US008785163B2

(12) United States Patent
Senger et al.

(10) Patent No.: US 8,785,163 B2
(45) Date of Patent: Jul. 22, 2014

(54) DESATURASES AND METHODS FOR PRODUCING POLYUNSATURATED FATTY ACIDS IN TRANSGENIC ORGANISMS

(75) Inventors: Toralf Senger, Weinheim (DE); Jörg Bauer, Limburgerhof (DE)

(73) Assignee: BASF Plant Science GmbH, Ludwigshafen (DE)

( * ) Notice: Subject to any disclaimer, the term of this patent is extended or adjusted under 35 U.S.C. 154(b) by 332 days.

(21) Appl. No.: 12/671,090

(22) PCT Filed: Jul. 30, 2008

(86) PCT No.: PCT/EP2008/059999

§ 371 (c)(1), (2), (4) Date: Jan. 28, 2010

(87) PCT Pub. No.: WO2009/016202

PCT Pub. Date: Feb. 5, 2009

(65) Prior Publication Data

US 2010/0199365 A1 Aug. 5, 2010

(30) Foreign Application Priority Data

| | | |
|---|---|---|
| Jul. 31, 2007 | (EP) | 07113506 |
| Dec. 20, 2007 | (EP) | 07123864 |
| Apr. 1, 2008 | (EP) | 08103294 |

(51) Int. Cl.

| | |
|---|---|
| ***C12P 7/64*** | (2006.01) |
| ***C12N 9/00*** | (2006.01) |
| ***C12N 9/02*** | (2006.01) |
| ***C12N 1/20*** | (2006.01) |
| ***C12N 15/00*** | (2006.01) |
| ***C07H 21/04*** | (2006.01) |

(52) U.S. Cl.

USPC ........ 435/134; 435/186; 435/189; 435/252.3; 435/320.1; 536/23.2

(58) Field of Classification Search

None

See application file for complete search history.

(56) References Cited

U.S. PATENT DOCUMENTS

| | | | | |
|---|---|---|---|---|
| 6,075,138 | A | 6/2000 | Kojima et al. | |
| 6,075,183 | A | 6/2000 | Knutzon et al. | |
| 2006/0094090 | A1 * | 5/2006 | Damude et al. | 435/134 |
| 2006/0115881 | A1 | 6/2006 | Damude et al. | |

FOREIGN PATENT DOCUMENTS

WO WO-03/099216 A2 12/2003

OTHER PUBLICATIONS

Chica et al. Curr Opin Biotechnol. Aug. 2005;16(4):378-84.*

Sen et al. Appl Biochem Biotechnol. Dec. 2007;143(3):212-23.*

Accession Q10W96. Aug. 22, 2006.*

Oura, T., et al., "*Saccharomyces kluyveri FAD3* Encodes an ω3 Fatty Acid Desaturase", Microbiology, vol. 150, (2004), pp. 1983-1990.

Wongwathanarat, P., et al., "Two Fatty Acid Δ9-desaturase Genes, *ole1* and *ole2*, from *Mortierella alpina* Complement the Yeast *ole1* Mutation", Microbiology, vol. 145, (1999), pp. 2939-2946.

* cited by examiner

*Primary Examiner* — Christian Fronda

(74) *Attorney, Agent, or Firm* — Drinker Biddle & Reath LLP

(57) ABSTRACT

The present invention relates to polynucleotides from *Helobdella robusta, Laccaria bicolor, Lottia gigantea, Microcoleus chthonoplastes, Monosiga brevicollis, Mycosphaerella fijiensis, Mycospaerella graminicola, Naegleria gruberi, Nectria haematococca, Nematostella vectensis, Phycomyces blakesleeanus, Trichoderma resii, Physcomitrella patens, Postia placenta, Selaginella moellendorffii* and *Microdochium nivale*, which code for desaturases and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production processes for the polyunsaturated fatty acids and for oil, lipid and fatty acid compositions and to their use as drugs, cosmetics, foodstuffs, feedstuffs, preferably fish food, or food supplements.

24 Claims, 12 Drawing Sheets

4D

4E

5D

5E

5F

6D

7D

Figure 1:
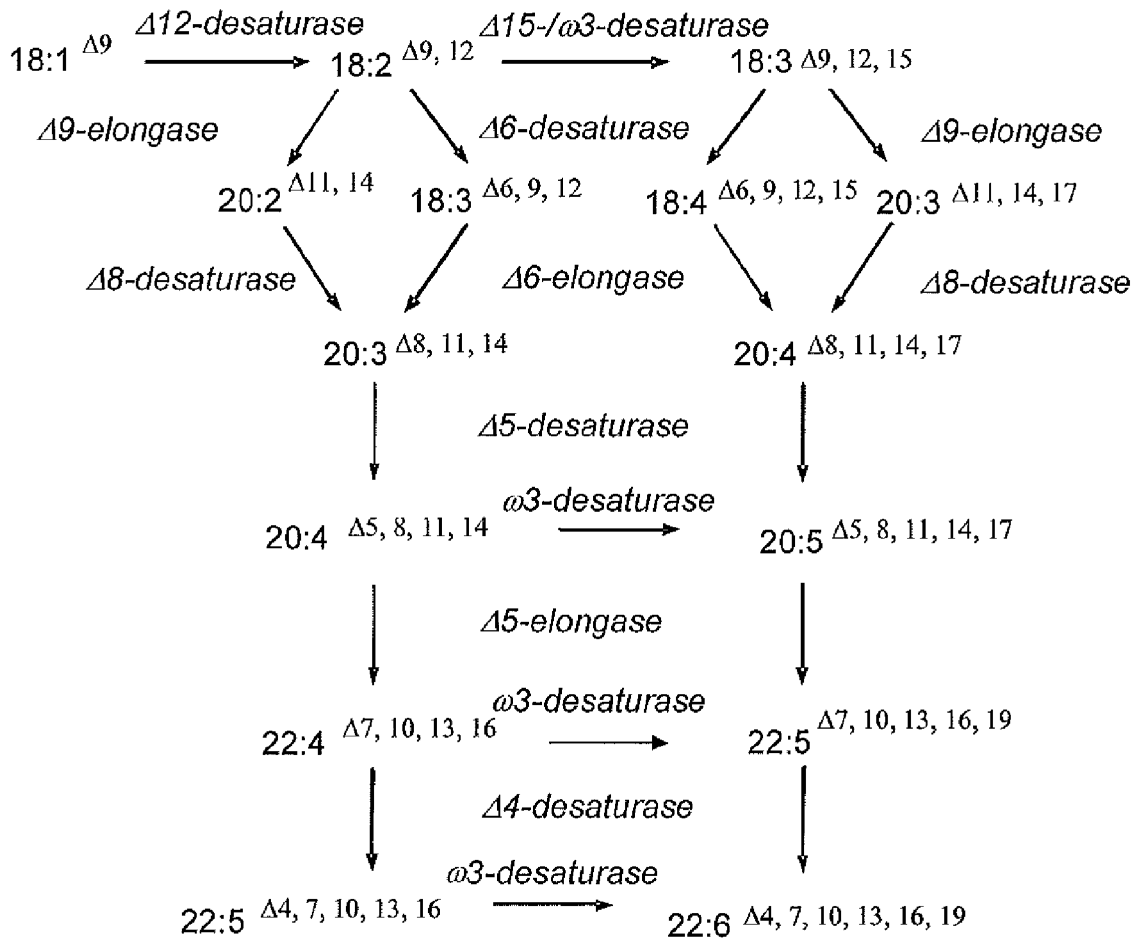

DESATURASES AND METHODS FOR PRODUCING POLYUNSATURATED FATTY ACIDS IN TRANSGENIC ORGANISMS

RELATED APPLICATIONS

This application is a national stage application (under 35 U.S.C. §371) of PCT/EP2008/059999, filed Jul. 30, 2008, which claims benefit of European application 07113506.5, filed Jul. 31, 2007, European application 07123864.6, filed Dec. 20, 2007 and European application 08103294.8, filed Apr. 1, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List__17418__00007_US. The size of the text file is 284 KB, and the text file was created on Jan. 26, 2010.

The present invention relates to polynucleotides from *Helobdella robusta, Laccaria bicolor, Lottia gigantea, Microcoleus chthonoplastes, Monosiga brevicollis, Mycosphaerella fijiensis, Mycospaerella graminicola, Naegleria gruberi, Nectria haematococca, Nematostella vectensis, Phycomyces blakesleeanus, Physcomitrella patens, Postia placenta, Selaginella moellendorffii, Microdochium nivale* and *Trichoderma resii* which code for desaturases and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production processes for the polyunsaturated fatty acids and for oil, lipid and fatty acid compositions and to their use as drugs, cosmetics, foodstuffs, feedstuffs, preferably fish food, or food supplements.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter themselves. Polyunsaturated ω3-fatty acids and ω6-fatty acids are therefore an important constituent in animal and human nutrition.

Polyunsaturated long-chain ω3-fatty acids such as eicosapentaenoic acid (=EPA, $C20:5^{\Delta5,8,11,14,17}$) or docosahexaenoic acid (=DHA, $C22:6^{\Delta4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the present-day composition of human food, an addition of polyunsaturated ω3-fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (polyunsaturated fatty acids, PUFA, long-chain polyunsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, $C20:4^{\Delta5,8,11,14}$) dihomo-γ-linolenic acid ($C20:3^{\Delta8,11,14}$) or docosapentaenoic acid (DPA, $C22:5^{\Delta7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, a stroke or hypertension can be reduced markedly by adding these ω3-fatty acids to food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to their positive characteristics, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, WO 96/21022, WO 00/21557 and WO 99/27111. Their application for production in transgenic organisms is described, for example, in WO 98/46763, WO 98/46764 and WO 98/46765. In this context, the expression of various desaturases and the formation of polyunsaturated fatty acids is also described and claimed; see, for example, WO 99/64616 or WO 98/46776, As regards the expression efficacy of desaturases and their effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricomutum, Porphiridium* species, *Thraustochytrium* species, *Schizochytrium* species or *Crypthecodinium* species, ciliates such as *Stylonychia* or *Colpidium*, fungi such as *Mortierella, Entomophthora* or *Mucor* and/or mosses such as *Physcomitrella*, preferably *Physcomitrella patens, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible. However, only limited amounts of the desired polyunsaturated fatty acids such as DPA, EPA or ARA can be produced with the aid of the abovementioned microorganisms. Moreover, depending on the microorganism used, these are generally generated as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA). Thus, EPA or DHA are produced in marine bacteria such as *Vibrio* sp. or *Shewanella* sp. via the polyketide pathway (Yu, R. et al, Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the pathway described in Zank et al. and in Sakuradani et al. via Δ6-desaturase, Δ6-elongase, Δ5-desaturase, Δ5-elongase and Δ4-desaturase is the Sprecher synthesis pathway (Sprecher 2000, Biochim. Biophys. Acta 1486: 219-231) in mammals. Instead of the Δ4-desaturation, a further elongation step is effected here to give $C_{24}$, followed by a further Δ6-desaturation and finally β-oxidation to give the $C_{22}$ chain length. What is known as the Sprecher synthesis pathway is, however, not suitable for the production in plants and microorganisms since the regulatory mechanisms are not yet known.

Depending on their desaturation pattern, the polyunsaturated fatty acids can be divided into two large classes, viz. ω6- or ω3-fatty acids, which differ with regard to their metabolic and functional activities. The starting material for the ω6-metabolic pathway is the fatty acid linoleic acid ($18:2^{\Delta 9,12}$), while the ω3-pathway proceeds via linolenic acid ($18:3^{\Delta 9,12,15}$). Linolenic acid is formed by the activity of a Δ15-desaturase (Tocher et al. 1998, Prog. Lipid Res. 37, 73-117; Domergue et al. 2002, Eur, J. Biochem. 269, 4105-4113).

Mammals, and thus also humans, have no corresponding desaturase activity (Δ12- and Δ15-desaturase) and must take up these fatty acids (essential fatty acids) via food. Starting with these precursors, the physiologically important polyunsaturated fatty acids arachidonic acid (=ARA, $20:4^{\Delta 5,8,11,14}$), an ω6-fatty acid, and the two ω3-fatty acids) eicosapentaenoic acid (=EPA, $20:5^{\Delta 5,8,11,14,17}$) and docosahexaenoic acid (DHA, $22:6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

Higher plants comprise polyunsaturated fatty acids such as linoleic acid (C18:2) and linolenic acid (C18:3). ARA, EPA and DHA are not found at all in the seed oil of higher plants, or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants (preferably in oil crops such as oilseed rape, linseed, sunflower and soybeans) would be advantageous since large amounts of high-quality LCPUFAs for the food industry, animal nutrition and pharmaceutical purposes can be obtained economically thereby. A potential route is via recombinant methods, where genes which code for enzymes of the biosynthesis of LCPUFAs are introduced and expressed into oil crops. These genes code for, for example, Δ6-desaturases, Δ6-elongases, Δ5-desaturases or Δ4-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans* (Zank, T. K. et al. Plant Journal 31:255-268, 2002, Beaudoin et al. Biochem Soc Trans 28:661-663, 2000).

The first transgenic plants which comprise and express genes coding for LCPUFA biosynthesis enzymes and which produce LCPUFAs were described, for example, in DE-A-102 19 203 (process for the production of polyunsaturated fatty acids in plants). However, these plants produce LCPUFAs in amounts which require further optimization for processing the oils which are present in the plants.

To make possible the fortification of food and of feed with these polyunsaturated fatty acids, there is therefore a great need in terms of means and measures for a simple, inexpensive process for the production of these polyunsaturated fatty acids, specifically in eukaryotic systems.

The object on which the present invention is based is the provision of such means and measures. This object is achieved by the embodiments which are described in the patent claims and hereinbelow.

The present invention thus relates to a polynucleotide comprising a nucleic acid sequence which is selected from the group consisting of:

(a) nucleic acid sequence as shown in any of SEQ ID NO. 1, 2, 4, 5, 7, 8, 10, 11, 13, 14, 16, 17, 19, 20, 22, 23, 25, 26, 90, 91, 122, 123, 125, 126, 128, 129, 131, 132, 134, 135, 142, 143, 145, 146, 148, 149, 151, 152, 154, 155 and 157;

(b) nucleic acid sequence which codes for a polypeptide which features an amino acid sequence as shown in any of SEQ ID No. 3, 6, 9, 12, 15, 18, 21, 24, 27, 92, 124, 127, 130, 133, 136, 144, 147, 150, 153, 156 and 158;

(c) nucleic acid sequence which has at least 70% identity to one of the nucleic acid sequences of (a) or (b), and which codes for a polypeptide with a desaturase activity; and (d) nucleic acid sequence for a fragment of a nucleic acid of (a), (b) or (c), where the fragment codes for a polypeptide with a desaturase activity.

The class of the ω6-fatty acids is based on the ω6-fatty acid linoleic acid (18:2Δ9,12), while the class of the ω3-fatty acids is based on the ω3-fatty acid linolenic acid (18:3Δ9,12,15); see FIG. 1. These two fatty acids are the substrates for the synthesis of long-chain ω6- and ω3-PUFAs, respectively. The increase of the content in these fatty acids according to the genes which are introduced leads to an increase of the content in long-chain PUFAs.

The present invention provides polynucleotide sequences which lead to an increase of the substrates 18:2Δ9,12 and 18:3Δ9,12,15, respectively. There have been identified polynucleotide sequences which code for enzymes with Δ12-desaturase activity, with Δ12- and Δ15-desaturase activity, with Δ15-desaturase activity or with ω3-desaturase activity.

According to the invention, the term "polynucleotide" refers to polynucleotides which comprise nucleic acid sequences which code for polypeptides with desaturase activity. The desaturase activities are preferably required for the biosynthesis of lipids or fatty acids. Especially preferably, they take the form of the following desaturase activities: Δ12-desaturase, Δ15-desaturase, Δ12- and Δ15-desaturase or omega-3-desaturase activity. The desaturases are preferably involved in the synthesis of polyunsaturated fatty acids (PUFAs) and especially preferably in the synthesis of long-chain PUFAs (LCPUFAs). Suitable detection systems for these desaturase activities are described in the examples or in WO 2005/083053. The desaturase according to the invention especially preferably have activities, substrate specificities and/or conversion rates which are comparable to those of the respective homologous desaturase enzymes from *Pythium irregulare, Ostreococcus tauri; Phytophthora sojae* or *Phytophthora infestans*. The specific polynucleotides according to the invention, i.e. the polynucleotides with a nucleic acid sequence as shown in SEQ ID No. 1, 2, 4, 5, 7, 8, 10, 11, 13, 14, 16, 17, 19, 20, 22, 23, 25, 26, 90, 91, 122, 123, 125, 126, 128, 129, 131, 132, 134, 135, 142, 143, 145, 146, 148, 149, 151, 152, 154, 155 or 157 have been obtained from *Nectria haematococca, Trichoderma resii, Monosiga brevicollis, Mycosphaerella fijiensis, Mycospaerella graminicola* (*Septoria tritici*), *Naegleria gruberi, Phycomyces blakesleeanus, Nematostella vectensis, Helobdella robusta, Lottia gigantea, Microcoleus chthonoplastes, Laccaria bicolor, Physcomitrella patens, Postia placenta, Selaginella moellendorffii* or *Microdochium nivale*. In particular, the nucleic acid sequences according to SEQ ID No. 1, 2, 4 and 5 originate from *Nectria haematococca*, the nucleic acid sequences according to SEQ ID No. 7 and 8 from *Trichoderma resii*, the nucleic acid sequences according to SEQ ID No. 10 and 11 from *Monosiga brevicollis*, the nucleic acid sequences according to SEQ ID No. 13, 14, 16 and 17 from *Mycosphaerella graminicola* (*Septoria tritici*), the nucleic acid sequences according to SEQ ID No. 19 and 20 from *Naegleria gruberi*, the nucleic acid sequences according to SEQ ID No. 22 and 23 from *Phycomyces blakesleeanus*, the nucleic acid sequences according to SEQ ID No. 25 and 26 from *Nematostella vectensis*, the nucleic acid sequences according to SEQ ID No. 90 and 91 from *Laccaria bicolor*, the nucleic acid sequences according to SEQ ID No. 134 and 135 from *Mycosphaerella fijiensis*, the nucleic acid sequences according to SEQ ID No. 122 and 123 from *Helobdella robusta*, the nucleic acid sequences according to SEQ ID No. 125, 126, 128 and 129 from *Lottia gigantea*, the nucleic acid sequences according to SEQ ID No. 131 and 132 from *Microcoleus chthonoplastes*, the nucleic acid sequences according to SEQ ID No. 142, 143, 145, 146, 148, 149 from *Physcomitrella patens*, the nucleic acid sequences according to SEQ ID No. 151, 152 from *Postia placenta*, the nucleic acid sequences according to SEQ ID No. 154, 155 from *Selaginella moellendorffii* and the nucleic acid sequence according to SEQ ID No. 157 from *Microdochium nivale*. The SEQ ID No. 1, 4, 7, 10, 13, 16, 19, 22, 25, 90, 122, 125, 128, 131, 134, 142, 145, 148, 151 and 154 are genomic sequences, while the SEQ ID No. 2, 5, 8, 11, 14, 17, 20, 23, 26, 91, 123, 126, 129, 132, 135, 143, 146, 149, 152, 155 and 157 are coding sequences (cds). The SEQ ID No. 3, 6, 9, 12, 15, 18, 21, 24, 27, 92, 124, 127, 130, 133, 136, 144, 147, 150, 153, 156 and 158 show the corresponding amino acid sequences.

Polynucleotides according to the invention are therefore in particular:

Polynucleotides which code for a polypeptide with Δ12-desaturase activity and which comprise (i) a nucleic acid sequence as shown in SEQ ID No. 1 or 2, (ii) a nucleic acid sequence which codes for a polypeptide as shown in SEQ ID No. 3, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ12-desaturase activity.

Polynucleotides which code for a polypeptide with Δ15-desaturase activity and which comprise (i) a nucleic acid sequence as shown in SEQ ID No. 4 or 5, (ii) a nucleic acid sequence which codes for a polypeptide as shown in SEQ ID No. 6, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 7 or 8, (ii) a nucleic acid sequence which codes for a polypeptide as shown in SEQ ID No. 9, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ12-desaturase activity and which comprise (i) a nucleic acid sequence as shown in SEQ ID No. 10 or 11, (ii) a nucleic acid sequence which codes for a polypeptide as shown in SEQ ID No. 12, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ12-desaturase activity.

Polynucleotides which code for a polypeptide with Δ15-desaturase activity and which comprise (i) a nucleic acid sequence as shown in SEQ ID No. 13 or 14, (ii) a nucleic acid sequence which codes for a polypeptide as shown in SEQ ID No. 15, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ12-desaturase activity and which comprise (i) a nucleic acid sequence as shown in SEQ ID No. 16 or 17, (ii) a nucleic acid sequence which codes for a polypeptide as shown in SEQ ID No. 18, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ12-desaturase activity.

Polynucleotides which code for a polypeptide with Δ15-desaturase activity and which comprise (i) a nucleic acid sequence as shown in SEQ ID No. 19 or 20, (ii) a nucleic acid sequence which codes for a polypeptide as shown in SEQ ID No. 21, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ12-desaturase activity.

Polynucleotides which code for a polypeptide with Δ12-desaturase activity and which comprise (i) a nucleic acid sequence as shown in SEQ ID No. 22 or 23, (ii) a nucleic acid sequence which codes for a polypeptide as shown in SEQ ID No. 24, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ12-desaturase activity.

Polynucleotides which code for a polypeptide with omega-3-desaturase (in particular Δ15-desaturase) activity and which comprise (i) a nucleic acid sequence as shown in SEQ ID No. 25 or 26, (ii) a nucleic acid sequence which codes for a polypeptide as shown in SEQ ID No. 27, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with an ω3-(omega-3)-desaturase (in particular Δ15-desaturase) activity.

Polynucleotides which code for a polypeptide with Δ15-desaturase activity and which comprise (i) a nucleic acid sequence as shown in SEQ ID No. 90 or 91, (ii) a nucleic acid sequence which codes for a polypeptide as shown in SEQ ID No. 92, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 122 or 123, (ii) a nucleic acid sequence which codes for a polypeptide as shown in SEQ ID No. 124, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 125 or 126, (ii) a nucleic acid sequence which codes for a polypeptide as shown in SEQ ID No. 127, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 128 or 129, (ii) a nucleic acid sequence which codes for a polypeptide as shown in SEQ ID No. 130, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 131 or 132, (ii) a nucleic acid sequence which codes for a polypeptide as shown in SEQ ID No. 133, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 134 or 135, (ii) a nucleic acid sequence which codes for a polypeptide as shown in SEQ ID No. 136, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 142 or 143, (ii) a nucleic acid sequence which codes for a polypeptide as shown in SEQ ID No. 144, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 145 or 146, (ii) a nucleic acid sequence which codes for a polypeptide as shown in SEQ ID No. 147, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 148 or 149, (ii) a nucleic acid sequence which codes for a polypeptide as shown in SEQ ID No. 150, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 151 or 152, (ii) a nucleic acid sequence which codes for a polypeptide as shown in SEQ ID No. 153, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 154 or 155, (ii) a nucleic acid sequence which codes for a polypeptide as shown in SEQ ID No. 156, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 157, (ii) a nucleic acid sequence which codes for a polypeptide as shown in SEQ ID No. 158, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

The term "delta-12-desaturase (or Δ12-desaturase or d-12-desaturase or d12-Des or d12Des)" or "delta-12-desaturase (or Δ12-desaturase or d-12-desaturase or d12-Des or d12Des) activity" as used in the present context refers to an enzyme with the enzymatic function for dehydrogenating C18-fatty acids which are already dehydrogenated on the C atom 9-10. Here, the C atoms C12 and C13 are dehydrogenated by in each case one hydrogen atom, giving rise to a double bond between these two C atoms.

The term "delta-15-desaturase (or Δ15-desaturase or d-15-desaturase or d15-Des or d15Des)" or "delta-15-desaturase (or Δ15-desaturase or d-15-desaturase or d15-Des or d15Des) activity" as used in the present context refers to an enzyme with the enzymatic function for dehydrogenating C18- and/or C20-fatty acids which are dehydrogenated on the C atoms 6-7, 8-9, 9-10, 12-13 and/or 13-14. Here, the C atoms C15-16 and/or C17-18 are dehydrogenated by in each case one hydrogen atom, giving rise to a double bond between the two C atoms.

The term "delta-12- and delta-15-desaturase (or Δ12- and Δ15-desaturase or as written hereinabove)" or "delta-12- and delta-15-desaturase (or Δ12- and Δ15-desaturase or as written hereinabove) activity" as used in the present context refers to an enzyme with the enzymatic function for dehydrogenating C18- and/or C20-fatty acids which are dehydrogenated on the C atoms 6-7, 8-9, 9-10 and/or 13-14. Here, the C atoms C12-13 and C15-16 and/or C17-18 are dehydrogenated by in each case one hydrogen atom, giving rise to a double bond between the two C atoms.

The term "omega-3-desaturase (or ω3-desaturase or ω3-Des or ω3Des or omega3 Des or o3Des)" or "omega-3-desaturase (or ω3-desaturase or ω3-Des or ω3Des or omega3 Des or o3Des) activity" as used in the present context refers to an enzyme with the enzymatic function for the dehydrogenation of C18-, C20- and/or C22-fatty acids which are dehydrogenated on the C atoms 4-5, 5-6, 6-7, 8-9, 9-10, 13-14 and/or 16-17. Here, the C atoms C15-16 and/or C17-18 and/or C19-20 are dehydrogenated by in each case one hydrogen atom, giving rise to a double bond between the two C atoms.

In this context, the polynucleotide sequences or polypeptide sequences according to the invention preferably originate from the abovementioned organisms.

It is clear that, in the light of the degeneracy of the genetic code, the abovementioned specific sequences can also be modified, where the modified polynucleotides still code for polypeptides with an amino acid sequence as shown in any of SEQ ID No. 3, 6, 9, 12, 15, 18, 21, 24, 27, 92, 124, 127, 130, 133, 136, 144, 147, 150, 153, 156, or 158 and which have the abovementioned desaturase activities.

The term "polynucleotide" also comprises variants of the abovementioned specific polynucleotides. These may take the form of homologous, orthologous or paralogous sequences. Such variants comprise nucleic acid sequences which feature at least one base substitution, one base addition or one base deletion, it being intended that the variants still code for a polypeptide with the abovementioned biological activity of the respective starting sequence. Variants comprise polynucleotides which are capable of hybridization with the abovementioned polynucleotides, preferably under stringent conditions. Especially preferred stringent conditions are known to the skilled worker and can be found in Current Protocols in Molecular Biology, John Wiley & Sons, N.Y. (1989), 6.3.1-6.3.6. A preferred example of stringent hybridization conditions are hybridizations in 6× sodium chloride/sodium citrate (=SSC) at approximately 45° C., preferably 50° C., 55° C., 60° C. and most preferably at 62° C., followed by one or more wash steps in 0.1×SSC, 0.1% SDS at 50 to 65° C., preferably 55 to 65° C., even more preferably at 60 to 65° C. The skilled worker knows that these hybridization conditions differ as a function of the type of nucleic acid and, for example when organic solvents are present, with regard to the temperature and the buffer concentration. Under "standard hybridization conditions", the temperature differs as a function of the type of nucleic acid between 42° C. and 58° C. in aqueous buffer with a concentration of from 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1×SSC and 30° C. to 55° C., preferably between 45° C. and 55° C. The abovementioned hybridization temperatures are determined for example for a nucleic acid of approximately 100 bp (=base pairs) in length and a G+C content of 50% in the absence of formamide. The skilled worker knows how to determine the hybridization conditions required with the aid of textbooks, such as the one mentioned hereinabove, or from the following textbooks: Sambrook et al., "Molecular Cloning", Cold Spring Harbor Laboratory, 1989; Hames and Higgins (eds.) 1985, "Nucleic Acids Hybridization: A Practical Approach", IRL Press at Oxford University Press, Oxford; Brown (ed.) 1991, "Essential Molecular Biology: A Practical Approach", IRL Press at Oxford University Press, Oxford. As an alternative, variants of the specific polynucleotides according to the invention may also be provided by polymerase chain reaction (PCR)-based methods. To this end, it is possible first to derive primers from conserved sequences (for example sequences which code for functional domains in the polypeptide). Conserved sequences can be determined by sequence comparisons with polynucleotides which code for polypeptides with a similar activity. The template used may be DNA or cDNA from bacteria, fungi, plants or animals. DNA fragments obtained by PCR can be used for screening suitable genomic libraries or cDNA libraries in order to—if required—isolate the complete open reading frame of the polynucleotide and to determine it by sequencing. Preferred variants comprise polynucleotides which comprise a nucleic acid sequence with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% (or a different percentage than mentioned herein) identity with one of the abovementioned specific nucleic acid sequences and which codes for a polypeptide with the respective biological activity. Equally preferably comprised are polynucleotides which comprise nucleic acid sequences which code for a polypeptide with an amino acid sequence with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% (or a different percentage than mentioned herein) identity with one of the abovementioned specific amino acid sequences and where the polypeptide has the respective biological activity of the starting sequence.

The percentage of identical nucleotides or amino acids preferably relates to a sequence segment of at least 50% of the sequences to be compared, and especially preferably over the entire length of the sequences to be compared. A multiplicity of programs which implement algorithms for such comparisons are described in the prior art and commercially available. In particular, reference may be made to the algorithms of Needleman and Wunsch or Smith and Waterman, which give particularly reliable results. These algorithms can preferably be implemented by the following programs: PileUp (J. Mol. Evolution., 25, 351-360, 1987, Higgins et al., 1989, CABIOS, 5: 151-153), Gap and BestFit (Needleman and Wunsch (J. Mol. Biol. 48; 443-453 (1970)) and Smith and Waterman (Adv. Appl. Math. 2; 482-489 (1981))), as part of the GCG software (Genetics Computer Group, 575 Science Drive, Madison, Wis., USA 53711, 1991). For the purposes of the present invention, it is especially preferred to determine the percentage (%) of the sequence identity with the GAP program over the entire sequence, with the following set parameters: Gap Weight: 50, Length Weight: 3, Average Match: 10.000 and Average Mismatch: 0.000.

A polynucleotide which only comprises a fragment of the abovementioned nucleic acid sequences is also a polynucleotide according to the invention. Here, it is intended that the fragment codes for a polypeptide which features the biological activity of the starting sequence, or of the polypeptide which the latter codes for. Polypeptides which are encoded by such polynucleotides therefore comprise, or consist of, domains of the abovementioned specific polypeptides (starting polypeptides) which confer the biological activity. A fragment for the purposes of the invention preferably comprises at least 50, at least 100, at least 250 or at least 500 consecutive nucleotides of the abovementioned specific sequences or codes for an amino acid sequence comprising at least 20, at least 30, at least 50, at least 80, at least 100 or at least 150 consecutive amino acids of one of the abovementioned specific amino acid sequences, and confers biological activity, preferably desaturase activity, as described above.

The polynucleotide variants according to the invention preferably feature at least 10%, at least 20%, at least 30%, at least 40%, at least 50%, at least 60%, at least 70%, at least 80% or at least 90% of the respective biological activity of the polypeptide which is encoded by the starting sequence. That is to say the polypeptides which are encoded by the polynucleotides according to the invention can participate in the metabolism of compounds required for the synthesis of fatty acids, fatty acid esters such as diacylglycerides and/or triacylglycerides in an organism, preferably in a plant or plant cell, or can participate in the transport of molecules across membranes, which means $C_{18}$-, $C_{20}$- or $C_{22}$-carbon chains in the fatty acid molecule with double bonds at least two, advantageously three, four, five or six positions.

The polynucleotides according to the invention either comprise the abovementioned specific nucleic acid sequences or consist of them. That is to say that the polynucleotides according to the invention may, in principle, also comprise further nucleotides. These may preferably be 3'- or 5'-untranslated regions of the genomic nucleic acid sequence. They preferably consist of at least 100, 200 or 500 nucleotides at the 5' terminus and of at least 20, 50 or 100 nucleotides at the 3' terminus of the coding region. Further polynucleotides which comprise additional nucleic acid sequences are those which code for fusion proteins. Such fusion proteins can code for further polypeptides or polypeptide portions, in addition to the abovementioned polypeptides. The additional polypeptide or polypeptide portion may take the form of further enzymes of lipid or fatty acid biosynthesis. Others which are feasible are polypeptides which may act as expression markers (green, yellow, red, blue fluorescent proteins, alkaline phosphatase and others) or so-called "tags" as labels or as an aid for purification (for example FLAG tags, 6-histidine tags, MYC tags and others).

Polynucleotide variants can be isolated from different natural or artificial sources. For example, they can be generated artificially by in-vitro or in-vivo mutagenesis. Homologs or orthologs of the specific sequences can be obtained from a wide range of animals, plants and microorganisms. They are preferably obtained from algae. Algae such as *Isochrysis, Euglena* or *Crypthecodinium*, algae/diatoms such as *Thalassiosira, Phaeodactylum* or *Thraustochytrium, Pythium*, mosses such as *Physcomitrella*, preferably *Physcomitrella patens* or *Ceratodon* are preferred, very especially preferred are the algae of the genus *Euglena* or the diatoms of the class Oomycota such as the genera *Pythium* or *Phytophthora* or fungi such as *Postia placenta* or *Microdochium nivale*, or from the division Zygomycota from the genera *Rhizopus*. The polynucleotides can also be obtained from plants, preferably from the family Selaginellaceae, such as *Selaginella moellendorffii*, or from higher plants such as Primulaceae such as *Aleuritia, Calendula stellate, Osteospermum spinescens* or *Osteospermum hyoseroides*, microorganisms such as fungi such as *Aspergillus, Thraustochytrium, Phytophthora, Entomophthora, Rhizopus, Mucor* or *Mortierella*, bacteria such as *Shewanella*, cyanobacteria such as *Synechococcus*, yeasts or animals such as nematodes, for example *Caenorhabditis*, molluscs, insects or fish. The polynucleotide variants are also preferably derived from an animal from the order vertebrates. Especially preferably, the polynucleotides are derived from the class Vertebrata; Euteleostomi, Actinopterygii; Neopterygii; Teleostei; Euteleostei, Protacanthopterygii, Salmoniformes; Salmonidae or *Oncorhynchus* and, very especially preferably, from the order Salmoniformes such as the family Salmonidae, such as the genus *Salmo*, for example from the genera and species *Oncorhynchus mykiss, Trutta trutta* or *Salmo trutta fario*. Here, the polynucleotides according to the invention can be isolated by means of standard techniques of molecular biology and of the sequence information provided herein. Also, it is possible, with the aid of comparative algorithms, to identify for example a homologous sequence or homologous, conserved sequence regions at the DNA or amino acid level. These can be employed as hybridization probe and standard hybridization techniques (such as, for example, those described in Sambrook et al., Molecular Cloning: A Laboratory Manual. 2nd Ed., Cold Spring Harbor Laboratory, Cold Spring Harbor Laboratory Press, Cold Spring Harbor, N.Y., 1989) for isolating further nucleic acid sequences which are useful in the process. Moreover, it is possible to isolate polynucleotides or fragments thereof by means of polymerase chain reaction (PCR), where oligonucleotide primers which are based on this sequence or parts thereof are employed (for example, a nucleic acid molecule comprising the complete sequence or part thereof can be isolated by polymerase chain reaction using oligonucleotide primers which have been generated on the basis of this same sequence). For example, it is possible to isolate mRNA from cells (for example by the guanidinium thiocyanate extractive method by Chirgwin et al. (1979) Biochemistry 18:5294-5299), and cDNA can be generated by means of reverse transcriptase (for example Moloney MLV reverse transcriptase, obtainable from Gibco/BRL, Bethesda, Md., or AMV reverse transcriptase, obtainable from Seikagaku America, Inc., St. Petersburg, Fla.). Synthetic oligonucleotide primers for the amplification by means of polymerase chain reaction can be generated on the basis of the polynucleotide and amino acid sequences shown in the SEQ ID numbers (SEQ ID No.). A nucleic acid according to the invention can be amplified using cDNA or, alternatively, genomic DNA as the template and suitable oligonucleotide primers, following standard PCR amplification techniques. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

The polynucleotides according to the invention can either be provided in the form of isolated polynucleotides (i.e. isolated from their natural origin, for example the genomic locus) or else in genetically modified form (i.e. the polynucleotides may also be present at their natural genetic locus, but, in such a case, must be genetically modified). An isolated polynucleotide preferably comprises less than 5 kb, 4 kb, 3 kb, 2 kb, 1 kb, 0.5 kb or 0.1 kb of nucleic acid sequence which occurs naturally in its environment. The polynucleotide according to the invention may be present as a single-stranded or double-stranded nucleic acid molecule and may take the form of genomic DNA, cDNA or RNA. Preferably, the polynucleotide according to the invention consists of RNA or DNA. The polynucleotides according to the invention comprise all orientations of the sequences shown in the SEQ ID numbers, i.e. also complementary strands and reverse, or reverse-complementary, orientations. The term furthermore also comprises chemically modified nucleic acids, such as the naturally occurring methylated DNA molecules, or artificial nucleic acids, for example biotinylated nucleic acids.

The invention also comprises oligonucleotides of at least 15 bp, preferably at least 20 bp, at least 25 bp, at least 30 bp, at least 35 bp or at least 50 bp, which are capable of specifically hybridizing under stringent conditions with one of the abovementioned polynucleotides. The oligonucleotides may consist of DNA or RNA or both. Such oligonucleotides can be employed as primers for the PCR, as expression-inhibitory antisense oligonucleotides, for RNA interference (RNAi) approaches or for chimeroplastic or genoplastic approaches. RNAi methods are described for example in Fire et al., Nature (1998) 391:806-811; Fire, Trends Genet. 15, 358-363 (1999); Sharp, RNA interference 2001. Genes Dev. 15, 485-490 (2001); Hammond et al. Nature Rev. Genet. 2, 1110-1119 (2001); Tuschl, Chem. Biochem, 2, 239-245 (2001); Hamilton et al., Science 286, 950-952 (1999); Hammond et al., Nature 404, 293-296 (2000); Zamore et al., Cell 101, 25-33 (2000); Bernstein et al., Nature 409, 363-366 (2001); Elbashir at al., Genes Dev. 15, 188-200 (2001); WO 01/29058; WO 99/32619; or Elbashir at al., 2001 Nature 411: 494-498 and serve for inhibiting gene expression by degrading the mRNA. Chimeroplastic or genoplastic approaches serve the in-vivo modification (for example the introduction of point mutations) into genes at their endogenous loci. Corresponding methods are disclosed in U.S. Pat. No. 5,565,350, U.S. Pat. No. 5,756,325, U.S. Pat. No. 5,871,984, U.S. Pat. No. 5,731,181, U.S. Pat. No. 5,795,972, U.S. Pat. No. 6,573,046, U.S. Pat. No. 6,211,351, U.S. Pat. No. 6,586,184, U.S. Pat. No. 6,271,360 and U.S. Pat. No. 6,479,292.

Advantageously, it has emerged that the polynucleotides according to the invention can be employed particularly effectively for the recombinant production of polyunsaturated fatty acids in host cells and in transgenic organisms. In particular, the polypeptides which are encoded by the polynucleotides according to the invention and which have Δ12-desaturase, Δ15-desaturase, Δ12- and Δ15-desaturase or omega-3-desaturase activity are capable of converting $C_{18}$-, $C_{20}$- and $C_{22}$-fatty acids with one, two, three, four or five double bonds and preferably polyunsaturated $C_{18}$-fatty acids with one, two or three double bonds such as $C18:1^{\Delta 9}$, $C18:2^{\Delta 9,12}$ or $C18:3^{\Delta 6,9,12}$, polyunsaturated $C_{20}$-fatty acids with three or four double bonds such as $C20:3^{\Delta 8,11,14}$, $C20:4^{\Delta 5,8,11,14}$ or $C20:4^{\Delta 8,11,14,17}$ or polyunsaturated $C_{22}$-fatty acids with four or five double bonds such as $C22:4^{\Delta 7,10,13,16}$ or $C22:5^{\Delta 7,10,13,16,19}$. Especially preferably, the polynucleotide and amino acid sequences according to the invention lead to an increase in the 18:2Δ9,12- or 18:3Δ9,12,15-fatty acids. FIG. 1 shows where the desaturases according to the invention engage in the biosynthesis of long-chain polyunsaturated fatty acids and/or how they can be used for producing these fatty acids.

In this context, it is especially preferred to employ the Δ6-desaturase encoded by the polynucleotide sequence with SEQ ID No. 28 (d6Des(Pir)), the Δ6-elongase encoded by the polynucleotide sequence with SEQ ID No. 31 (d6Elo(Pp)), the Δ5-desaturase encoded by the polynucleotide sequence with SEQ ID No. 29 (d5Des(Tc)), the Δ5-elongase encoded by the polynucleotide sequence with SEQ ID No. 32 (d5Elo (Ot)), the Δ4-desaturase encoded by the polynucleotide sequence with SEQ ID No. 33 (d4Des(Tc)), the Δ6-elongase encoded by the polynucleotide sequence with SEQ ID No. 138 (d6Elo(Tp)), the Δ6-desaturase encoded by the polynucleotide sequence with SEQ ID No. 139 (d6Des(Ot)) with one or more of the desaturases according to the invention in order to synthesize long-chain polyunsaturated fatty acids; see in this context for example WO2006/100241. Alternatively, it is also possible to employ a Δ9-elongase and a Δ8-desaturase instead of the abovementioned Δ6-desaturase and the Δ6-elongase as described in WO2004/057001. Depending on the fatty acid which is to be prepared, it is possible to coexpress, in the host cells or transgenic organisms described hereinbelow, or to use in the methods according to the invention, a variety of combinations of the polynucleotides according to the invention with the abovementioned desaturases or elongases. Especially preferred combinations for the production of eicosapentaenoic acid are shown in tables 5 and 8 and for docosahexaenoic acid in table 6 hereinbelow. For example, it is possible to use a Δ12-desaturase, Δ15-desaturase, Δ12- and Δ15-desaturase, or omega-3-desaturase according to the invention, alone or in a suitable combination (for example a Δ12-desaturase and a Δ15-desaturase), together with d6Des(Pir) and/or d6Des(Ot), d6Elo(Pp), d5Des(Tc) and ω3Des(Pi) for the production of EPA. Equally, a Δ12-desaturase, Δ15-desaturase, Δ12- and Δ15-desaturase, or omega-3-desaturase according to the invention, alone or in a suitable combination, can be used together with d6Des(Pir) and/or d6Des(Ot), d6Elo(Pp), d5Des(Tc), ω3Des(Pi), d5Elo(Ot), d4Des(Tc) for the production of docosahexaenoic acid.

Preferably, it is the fatty acids in phospholipids or CoA fatty acid esters which are desaturated, advantageously in the CoA fatty acid esters. Thus, a simple, inexpensive production of these polyunsaturated fatty acids is possible, specifically in eukaryotic systems. The unsaturated fatty acids produced by means of the polynucleotides according to the invention can then be formulated as oil, lipid and fatty acid compositions and can be employed in a suitable manner.

The present invention furthermore relates to a vector which comprises the polynucleotide according to the invention.

The term "vector" refers to a nucleic acid molecule which is capable of transporting another nucleic acid molecule, such as the polynucleotides according to the invention, to which it is bound. One type of vector is a plasmid, a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicated together with the host genome. Moreover, certain vectors can govern the expression of genes with which they are in operable linkage. These vectors are referred to in the present context as expression vectors. Usually, expression vectors which are suitable for DNA recombination techniques take the form of plasmids. In the present description, "plasmid" and "vector" can be used exchangeably since the plasmid is the form of vector which is most frequently used. However, the invention is also intended to comprise other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA, artificial chromosomes. Finally, the term also comprises constructs for the targeted, i.e. homologous, recombination, or the heterologous insertion of polynucleotides.

Vectors can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Suitable cloning vectors are generally known to the skilled worker. In particular, they include vectors which can replicate in microbial systems, that is mainly vectors which ensure efficient cloning in yeasts or fungi, and which make possible the stable transformation of plants. Those which must be mentioned are in particular various binary and cointegrated vector systems which are suitable for the T-DNA-mediated transformation. Such vector systems are, as a rule, characterized in that they comprise at least the vir genes, which are required for the *agrobacterium*-mediated transformation, and the T-DNA-bordering sequences (T-DNA border). Preferably, these vector systems also comprise further cis-regulatory regions such as promoters and terminators and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, and the other bears T-DNA, but no vir gene. As a result, the last-mentioned vectors are relatively small, easy to manipulate and to replicate both in *E. coli* and in *Agrobacterium*. These binary vectors include vectors from the pBIB-HYG series, the pPZP series, the pBecks series and the pGreen series. Preferably used according to the invention are Bin19, pBl101, pBinAR, pGPTV and pCAMBIA. An overview of binary vectors and their use is found in Hellens et al, Trends in Plant Science (2000) 5, 446-451. The vectors with the inserted polynucleotides according to the invention can be propagated stably under selective conditions in microorganisms, in particular *Escherichia coli* and *Agrobacterium tumefaciens*, and make possible a transfer of heterologous DNA into plants or microorganisms. The polynucleotides according to the invention can be introduced into organisms such as microorganisms or plants by means of the cloning vectors and thus used for transforming plants. Vectors which are suitable for this purpose are published in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, eds.: Kung and R. Wu, Academic Press, 1993, 15-38; B. Jenes et al., Techniques for Gene Transfer, in: Transgenic Plants, vol. 1, Engineering and Utilization, eds.: Kung and R. Wu, Academic Press (1993), 128-143; Potrykus, Annu. Rev. Plant Physiol. Plant Molec. Biol. 42 (1991), 205-225.

The vector is preferably an expression vector. The polynucleotide is present in the expression vector according to the invention in operative (i.e. functional) linkage with an expression control sequence. The expression control sequence together with the polynucleotide and optionally further sequence elements of the vector is also referred to as the expression cassette. The expression control sequence ensures that, after transformation or transfection into a host cell, the polynucleotide can be expressed. The expression control sequence to be used preferably comprises cis-regulatory elements such as promoter and/or enhancer nucleic acid sequences, which are recognized by the transcription machinery of the host cells. The term furthermore comprises other expression control elements, for example polyadenylation signals and RNA-stabilizing sequences. These regulatory sequences are described for example in Goeddel: Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick and Thompson, chapter 7, 89-108, including the literature cited therein. Expression control sequences comprise those which govern the constitutive expression of a nucleotide sequence in many types of host cells, and those which govern the direct expression of the nucleotide sequence only in certain host cells under certain conditions. The skilled worker knows that the design of the expression vector may depend on factors such as the choice of the host cell to be transformed, the extent of the expression of the desired protein and the like. The polynucleotides according to the invention may be present in one or more copies in the expression cassette or in the expression vector according to the invention (for example in the form of several expression cassettes). Here, the regulatory sequences or factors can preferably have a positive effect on the gene expression of the introduced genes, as described above, and thereby increase it. Thus, it is possible to enhance the regulatory elements advantageously at the transcription level by using strong transcription signals such as promoters and/or "enhancers". Besides, it is also possible to enhance the translation, for example by improving the mRNA stability. Further expression control sequences within the meaning of the present invention are translation terminators at the 3' end of the polynucleotides to be translated. An example which can be used here is the OCS1 terminator. As in the case of the promoters, a different terminator sequence should be used for each polynucleotide to be expressed.

Preferred expression control sequences or regulatory sequences are present in promoters such as the cos, tac, trp, tet, trp-tet, lpp, lac, lpp-lac, laclq, T7, T5, T3, gal, trc, ara, SP6, λ-PR or λ-PL promoters and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscisic acid-inducible) or WO 93/21334 (ethanol- or cyclohexenol-inducible). Further suitable plant promoters are the cytosolic FBPase promoter or the ST-LSI promoter of potato (Stockhaus et al., EMBO J. 8, 1989, 2445), the *glycine max* phosphoribosyl-pyrophosphate amidotransferase promoter (Genbank Accession No. 087999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arobidopsis oleosin* promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890. In principle, it is possible to use all natural promoters together with their regulatory sequences, such as those mentioned above, as expression control sequences. It is also possible to use synthetic promoters, either in addition or alone, in particular when they mediate seed-specific expression, as described, for example, in WO 99/16890.

In order to achieve a particularly high PUFA content, especially in transgenic plants, the polynucleotides of the present invention should preferably be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vida faba*) [Bäumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2, 2, 1992], Lpt2 and lpt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see a review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure stable integration of the various biosynthesis genes into the transgenic plant over a plurality of generations, each of the polynucleotides according to the invention should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site (advantageously in a polylinker) for insertion of the nucleic acid to be expressed and, if appropriate, a terminator is then positioned behind the polylinker. This sequence is repeated several times, preferably three, four or five times, so that up to five genes are combined in one construct and can thus be introduced into the transgenic plant in order to be expressed. Advantageously, the sequence is repeated up to three times. To express the nucleic acid sequences, the latter are inserted behind the promoter via the suitable cleavage site, for example in the polylinker. Advantageously, each nucleic acid sequence has its own promoter and, if appropriate, its own terminator. Such advantageous constructs are disclosed, for example, in DE 101 02 337 or DE 101 02 338. However, it is also possible to insert a plurality of nucleic acid sequences behind a promoter and, if appropriate, in front of a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoters, and different terminators can be used in the expression cassette. However, it is also possible to use only one type of promoter in the cassette. This, however, may lead to undesired recombination events.

The recombinant expression vectors used can be designed for the expression in prokaryotic or eukaryotic cells. This is advantageous since intermediate steps of the vector construction are frequently carried out in microorganisms for the sake of simplicity. For example, the Δ12-desaturase, Δ15-desaturase, Δ12- and Δ15-desaturase, ω3-desaturase, Δ6-desaturase, Δ6-elongase, Δ9-elongase, Δ8-desaturase, Δ5-desaturase, Δ5-elongase and/or Δ4-desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M.

J. J., et al. (1991) "Heterologous gene expression in filamentous fungi", in: More Gene Manipulations in Fungi, J. W. Bennet & L. L. Lasure, Eds., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Eds., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Eds.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the vector pTrc is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophagene which harbors a T7 gn1 gene under the transcriptional control of the lacUV 5 promoter. Other vectors which are suitable for prokaryotic organisms are known to the skilled worker, these vectors are, for example, in *E. coli* pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Eds., pp. 396-428: Academic Press: San Diego]. Further suitable yeast vectors are, for example, pAG-1, YEp6, YEp13 or pEMBLYe23.

As an alternative, the polynucleotides of the present invention can also be expressed in insect cells using Baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

Preferred plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Eds.: Kung and R. Wu, Academic Press, 1993, pp. 15-38. A plant expression cassette preferably comprises expression control sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable. Since plant gene expression is very often not limited to transcriptional levels, a plant expression cassette preferably comprises other sequences which are linked operably, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711). As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CAMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028. Other preferred sequences for use in operable linkage in plant gene expression cassettes are targeting sequences, which are required for steering the gene product into its corresponding cell compartment (see a review in Kermode, Crit. Rev, Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, oil bodies, peroxisomes and other compartments of plant cells.

As described above, plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable, for example the pathogen-induced PRP1 gene promoter (Ward et al., Plant. Mal. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as the cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the *sorghum kasirin* gene or the rye secalin gene, which are described in WO 99/16890. Especially suitable promoters are likewise those which bring about the plastid-specific expression, since plastids are the compartment in which the precursors and some of the end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

The abovementioned vectors are only a small overview of possible vectors which are suitable. Further plasmids are known to the skilled worker and are described for example in: Cloning Vectors (eds. Pouwels, P. H., et al., Elsevier, Amsterdam-New York-Oxford, 1985, ISBN 0 444 904018). Further suitable expression systems for prokaryotic and eukaryotic cells, see chapters 16 and 17 of Sambrook, J., Fritsch, E. F., and Maniatis, T., Molecular Cloning: A Laboratory Manual, 2nd ed., Cold Spring Harbor Laboratory, Cold Spring Harbor Laboratory Press, Cold Spring Harbor, N.Y., 1989.

As described above, the expression vector cart, in addition to the polynucleotides according to the invention, also comprise further genes which are to be introduced into the organisms. It is possible and preferred to introduce into the host organisms, and express in them, regulatory genes, such as genes for inductors, repressors or enzymes which, as a result of their enzymatic activity, engage in the regulation of one or more genes of a biosynthetic pathway. These genes can be of heterologous or homologous origin. Heterologous genes or polynucleotides are derived from an organism of origin which differs from the target organism into which the genes or polynucleotides are to be introduced. In the case of homologous genes or polynucleotides, target organism and organism of origin are identical. The vector therefore preferably comprises at least one further polynucleotide which codes for a further enzyme which is involved in the biosynthesis of lipids or fatty acids. The enzyme is preferably selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ15-desaturase(s), Δ12- and Δ15-desaturase(s), ω3-desaturase, Δ5-elongase(s), Δ6-elongase(s) and Δ9-elongase(s). Especially preferred gene combinations are listed in tables 5 and 6 and in the examples which follow.

The invention also relates to a host cell which comprises the polynucleotide according to the invention or the vector according to the invention.

In principle, host cells for the purposes of the present invention may be all eukaryotic or prokaryotic cells. They may be primary cells from animals, plants or multi-celled microorganisms, for example from those which are mentioned in another place in the description. The term furthermore also comprises cell lines which can be obtained from these organisms.

However, host cells for the purposes of the invention may also be single-celled microorganisms, for example bacteria or fungi. Especially preferred microorganisms are fungi selected from the group of the families Chaetomiaceae, Choanephoraceae, Cryptococcaceae, Cunninghamellaceae, Demetiaceae, Hydnangiaceae (genus *Laccaria*), Moniliaceae, Mortierellaceae, Mucoraceae, Pythiaceae, Saccharomycetaceae, Saprolegniaceae, Schizosacharomycetaceae, Sodariaceae or Tuberculariaceae. Further preferred microorganisms are selected from the group: Choanephoraceae, such as the genera *Blakeslea, Choanephora*, for example the genera and species *Blakeslea trispora, Choanephora cucurbitarum, Choanephora infundibulifera* var. *cucurbitarum*, Hydnangiaceae (for example genus *Laccaria*, in particular species *Laccaria bicolor*), Mortierellaceae, such as the genus *Mortierella*, for example the genera and species *Mortierella isabellina, Mortierella polycephala, Mortierella ramanniana, Mortierella vinacea, Mortierella zonata*, the family Mucorales, such as the genera and species *Rhizopus oryzae, Rhizopus stolonifer, Fusarium graminearium*, Pythiaceae, such as the genera *Phytium, Phytophthora*, for example the genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Saccharomycetaceae, such as the genera *Hansenula, Pichia, Saccharomyces, Saccharomycodes, Yarrowia*, for example the genera and species *Hansenula anomala, Hansenula californica, Hansenula canadensis, Hansenula capsulate, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wicker-*

*hamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica*, Schizosaccharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe*, Thraustochytriaceae such as the genera *Althornia, Aplanochytrium, Japonochytrium, Schizochytrium, Thraustochytrium*, e.g. *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense.*

Equally preferred as microorganisms are bacteria selected from the group of the families Bacillaceae, Enterobacteriacae or Rhizobiaceae. It is especially preferred to mention the following bacteria selected from the group: Bacillaceae, such as the genus *Bacillus*, for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia*, for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli-mutabile, Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae, such as the genera *Agrobacterium, Carbophilus, Chelatobacter, Ensifer, Rhizobium, Sinorhizobium*, for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri, Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris,*

*Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense.*

Further utilizable host cells are detailed in: Goeddel, Gene Expression Technology: Methods in Enzymology 185, Academic Press, San Diego, Calif. (1990). Expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, crop material, plant tissue, reproductive tissue and cell cultures which are derived from the actual transgenic plant and/or can be used for giving rise to the transgenic plant.

Polynucleotides or vectors can be introduced into the host cell as described above by means of transformation or transfection methods which are known in the prior art. Conditions and media for the cultivation of the host cells are also known to the skilled worker.

The host cell according to the invention preferably additionally comprises at least one further enzyme which is involved in the biosynthesis of lipids or fatty acids. Preferred enzymes have already been mentioned in another place in the description. The enzyme can be present in the host cell in endogenous form, i.e. the host cell already naturally expresses a gene which codes for a corresponding enzyme. Alternatively, it is also possible to introduce, into the host cell, a heterologous polynucleotide which codes for the enzyme. Suitable methods and means for the expression of a heterologous polynucleotide are known in the prior art and are described herein in connection with the polynucleotides, vectors and host cells according to the invention.

The invention also relates to a method of generating a polypeptide with desaturase activity, comprising the steps:

(a) expressing a polynucleotide according to the invention as defined above in a host cell; and (b) obtaining, from the host cell, the polypeptide which is encoded by the polynucleotide in (a).

In this context, the polypeptide can be obtained or isolated by all current protein purification methods. The methods comprise, for example, affinity chromatography, molecular sieve chromatography, high-pressure liquid chromatography or else protein precipitation, if appropriate with specific antibodies. Although this is preferred, the method need not necessarily provide a pure polypeptide preparation.

The invention therefore also relates to a polypeptide which is encoded by the polynucleotide according to the invention or which is obtainable by the abovementioned method according to the invention.

The term "polypeptide" refers both to an essentially pure polypeptide, and also to a polypeptide preparation which additionally comprises further components or impurities. The term is also used for fusion proteins and protein aggregates which comprise the polypeptide according to the invention and additionally further components. The term also refers to chemically modified polypeptides. In this context, chemical modifications comprise artificial modifications or naturally occurring modifications, for example posttranslational modifications such as phosphorylation, myristylation, glycosylation and the like. The terms polypeptide, peptide and protein are interchangeable and are used accordingly in the description and in the prior art. The polypeptides according to the invention have the abovementioned biological activities, that is to say desaturase activities, and can influence the biosynthesis of polyunsaturated fatty acids (PUFAs), preferably the long-chain PUFAs (LCPUFAs), as herein described.

The invention also comprises an antibody which specifically recognizes the polypeptide according to the invention.

Antibodies against the polypeptide according to the invention can be prepared by means of known methods, where purified polypeptide or fragments thereof with suitable epitopes are used as the antigen. Suitable epitopes can be determined by means of known algorithms for the antigenicity determination, based on the amino acid sequences of the polypeptides according to the invention provided herein. The relevant polypeptides or fragments can then be synthesized or obtained by recombinant techniques. After suitable animals, preferably mammals, for example hares, rats or mice, have been immunized, the antibodies can then be obtained from the serum, using known methods. Alternatively, monoclonal antibodies or antibody fragments can be provided with the known methods; see, for example, Harlow and Lane "Antibodies, A Laboratory Manual", CSH Press, Cold Spring Harbor, 1988 or Köhler and Milstein, Nature 256 (1975), 495, and Galfré, Meth. Enzymol. 73 (1981), 3.

The antibodies preferably take the form of monoclonal or polyclonal antibodies, single-chain antibodies or chimeric antibodies, and fragments of these such as Fab, Fv or scFv. Further antibodies within the meaning of the invention are bispecific antibodies, synthetic antibodies or their chemically modified derivatives.

The antibodies according to the invention specifically recognize the polypeptides according to the invention, that is to say they do not cross-react significantly with other proteins. For example, an antibody according to the invention which specifically binds a Δ12-desaturase will not react with a Δ6-desaturase. This can be assayed by means of methods known in the prior art. For example, the antibodies can be employed for the purposes of detection reactions, immunoprecipitation, immunhistochemistry or protein purification (for example affinity chromatography).

The invention furthermore relates to a transgenic, nonhuman organism which comprises the polynucleotide, the vector or the host cell of the present invention. The transgenic, nonhuman organism preferably takes the form of an animal, a plant or a multicellular microorganism.

The term "transgenic" is understood as meaning that a heterologous polynucleotide, that is to say a polynucleotide which does not occur naturally in the respective organism, is introduced into the organism. This can be achieved either by random insertion of the polynucleotide or by homologous recombination. Naturally, it is also possible to introduce the vector according to the invention instead of the polynucleotide. Methods of introducing polynucleotides or vectors for the purposes of random insertion or homologous recombination are known in the prior art and also described in greater detail hereinbelow. Host cells which comprise the polynucleotide or the vector can also be introduced into an organism and thus generate a transgenic organism. In such a case, such an organism takes the form of a chimeric organism, where only those cells which are derived from the introduced cells are transgenic, i.e. comprise the heterologous polynucleotide.

The transgenic nonhuman organisms are preferably oil-producing organisms, which means organisms which are used for the production of oils, for example fungi such as *Rhizopus* or *Thraustochytrium*, algae such as *Euglena, Nephroselmis*, Pseudoscourfielda, *Prasinococcus, Scherffelia, Tetraselmis, Mantoniella, Ostreococcus, Crypthecodinium, Phaeodactylum*, or diatoms such as *Pythium* or *Phytophthora* or plants.

Transgenic plants which can be used are, in principle, all plants, that is to say both dicotyledonous and monocotyledonous plants. They preferably take the form of oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, verbascum, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, tobacco, verbascum, sesame, cotton, pumpkin/squash, poppy, evening primrose, walnut, linseed, hemp, thistle or safflower. Very especially preferred plants are plants such as safflower, sunflower, poppy, evening primrose, walnut, linseed or hemp. In principle, however, all plants which are capable of synthesizing fatty acids are suitable, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*.

Examples which may especially preferably be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp, *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [African or French marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis, Brassica juncea, Brassica juncea* var. *juncea, Brassica juncea* var. *crispifolia, Brassica juncea* var. *foliose, Brassica nigra, Brassica sinapioides, Camelina sativa, Melanosinapis communis* [mustard], *Brassica oleracea* [fodder beet] or *Arabidopsis thaliana*, Bromeliaceae, such as the genera *Ananas, Bromelia* (pineapple), for example the genera and species *Ananas comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis saliva* [hemp], Convolvulaceae, such as the genera *Ipomea, Convolvulus*, for example the genera and species *Ipomoea batatas, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var *vulgaris, Beta maritima, Beta vulgaris* var *perennis, Beta vulgaris* var, *conditiva* or *Beta vulgaris* var. *esculenta* [sugarbeet], Crypthecodiniaceae, such as the genus *Crypthecodinium*, for example the genus and species *Crypthecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricornutum*, Ditrichaceae, such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Cerafodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum montanum, Ditrichum pallidum, Ditrichum punctulatum, Ditrichum pusillum, Ditrichum pusfilum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicago, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizia berteriana, Cathormion berteriana, Feuillea berteriana, Inga fragrans, Pithecello-*

*bium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericandra julibrissin, Acacia lebbeck, Acacia macrophylla, Albizia lebbeck, Feuilleea lebbeck, Mimosa lebbeck, Mimosa speciosa* [silk tree], *Medicago saliva, Medicago falcata, Medicago varia* [alfalfa] *Glycine max Dolkhos soja, Glycine gracilis, Glycine hispida, Phaseolus max, Soja hispida* or *Soja max* [soybean], Funariaceae, such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminate, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elaeis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum mlliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridiurn, Rhodella, Rhodosorus, Vanhoeffenia*, for example the genus and species *Porphyridium cruentum*, Proteaceae, such as the genus *Macadamia*, for example the genus and species *Macadamia intergrifolia [macadamia*], Prasinophyceae, such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantonielia squamata, Ostreococcus tauri*, Rubiaceae, such as the genus *Coffea*, for example the genera and species *Coffea* spp., *Coffea arabica, Coffea canephora* or *Coffea liberica* [coffee], Scrophulariaceae, such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lyco-*

*persicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Multicellular microorganisms which can be employed as transgenic nonhuman organisms are preferably protists or diatoms selected from the group of the families Dinophyceae, Turaniellidae or Oxytrichidae, such as the genera and species: *Crypthecodinium cohnii, Phaeodactylum tricornutum, Stylonychia mytilus, Stylonychia pustulata, Stylonychia putrina, Stylonychia notophora, Stylonychia* sp., *Colpidium campylum* or *Colpidium* sp.

The invention further relates to a process for the production of a substance which has the structure shown in the general formula I hereinbelow (I)

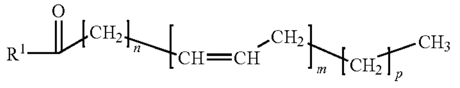

where the variables and substituents are as follows:

$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II (II)

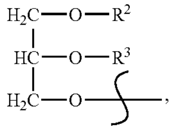

$R^2$=hydrogen, lysophosphatidylcholine, lysophosphatidylethanolamine, lysophosphatidylglycerol, lysodiphosphatidyiglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

(Ia)

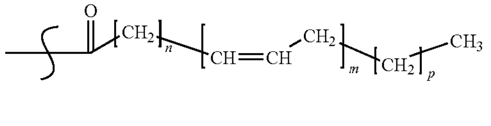

n=2, 3, 4, 5, 6, 7 or 9, m=2, 3, 4, 5 or 6 and p=0 or 3;

and wherein the process comprises the cultivation of (i) a host cell according to the invention or (ii) of a transgenic, nonhuman organism according to the invention under conditions which permit the biosynthesis of the substance. Preferably, the abovementioned substance is provided in an amount of at least 1% by weight based on the total lipid content in the host cell or the transgenic organism.

$R^1$ in the general formula I is hydroxyl, coenzyme A (thioester), lysophosphatidylcholine, lysophosphatidylethanolamine, lysophosphatidyiglycerol, lysodiphosphatidylglycerol, lysophosphatidylserine, lysophosphatidylinositol, sphingo base or a radical of the general formula II (II)

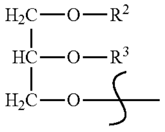

The abovementioned radicals of $R^1$ are always bonded to the compounds of the general formula I in the form of their thioesters.

$R^2$ in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

$R^3$ in the general formula II is hydrogen, saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds.

Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise four, five or six double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, with the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% in comparison with polyunsaturated fatty acids. These fatty acids which have been produced can be produced in the process as a single product or be present in a fatty acid mixture.

Advantageously, the substituents $R^2$ or $R^3$ in the general formulae I and II are, independently of one another, saturated or unsaturated $C_{18}$-$C_{22}$-alkylcarbonyl, especially advantageously, they are, independently of one another, unsaturated $C_{18}$-, $C_{20}$- or $C_{22}$-alkylcarbonyl with at least two double bonds.

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are long-chain fatty acids, more preferably long-chain fatty acids LCPUFAs of $C_{18}$-, $C_{20}$- and/or $C_{22}$-fatty acids.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, $C18:2^{\Delta 9,12}$), γ-linolenic acid (=GLA, $C18:3^{\Delta 6,9,12}$), stearidonic acid (=SDA, $C18:4^{\Delta 6,9,12,15}$), dihomo-γ-linolenic acid (=DGLA, $20:3^{\Delta 8,11,14}$), ω3-eicosatetraenoic acid (=ETA, $C20:4^{\Delta 5,8,11,14}$), arachidonic acid (ARA, $C20:4^{\Delta 5,8,11,14}$), eicosapentaenoic acid (EPA, $C20:5^{\Delta 5,8,11,14,17}$), ω6-docosapentaenoic acid ($C22:5^{\Delta 4,7,10,13,16}$), ω6-docosatetraenoic acid ($C22:4^{\Delta 7,10,13,16}$), ω3-docosapentaenoic acid (=DPA, $C22:5^{\Delta 7,10,13,16,19}$), docosahexaenoic acid (=DHA, $C22:6^{\Delta 4,7,10,13,16,19}$) or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, three, four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. In this context, it is advantageous to convert $C_{18}$- and/or $C_{20}$-fatty acids which are present in the host organisms to at least 10%, advantageously to at least 20%, especially advantageously to at least 30%, most advantageously to at least 40% to give the corresponding products such as DPA or DHA, to mention just two examples. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA), ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant in the process according to the invention. If the compounds ARA, EPA and DHA are produced simultaneously, they are advantageously produced in a ratio of at least 1:1:2 (EPA:ARA:DHA), advantageously of at least 1:1:3, preferably 1:1:4, especially preferably 1:1:5.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernonic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$).

Owing to the nucleic acid sequences of the invention, or the nucleic acid sequences used in the process according to the invention, an increase in the yield of polyunsaturated fatty acids of at least 50%, advantageously of at least 80%, especially advantageously of at least 100%, very especially advantageously of at least 150%, in comparison with the nontransgenic starting organism, for example a yeast, an alga, a fungus or a plant such as *Arabidopsis* or linseed can be obtained in a comparison by GC analysis.

Chemically pure polyunsaturated fatty acids or fatty acid compositions can also be prepared by the processes described above. To this end, the fatty acids or the fatty acid compositions are isolated from the organism, such as the microorganisms or the plants or the culture medium in or on which the organisms have been grown, or from the organism and the culture medium, in a known manner, for example via extraction, distillation, crystallization, chromatography or combinations of these methods. These chemically pure fatty acids or fatty acid compositions are advantageous for applications in the food industry sector, the cosmetic industry sector and especially the pharmacological industry sector.

In principle, all genes of the fatty acid or lipid metabolism can be used in the process for the production of polyunsaturated fatty acids, advantageously in combination with the inventive polynucleotide(s) (for the purposes of the present application, the plural is understood as encompassing the singular and vice versa). Genes of the fatty acid or lipid metabolism which are used are advantageously selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Genes selected from the group of the Δ4-desaturases, Δ5-desaturases, Δ6-desaturases, Δ8-desaturases, Δ9-desaturases, Δ12-desaturases, Δ15-desaturases, Δ12- and Δ15-desaturases, ω3-desaturases, Δ6-elongases, Δ9-elongases or Δ5-elongases in combination with the polynucleotides according to the invention are preferably used, it being possible to use individual genes or a plurality of genes in combination. For especially preferred gene combinations, reference is made here to tables 5 and 6, which are shown in the examples.

Advantageously, the desaturases used in the process according to the invention convert their respective substrates in the form of the CoA-fatty acid esters. If preceded by an elongation step, this advantageously results in an increased product yield. The respective desaturation products are thereby synthesized in greater quantities, since the elongation step is usually carried out with the CoA-fatty acid esters, while the desaturation step is predominantly carried out with the phospholipids or the triglycerides. Therefore, a substitution reaction between the CoA-fatty acid esters and the phospholipids or triglycerides, which would require a further, possibly limiting, enzyme reaction, is not necessary.

Owing to the enzymatic activity of the polypeptides used in the process according to the invention, a wide range of polyunsaturated fatty acids can be produced in the process according to the invention. Depending on the choice of the organisms, such as the preferred plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta 9,12}$) is present as unsaturated fatty acid in the plant used for the process, the process can only afford GLA, DGLA and ARA as products, all of which can be present as free fatty acids or in bound form. If only α-linolenic acid (=ALA, C18:$3^{\Delta 9,12,15}$) is present as unsaturated fatty acid in the plant used for the process, the process can only afford SDA, ETA, EPA and/or DHA as products, all of which can be present as free fatty acids or in bound form, as described above. Owing to the modification of the activity of the enzymes Δ5-desaturase, Δ6-desaturase, Δ4-desaturase, Δ12-desaturase, Δ15-desaturase, ω3-desaturase, Δ5-elongase and/or Δ6-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase, Δ5-elongase and Δ4-desaturase are additionally introduced into the organisms, advantageously into the plant, ARA, EPA and/or DHA are additionally formed. Advantageously, only ARA, EPA or DHA or mixtures of these are synthesized, depending on the fatty acids present in the organism, or in the plant, which acts as starting substance for the synthesis. Since biosynthetic cascades are involved, the end products in question are not present as pure substances in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end product DGLA, ETA or their mixtures, or ARA, EPA, DHA or their mixtures, advantageously EPA or DHA or their mixtures.

In addition to the production, directly in the organism, of the starting fatty acids for the polypeptides used in the process of the invention, the fatty acids can also be fed externally. The production in the organism is preferred for reasons of economy, Preferred substrates are linoleic acid (C18:$2^{\Delta 9,12}$), γ-linolenic acid (C18:$3^{\Delta 6,9,12}$), eicosadienoic acid (C20:$2^{\Delta 11,14}$), dihomo-γ-linolenic acid (C20:$3^{\Delta 8,11,14}$), arachidonic acid (C20:$4^{\Delta 5,8,11,14}$), docosatetraenoic acid (C22:$4^{\Delta 7,10,13,16}$) and docosapentaenoic acid (C22:$5^{\Delta 4,7,10,13,15}$).

To increase the yield in the described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which codes for a polypeptide with a Δ12-desaturase and/or Δ15-desaturase according to the invention. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the abovementioned Δ12-desaturases and/or Δ15-desaturases according to the invention for producing the starting material linoleic acid is advantageous.

The process according to the invention advantageously employs the abovementioned nucleic acid sequences or their derivatives or homologs which code for polypeptides which retain the enzymatic activity of the proteins encoded by nucleic acid sequences. These sequences, individually or in combination with the polynucleotides according to the invention, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a polynucleotide according to the invention, a gene construct or a vector as described below, alone or in combination with further nucleic acid sequences which code for proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a hothouse- or field-grown culture of a plant. The cell or the organism thus produced is advantageously a cell of an oil-producing organism, such as an oil crop, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

Suitable organisms or host cells for the process according to the invention are those which are capable of synthesizing fatty acids, specifically unsaturated fatty acids, and/or which are suitable for the expression of recombinant genes. Examples which may be mentioned are plants such as *Arabidopsis, Asteraceae* such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophthora* or *Pythium*, bacteria, such as the genus *Escherichia* or *Shewanella*, yeasts, such as the genus *Saccharomyces*, cyanobacteria, ciliates, algae such as *Mantoniella* or *Ostreococcus*, or protozoans such as dinoflagellates, such as *Thalassiosira* or *Crypthecodinium*. Preferred organisms are those which are naturally capable of synthesizing substantial amounts of oil, such as fungi, such as *Mortierella alpina, Pythium insidiosum, Phytophthora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula, Mortierella* or *Saccharomyces cerevisiae* being especially preferred. In principle, suitable as host organisms are, in addition to the abovementioned transgenic organisms, also transgenic animals, advantageously nonhuman animals, for example *Caenorhabditis elegans*. Further suitable host cells and organisms have already been described extensively above.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, crop material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably of the plant seeds. In this context, the oils, fats, lipids and/or free fatty acids can be obtained by pressing by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, for example the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using fuller's earth or active charcoal. At the end, the product is deodorized, for example using steam.

The PUFAs or LCPUFAs produced by this process are preferably $C_{18}$-, $C_{20}$- or $C_{22}$-fatty acid molecules, advantageously $C_{20}$- or $C_{22}$-fatty acid molecules, with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the above described process, especially preferably oil, lipid or a fatty acid composition comprising PUFAs and being derived from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid ester or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernonic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid ester or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$).

The oils, lipids or fatty acids according to the invention preferably comprise at least 0.5%, 1%, 2%, 3%, 4% or 5%, advantageously at least 6%, 7%, 8%, 9% or 10%, especially advantageously at least 11%, 12%, 13%, 14% or 15% of ARA or at least 0.5%, 1%, 2%, 3%, 4% or 5%, advantageously at least 6% or 7%, especially advantageously at least 8%, 9% or 10% of EPA and/or DHA, based on the total fatty acid content of the production organism, advantageously of a plant, especially advantageously of an oil crop plant such as soybean, oilseed rape, coconut, oil palm, safflower, flax, hemp, castor-oil plant, *Calendula*, peanut, cacao bean, sunflower, or the abovementioned further mono- or dicotyledonous oil crop plants.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in "trans", so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains that also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates which are suitable for the polypeptides according to the invention of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA: lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) are preferably $C_{16}$-, $C_{18}$- or $C_{20}$-fatty acids. The fatty acids converted as substrates in the process are preferably converted in the form of their acyl-CoA esters and/or their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles, $C_{22}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to $C_{20}$- and/or $C_{22}$-fatty acids with at least two double bonds in the fatty acid molecule, preferably with three, four, five or six double bonds, very especially preferably with five or six double bonds in the molecule. After a first desaturation and the elongation have taken place, further desaturation and elongation steps such as, for example, such a desaturation in the Δ5 and Δ4 positions may take place. Products of the process according to the invention which are especially preferred are dihomo-γ-linolenic acid, arachidonic acid, eicosapentaenoic acid, docosapentaenoic acid and/or docosahexaenoic acid. The $C_{20}$-fatty acids with at least two double bonds in the fatty acid can be desaturated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the process is sensible. However, it is obvious that the biosynthesis of fatty acids, oils or lipids need not be limited to the seed tissue, but can also take place in a tissue-specific manner in all the other parts of the plant—for example in epidermal cells or in the tubers.

If microorganism such as yeasts, such as *Saccharomyces* or *Schizosaccharomyces*, fungi such as *Mortierella, Aspergillus, Phytophthora, Entomophthora, Mucor* or *Thraustochytrium*, algae such as *Isochrysis, Mantoniella, Ostreococcus, Phaeodactylum* or *Crypthecodinium* are used as organisms in the process according to the invention, these organisms are advantageously grown in fermentation cultures.

Owing to the use of the nucleic acids according to the invention which code for a desaturase, the polyunsaturated fatty acids produced in the process can be increased by at least 5%, preferably by at least 10%, especially preferably by at least 20%, very especially preferably by at least 50% in comparison with the wild type of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in a manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while introducing oxygen gas. The pH of the nutrient liquid can either be kept constant, that is to say regulated during the culturing period, or not.

The cultures can be grown batchwise, semibatchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview of known cultivation methods can be found in the textbook by Chmiel (Bioprozeβtechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for cultivating microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds depends heavily on the particular experiment and is decided upon individually for each specific case. Information on the optimization of media can be found in the textbook "Applied Microbial. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air, into the culture. The temperature of the culture is normally 20° C. to 45° C. and preferably 25° C. to 40° C. The culture is continued until formation of the desired product is at a maximum. This aim is normally achieved within 10 hours to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The polynucleotides or polypeptides of the present invention which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and Tagetes, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only easily incorporated into triacylglycerol but also into membrane lipids.

Brassicaceae, Boraginaceae, Primulaceae, or Linaceae are particularly suitable for the production of PUFAs, for example stearidonic acid, eicosapentaenoic acid and docosahexaenoic acid. Linseed (*Linum usitatissimum*) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydration reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool from the phospholipids. This is made possible by acyl-CoA:lysophospholipid acyltransferases. Moreover, these enzymes are capable of transferring the elongated fatty acids from the CoA esters back to the phospholipids. If appropriate, this reaction sequence can be traversed repeatedly.

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the desaturases used in the process, such as the Δ12-, Δ15-, Δ12- and Δ15-, ω3-, Δ4-, Δ5- and Δ6-desaturases and/or the Δ5-, Δ6-elongases, arachidonic acid, eicosapentaenoic acid, docosapentaenoic acid or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least three, four, five or six, double bonds in the fatty acid molecule, preferably $C_{20}$- or $C_{22}$-fatty acids with advantageously four, five or six double bonds in the fatty acid molecule, can be prepared using the abovementioned enzymes. Desaturation may take place before or after elongation of the fatty acid in question. This is why the products of the desaturase activities and of the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the process according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid. The synthesized $C_{20}$- or $C_{22}$-fatty acids with at least two, three, four, five or six double bonds in the fatty acid are obtained in the process according to the invention in the form of the free fatty acid or in the form of their esters, for example in the form of their glycerides.

The term "glyceride" is understood as meaning a glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the process according to the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

For publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantities and must therefore take up additional quantities, although they can be synthesized readily by other organisms such as bacteria; for example, cats are no longer capable of synthesizing arachidonic acid.

"Phospholipids" for the purposes of the invention are understood as meaning phosphatidylcholine, phosphatidylethanolamine, phosphatidylserine, phosphatidyl-glycerol and/or phosphatidylinositol, advantageously phosphatidylcholine. The terms "production or productivity" are known in the art and encompass the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term "production efficiency" comprises the time required for obtaining a specific production quantity (for example the time required by the cell to establish a certain throughput rate of a fine chemical). The term "yield or product/carbon yield" is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained, in a specific culture quantity over a specified period of time is increased. The terms "biosynthesis or biosynthetic pathway" are known in the art and comprise the synthesis of a compound, preferably an organic compound, by a cell from intermediates, for example in a multi-step and strongly regulated process. The terms "catabolism or catabolic pathway" are known in the art and comprise the cleavage of a compound, preferably of an organic compound, by a cell to give catabolites (in more general terms, smaller or less complex molecules), for example in a multi-step and strongly regulated process. The term "metabolism" is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

By employing, in the process according to the invention, the polynucleotides according to the invention and optionally further polynucleotides which code for enzymes of the lipid or fatty acid metabolism it is possible to achieve various advantageous effects. Thus, it is possible to influence the yield, production and/or production efficiency of the polyunsaturated fatty acids in a plant, preferably in an oil crop plant, or in a microorganism. The number or activity of the polypeptides or polynucleotides according to the invention can be increased, so that larger amounts of the gene products and, ultimately, larger amounts of the compounds of the general formula I are produced. A de novo synthesis in an organism, which, before the gene(s) in question was/were introduced, had been lacking the activity and ability to biosynthesize the compounds, is also possible. The same applies analogously to the combination with further desaturases or elongases or further enzymes of the fatty acid and lipid metabolism. The use of a variety of divergent sequences, i.e. sequences which differ at the DNA sequence level, may also be advantageous in this context, or else the use of gene expression promoters which makes possible a different gene expression as far as timing is concerned, for example as a function of the degree of maturity of a seed or oil-storing tissue.

By introducing, into an organism, a polynucleotide according to the invention alone or in combination with other genes in a cell it is possible not only to increase the biosynthetic flow towards the end product, but also to increase, or to create de novo, the corresponding triacylglycerol composition. Equally, the number or activity of other genes which are required for the import of nutrients for the biosynthesis of one or more fatty acids, oils, polar and/or neutral lipids can be increased, so that the concentration of these precursors, cofactors or intermediates within the cells or within the storage compartment is increased, whereby the ability of the cells to produce PUFAs is further enhanced. By optimizing the activity, or increasing the number, of one or more polynucleotides or polypeptides according to the invention which are involved in the biosynthesis of these compounds, or by destroying the activity of one or more genes which are involved in the degradation of these compounds, it may be possible to increase the yield, production and/or production efficiency of fatty acid and lipid molecules from organisms, in particular from plants. The fatty acids obtained in the process are suitable as starting materials for the chemical synthesis of further products of interest. For example, they can be used for the preparation of pharmaceuticals, foodstuffs, animal feeds or cosmetics, either alone or in combination with one another.

It can be seen from what has been said above that the invention also relates to a process for the production of an oil, lipid or fatty acid composition, comprising the steps of the process according to the invention and the further step of formulating the substance as an oil, lipid or fatty acid composition.

In a preferred embodiment of this process, the oil, lipid or fatty acid composition is formulated further to give a drug, a cosmetic product, a foodstuff, a feedstuff, preferably fish food, or a food supplement.

Finally, the invention relates to the principle of using the polynucleotide, the vector, the host cell, the polypeptide or the transgenic, nonhuman organism of the present invention for the production of an oil, lipid or fatty acid composition. The latter should then preferably be employed as drug, cosmetic product, foodstuff, feedstuff, preferably fish food, or food supplement.

The content of all the references, patent applications, patents and published patent applications cited in the present patent application is hereby incorporated by reference to the respective specific disclosure.

FIGURES

FIG. 1: Biosynthetic pathways for the production of long-chain, polyunsaturated fatty acids such as arachidonic acid (=ARA, $C20:4^{\Delta 5,8,11,14}$), eicosapentaenoic acid (=EPA, $C20:5^{\Delta 5,8,11,14,17}$) or docosahexaenoic acid (=DHA, $C22:6^{\Delta 4,7,10,13,16,19}$).

Figure 2:
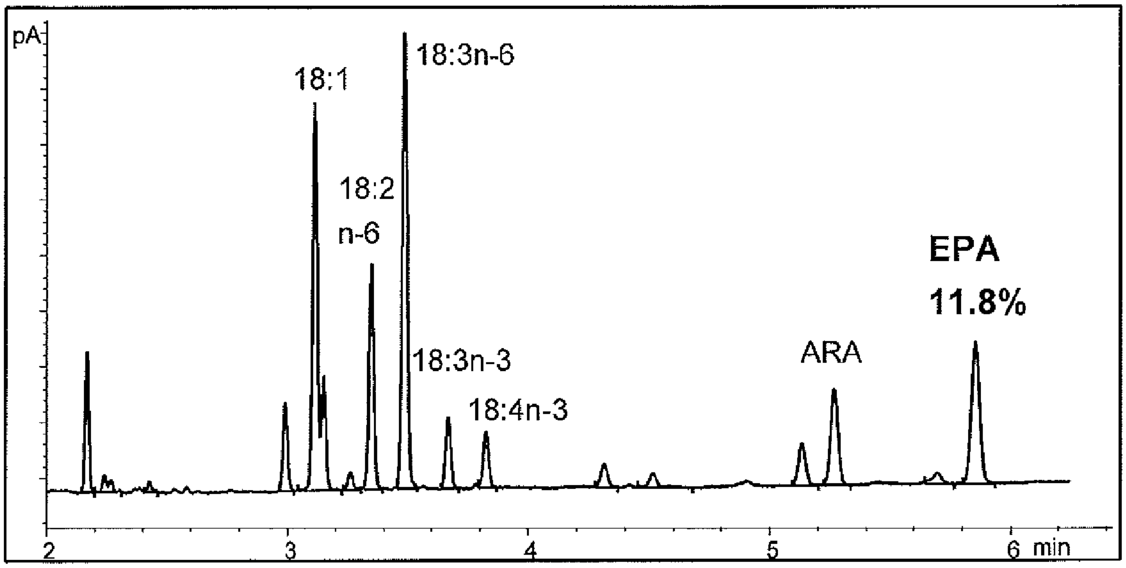

FIG. 2: Chromatogram of seeds of an oilseed rape plant transformed with the construct LJB765, which is described in the examples. Only 16:0, 16:1, 18:0, 18:1, 18:2n-6, 18:3n-3, 20:0, 20:1, 20:2n-6 and 22:0 can be detected in untransformed rapeseed. The chromatogram proves the production of novel fatty acids in the transgenic rapeseed. These novel fatty acids can be attributed to the activity of the introduced genes (see EPA, eicosapentaenoic acid). In comparison with the untransformed control, the seeds of the transgenic plant show increased contents of Δ12-desaturated product (C18:2n-6, linoleic acid) and Δ15-desaturated products (18:3n-3; 18:4n-3; EPA), which can be attributed to the activity of the introduced Δ12- and Δ15-desaturase.

Figure 3:
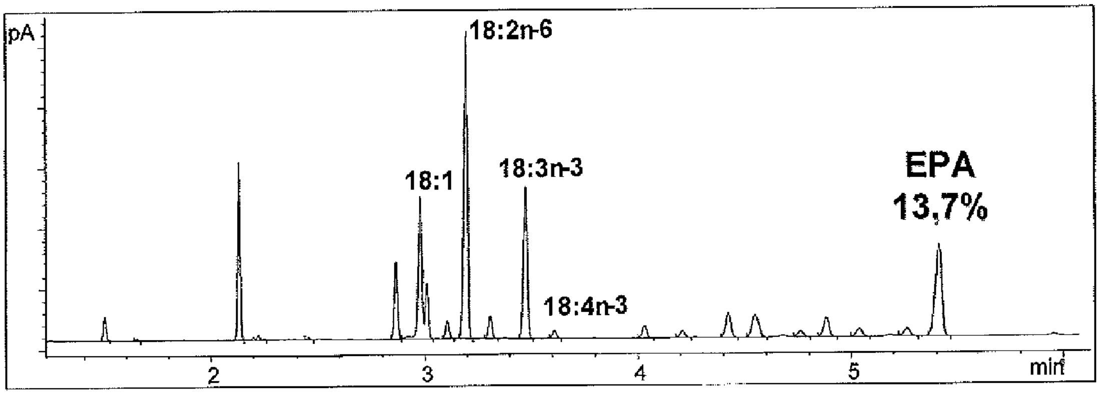

FIG. 3: Chromatogram of seeds of transgenic *Arabidopsis* plants transformed with the plasmid LJB765, which is described in the examples. Similar values as for oilseed rape were obtained for the omega3-fatty acid EPA.

Figure 4:
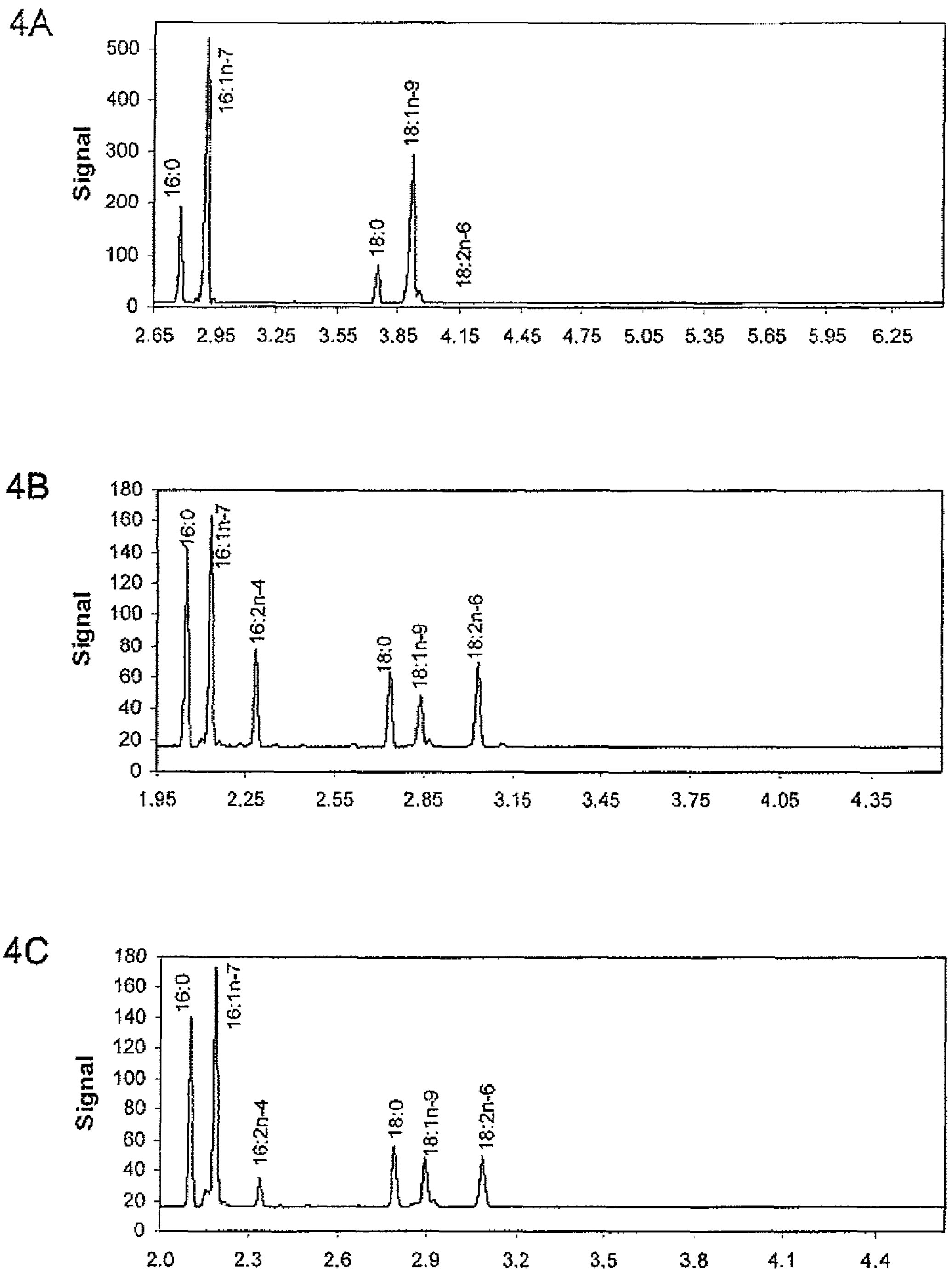
Figure 4:
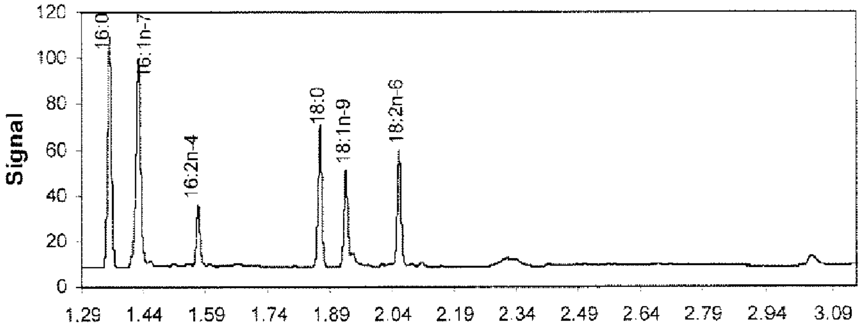
Figure 4:
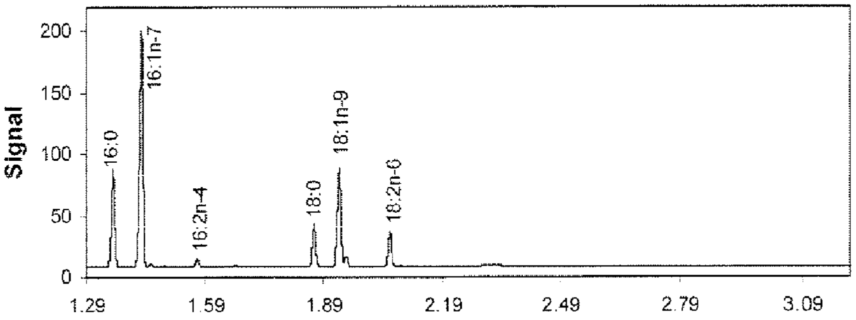

FIG. 4: Gas-chromatographic determination of the fatty acids from yeasts which have been transformed with the plasmid pYES (A) and pYES-d12Des(Nh) (B), pYES-d12Des(Mb) (C), pYES-d12Des(Mg) (D) and pYES-d12Des (Pb) (E).

Figure 5:
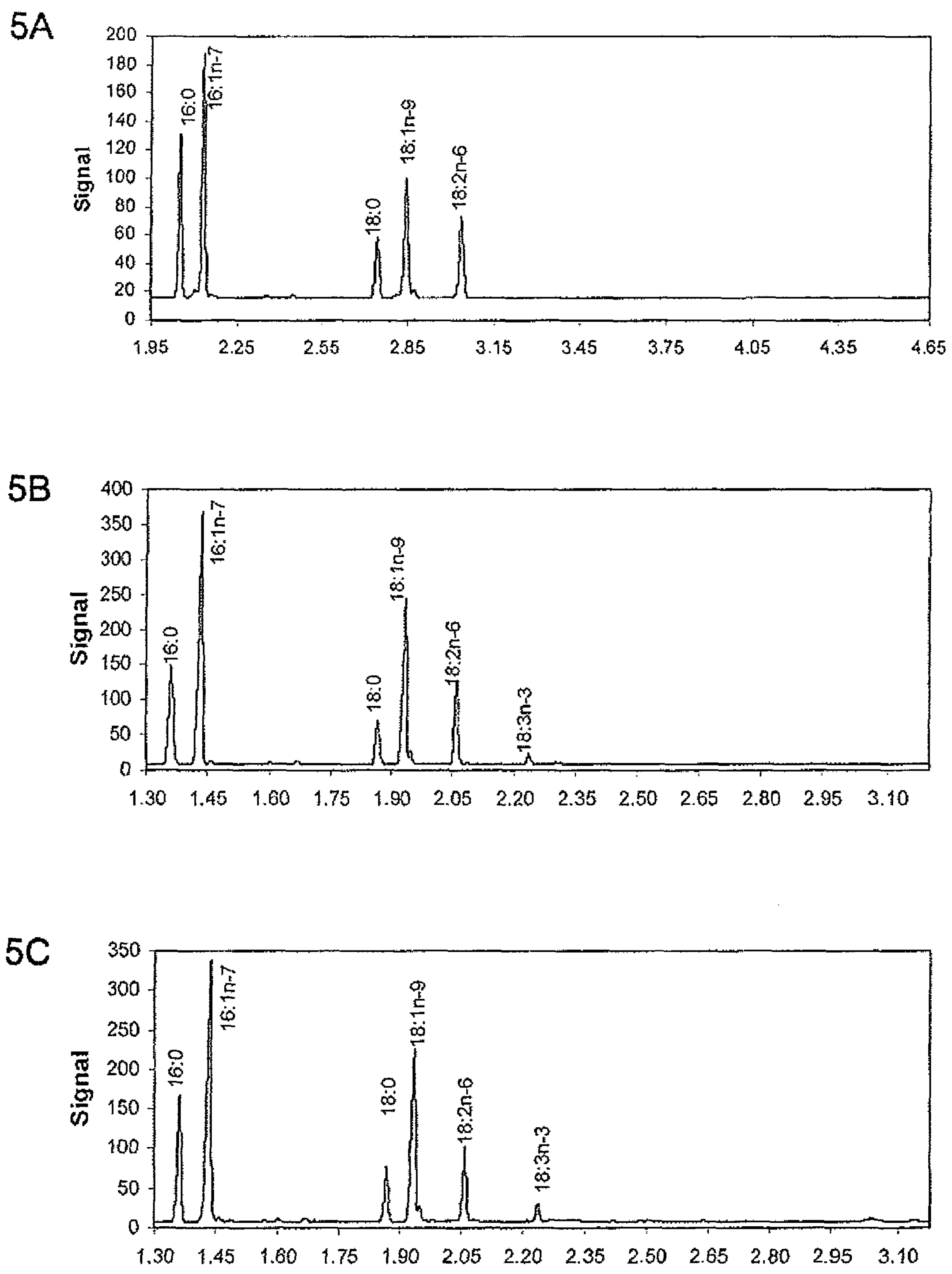
Figure 5:
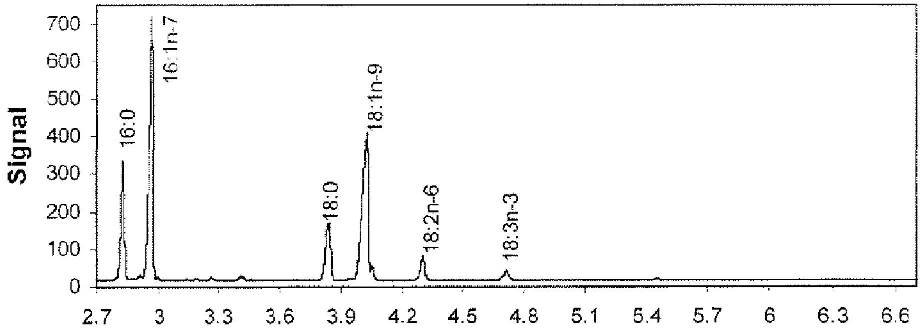
Figure 5:
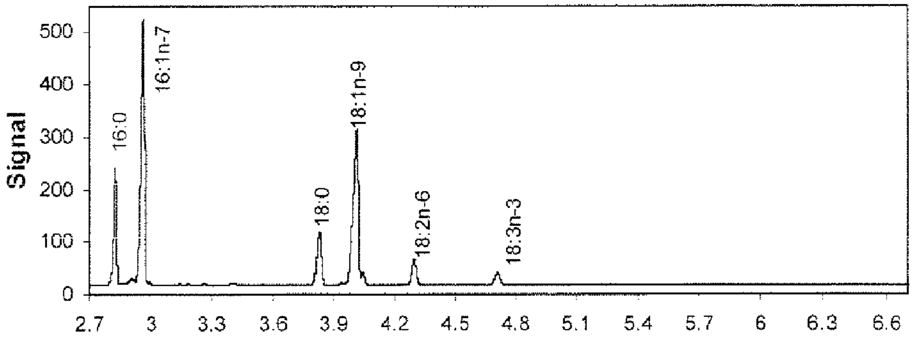
Figure 5:
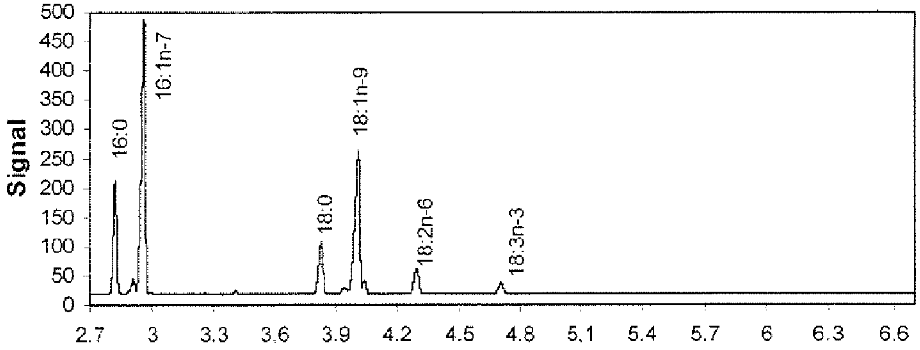

FIG. 5: Gas-chromatographic determination of the fatty acids from yeasts which have been transformed with the plasmid pYES (A) and pYES-d15Des(Nh)2 (B), pYES-d15Des(Mg) (C), pYES-d15Des(Hr) (D), pYES-d15Des(Lg) (E) and pYES-d15Des(Mc) (F). The fatty acid 18:2n-6 was fed.

Figure 6:
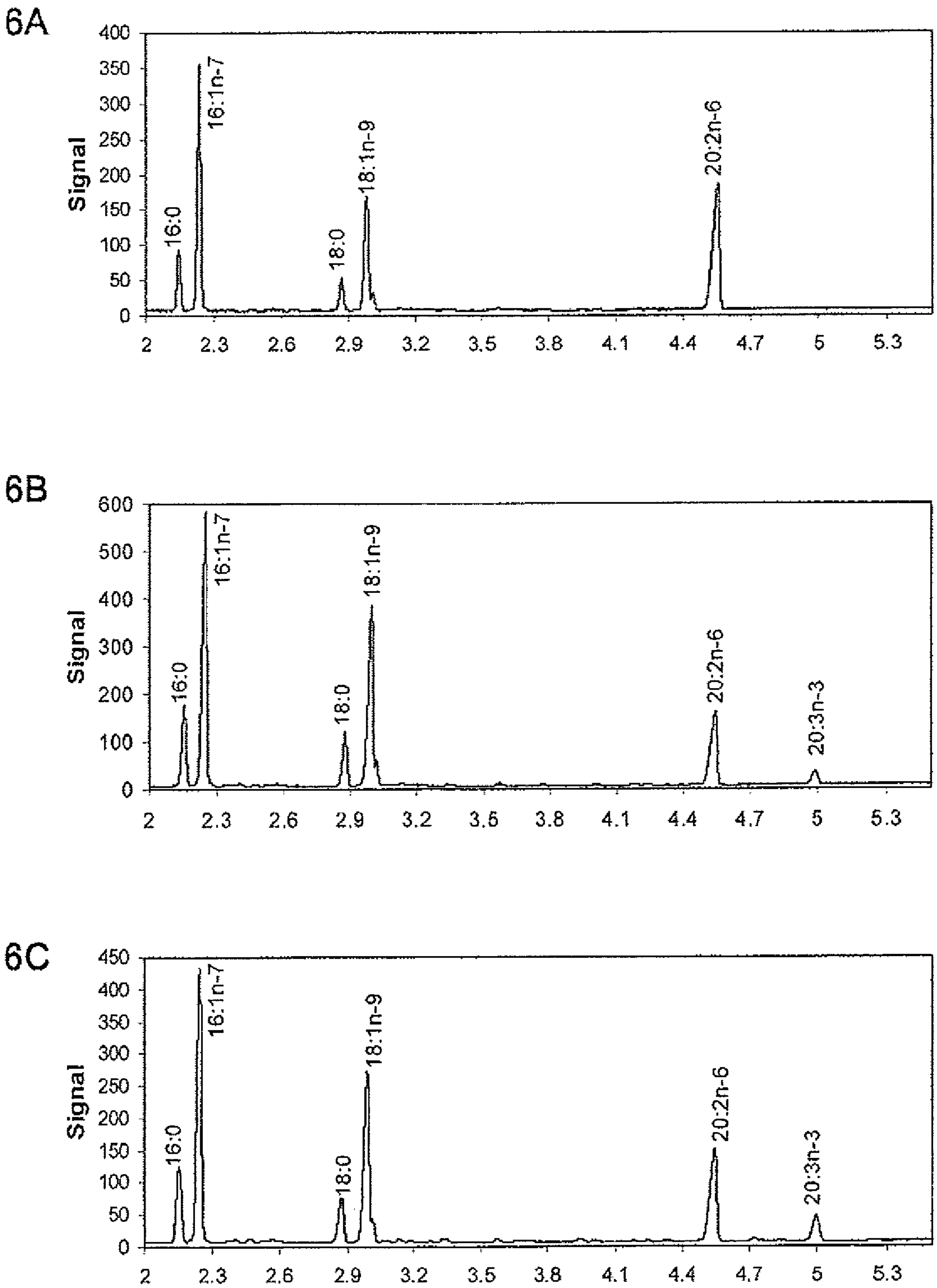
Figure 6:
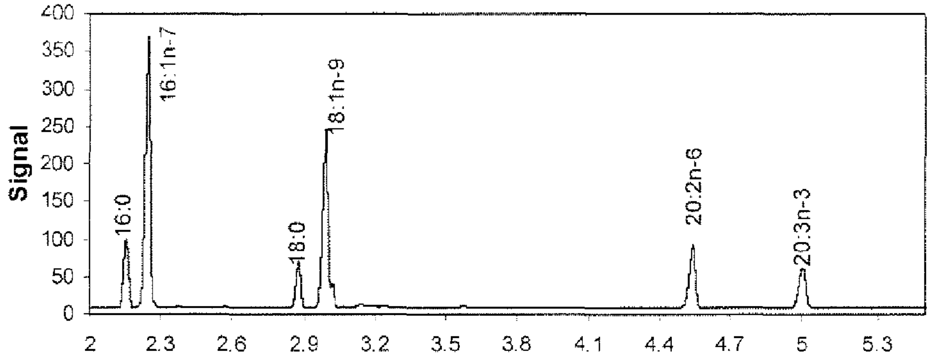

FIG. 6: Gas-chromatographic determination of the fatty acids from yeasts which have been transformed with the plasmid pYES (A) and pYES-d15Des(Hr) (B), pYES-d15Des(Lg) (C) and pYES-d15Des(Mc) (D), The fatty acid 20:2n-6 was fed.

Figure 7:
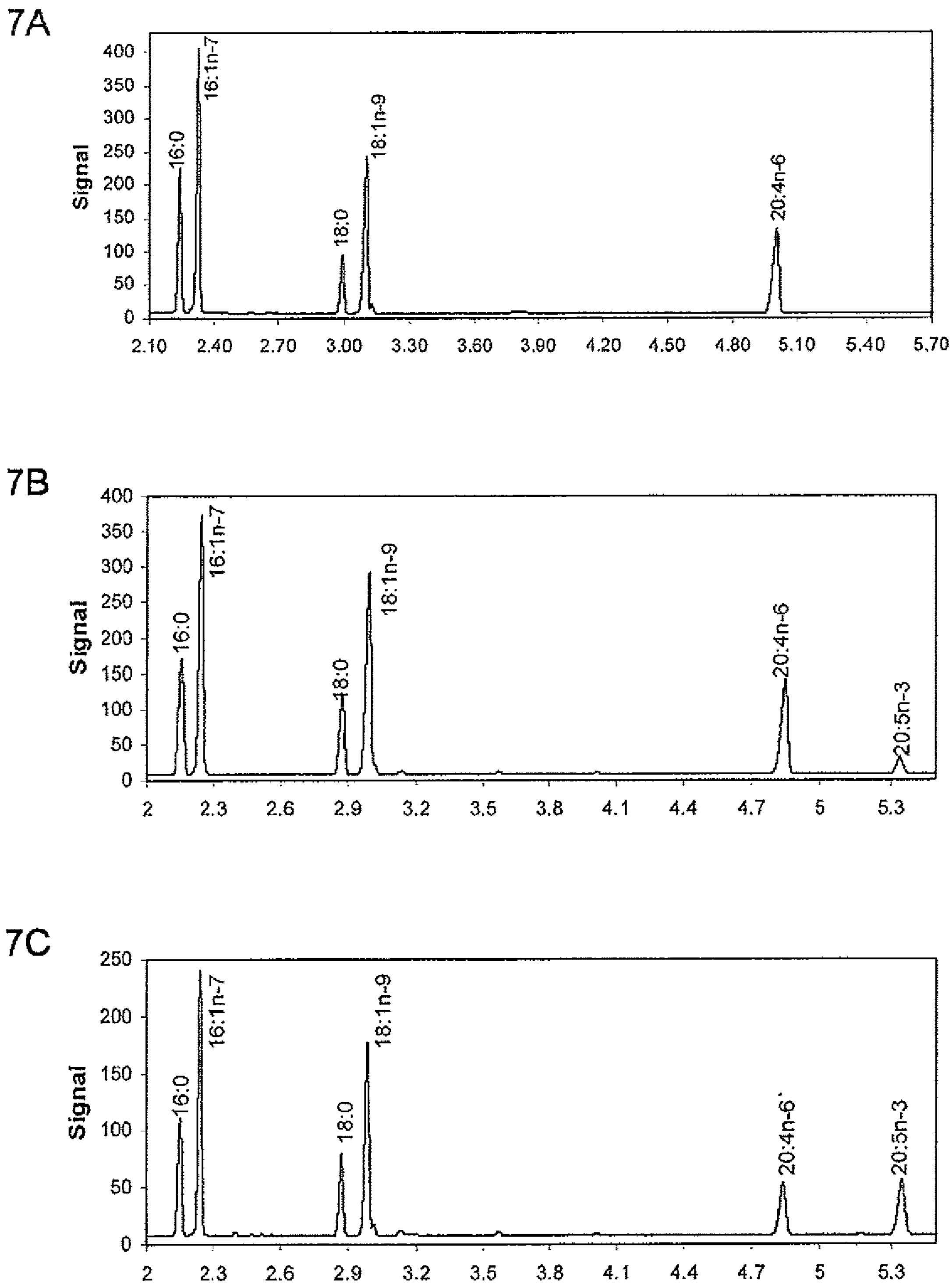
Figure 7:
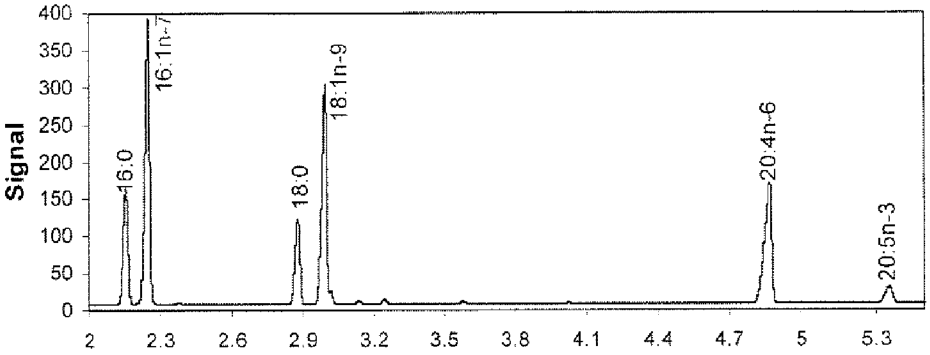

FIG. 7: Gas-chromatographic determination of the fatty acids from yeasts which have been transformed with the plasmid pYES (A) and pYES-d15Des(Hr) (B), pYES-d15Des(Lg) (C) and pYES-d15Des(Mc) (D). The fatty acid 22:4n-6 was fed.

Figure 8:
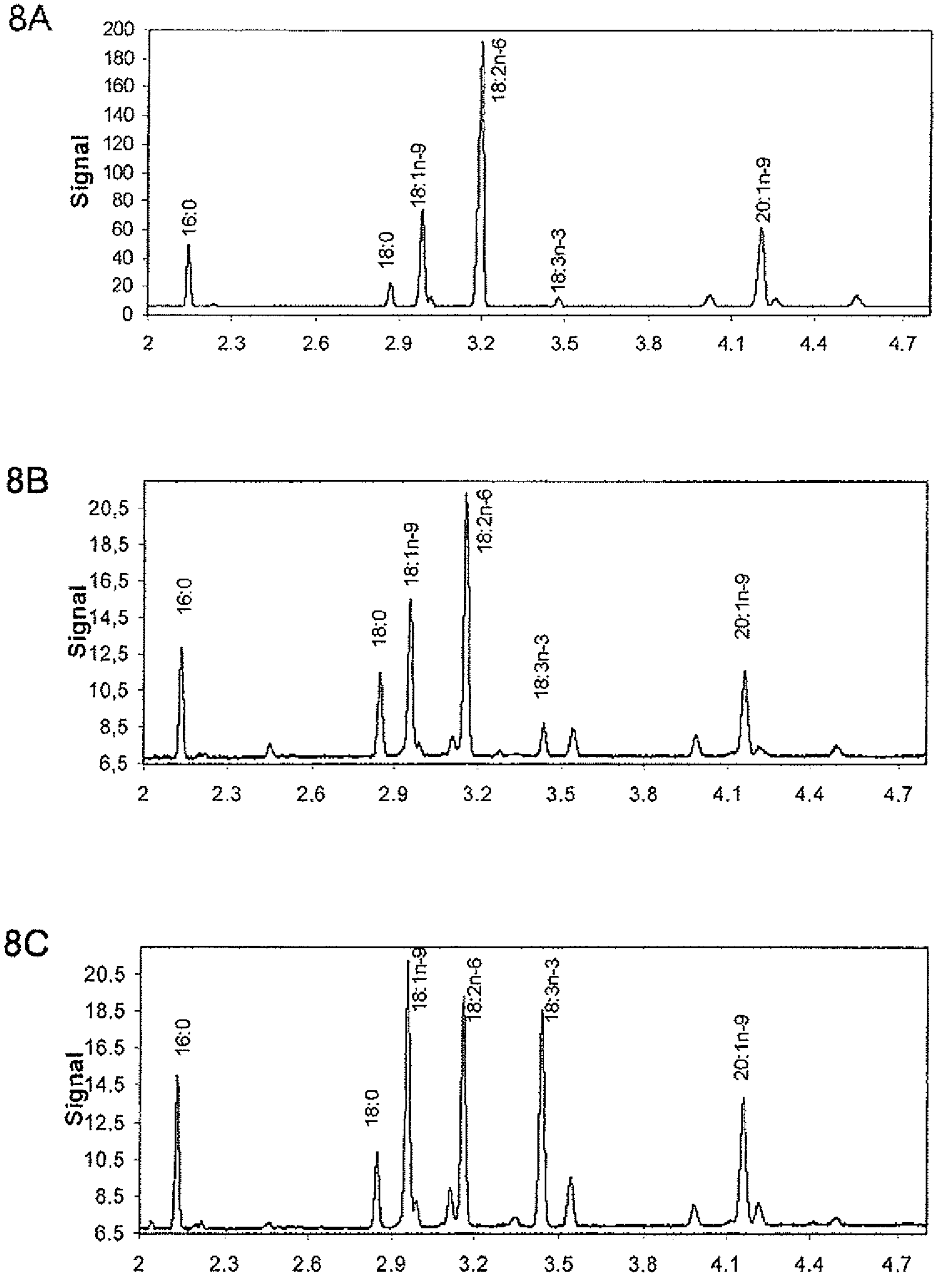

FIG. 8: Gas-chromatographic determination of the fatty acids from *Arabidopsis* seeds of the fad3 mutant which had been transformed with the plasmid pSUN (A) and pSUN-d15Des(Mg) (SEQ ID No. 183; B) and pYES-d15Des(Nh)2 (SEQ ID No. 184; C).

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA 74, 5463-5467). Fragments obtained by polymerase chain reaction were sequenced and verified to avoid polymerase errors in constructs to be expressed.

Example 3

Lipid Extraction from Yeasts

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research", Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

Unambiguous proof for the presence of fatty acid products can be obtained by analyzing recombinant organisms using standard analytical methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipide 33:343-353).

The material to be analyzed can be disrupted by sonication, grinding in the glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 micrometer, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Example 4

Cloning Desaturase Genes

By searching for conserved regions in the protein sequences of the organisms *Nectria haematococca, Trichoderma resii, Monosiga brevicollis, Mycosphaerella fijiensis, Mycospaerella graminicola, Naegleria gruberi, Phycomyces blakesleeanus, Laccaria bicolor, Helobdella robusta, Lottia gigantea, Microcoleus chthonoplastes, Nematostella vectensis, Physcomitrella patens, Postia placenta, Selaginella moellendorffii* and *Microdochium nivale*, it is possible to identify sequences with corresponding motives for Δ12- and/or Δ15-desaturases: These motives are, in particular, the desaturase motive 1 "LXXITXLXH" (SEQ ID No. 83), the desaturase motive 2 "GAXXTXDR" (SEQ ID NO. 84) and the desaturase motive 3 "HVXHH" (SEQ ID No. 85), where X denotes any amino acid. To distinguish between Δ12, Δ15 and omega 3-desaturases, the following motives, which are located at the same position in the alignment of the protein sequences of these desaturases, were used: Δ12-desaturases were identified with the aid of motive 4 "TXXQHXX" (SEQ ID No. 113), in particular with the aid of motive 5 "T(YF)(LM)QH(TSQ)(DHN)" (SEQ ID No. 114), more specifically with the aid of motive 6 "T(YF)LQH(TS)(DH)" (SEQ ID No. 115).

Δ15-desaturases were identified with the aid of motive 7 "TXXHHX(G-)(X-)X" (SEQ ID No. 116), in particular with the aid of motive 8 "T(YF)(LM)HH(HTSV)(G-)(HY-)(HDEG)" (SEQ ID No. 117), in particular with the aid of motive 9 "T(YF)(LM)HH(HTS)(HDE)" (SEQ ID No. 118) or, alternatively, with the aid of motive 10 "T(YF)(LM)HH(HTSV)G(HY)(HDEG)" (SEQ ID 119).

Omega 3-desaturases were identified preferably with the aid of motive 11 "TXXHHNX" (SEQ ID No. 120), in particular with the aid of motive 12 "T(YF)(LM)HHN(HDEG)" (SEQ ID No. 121).

In a first step, complete genomic sequences were identified according to database entries. In a further step, the coding sequence was extracted with the aid of methods of bioinformatics. In order to obtain the corresponding coding sequence from the organisms, can be amplified in a PCR reaction from cDNA preparations, using the primer sequences defined in table 1. This allows fragments as described in table 2 to be obtained.

TABLE 1

Primer sequences for cloning the desaturases which have been identified.

| Name of gene | Organism | Primer sequence (5'-3') | SEQ ID No. |
|---|---|---|---|
| D12Des(Nh) | *Nectria haematococca* | Forward: atggcttctacggctgtgcc | 34 |
| | | Reverse: ttaggcggcgggagggtcg | 35 |
| D15Des(Nh) | *Nectria haematococca* | Forward: atggctactcgacagcgtac | 36 |
| | | Reverse: ctactccttggcccatcgcatg | 37 |
| D15Des(Tr) | *Trichoderma resii* | Forward: atggctactaccacgacggt | 38 |
| | | Reverse: tcattgcgcccagtgcagagctc | 39 |
| D12Des(Mb) | *Monosiga brevicollis* | Forward: atgacggtggcttcccaggtg | 40 |
| | | Reverse: ttacctgtccttgaaccaaag | 41 |
| D15Des(Mg) | *Mycospaerella graminicola* | Forward: atgagcagaacagtcacatta | 42 |
| | | Reverse: tcacgcgctcttaacatgcg | 43 |
| D12Des(Mg) | *Mycospaerella graminicola* | Forward: atgagcaccaccgccctctc | 44 |
| | | Reverse: ctattcggaatcatcctca | 45 |
| D15Des(Ng) | *Naegleria gruberi* | Forward: atgtcagctgccacatcaga | 46 |
| | | Reverse: ttaatgatcccaccacaaaa | 47 |

TABLE 1-continued

Primer sequences for cloning the desaturases which have been identified.

| Name of gene | Organism | Primer sequence (5'-3') | SEQ ID No. |
|---|---|---|---|
| D12Des(Pb) | *Phycomyces blakesleeanus* | Forward: atgtcggataacactgaatc | 48 |
| | | Reverse: ttaattcttgaggaaacgaa | 49 |
| D15Des(Nv) | *Nematostella vectensis* | Forward: atgccgccgtgtcacgcaac | 50 |
| | | Reverse: ttagtccttttcacagttttc | 51 |
| D15Des(Lb) | *Laccaria bicolor* | Forward: atggctgttaaaacggac | 88 |
| | | Reverse: ctatttttcaacctcaatac | 89 |
| d15Des(Hr) | *Helobdella robusta* | Forward: atgaactgtgtaactgagg | 93 |
| | | Reverse: tatttgtaataaacctctaac | 94 |
| d15Des(Lg)1 | *Lottia gigantea* | Forward: atggaaaccaaatcaggaag | 95 |
| | | Reverse: ttatgtataaatatgtac | 96 |
| d15Des(Lg)2 | *Lottia gigantea* | Forward: atgaatgaagccaataaccac | 97 |
| | | Reverse: ttatttatagtaatgaattttg | 98 |
| d15Des(Mc) | *Microcoleus chthonoplastes* | Forward: atgcaatcaaacacagttc | 99 |
| | | Reverse: ttagtttgatcgcggatgtttg | 100 |
| d15Des(Mf) | *Mycosphaerella fijiensis* | Forward: atgtttctcgccggaagtgatg | 101 |
| | | Reverse: tcaggctcctagatctttcc | 102 |
| d15Des(Pp) | *Physcomitrella patens* | Forward: atggatcaagccagtaagattg | 159 |
| | | Reverse: ttatctgcaattgcactgttttg | 160 |
| d15Des(Pp2) | *Physcomitrella patens* | Forward: atgcggagcgcggaggatga tg | 161 |
| | | Reverse: tcactgctttacatcgttctg | 162 |
| d15Des(Pp3) | *Physcomitrella patens* | Forward: atgtccgtgaagcatgagat | 163 |
| | | Reverse: tcacttagcatttgtgctcttc | 164 |
| d15Des(Ppla) | *Postia placenta* | Forward: atggctaccacggctgattctg | 165 |
| | | Reverse: tcacttagcatttgtgctcttc | 166 |
| d15Des(Sm) | *Selaginella moellendorffii* | Forward: atggtcgctgttccactccg | 167 |
| | | Reverse: ttacttcaagcctggatcgctc | 168 |
| d15Des(Mn) | *Microdochium nivale* | Forward: atgattgcga ccacccagacc | 169 |
| | | Reverse: ctaaaggtccttgcggggtg | 170 |

TABLE 2

Coding polynucleotide or amino acid sequences of the desaturases which have been identified.

| Name of gene | Organism | Nucleotides in bp | SEQ ID No. | Amino acid | SEQ ID |
|---|---|---|---|---|---|
| D12Des(Nh) | *Nectria haematococca* | 1437 | 2 | 478 | 3 |
| D15Des(Nh) | *Nectria haematococca* | 1203 | 5 | 400 | 6 |
| D15Des(Tr) | *Trichoderma resii* | 1173 | 8 | 390 | 9 |
| D12Des(Mb) | *Monosiga brevicollis* | 1149 | 11 | 382 | 12 |
| D15Des(Mg) | *Mycospaerella graminicola* | 1191 | 14 | 396 | 15 |
| D12Des(Mg) | *Mycospaerella graminicola* | 1449 | 17 | 482 | 18 |
| D15Des(Ng) | *Naegleria gruberi* | 1197 | 20 | 398 | 21 |
| D12Des(Pb) | *Phycomyces blakesleeanus* | 1170 | 23 | 389 | 24 |
| D15Des(Nv) | *Nematostella vectensis* | 990 | 26 | 329 | 27 |

TABLE 2-continued

Coding polynucleotide or amino acid sequences of the desaturases which have been identified.

| Name of gene | Organism | Nucleotides in bp | SEQ ID No. | Amino acid | SEQ ID |
|---|---|---|---|---|---|
| D15Des(Lb) | *Laccaria bicolor* | 1323 | 91 | 440 | 92 |
| d15Des(Hr) | *Helobdella robusta* | 1128 | 123 | 375 | 124 |
| d15Des(Lg)1 | *Lottia gigantea* | 1101 | 126 | 366 | 127 |
| d15Des(Lg)2 | *Lottia gigantea* | 1113 | 129 | 370 | 130 |
| d15Des(Mc) | *Microcoleus chthonoplastes* | 1077 | 132 | 358 | 133 |
| d15Des(Mf) | *Mycosphaerella fijiensis* | 1191 | 135 | 396 | 136 |
| d15Des(Pp) | *Physcomitrella patens* | 1185 | 143 | 394 | 144 |
| d15Des(Pp2) | *Physcomitrella patens* | 1143 | 146 | 380 | 147 |
| d15Des(Pp3) | *Physcomitrella patens* | 1095 | 149 | 364 | 150 |

TABLE 2-continued

Coding polynucleotide or amino acid sequences of the desaturases which have been identified.

| Name of gene | Organism | Nucleotides in bp | SEQ ID No. | Amino acid | SEQ ID |
|---|---|---|---|---|---|
| d15Des(Ppla) | *Postia placenta* | 1284 | 152 | 427 | 153 |
| d15Des(Sm) | *Selaginella moellendorffii* | 1125 | 155 | 374 | 156 |
| d15Des(Mn) | *Microdochium nivale* | 1209 | 157 | 402 | 158 |

TABLE 3

Genomic sequences of the desaturases which have been identified.

| Name of gene | Organism | Nucleotides in bp | SEQ ID |
|---|---|---|---|
| D12Des(Nh) | *Nectria haematococca* | 2258 | 1 |
| D15Des(Nh) | *Nectria haematococca* | 1996 | 4 |
| D15Des(Tr) | *Trichoderma resii* | 1988 | 7 |
| D12Des(Mb) | *Monosiga brevicollis* | 2520 | 10 |
| D15Des(Mg) | *Mycospaerella graminicola* | 1179 | 13 |
| D12Des(Mg) | *Mycospaerella graminicola* | 2301 | 16 |
| D15Des(Ng) | *Naegleria gruberi* | 1906 | 19 |
| D12Des(Pb) | *Phycomyces blakesleeanus* | 1740 | 22 |
| D15Des(Nv) | *Nematostella vectensis* | 2243 | 25 |
| D15Des(Lb) | *Laccaria bicolor* | 2336 | 90 |
| d15Des(Hr) | *Helobdella robusta* | 1975 | 122 |
| d15Des(Lg)1 | *Lottia gigantea* | 1390 | 125 |
| d15Des(Lg)2 | *Lottia gigantea* | 1513 | 128 |
| d15Des(Mc) | *Microcoleus chthonoplastes* | 3060 | 131 |
| d15Des(Mf) | *Mycosphaerella fijiensis* | 1191 | 134 |
| d15Des(Pp) | *Physcomitrella patens* | 3201 | 142 |
| d15Des(Pp2) | *Physcomitrella patens* | 1543 | 145 |
| d15Des(Pp3) | *Physcomitrella patens* | 1495 | 148 |
| d15Des(Ppla) | *Postia placenta* | 2468 | 151 |
| d15Des(Sm) | *Selaginella moellendorffii* | 4066 | 154 |

To characterize the functions of the individual sequences, the open reading frame of the DNA (table 2) is cloned downstream of the galactose-inducible GAL1 promoter of pYES2.1/V5-His-TOPO (Invitrogen), giving rise to the plasmids pYES-D12Des(Nh), pYES-D15Des(Nh), pYES-D15Des(Tr), pYES-D12Des(Mb), pYES-D15Des(Mg), pYES-D12Des(Mg), pYES-D15Des(Ng), pYES-D12Des (Pb), pYES-D15Des(Nv), pYES-D15Des(Lb), pYES-D15Des(Hr), pYES-D15Des(Lg)1, pYES-D15Des(Lg)2, pYES-D15Des(Mc), pYES-D15Des(Mf), pYes-D15Des (Pp), pYes-D15Des(Pp2), pYes-D15Des(Pp3), pYes-D15Des(Ppla) or pYes-D15Des(Sm). Then, following manufacturers' instructions, these plasmids can be transformed into the yeast stream INVSC-1 (Invitrogen) and selected for uracil auxotrophism on plates with DOB-U agar. Positive colonies are identified by PCR. To this end, is carried out in each case with 1 μl of defrosted cells, 200 μM of dNTPs, 2.5 U Taq polymerase and 100 pmol of each primer in a total volume of 50 μl. The PCR conditions are as follows: first denaturation at 95° C. for 5 minutes, followed by 30 cycles at 94° C. for 30 seconds, 55° C. for 1 minute and 72° C. for 2 minutes, and a last elongation step at 72° C. for 10 minutes. In parallel, the empty vector pYES2.1/V5-His-TOPO is transformed in the above-described manner into competent yeast cells of strain INVSC-1. Yeast cells with the plasmids pYES-D12Des(Nh), pYES-D15Des(Nh), pYES-D15Des(Tr), pYES-D12Des(Mb), pYES-D15Des(Mg), pYES-D12Des (Mg), pYES-D15Des(Ng), pYES-D12Des(Pb), pYES-D15Des(Nv), pYES-D15Des(Lb), pYES-D15Des(Hr), pYES-D15Des(Lg)1, pYES-D15Des(Lg)2, pYES-D15Des (Mc), pYES-D15Des(Mf), pYes-D15Des(Pp), pYes-D15Des (Pp2), pYes-D15Des(Pp3), pYes-D15Des(Ppla) or pYes-D15Des(Sm) are incubated for 12 h in liquid DOB-U medium at 28° C. and 200 rpm and then grown for a further 12 h in induction medium (DOB-U+2% (w/v) galactose+2% (w/v) raffinose) and 250 μM of fatty acids which are added into the medium. The specificity and activity of the gene to be characterized can be determined with reference to the added fatty acids.

Yeasts transformed with the plasmids pYES2/V5-His-TOPO or pYES-D12Des(Nh), pYES-D15Des(Nh), pYES-D15Des(Tr), pYES-D12Des(Mb), pYES-D15Des(Mg), pYES-D12Des(Mg), pYES-D15Des(Ng), pYES-D12Des (Pb), pYES-D15Des(Nv), pYES-D15Des(Lb), pYES-D15Des(Hr), pYES-D15Des(Lg)1, pYES-D15Des(Lg)2, pYES-D15Des(Mc), pYES-D15Des(Mf), pYes-D15Des (Pp), pYes-D15Des(Pp2), pYes-D15Des(Pp3), pYes-D15Des(Ppla) or pYes-D15Des(Sm) are analyzed as follows:

The yeast cells from the main cultures are harvested by centrifugation (100×g, 5 min, 20° C.) and washed with 100 mM $NaHCO_3$, pH 8.0 to remove residual medium and fatty acids. Starting with the yeast cell sediments, fatty acid methyl esters (FAMEs) are prepared by acid methanolysis. To this end, the cell sediments are incubated for one hour at 80° C. together with 2 ml of 1 N methanolic sulfuric acid and 2% (v/v) of dimethoxypropane. The FAMEs are extracted twice with petroleum ether (PE). To remove nonderivatized fatty acids, the organic phases are washed in each case once with 2 ml of 100 mM $NaHCO_3$, pH 8.0 and 2 ml of distilled water. Thereafter, the PE phases were dried with $Na_2SO_4$, evaporated under argon and taken up in 100 μl of PE. The samples are separated on a DB-23 capillary column (30 m, 0.25 mm, 0.25 μm, Agilent) in a Hewlett-Packard 6850 gas chromatograph equipped with flame ionization detector. The conditions for the GLC analysis are as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch, Biochem. Biophys. 388(2):293-298 and Michaelson at al., 1998, FEBS Letters. 439(3):215-218.

Activity and Substrate Determination of the Desaturases which have been Identified The substrate specificity of D12Des(Nh), D15Des(Nh), D15Des(Tr), D12Des(Mb), D15Des(Mg), D12Des(Mg), D15Des(Ng), D12Des(Pb), D15Des(Nv), D15Des(Lb), D15Des(Hr), D15Des(Lg)1, D15Des(Lg2), D15Des(Mc), D15Des(Mf), D15Des(Pp), D15Des(Pp2), D15Des(Pp3), D15Des(Ppla) or D15Des(Sm) can be determined after expression and after the feeding of various fatty acids. Departing from the conserved elements, the following activity was found for the coding sequences (table 4).

TABLE 4

Activity of the desaturases which have been identified

| Name of gene | Organism | Activity | Polynucleotide SEQ ID No. | Polypeptide SEQ ID No. |
|---|---|---|---|---|
| D12Des(Nh) | Nectria haematococca | Δ12-desaturase | 2 | 3 |
| D15Des(Nh) | Nectria haematococca | Δ15-desaturase | 5 | 6 |
| D15Des(Tr) | Trichoderma resii | Δ15-desaturase | 8 | 9 |
| D12Des(Mb) | Monosiga brevicollis | Δ12-desaturase | 11 | 12 |
| D15Des(Mg) | Mycospaerella graminicola | Δ15-desaturase | 14 | 15 |
| D12Des(Mg) | Mycospaerella graminicola | Δ12-desaturase | 17 | 18 |
| D15Des(Ng) | Naegleria gruberi | Δ15-desaturase | 20 | 21 |
| D12Des(Pb) | Phycomyces blakesleeanus | Δ12-desaturase | 23 | 24 |
| D15Des(Nv) | Nematostella vectensis | Δ15-desaturase | 26 | 27 |

TABLE 4-continued

Activity of the desaturases which have been identified

| Name of gene | Organism | Activity | Polynucleotide SEQ ID No. | Polypeptide SEQ ID No. |
|---|---|---|---|---|
| D15Des(Lb) | Laccaria bicolor | Δ15-desaturase | 91 | 92 |
| d15Des(Hr) | Helobdella robusta | Δ15-desaturase | 123 | 124 |
| d15Des(Lg)1 | Lottia gigantea | (15-desaturase | 126 | 127 |
| d15Des(Lg)2 | Lottia gigantea | (15-desaturase | 129 | 130 |
| d15Des(Mc) | Microcoleus chthonoplastes | (15-desaturase | 132 | 133 |
| d15Des(Mf) | Mycosphaerella fijiensis | (15-desaturase | 135 | 136 |
| d15Des(Pp) | Physcomitrella patens | (15-desaturase | 143 | 144 |
| d15Des(Pp2) | Physcomitrella patens | (15-desaturase | 146 | 147 |
| d15Des(Pp3) | Physcomitrella patens | (15-desaturase | 149 | 150 |
| d15Des(Ppla) | Postia placenta | (15-desaturase | 152 | 153 |
| d15Des(Sm) | Selaginella moellendorffii | (15-desaturase | 155 | 156 |
| d15Des(Mn) | Microdochium nivale | (15-desaturase | 157 | 158 |

These activities which have been found were additionally verified by expressing the desaturases in yeast. Table 4A lists the conversion of various fatty acid substrates into the expected fatty acid products. Except for the fatty acid 18:1n-9, all substrates were fed in the experiment and are therefore present in excess. FIGS. 4, 5, 6 and 7 show the chromatograms of the individual experiments.

TABLE 4A

Feeding of yeasts

| Sample name/fatty acid fed | Reaction step observed | | | | Activity observed | Fig. |
|---|---|---|---|---|---|---|
| | Substrate (units of area) | Product (units of area) | Conversion rate (%) Expected | Conversion rate (%) Observed | | |
| pYES2 empty vector | 18:1n-9 169.3 | 18:2n-6 0.7 | — | — | — | 4a |
| d12Des(Nh) | 18:1n-9 10.5 | 18:2n-6 14.8 | >0 | 59 | Δ12-Des. | 4b |
| d12Des(Mb) | 18:1n-9 12.0 | 18:2n-6 9.9 | >0 | 45 | Δ12-Des. | 4c |
| d12Des(Mg) | 18:1n-9 33.8 | 18:2n-6 36.0 | >0 | 52 | Δ12-Des. | 4d |
| d12Des(Pb) | 18:1n-9 55.3 | 18:2n-6 18.0 | >0 | 25 | Δ12-Des. | 4e |
| pYES2 empty vector/18:2n-9 | 18:2n-6 49.3 | 18:3n-3 0.0 | — | — | — | 5a |
| d15Des(Nh)2/18:2n-9 | 18:2n-6 79.3 | 18:3n-3 9.1 | >0 | 10 | Δ15-Des. | 5b |
| d15Des(Mg)/18:2n-9 | 18:2n-6 66.0 | 18:3n-3 15.3 | >0 | 19 | Δ15-Des. | 5c |
| d15Des(Hr)/18:2n-9 | 18:2n-6 3.8 | 18:3n-3 1.5 | >0 | 29 | Δ15-Des. | 5d |
| d15Des(Lg)2/18:2n-9 | 18:2n-6 4.3 | 18:3n-3 2.2 | >0 | 34 | Δ15-Des. | 5e |
| d15Des(Mc)/18:2n-9 | 18:2n-6 3.2 | 18:3n-3 2.1 | >0 | 40 | Δ15-Des. | 5f |
| pYES2 empty vector/20:2n-6 | 20:2n-6 27.7 | 20:3n-6 0.0 | — | — | — | 6a |
| d15Des(Hr)/20:2n-6 | 20:2n-6 17.4 | 20:3n-6 2.3 | >0 | 12 | ω3-Des. | 6b |
| d15Des(Lg)2/20:2n-6 | 20:2n-6 17.0 | 20:3n-6 4.6 | >0 | 21 | ω3-Des. | 6c |
| d15Des(Mc)/20:2n-6 | 20:2n-6 11.2 | 20:3n-6 7.5 | >0 | 40 | ω3-Des. | 6d |
| pYES2 empty vector/20:4n-6 | 20:4n-6 14.1 | 20:5n-3 | — | — | — | 7a |
| d15Des(Hr)/20:4n-6 | 20:4n-6 15.6 | 20:5n-3 2.8 | >0 | 15 | ω3-Des. | 7b |
| d15Des(Lg)2/20:4n-6 | 20:4n-6 9.3 | 20:5n-3 10.7 | >0 | 54 | ω3-Des. | 7c |
| d15Des(Mc)/20:4n-6 | 20:4n-6 19.4 | 20:5n-3 2.6 | >0 | 12 | ω3-Des. | 7d |

By way of control for the assay for Δ12-desaturase activity, yeasts were transformed exclusively with the pYES empty vector, and the fatty acid profile was analyzed (FIG. 4A). In comparison, the additional fatty acid 18:2n-6 can be observed in yeasts which express the desaturases Δ12Des(Nh), Δ12Des(Mb), Δ12Des(Mg) and Δ12Des(Pb) (FIGS. 4B, 4C, 4D, 4E). These desaturases which have been assayed therefore have Δ12-desaturase activity.

By way of control for the assay for Δ15-desaturase activity, yeasts were transformed with the pYES empty vector, the fatty acid 18:2n-6 was fed, and the fatty acid profile was analyzed (FIG. 5A). In comparison, the additional fatty acid 18:3n-3 can be observed in yeasts which express the desaturases Δ15Des(Nh)2, Δ15Des(Mg), Δ15Des(Hr), Δ15Des(Lg)

and Δ15Des(Mc) (FIGS. 5B, 5C, 5D, 5E, 5F). These desaturases which have been assayed therefore have Δ15-desaturase activity.

By way of control for the assay for ω3-desaturase activity, and when using 20:2n-6 as the substrate, yeasts were transformed with the pYES empty vector, the fatty acid 20:2n-6 was fed, and the fatty acid profile was analyzed (FIG. 6A). In comparison, the additional fatty acid 20:3n-3 can be observed in yeasts which express the desaturases Δ15Des(Hr), Δ15Des (Lg), Δ15Des(Mc) (FIGS. 6B, 6C, 6D). These desaturases which have been assayed and for which 20:2n-6 acts as the substrate therefore have ω3-desaturase activity.

By way of control for the assay for ω3-desaturase activity, and when using 22:4n-6 as the substrate, yeasts were transformed with the pYES empty vector, the fatty acid 20:4n-6 was fed, and the fatty acid profile was analyzed (FIG. 7A). In comparison, the additional fatty acid 22:5n-3 can be observed in yeasts which express the desaturases Δ15Des(Hr), Δ15Des (Lg), Δ15Des(Mc) (FIGS. 7B, 7C, 7D). These desaturases which have been assayed and for which 20:4n-6 acts as the substrate therefore have ω3-desaturase activity.

Moreover, the activities detected in yeast were verified in plants which expressed the desaturases in a seed-specific manner. The fad3 mutant of *Arabidopsis* which, in comparison with the Col-0 wild-type, only produces very little 18:3n-3 in the seed was used for this purpose (see table 4A and FIG. 8A). In comparison, drastically increased amounts of 18:3n-3 can be observed in fad3 mutants which express the desaturase Δ15Des(Mg) (see table 4B) and Δ15Des(Nh) (see table 4C) in the seed (FIGS. 8B, 8C). These desaturases which have been assayed therefore have Δ15-desaturase activity in plants.

TABLE 4B

Position of the region of the binary vector pSUN-Δ15Des(Mg) (16093 bp, DNA, circular) which codes for the desaturase Δ15Des(Mg) (SEQ ID No. 15), and the position of the corresponding promoter which regulates the expression and of the terminator. The basic vector on which this is based is pSUN. The position indicated describes the start and end of the corresponding element in base pairs (bp) based on SEQ ID No. 183. The following elements are characterized by a prefix: p—(promoter),: c—(coding sequence), t—(terminator).

| Element | Description | Position |
|---|---|---|
| p-SBP | Promoter of the *Vicia faba* ViSBP | 263-2061 |
| c-d15Des(Mg_GA) | Codes for the *Mycosphaerella graminicola* Δ15-desaturase (SEQ ID No. 15) | 2071-3261 |
| t-CatpA | *Vicia faba* terminator | 3291-3526 |

TABLE 4B

Position of the region of the binary vector pSUN-Δ15Des(Nh)2 (16097 bp, DNA, circular) which codes for the desaturase Δ15Des(Nh)2 (SEQ ID No. 6), and the position of the corresponding promoter which regulates the expression and of the terminator. The basic vector on which this is based is pSUN. The position indicated describes the start and end of the corresponding element in base pairs (bp) based on SEQ ID No. 184. The following elements are characterized by a prefix: p—(promoter),: c—(coding sequence), t—(terminator).

| Element | Description | Position |
|---|---|---|
| p-SBP | Promoter of the *Vicia faba* ViSBP | 263-2061 |
| c-d15Des(Nh_GA)2 | Codes for the *Nectria haematococca* Δ15-desaturase (SEQ ID No. 6) | 2063-3265 |
| t-CatpA | *Vicia faba* terminator | 3296-3530 |

Example 5

Production of Transgenic Plants for the Production of Long-Chain Polyunsaturated Fatty Acids To produce long-chain polyunsaturated fatty acids in plants, various genes of the metabolic pathway are combined on a binary vector. To produce the fatty acid eicosapentaenoic acid (20:5Δ5,8,11,14,17), genes as described in table 5 are combined. Analogously, the genes as described in table 6 are combined for producing the fatty acid docosahexaenoic acid (22:6Δ4,7,10,13,16,19).

TABLE 5

Gene combination for the production of eicosapentaenoic acid

| Gene | Activity | SEQ ID No. |
|---|---|---|
| D6Des(Pir) | Δ6-desaturase | 28 |
| D6Elo(Pp) | Δ6-elongase | 31 |
| D5Des(Tc) | Δ5-desaturase | 29 |
| ω3-Des(Pi) | omega 3-desaturase | 30 |
| D12Des(Nh) | Δ12-desaturase | 2 |
| D15Des(Nh) | Δ15-desaturase | 5 |
| D15Des(Tr) | Δ12-/Δ15-desaturase | 8 |
| D12Des(Mb) | Δ12-desaturase | 11 |
| D15Des(Mg) | Δ15-desaturase | 14 |
| D12Des(Mg) | Δ12-desaturase | 17 |
| D15Des(Ng) | Δ15-desaturase | 20 |
| D12Des(Pb) | Δ12-desaturase | 23 |
| D15Des(Nv) | Δ15-desaturase | 26 |
| D15Des(Lb) | Δ15-desaturase | 91 |
| d15Des(Hr) | Δ15-desaturase | 123 |
| d15Des(Lg)1 | Δ15-desaturase | 126 |
| d15Des(Lg)2 | Δ15-desaturase | 129 |
| d15Des(Mc) | Δ15-desaturase | 132 |
| d15Des(Mf) | Δ15-desaturase | 135 |
| d15Des(Pp) | Δ15-desaturase | 143 |
| d15Des(Pp2) | Δ15-desaturase | 146 |
| d15Des(Pp3) | Δ15-desaturase | 149 |
| d15Des(Ppla) | Δ15-desaturase | 152 |
| d15Des(Sm) | Δ15-desaturase | 155 |
| d15Des(Mn) | Δ15-desaturase | 157 |

TABLE 6

Gene combination for the production of docosahexaenoic acid

| Gene | Activity | SEQ ID No. |
|---|---|---|
| D6Des(Pir) | Δ6-desaturase | 28 |
| D6Elo(Pp) | Δ6-elongase | 31 |
| D5Des(Tc) | Δ5-desaturase | 29 |
| ω3-Des(Pi) | omega 3-desaturase | 30 |
| D12Des(Nh) | Δ12-desaturase | 2 |
| D15Des(Nh) | Δ15-desaturase | 5 |
| D15Des(Tr) | Δ12-/(15-desaturase | 8 |
| D12Des(Mb) | (12-desaturase | 11 |
| D15Des(Mg) | (15-desaturase | 14 |
| D12Des(Mg) | (12-desaturase | 17 |
| D15Des(Ng) | (15-desaturase | 20 |
| D12Des(Pb) | (12-desaturase | 23 |
| D15Des(Nv) | (15-desaturase | 26 |
| D15Des(Lb) | (15-desaturase | 91 |
| d15Des(Hr) | (15-desaturase | 123 |
| d15Des(Lg)1 | (15-desaturase | 126 |
| d15Des(Lg)2 | (15-desaturase | 129 |
| d15Des(Mc) | (15-desaturase | 132 |
| d15Des(Mf) | (15-desaturase | 135 |
| d15Des (Pp) | (15-desaturase | 143 |
| d15Des (Pp2) | (15-desaturase | 146 |
| d15Des (Pp3) | (15-desaturase | 149 |
| d15Des (Ppla) | (15-desaturase | 152 |
| d15Des (Sm) | (15-desaturase | 155 |
| d15Des (Mn) | (15-desaturase | 157 |

TABLE 6-continued

| Gene combination for the production of docosahexaenoic acid | | |
|---|---|---|
| Gene | Activity | SEQ ID No. |
| D5Elo (Ot) | (5-elongase | 32 |
| D4Des (Tc) | (4-desaturase | 33 |

Further transformation vectors based on pSUN-USP are generated for the transformation of plants. To this end, NotI cleavage sites are introduced at the 5' and at the 3' end of the coding sequence, using the following primer pairs (see table 7).

Composition of the PCR mix (50 μl):

5.00 μl template cDNA 5.00 μl 10× buffer (Advantage polymerase)+25 mM $MgCl_2$ 5.00 μl 2 mM dNTP 1.25 μl of each primer (10 pmol/μl)

0.50 μl Advantage polymerase

The Advantage polymerase from Clontech is employed.

PCR reaction conditions:

Annealing temperature: 1 min 55° C.

Denaturation temperature: 1 min 94° C.

Elongation temperature: 2 min 72° C.

Number of cycles: 35

TABLE 7

| Primer sequences (for cloning transformation vectors based on pSUN-USP) | | |
|---|---|---|
| Gene | Primer | SEQ ID No. |
| D6-Des(Pir) | Fwd: gcggccgcgccatggtggacctcaagcctgg | 52 |
| | Rvs: gcggccgttacatcgctgggaactcgg | 53 |
| D5-Des(Tc) | Fwd: gcggccgcgccatgggcaagggcagcgaggg | 54 |
| | Rvs: gcggccgcgcctcagtcctgcttcttggtgtc | 55 |
| O3-Des(Pi) | Fwd: gcggccgcgccatggcgacgaaggaggcgta | 56 |
| | Rvs: gcggccgcgttacgtggacttggtcttggcc | 57 |
| D6-Elo(Pp) | Fwd: gcggccgcgccatggaggtcgtggagagattc | 58 |
| | Rvs: gcggccgcgtcactcagttttagctccc | 59 |
| D12Des(Nh) | Fwd: gcggccgcgccatggcttctacggctgtgcc | 60 |
| | Rvs: gcggccgcgttaggcggcgggagggtcga | 61 |
| D15Des(Nh) | Fwd: gcggccgcgccatggctactcgacagcgtac | 62 |
| | Rvs: gcggccgcgctactccttggcccatcgcatg | 63 |
| D15Des(Tr) | Fwd: gcggccgcgccatggctactaccacgacggtc | 64 |
| | Rvs: gcggccgcgtcattgcgcccagtgcagag | 65 |
| D12Des(Mb) | Fwd: gcggccgcgccatgacggtggcttcccaggtg | 66 |
| | Rvs: gcggccgcgttacctgtccttgaaccaaag | 67 |
| D15Des(Mg) | Fwd: gcggccgcgccatgagcagaacagtcacatta | 68 |
| | Rvs: gcggccgcgtcacgcgctcttaacatgcg | 69 |
| D12Des(Mg) | Fwd: gcggccgcgccatgagcaccaccgccctctc | 70 |
| | Rvs: gcggccgcgctattcggaatcatcctcaac | 71 |
| D15Des(Ng) | Fwd: gcggccgcgccatgtcagctgccacatcag | 72 |
| | Rvs: gcggccgcgttaatgatcccaccacaaaa | 73 |
| D12Des(Pb) | Fwd: gcggccgcgccatgtcggataacactgaatc | 74 |
| | Rvs: gcggccgcgttaattcttgaggaaacgaa | 75 |
| D15Des(Nv) | Fwd: gcggccgcgccatgccgccgtgtcacgcaac | 76 |
| | Rvs: gcggccgcgttagtccttttcacagttttc | 77 |
| D15Des(Lb) | Fwd: gcggccgcgccatggctgttaaaacggac | 86 |
| | Rvs: gcggccgcgctatttttcaacctcaatac | 87 |
| d15Des(Hr) | Fwd: gcggccgcgccatgaactgtgtaactgagg | 103 |
| | Rvs: gcggccgcgtatttgtaataaacctctaac | 104 |
| d15Des(Lg)1 | Fwd: gcggccgcgccatggaaaccaaatcaggaag | 105 |
| | Rvs: gcggccgcgttatgtataaatatgtac | 106 |
| d15Des(Lg)2 | Fwd: gcggccgcgccatgaatgaagccaataaccac | 107 |
| | Rvs: gcggccgcgttatttatagtaatgaattttg | 108 |
| d15Des(Mc) | Fwd: gcggccgcgccatgcaatcaaacacagttc | 109 |
| | Rvs: gcggccgcgttagtttgatcgcggatgtttg | 110 |
| d15Des(Mf) | Fwd: gcggccgcgccatgtttctcgccggaagtgatg | 111 |
| | Rvs: gcggccgcgtcaggctcctagatctttcc | 112 |

TABLE 7-continued

Primer sequences (for cloning transformation vectors based on pSUN-USP)

| Gene | Primer | SEQ ID No. |
|---|---|---|
| d15Des(Pp) | Fwd: gcggccgcgccatggatcaagccagtaaga ttg | 171 |
| | Rvs: gcggccgcgttatctgcaattgcactgttttg | 172 |
| d15Des(Pp2) | Fwd: gcggccgcgccatgcggagcgcggaggatg atg | 173 |
| | Rvs: gcggccgcgt cactgcttta catcgttctg | 174 |
| d15Des(Pp3) | Fwd: gcggccgcgc catgtccgtg aagcatgaga t | 175 |
| | Rvs: gcggccgcgt cacttagcat ttgtgctctt c | 176 |
| d15Des(Ppla) | Fwd: gcggccgcgc catggctacc acggctgatt ctg | 177 |
| | Rvs: gcggccgcgt caacgagaca cgctcgctg | 178 |
| d15Des(Sm) | Fwd: gcggccgcgc catggtcgct gttccactcc g | 179 |
| | Rvs: gcggccgcgt tacttcaagc ctggatcgct c | 180 |
| d15Des(Mn) | Fwd: gcggccgcgc catgattgcg accacccaga cc | 181 |
| | Rvs: gcggccgcgc taaaggtcct tgcggggtg | 182 |
| D5Elo(Ot) | Fwd: gcggccgcgccatgagcgcctccggtgcgctg | 78 |
| | Rvs: gcggccgcgttagtcaatttttc | 79 |
| D4Des(Tc) | Fwd: gcggccgcgccatgacggtcggctacgacgag | 80 |
| | Rvs: gcggccgcgtcaggcagcgcgctgccagg | 81 |

The PCR products are incubated with the restriction enzyme NotI for 4 h at 37° C. The plant expression vector pSUN300-USP is incubated in the same manner. Thereafter, the PCR products and the 7624 bp vector are separated by agarose gel electrophoresis, and the corresponding DNA fragments are excised. The DNA is purified by means of the Qiagen gel purification kit, following the manufacturer's instructions. Thereafter, vector and PCR products are ligated. The Rapid Ligation kit from Roche is used for this purpose. The plasmids generated are verified by sequencing.

pSUN300 is a derivative of the plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP originated from pSUN300, by inserting a USP promoter into pSUN300 in the form of an EcoRI fragment. The polyadenylation signal is that of the OCS gene from the *A. tumefaciens* Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982). The USP promoter corresponds to nucleotides 1 to 684 (Genbank Accession X56240), where part of the noncoding region of the USP gene is present in the promoter. The promoter fragment which is 684 base pairs in size was amplified by a PCR reaction using standard methods with the aid of a synthesized primer and by means of a commercially available T7 standard primer (Stratagene)

[SEQ ID No. 82]
(Primer sequence: 5'-GTCGACCCGCGGACTAGTGGGCCCTCTAG

ACCCGGGGGATCCGGATCTGCTGGCTATGAA-3').

The PCR fragment was recut with EcoRI/SalI and inserted into the vector pSUN300 with OCS terminator. This gave rise to the plasmid named pSUN-USP, which can be employed for transforming plants by means of *Agrobacterium tumefaciens*.

a) Generation of transgenic oilseed rape plants (modified method of Moloney et al., 1992, Plant Cell Reports, 8:238-242)

To generate transgenic oilseed rape plants, binary vectors such as the pSUN plasmids described hereinabove were transformed into *Agrobacterium tumefaciens* C58C1: pGV2260 using the appropriately combined genes (Deblaere et al, 1984, Nucl. Acids. Res. 13, 4777-4788). As an example for the use and analysis of Δ15-desaturases and Δ12-desaturases, the generation of plants transformed with the construct LJB765 (SEQ ID 137), which contains a Δ15-desaturase and a Δ12-desaturase (elements c-d15Des(Fm_GA) with the SEQ ID No. 140 and c-d12-Des(Co) with SEQ ID No. 141 in table 8 hereinbelow) will now be described. The Δ15-desaturase and Δ12-desaturase used in the construct can be replaced by the Δ15-desaturases or Δ12-desaturases according to the invention. The binary vector LJB765 with the SEQ ID No. 137 comprises the elements listed in table 8.

TABLE 8

Description of the binary vector LJB765: (28 346 bp, DNA, circular). The position indicated describes the start and end of the corresponding element in base pairs (bp) based on SEQ ID No. 137. The following elements are characterized by a prefix: p—(promoter), o—(origin of replication), c—(coding sequence), t—(terminator).

| Element | Description | Position |
|---|---|---|
| c-d6-Elo(Pp_GA) SEQ ID No. 31 | *Physcomitrella patens* Δ6-elongase | 980-1852 |
| c-d6-Des(Pir) SEQ ID No. 28 | *Pythium irregulare* Δ6-desaturase | 2953-4332 |
| c-o3Des(Pi_GA2) SEQ ID No. 30 | *Phytophthora infestans* omega3-desaturase | 5402-6487 |
| c-d6Elo(Tp_GA) SEQ ID No. 138 | *Thalassiosira pseudonana* Δ6-elongase | 8854-9672 |
| c-d6Des(Ot_GA2) SEQ ID 139 | *Ostreococcus tauri* Δ6-desaturase | 10543-11913 |
| c-d15Des(Fm_GA) SEQ ID 140 | *Fusarium, monoliforme* Δ15-desaturase | 12939-14147 |
| c-d5Des(Tc_GA) SEQ ID No. 29 | *Thraustochytrium* ssp. Δ5-desaturase | 15582-16901 |

TABLE 8-continued

Description of the binary vector LJB765: (28 346 bp, DNA, circular). The position indicated describes the start and end of the corresponding element in base pairs (bp) based on SEQ ID No. 137. The following elements are characterized by a prefix: p—(promoter), o—(origin of replication), c—(coding sequence), t—(terminator).

| Element | Description | Position |
|---|---|---|
| c-d12-Des(Co) SEQ ID No. 141 | *Calendula officinalis* Δ12-desaturase | 18900-20051 |
| c-NptII | Neomycin phosphotransferase | 21425-22219 |
| c-PVS1 | Partitioning protein | 23248-24248 |
| c-StaA | PVS partitioning protein | 23487-24116 |
| c-VS1 | VS1 orf3 | 24137-24352 |
| c-RepA | Replication protein | 24511-25618 |
| c-aadA | Adenylate transferase | 27382-28173 |
| o-BOM | pBR322 replication origin | 26252-26512 |
| o-ColE1 | Origin of replication | 26367-27213 |
| p-VfUSP | *Vicia faba* VfUSP promoter | 299-972 |
| p-LeB4 | *Vicia faba* LeB4 promoter | 2163-2918 |
| p-Napin | *Brassica napus* Napin promoter | 4735-5398 |
| p-VfSBP | *Vicia faba* VfSBP promoter | 7054-8852 |
| p-BnGLP | *Brassica napus* BnGLP promoter | 9914-10539 |
| p-VfUSP | *Vicia faba* VfUSP promoter | 12250-12923 |
| p-Conlinin | *Linum usitatissimum* Conlinin promoter | 14505-15543 |
| p-LuPXR | *Linum usitatissimum* LuPXR promoter | 17150-18876 |
| p-NOS | *Agrobacterium tumefaciens* promoter | 21106-21393 |
| RB | Right border of the T plasmid | 83-106 |
| LB | Left border of the T plasmid | 22732-22756 |
| t-35S | CamV35S terminator | 1903-2124 |
| t-LeB | *Vicia faba* terminator | 4375-4671 |
| t-E9 | *Pisum sativum* terminator | 6488-7045 |
| t-CatpA | *Vicia faba* terminator | 9673-9907 |
| t-AtGLP | *Arabidopsis thaliana* terminator | 11914-12186 |
| t-35S | CamV35S terminator | 14201-14416 |
| t-OCS | *Agrobacterium tumefaciens* terminator | 16949-17147 |
| t-AtPXR | *Arabidopsis thaliana* terminator | 20117-20516 |
| t-NOS | *Agrobacterium tumefaciens* terminator | 20743-20998 |
| t-NOS | *Agrobacterium tumefaciens* terminator | 22318-22570 |

After transformation of the binary plasmid LJB765 into *agrobacterium* (see above), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used for transforming oilseed rape plants (cv. Westar). Petioles or hypocotyls of freshly germinated sterile oilseed rape plants (in each case approx. 1 $cm^2$) are incubated with a 1:50 agrobacterial dilution for 5-10 minutes in a Petri dish. This is followed by 3 days of coincubation in the dark at 25° C. on 3MS medium supplemented with 0.8% Bacto agar. After 3 days, the cultivation is continued with 16 hours light/8 hours dark and is continued, in a 1-week rhythm, on MS medium supplemented with 500 mg/l Claforan (cefotaxim-sodium), 50 mg/l kanamycin, 20 μm benzylaminopurine (BAP) and 1.6 g/l glucose. Growing shoots are transferred to MS medium supplemented with 2% sucrose, 250 mg/l Claforan and 0.8% Bacto agar. If no roots have formed after three weeks, the growth hormone 2-indolebutyric acid is added to the medium to promote rooting.

Regenerated shoots are obtained on 2MS medium supplemented with kanamycin and Claforan, transferred into soil once rooted, and after cultivation for two weeks grown in a controlled-environment cabinet or in a greenhouse, flowering is induced, mature seeds are harvested and analyzed for expression of the desaturase or elongase genes by means of lipid analyses as described by way of example in Qiu et al. 2001, J. Biol. Chem. 276, 31561-31566. FIG. 2 shows a chromatogram of rapeseed harvested from plants which have been transformed with the construct LJB765. Here, the generation of novel fatty acids in the rapeseed can be observed. These novel fatty acids can be attributed to the activity of the genes which have been introduced (see EPA, eicosapentaenoic acid). In comparison to the untransformed control, the seeds of the transgenic plant (FIG. 2) show increased contents of Δ12-desaturated product (C18:2n-6, linoleic acid) and Δ15-desaturated products (18:3n-3; 18:4n-3; EPA), which can be attributed to the activity of the Δ12- and Δ15-desaturase which have been introduced. In total, 18.4% of omega3-fatty acids is produced, of which 11.8% EPA, 3.0% 18:4n-3 and 3.6% 18:3n-3. The untransformed control plant contains between 5 and 6% omega3-fatty acids, i.e. the content of omega3-fatty acids was tripled in the transgenic plants.

In another example, the construct LJB765 was transformed into *Arabidopsis thaliana*. The Floral Dip method of (Clough and Bent, 1998, Plant Journal 16: 735-743) was used for this purpose. Transgenic plants were selected on agar plates with kanamycin, and the harvested seeds were studied by gas-chromatographic analysis as described by Sayanova et al., 2003, FEBS Letters, 542, 100-104. Similar data as for oilseed rape were obtained (FIG. 3). In comparison to the untransformed control, the seeds of the transgenic plant show increased contents of Δ12-desaturated product (C18:2n-6, linoleic acid). The transformed plants also show a markedly increased content (i.e. a doubling) of omega3-fatty acids in comparison with the untransformed plants. Thus, for example, 13.7% EPA was obtained. In total, 28.6% of omega3-fatty acids was produced, of which 13.7% EPA, 0.6% 18:3n-3, 13.3% 18:3n-3 and 1.0% 20:4n-3.

In a similar manner, the Δ12- and Δ15-desaturases according to the invention may also be characterized and used for the production of polyunsaturated long-chain omega3-fatty acids (such as eicosapentaenoic acid and/or docosahexaenoic acid).

b) Generation of Transgenic Linseed Plants

Transgenic linseed plants can be generated for example by the method of Bell et al., 1999, In Vitro Cell. Dev. Biol.-Plant. 35(6):456-465 by means of particle bombardment. *Agrobacteria*-mediated transformations can be effected for example as described by Mlynarova et al. (1994), Plant Cell Report 13: 282-285.

We claim:

1. An isolated polynucleotide comprising a nucleic acid sequence operably linked to a heterologous expression control sequence, wherein said nucleic acid sequence encodes a polypeptide having delta-15 desaturase activity and comprising an amino acid sequence having at least 85% sequence identity to SEQ ID NO: 133, and wherein said amino acid sequence further comprises the amino acid motif of SEQ ID NO: 116 and any of the amino acid motifs of SEQ ID NO: 83, SEQ ID NO: 84 and SEQ ID NO: 85.

2. The isolated polynucleotide of claim 1, wherein the polynucleotide consists of RNA or DNA.

3. A vector comprising the isolated polynucleotide of claim 1.

4. The vector according to claim 3, wherein the vector is an expression vector.

5. The vector according to claim 3, wherein the vector comprises at least one further polynucleotide which codes for a further enzyme which is involved in the biosynthesis of lipids or fatty acids.

6. The vector of claim 5, wherein the enzyme is selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ5-elongase(s), Δ6-elongase(s), and Δ9-elongase(s).

7. A host cell comprising:

(a) the isolated polynucleotide of claim 1, or (b) a vector comprising said isolated polynucleotide.

8. The host cell according to claim 7, wherein the host cell additionally comprises at least one further enzyme which is involved in the biosynthesis of lipids or fatty acids.

9. A host cell comprising the vector of claim 3.

10. The host cell of claim 8, wherein the enzyme is selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ5-elongase(s), Δ6-elongase(s) and Δ9-elongase(s).

11. A method of generating a polypeptide with delta-15 desaturase activity, comprising:

(a) expressing the isolated polynucleotide of claim 1 in a host cell; and (b) obtaining, from the host cell, the polypeptide which is encoded by the polynucleotide according to (a).

12. An isolated polypeptide which is encoded by the polynucleotide according to claim 1.

13. A transgenic, nonhuman organism comprising the polynucleotide of claim 1.

14. The transgenic, nonhuman organism according to claim 13, wherein the organism is an animal, a plant or a multicellular microorganism.

15. A process for the production of a substance which has the structure shown in the general formula I (I)

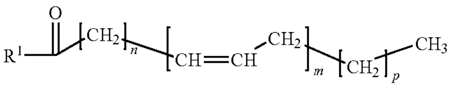

where $R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II (II)

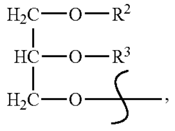

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

(Ia)

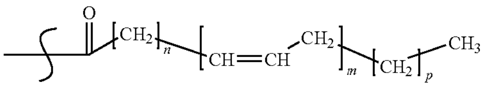

n=2, 3, 4, 5, 6, 7 or 9, m=2, 3, 4, 5 or 6; and p=0 or 3; and wherein the process comprises cultivating the host cell of claim 7 under conditions which permit the biosynthesis of the substance.

16. A process for the production of an oil, lipid or fatty acid composition, comprising the steps of the process according to claim 15 and the further step of formulating the substance as an oil, lipid or fatty acid composition.

17. The process according to claim 16, wherein the oil, lipid or fatty acid composition is formulated further to give a drug, a cosmetic product, a foodstuff, a feedstuff, a fish food, or a food supplement.

18. A process for the production of a substance which has the structure shown in the general formula I (I)

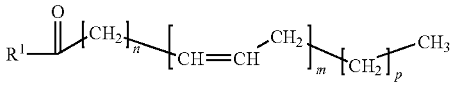

where $R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II (II)

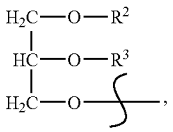

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

(Ia)

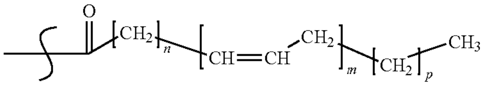

n=2, 3, 4, 5, 6, 7 or 9, m=2, 3, 4, 5 or 6; and p=0 or 3;

and wherein the process comprises cultivating the transgenic, non-human organism of claim 13 under conditions which permit the biosynthesis of the substance.

19. A process for the production of an oil, lipid or fatty acid composition, comprising the steps of the process according to claim 18 and the further step of formulating the substance as an oil, lipid or fatty acid composition.

20. The process according to claim 19, wherein the oil, lipid or fatty acid composition is formulated further to give a drug, a cosmetic product, a foodstuff, a feedstuff, a fish food, or a food supplement.

21. The isolated polynucleotide of claim 1, wherein the nucleic acid sequence is selected from the group consisting of:

(a) the nucleic acid sequence of SEQ ID NO: 132;

(b) a nucleic acid sequence which encodes a polypeptide comprising the amino acid sequence of SEQ ID NO: 133; and (c) a nucleic acid sequence which encodes a polypeptide comprising an amino acid sequence having at least 90% sequence identity to the amino acid sequence of SEQ ID NO: 133 and having delta-15 desaturase activity.

22. The isolated polynucleotide of claim 21, wherein the nucleic acid sequence encodes a polypeptide comprising an amino acid sequence having at least 95% sequence identity to the amino acid sequence of SEQ ID NO: 133 and having delta-15 desaturase activity.

23. The isolated polynucleotide of claim 1, wherein the nucleic acid sequence comprises:

(a) the nucleic acid sequence of SEQ ID NO: 132; or (b) a nucleic acid sequence which encodes a polypeptide comprising the amino acid sequence of SEQ ID NO: 133.

24. The isolated polynucleotide of claim 1, wherein the amino acid motif of SEQ ID NO: 116 is the amino acid motif of SEQ ID NO: 117, SEQ ID NO: 118, or SEQ ID NO: 119.

* * * * *

SEQUENCE LISTING

```
<160> NUMBER OF SEQ ID NOS: 184

<210> SEQ ID NO 1
<211> LENGTH: 2258
<212> TYPE: DNA
<213> ORGANISM: Nectria haematococca

<400> SEQUENCE: 1
```

-continued

```
tgtgcctggt ctgcttcact gcttgcctgt ccgttctccc gtggctgcca ggctttgagt     60
gggctccacg gcacttcccc caacaaaacg ttcctgccga gcaagcggaa tcgcattgca    120
tccataaaac ttcaacccc cccttattat aacacactcc cgtcagcctc ttccttcttc    180
ttcacctccc ctctttctct cttcgactct tgtcctttgg ccaatccgac caattgactc    240
ttctctcttt gtcggtcgtc ctcccttccc ccccgcaaca atggcttcta cggctgtgcc    300
caggcagaac cctgcccttc gacgcaccgt cacctctacc acggctaccg actccgaaac    360
gtcagctgcc gtctctccct cggactctcc tcgtccctcg gcttcctcta cttcgctctc    420
ctccctgtct gaggtggaca ttgcgaagcc caagtccagc tatggccgcc tgatcgacac    480
atacggcaac gagttcgagg tgcccgactt taccatcaag gacatccacg atgccatccc    540
caagcactgc ttcaagcgct ccgccatcag gggctacggc tacatcctcc gcgacattgt    600
cctcctcacc accactttca ccatctggca caactttgtg acccccgagt acatcccctc    660
cactcccgcc cgtgctggtc tctgggccgt ctacaccgtc ctccagggtc tctttggaac    720
tggtctctgg gtcattgccc acgagtgcgg ccacggcgcc ttctccgact ctcgcctcgt    780
caacgacatc accggctggg tcctccactc gtccctgctc gtcccctact tcagctggca    840
gatctcgcac cgaaagcacc acaaggccac cggcaacatg gagcgtgaca tggtctttgt    900
tccccgaacc agggagcagc aggctactcg tctcggcaag atggctcacg agctcgctca    960
cctcaccgag gagacccccg ccttcaccct gctcatgctg gtcatgcagc agctcgttgg   1020
ctggcccaat tacctcctga ccaacgtcac tggccacaac ttccacgagc gccagcgcga   1080
gggtcgcggc aagggcaaga agaacggcct cggcggtggt gtcaaccact tcgatccccg   1140
cagccctctg tacgagaacc gtgatgctaa gctcatcgtc ctgagcgata tcggtattgg   1200
tctggtcgct accggtctgt acttcctcgt gcagaagttt ggcttctaca acatggccat   1260
ctggtacttt gttccctacc tctgggtcaa ccactggctg ggtaagctcc tctcgtcttc   1320
tttcacttgt taatcaatac tgacctgtct agttgccatc actttccttc agcacaccga   1380
ccctaccctc cctcactacc acaacgagga gtggaacttt gtccgcggcg ccgctgccac   1440
catcgatcgt gagatgggct tcatcggccg acacctgctc cacggcatca tcgagaccca   1500
cgtcctccac cactacgtca gcagcatccc cttctacaac gctgatgagg ccaccgaggc   1560
tatcaagcct gtcatgggca agcactaccg cgctgacgtc aaggacggtc ctcgtggttt   1620
catccgtgcc atgtacaaca gcgcccgtat gtgccagtgg gttgagccca gtgctgaggc   1680
tgagggtgct ggcaagaaca ttctcttctt ccgcaaccgc aacaacctgg gcactaagcc   1740
tgccatcatc gaccctcccg ccgcctaagg gtgctatatc ggtccgctcg cagggtgtct   1800
gcacacccac agatgttttc agcgttgatt gttccaagtt tggtcatggg agtcgtcgga   1860
ttcggttgtt tgggtcggag caagaccgta catgaaacag gtcttgccag tcggttaaat   1920
tgatatggcc catggacatg gtggaggatg gaagaggagg taaaataatc gaaggaacaa   1980
agactcaaag agtgatgaac tagatgatgg agagcagcaa ggatatgaaa cctaatgaag   2040
ccactcaatt tcttggatca aggactgtct tgtgatgttt ctcgaggttt gttgacgctg   2100
aaatgacgga tgccccggac tatcaagtga tctgatgcgg ggaaagccac acgtgctcac   2160
gggtcatatt tggagtccga ccgccgaagg tctttatctt gaagctgtcg agattgtgat   2220
ttggtggttt ctgtggggtt tgagaactgc cgttgggt                           2258
```

<210> SEQ ID NO 2
<211> LENGTH: 1437

<212> TYPE: DNA
<213> ORGANISM: Nectria haematococca

<400> SEQUENCE: 2

```
atggcttcta cggctgtgcc caggcagaac cctgcccttc gacgcaccgt cacctctacc     60
acggctaccg actccgaaac gtcagctgcc gtctctccct cggactctcc tcgtccctcg    120
gcttcctcta cttcgctctc ctccctgtct gaggtggaca ttgcgaagcc caagtccagc    180
tatggccgcc tgatcgacac atacggcaac gagttcgagg tgcccgactt taccatcaag    240
gacatccacg atgccatccc caagcactgc ttcaagcgct ccgccatcag gggctacggc    300
tacatcctcc gcgacattgt cctcctcacc accactttca ccatctggca caactttgtg    360
acccccgagt acatcccctc cactcccgcc cgtgctggtc tctgggccgt ctacaccgtc    420
ctccagggtc tctttggaac tggtctctgg gtcattgccc acgagtgcgg ccacggcgcc    480
ttctccgact ctcgcctcgt caacgacatc accggctggg tcctccactc gtccctgctc    540
gtcccctact tcagctggca gatctcgcac cgaaagcacc acaaggccac cggcaacatg    600
gagcgtgaca tggtctttgt tccccgaacc agggagcagc aggctactcg tctcggcaag    660
atggctcacg agctcgctca cctcaccgag gagacccccg ccttcaccct gctcatgctg    720
gtcatgcagc agctcgttgg ctggcccaat tacctcctga ccaacgtcac tggccacaac    780
ttccacgagc gccagcgcga gggtcgcggc aagggcaaga agaacggcct cggcggtggt    840
gtcaaccact tcgatccccg cagccctctg tacgagaacc gtgatgctaa gctcatcgtc    900
ctgagcgata tcggtattgg tctggtcgct accggtctgt acttcctcgt gcagaagttt    960
ggcttctaca acatggccat ctggtacttt gttccctacc tctgggtcaa ccactggctg   1020
gttgccatca ctttccttca gcacaccgac cctaccctcc ctcactacca caacgaggag   1080
tggaactttg tccgcggcgc cgctgccacc atcgatcgtg agatgggctt catcggccga   1140
cacctgctcc acggcatcat cgagacccac gtcctccacc actacgtcag cagcatcccc   1200
ttctacaacg ctgatgaggc caccgaggct atcaagcctg tcatgggcaa gcactaccgc   1260
gctgacgtca aggacggtcc tcgtggtttc atccgtgcca tgtacaacag cgcccgtatg   1320
tgccagtggg ttgagcccag tgctgaggct gagggtgctg gcaagaacat tctcttcttc   1380
cgcaaccgca acaacctggg cactaagcct gccatcatcg accctcccgc cgcctaa      1437
```

<210> SEQ ID NO 3
<211> LENGTH: 478
<212> TYPE: PRT
<213> ORGANISM: Nectria haematococca

<400> SEQUENCE: 3

```
Met Ala Ser Thr Ala Val Pro Arg Gln Asn Pro Ala Leu Arg Arg Thr
1               5                   10                  15

Val Thr Ser Thr Thr Ala Thr Asp Ser Glu Thr Ser Ala Ala Val Ser
            20                  25                  30

Pro Ser Asp Ser Pro Arg Pro Ser Ala Ser Ser Thr Ser Leu Ser Ser
        35                  40                  45

Leu Ser Glu Val Asp Ile Ala Lys Pro Lys Ser Ser Tyr Gly Arg Leu
    50                  55                  60

Ile Asp Thr Tyr Gly Asn Glu Phe Glu Val Pro Asp Phe Thr Ile Lys
65                  70                  75                  80

Asp Ile His Asp Ala Ile Pro Lys His Cys Phe Lys Arg Ser Ala Ile
                85                  90                  95
```

```
Arg Gly Tyr Gly Tyr Ile Leu Arg Asp Ile Val Leu Leu Thr Thr Thr
            100                 105                 110

Phe Thr Ile Trp His Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Leu Val Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Ala His Glu
    210                 215                 220

Leu Ala His Leu Thr Glu Glu Thr Pro Ala Phe Thr Leu Leu Met Leu
225                 230                 235                 240

Val Met Gln Gln Leu Val Gly Trp Pro Asn Tyr Leu Leu Thr Asn Val
                245                 250                 255

Thr Gly His Asn Phe His Glu Arg Gln Arg Glu Gly Arg Gly Lys Gly
            260                 265                 270

Lys Lys Asn Gly Leu Gly Gly Gly Val Asn His Phe Asp Pro Arg Ser
        275                 280                 285

Pro Leu Tyr Glu Asn Arg Asp Ala Lys Leu Ile Val Leu Ser Asp Ile
    290                 295                 300

Gly Ile Gly Leu Val Ala Thr Gly Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr His Asn Glu Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Val Met Gly
                405                 410                 415

Lys His Tyr Arg Ala Asp Val Lys Asp Gly Pro Arg Gly Phe Ile Arg
            420                 425                 430

Ala Met Tyr Asn Ser Ala Arg Met Cys Gln Trp Val Glu Pro Ser Ala
        435                 440                 445

Glu Ala Glu Gly Ala Gly Lys Asn Ile Leu Phe Phe Arg Asn Arg Asn
    450                 455                 460

Asn Leu Gly Thr Lys Pro Ala Ile Ile Asp Pro Pro Ala Ala
465                 470                 475
```

<210> SEQ ID NO 4
<211> LENGTH: 1996
<212> TYPE: DNA
<213> ORGANISM: Nectria haematococca

<400> SEQUENCE: 4

-continued

```
ggggaggagg agagagggac aagctatggg tttaaagcta ggaggagagc cgcgcaaaca      60
gggagggagc ccaaggagaa gaaaaatttc ccacctttct ttctcttccc ttttctctct     120
agcaaacatc aattggtcag aggtcgctgg ctcgtcttct acgtctccca attgcattgt     180
tctgtctaga tcagctcaac atggctactc gacagcgtac ttcgaccact gttgtggttg     240
agaagccttc tgccaaggta agtttctact gtctcaccct cttgtctctt caggtggctg     300
actctgtcgc aaaaggttac tctcgagcct cagcagcagc ctcaattccc cgatatcaag     360
accatcaagg atgccatccc cgcccactgc ttccagccct cgctcttcac ctccttctac     420
tatgtcttcc gcgactttgc catggtggcc accctcgtct gggctgccct gacctacatt     480
cccgccattc ctgaccagag gctgcgcgtc gccgcctgga tggtctacgg ctttgtccaa     540
ggcctcgtgt gcactggtgt ctggatcctg ggccacgagt gcggtcacgg tgctttctct     600
acccacggaa agctcaacaa tgtcgtcgga tggttcctcc actcgttcct cctcgtgccc     660
tacttctcgt ggaagtactc tcaccaccgc caccaccgct tcaccggcca catggacctc     720
gacatggcct ttgtccccgc cacccagccc aagaagcaca gcatccttgc cggcatcgac     780
ctgaacgagc tgtttgagga cacccccatc gcccagctca tcaggatcgt cttccaccag     840
ctgttcggct ggcaggtgta cctcctgttc aacgccagcg ctggtaaggg cagcaagcag     900
tgggagccta ctggtctggc caagtggttc cgtgtcagcc actttgagcc caccagcgcc     960
gtgttccgac ccagcgaggc catcttcatc ttcatctctg acctcggcct ggccatcacc    1020
ttcaccgccc tgtactttgc ctccaaggct gtgggaacct cgactgttct gttcctctac    1080
gccgtcccct acttctgggt gcaccactgg ctgggtaaga tttctgatgg caacaaaatt    1140
gaatagccgc tgacgtgatt tttagtcgcc atcacctacc tccaccacca ccacaccgag    1200
gtccctcact acactaacga gggctggacc tatgtcaagg gcgctctcgc taccgttgac    1260
cgtgagtttg gcttcattgg caagcacctg ttccacggca tcattgagaa gcacgttgtc    1320
caccaccttt tcccgtgagt actccccgct atttggggtg aaccaatcta accatctcag    1380
ccgcatcccc ttctacaagg ccgacgaggc taccgaggcc atcaagcctc tcctgggcga    1440
cctctactac cacgacgagc gcaacttcat cggccagctc tggtccgtct ttggctcgct    1500
caagtacgtc gagcacgacc ccaccaacca gggtgccatg cgatgggcca aggagtagag    1560
ctccaaggct gtcggagccc catgcgaaga gacatagaga gattagacga tgggattaga    1620
cacgatagac caaacgacta gacacacaat gctatagatc tagagcaatt gctttctcgg    1680
ctggtatcgg atttagacgc tctgagataa aggtcaaatc ggatgatgaa acaaaatgga    1740
ggcttgcttg tcctgttgga ctgcaatgta ttataccaat agaagctgaa tcaatgacct    1800
gacttgtgca acatcttgag ttggtgttca aattggctca atttgaggca tcctctgcga    1860
ttgggcagag atgaacttgc tttatcgatc tagatccatc caatcctgag acaatctctt    1920
gcatgagatt gagatggtca tggaggtgtg gagactctct cctcaacaac gccaagacca    1980
atcggcttga ttagta                                                    1996
```

```
<210> SEQ ID NO 5
<211> LENGTH: 1203
<212> TYPE: DNA
<213> ORGANISM: Nectria haematococca

<400> SEQUENCE: 5

atggctactc gacagcgtac ttcgaccact gttgtggttg agaagccttc tgccaaggtt      60
```

```
actctcgagc ctcagcagca gcctcaattc cccgatatca agaccatcaa ggatgccatc    120

cccgcccact gcttccagcc ctcgctcttc acctccttct actatgtctt ccgcgacttt    180

gccatggtgg ccaccctcgt ctgggctgcc ctgacctaca ttcccgccat tcctgaccag    240

aggctgcgcg tcgccgcctg gatggtctac ggctttgtcc aaggcctcgt gtgcactggt    300

gtctggatcc tgggccacga gtgcggtcac ggtgctttct ctacccacgg aaagctcaac    360

aatgtcgtcg gatggttcct ccactcgttc ctcctcgtgc cctacttctc gtggaagtac    420

tctcaccacc gccaccaccg cttcaccggc cacatggacc tcgacatggc ctttgtcccc    480

gccacccagc ccaagaagca cagcatcctt gccggcatcg acctgaacga gctgtttgag    540

gacaccccca tcgcccagct catcaggatc gtcttccacc agctgttcgg ctggcaggtg    600

tacctcctgt tcaacgccag cgctggtaag ggcagcaagc agtgggagcc tactggtctg    660

gccaagtggt tccgtgtcag ccactttgag cccaccagcg ccgtgttccg acccagcgag    720

gccatcttca tcttcatctc tgacctcggc ctggccatca ccttcaccgc cctgtacttt    780

gcctccaagg ctgtgggaac ctcgactgtt ctgttcctct acgccgtccc ctacttctgg    840

gtgcaccact ggctggtcgc catcacctac ctccaccacc accacaccga ggtccctcac    900

tacactaacg agggctggac ctatgtcaag ggcgctctcg ctaccgttga ccgtgagttt    960

ggcttcattg gcaagcacct gttccacggc atcattgaga agcacgttgt ccaccacctt   1020

ttcccccgca tccccttcta caaggccgac gaggctaccg aggccatcaa gcctctcctg   1080

ggcgacctct actaccacga cgagcgcaac ttcatcggcc agctctggtc cgtctttggc   1140

tcgctcaagt acgtcgagca cgaccccacc aaccagggtg ccatgcgatg ggccaaggag   1200

tag                                                                 1203
```

```
<210> SEQ ID NO 6
<211> LENGTH: 400
<212> TYPE: PRT
<213> ORGANISM: Nectria haematococca

<400> SEQUENCE: 6

Met Ala Thr Arg Gln Arg Thr Ser Thr Thr Val Val Val Glu Lys Pro
1               5                   10                  15

Ser Ala Lys Val Thr Leu Glu Pro Gln Gln Gln Pro Gln Phe Pro Asp
            20                  25                  30

Ile Lys Thr Ile Lys Asp Ala Ile Pro Ala His Cys Phe Gln Pro Ser
        35                  40                  45

Leu Phe Thr Ser Phe Tyr Tyr Val Phe Arg Asp Phe Ala Met Val Ala
    50                  55                  60

Thr Leu Val Trp Ala Ala Leu Thr Tyr Ile Pro Ala Ile Pro Asp Gln
65                  70                  75                  80

Arg Leu Arg Val Ala Ala Trp Met Val Tyr Gly Phe Val Gln Gly Leu
                85                  90                  95

Val Cys Thr Gly Val Trp Ile Leu Gly His Glu Cys Gly His Gly Ala
            100                 105                 110

Phe Ser Thr His Gly Lys Leu Asn Asn Val Val Gly Trp Phe Leu His
        115                 120                 125

Ser Phe Leu Leu Val Pro Tyr Phe Ser Trp Lys Tyr Ser His His Arg
    130                 135                 140

His His Arg Phe Thr Gly His Met Asp Leu Asp Met Ala Phe Val Pro
145                 150                 155                 160

Ala Thr Gln Pro Lys Lys His Ser Ile Leu Ala Gly Ile Asp Leu Asn
```

-continued

```
                165                 170                 175

Glu Leu Phe Glu Asp Thr Pro Ile Ala Gln Leu Ile Arg Ile Val Phe
            180                 185                 190

His Gln Leu Phe Gly Trp Gln Val Tyr Leu Leu Phe Asn Ala Ser Ala
        195                 200                 205

Gly Lys Gly Ser Lys Gln Trp Glu Pro Thr Gly Leu Ala Lys Trp Phe
    210                 215                 220

Arg Val Ser His Phe Glu Pro Thr Ser Ala Val Phe Arg Pro Ser Glu
225                 230                 235                 240

Ala Ile Phe Ile Phe Ile Ser Asp Leu Gly Leu Ala Ile Thr Phe Thr
                245                 250                 255

Ala Leu Tyr Phe Ala Ser Lys Ala Val Gly Thr Ser Thr Val Leu Phe
            260                 265                 270

Leu Tyr Ala Val Pro Tyr Phe Trp Val His His Trp Leu Val Ala Ile
        275                 280                 285

Thr Tyr Leu His His His His Thr Glu Val Pro His Tyr Thr Asn Glu
    290                 295                 300

Gly Trp Thr Tyr Val Lys Gly Ala Leu Ala Thr Val Asp Arg Glu Phe
305                 310                 315                 320

Gly Phe Ile Gly Lys His Leu Phe His Gly Ile Ile Glu Lys His Val
                325                 330                 335

Val His His Leu Phe Pro Arg Ile Pro Phe Tyr Lys Ala Asp Glu Ala
            340                 345                 350

Thr Glu Ala Ile Lys Pro Leu Leu Gly Asp Leu Tyr Tyr His Asp Glu
        355                 360                 365

Arg Asn Phe Ile Gly Gln Leu Trp Ser Val Phe Gly Ser Leu Lys Tyr
    370                 375                 380

Val Glu His Asp Pro Thr Asn Gln Gly Ala Met Arg Trp Ala Lys Glu
385                 390                 395                 400


<210> SEQ ID NO 7
<211> LENGTH: 1988
<212> TYPE: DNA
<213> ORGANISM: Trichoderma resii

<400> SEQUENCE: 7

ccccgttagc agggggtacc tcccaacgcc agcagtgccg ccaccactcc gcaggtcaca      60

ggtgttaacg ccaccaacca gatgccgcca gataagggac acgacacgaa aaatggatca     120

ggacgaccaa gctagagggc gaaaggggaa gtggaagtgg aaaatttgat gccgtgcctg     180

actatggagc tccctttttc ccagcgtttt ctgccttaca gttgggctgc tggtgtgggt     240

ttaaaaggca atcaggacgg ctgttctcgc tcaggaagag tcctcagttc atactcccaa     300

ctttcttcat ccattgagtt gctggccttt gtccacttca cgatggctac taccacgacg     360

gtcaccaaga ggggaggcgc cgtgggctca atgtcagtag tcctgctagt ctcatgaagg     420

ctttttctgc cccgaaaagt tttcacccgt tgctctgttt tttttgctga ctccagatac     480

agcaagctgc ctgaggagga cagtcggttc cccgatatca acacgattcg ggccgccatc     540

cccaagcact gctttgagcc gtctgtggcc atctccatgg gctacctggt gcgcgatgtg     600

gtcatgattg gagcccttgg ctgggctgcc cttacttaca ttcccaccat tcctgatgcc     660

acccttcgga ccattgcctg gatcgtctac ggcttcgtcc agggcctcgt ctgcactggt     720

ctctggattc tgggccacga ggccggccac ggcgcctttt cccagcactc tctgctgaac     780

cacgtcgtcg gcttcttctc tcactccgtc ctgctggtgc cgtactactc ctggaagttc     840
```

tctcaccacc gccaccacaa gtacaccggc cacatggaga aggacatggc ctttgtcccc 900
cggaccaagc ccgactacgc caagcgaacc ctggccgccc ttgagatgct cgaggacacg 960
cccgcctacc agttcgtgac gctcatgttc caccagctgt ttgcgtggca gatctacctg 1020
ctgttcaaca tctccgccgg ccgcaacagc ctgcagaagt ctgccacgac catgttcggc 1080
aagagccact ttggccccaa cagcgccgtc ttccgccgca gcgaggctcc cttcatcttc 1140
ctgtctgacg tcggccttgc catgacggcg tttgcgctgt acaagctcgc gggagccgtg 1200
ggaacgggca ccatgctgct tgtttacgcg cagccttact tctgggttca ccactggttg 1260
agtatgtttt ctcctaaaca aacgcccaag caaacgcaca gtcacactca agcctgatgc 1320
aaacgcaaac acggcgtgtc aatgtcaaaa cagggaataa gattgctgac gggagtgcca 1380
ttttttagtt gccatcactt accttcacca cactcacatg gaggtgcctc actatgatgc 1440
cgagaactgg acctttgtca agggtgctct ggccactgtt gaccgcgagt ttggctttgt 1500
cggccgccac ctcttccact gcattattga gcaccacgtt gttcaccacc ttttcccgta 1560
agtcttcagc tggacctata gctgccaatt gccattcact aacattcttc tagtcgcatt 1620
cccttctact atgccggaga agccaccgag gccatcaagc ccgtgcttgg cgacctgtac 1680
taccgcgatg agcgatcttt cctgggccag ctctggagca actttaccaa gtgcaagtac 1740
gtcgtggccg atgagaagac gcccggagct ctgcactggg cgcaatgatt gaatgaatga 1800
gaacatggtt taaatggatc gcgttgggtt gctctgcttt gtctttctcg gtgggaagga 1860
taatggcttt caaaagggga taaaagtatc tcggattaga ctcttctgtg tgctctctcg 1920
tatgatgaga tggccttggg ggggaaatct ttgttttgcg gttttagatg atacacgata 1980
gacttcgt 1988

<210> SEQ ID NO 8
<211> LENGTH: 1173
<212> TYPE: DNA
<213> ORGANISM: Trichoderma resii

<400> SEQUENCE: 8
atggctacta ccacgacggt caccaagagg ggaggcgccg tgggctcaat caagctgcct 60
gaggaggaca gtcggttccc cgatatcaac acgattcggg ccgccatccc caagcactgc 120
tttgagccgt ctgtggccat ctccatgggc tacctggtgc gcgatgtggt catgattgga 180
gcccttggct gggctgccct tacttacatt cccaccattc ctgatgccac ccttcggacc 240
attgcctgga tcgtctacgg cttcgtccag ggcctcgtct gcactggtct ctggattctg 300
ggccacgagg ccggccacgg cgccttttcc cagcactctc tgctgaacca cgtcgtcggc 360
ttcttctctc actccgtcct gctggtgccg tactactcct ggaagttctc tcaccaccgc 420
caccacaagt acaccggcca catggagaag gacatggcct ttgtcccccg gaccaagccc 480
gactacgcca agcgaaccct ggccgccctt gagatgctcg aggacacgcc cgcctaccag 540
ttcgtgacgc tcatgttcca ccagctgttt gcgtggcaga tctacctgct gttcaacatc 600
tccgccggcc gcaacagcct gcagaagtct gccacgacca tgttcggcaa gagccacttt 660
ggccccaaca gcgccgtctt ccgccgcagc gaggctccct tcatcttcct gtctgacgtc 720
ggccttgcca tgacggcgtt tgcgctgtac aagctcgcgg gagccgtggg aacgggcacc 780
atgctgcttg tttacgcgca gccttacttc tgggttcacc actggttgat tgccatcact 840
taccttcacc acactcacat ggaggtgcct cactatgatg ccgagaactg gacctttgtc 900

-continued

```
aagggtgctc tggccactgt tgaccgcgag tttggctttg tcggccgcca cctcttccac    960

tgcattattg agcaccacgt tgttcaccac cttttccctc gcattccctt ctactatgcc   1020

ggagaagcca ccgaggccat caagcccgtg cttggcgacc tgtactaccg cgatgagcga   1080

tctttcctgg gccagctctg gagcaacttt accaagtgca agtacgtcgt ggccgatgag   1140

aagacgcccg gagctctgca ctgggcgcaa tga                                1173


<210> SEQ ID NO 9
<211> LENGTH: 390
<212> TYPE: PRT
<213> ORGANISM: Trichoderma resii

<400> SEQUENCE: 9

Met Ala Thr Thr Thr Thr Val Thr Lys Arg Gly Gly Ala Val Gly Ser
1               5                   10                  15

Ile Lys Leu Pro Glu Glu Asp Ser Arg Phe Pro Asp Ile Asn Thr Ile
            20                  25                  30

Arg Ala Ala Ile Pro Lys His Cys Phe Glu Pro Ser Val Ala Ile Ser
        35                  40                  45

Met Gly Tyr Leu Val Arg Asp Val Val Met Ile Gly Ala Leu Gly Trp
    50                  55                  60

Ala Ala Leu Thr Tyr Ile Pro Thr Ile Pro Asp Ala Thr Leu Arg Thr
65                  70                  75                  80

Ile Ala Trp Ile Val Tyr Gly Phe Val Gln Gly Leu Val Cys Thr Gly
                85                  90                  95

Leu Trp Ile Leu Gly His Glu Ala Gly His Gly Ala Phe Ser Gln His
            100                 105                 110

Ser Leu Leu Asn His Val Val Gly Phe Phe Ser His Ser Val Leu Leu
        115                 120                 125

Val Pro Tyr Tyr Ser Trp Lys Phe Ser His His Arg His His Lys Tyr
    130                 135                 140

Thr Gly His Met Glu Lys Asp Met Ala Phe Val Pro Arg Thr Lys Pro
145                 150                 155                 160

Asp Tyr Ala Lys Arg Thr Leu Ala Ala Leu Glu Met Leu Glu Asp Thr
                165                 170                 175

Pro Ala Tyr Gln Phe Val Thr Leu Met Phe His Gln Leu Phe Ala Trp
            180                 185                 190

Gln Ile Tyr Leu Leu Phe Asn Ile Ser Ala Gly Arg Asn Ser Leu Gln
        195                 200                 205

Lys Ser Ala Thr Thr Met Phe Gly Lys Ser His Phe Gly Pro Asn Ser
    210                 215                 220

Ala Val Phe Arg Arg Ser Glu Ala Pro Phe Ile Phe Leu Ser Asp Val
225                 230                 235                 240

Gly Leu Ala Met Thr Ala Phe Ala Leu Tyr Lys Leu Ala Gly Ala Val
                245                 250                 255

Gly Thr Gly Thr Met Leu Leu Val Tyr Ala Gln Pro Tyr Phe Trp Val
            260                 265                 270

His His Trp Leu Ile Ala Ile Thr Tyr Leu His His Thr His Met Glu
        275                 280                 285

Val Pro His Tyr Asp Ala Glu Asn Trp Thr Phe Val Lys Gly Ala Leu
    290                 295                 300

Ala Thr Val Asp Arg Glu Phe Gly Phe Val Gly Arg His Leu Phe His
305                 310                 315                 320

Cys Ile Ile Glu His His Val Val His His Leu Phe Pro Arg Ile Pro
```

-continued

```
            325                 330                 335

Phe Tyr Tyr Ala Gly Glu Ala Thr Glu Ala Ile Lys Pro Val Leu Gly
            340                 345                 350

Asp Leu Tyr Tyr Arg Asp Glu Arg Ser Phe Leu Gly Gln Leu Trp Ser
        355                 360                 365

Asn Phe Thr Lys Cys Lys Tyr Val Val Ala Asp Glu Lys Thr Pro Gly
    370                 375                 380

Ala Leu His Trp Ala Gln
385                 390
```

<210> SEQ ID NO 10
<211> LENGTH: 2520
<212> TYPE: DNA
<213> ORGANISM: Monosiga brevicollis

<400> SEQUENCE: 10

```
agatcttgca tcaccggtcg ctctcgtgtg cagagggcag ccggggtctg cgcgttgagg      60

ccgtggaaga agacgtactt gttgtgcagg gggaaaaact aaaaagctgg ctggttgtat     120

caagccggct tcagggttca gcagatcatg cacggctgcg ctgccgtttt gacaggttgc     180

gcgttgtccg tgtcatacag ggagatggtg caaggtgcgt atgcaggtgt gatcacttca     240

aggtatagtc aagctaaacg tcacgtgcat gtgtgcaagc cacccaaagt gaggaaagca     300

tgtgatgaga tcgcacatgt cacgccattg cagtctctca cttgtctctg gtttagatct     360

ggctacagga ctattctctg aaatcaacgt tatatcccat tgccacgacg acactttgat     420

gactcacgtc tccctctctc tctgcttgaa ccactcgccc cccggccttt ctctgacacg     480

acactgtcaa cgacttcact ttttttttc tctcgacgcc gacgccgacg ccgacgccga     540

cgccgaaccc ttcaaggtca gtcccgccac cccggcccgg ccagatccgc gccgcaaacg     600

ggccttgtcg taatcgggtt cttgagtatc attcgccacg gcctggcttg gtttcctgtc     660

gtcgaatcta cacggctgct ctgccatcgc ttctcgagtg tcgctcacgt gctcgtgcgg     720

gtttcgcttg tggggaatgt agatgacggt ggcttcccag gtgaccgagg aggtggcagc     780

cgtgcccacc aagcaccccc gcatgcccac ggacactccg ccttttaccc ttggccaact     840

caaggtgatt caccgcgtct ttccgcgtct ttccttgtta ctcgtcatgc tctcgctgga     900

cgtaaactca tcttcttgca tcatccggtt ccgcaaccat ggcccgttag gcagccatcc     960

cgccccactg ctttgagcgc aacctcttca cttcgatgcg ctatgtgttc caagaccttg    1020

ctggtgttgc cactctctac tacctctcca cctttattga tcaactgccc tcgttcgccg    1080

gccttttcct ctggcctctc tattggtacc tccaggtcag tctctgtttc ccctcttctt    1140

cttcttctcg acgttggccc ttccttttca atccctcccc aagcgccatc cctccccttt    1200

gtcttgccat gcaccaattg ctgcccacgc acatgctcgc tggtttgcgt ttcctctatt    1260

cctcaacttt gaacccgcct tttcccttcg ttcatagggt gccgtcatga ctggtttgtg    1320

ggttctggcc catgagtgtg gccaccgcgc gttttgcgac aacgagacca ttggcgatgc    1380

cgtgggcatg atcctccact ctgtacgtgc tttctgccat tggacccccg catgcacttg    1440

atctcccccc cctctttctt tttctcggcc gtcctcaaat accatggtgg tcgggcacga    1500

tgaagccaaa cgcatcctcg agtcctctca ttgacttttt gttttggtct ccctctacct    1560

tgacaggctc tcttggtgcc ctaccacccc tggcgtatct cccaccgcaa gcaccactcg    1620

cgcaccaacc acatgaccga ggatgaggtc ttcatccctg acacccgtgg tcacgagcac    1680

attgtcccct acgatgagat ggtcggcccc gtctcggtcg ccctgcgcgt cttcttctgc    1740
```

gctcgtatgc ttctctttgg ctggcccgcc tacctcttga cccatgttac tggtcgtcaa 1800
tacggtcgcc gcaccaacca ttttgagccc gagtctcctc tcttcgacaa gaaggagcgc 1860
ggtggcgtgg tcctcagtga cctggtcctc ttctcctgga tcggctgcct tctctacgct 1920
ggtcagaccg ctggctgggg ctggctcttc aagtcttact ttgttcctta catcatcgtc 1980
aacttttggc tcgtcctcat cacccacctc caacacacgg acgtccgcct tccccactat 2040
cgctcccaag agtggacctg gctcaagggt gccctctgca ccatggaccg cgactatggt 2100
cacctcaaca tccttcacca tcacatctcc gatacccacg tcgtccatca cctcttcagc 2160
tacctccccc actatcatgc cgaagaggct ttggccgcca tcaagcccat tctgggcgag 2220
tattacctca aggactccgt ttcccccggt ctgcagggcg ttatggaggc cctctggaac 2280
agcatgacct actgccgcgt cgtcgagaac accggtgagg tcctttggtt caaggacagg 2340
taaaacggct tgccctcttt gtcttcttgt gccccaaacc cgatttgcgg ttggatgagc 2400
atgagagaat cggtggcagt accggttgcc ggagaatgag cgcctctgta catgaccaca 2460
cccacccatg ttcttttcct actctgactt gcgttgccgg tgatagctgc agcgctctct 2520

<210> SEQ ID NO 11
<211> LENGTH: 1149
<212> TYPE: DNA
<213> ORGANISM: Monosiga brevicollis

<400> SEQUENCE: 11
atgacggtgg cttcccaggt gaccgaggag gtggcagccg tgcccaccaa gcacccccgc 60
atgcccacgg acactccgcc ttttaccctt ggccaactca aggcagccat cccgccccac 120
tgctttgagc gcaacctctt cacttcgatg cgctatgtgt tccaagacct tgctggtgtt 180
gccactctct actacctctc cacctttatt gatcaactgc cctcgttcgc cggccttttc 240
ctctggcctc tctattggta cctccagggt gccgtcatga ctggtttgtg ggttctggcc 300
catgagtgtg gccaccgcgc gttttgcgac aacgagacca ttggcgatgc cgtgggcatg 360
atcctccact ctgctctctt ggtgccctac cacccctggc gtatctccca ccgcaagcac 420
cactcgcgca ccaaccacat gaccgaggat gaggtcttca tccctgacac ccgtggtcac 480
gagcacattg tcccctacga tgagatggtc ggccccgtct cggtcgccct gcgcgtcttc 540
ttctgcgctc gtatgcttct ctttggctgg cccgcctacc tcttgaccca tgttactggt 600
cgtcaatacg gtcgccgcac caaccatttt gagcccgagt ctcctctctt cgacaagaag 660
gagcgcggtg gcgtggtcct cagtgacctg gtcctcttct cctggatcgg ctgccttctc 720
tacgctggtc agaccgctgg ctggggctgg ctcttcaagt cttactttgt tccttacatc 780
atcgtcaact tttggctcgt cctcatcacc cacctccaac acacggacgt ccgccttccc 840
cactatcgct cccaagagtg gacctggctc aagggtgccc tctgcaccat ggaccgcgac 900
tatggtcacc tcaacatcct tcaccatcac atctccgata cccacgtcgt ccatcacctc 960
ttcagctacc tcccccacta tcatgccgaa gaggctttgg ccgccatcaa gcccattctg 1020
ggcgagtatt acctcaagga ctccgtttcc cccggtctgc agggcgttat ggaggccctc 1080
tggaacagca tgacctactg ccgcgtcgtc gagaacaccg gtgaggtcct ttggttcaag 1140
gacaggtaa 1149

<210> SEQ ID NO 12
<211> LENGTH: 382
<212> TYPE: PRT

<213> ORGANISM: Monosiga brevicollis

<400> SEQUENCE: 12

```
Met Thr Val Ala Ser Gln Val Thr Glu Glu Val Ala Ala Val Pro Thr
1               5                   10                  15

Lys His Pro Arg Met Pro Thr Asp Thr Pro Pro Phe Thr Leu Gly Gln
            20                  25                  30

Leu Lys Ala Ala Ile Pro Pro His Cys Phe Glu Arg Asn Leu Phe Thr
        35                  40                  45

Ser Met Arg Tyr Val Phe Gln Asp Leu Ala Gly Val Ala Thr Leu Tyr
    50                  55                  60

Tyr Leu Ser Thr Phe Ile Asp Gln Leu Pro Ser Phe Ala Gly Leu Phe
65                  70                  75                  80

Leu Trp Pro Leu Tyr Trp Tyr Leu Gln Gly Ala Val Met Thr Gly Leu
                85                  90                  95

Trp Val Leu Ala His Glu Cys Gly His Arg Ala Phe Cys Asp Asn Glu
            100                 105                 110

Thr Ile Gly Asp Ala Val Gly Met Ile Leu His Ser Ala Leu Leu Val
        115                 120                 125

Pro Tyr His Pro Trp Arg Ile Ser His Arg Lys His His Ser Arg Thr
    130                 135                 140

Asn His Met Thr Glu Asp Glu Val Phe Ile Pro Asp Thr Arg Gly His
145                 150                 155                 160

Glu His Ile Val Pro Tyr Asp Glu Met Val Gly Pro Val Ser Val Ala
                165                 170                 175

Leu Arg Val Phe Phe Cys Ala Arg Met Leu Leu Phe Gly Trp Pro Ala
            180                 185                 190

Tyr Leu Leu Thr His Val Thr Gly Arg Gln Tyr Gly Arg Arg Thr Asn
        195                 200                 205

His Phe Glu Pro Glu Ser Pro Leu Phe Asp Lys Lys Glu Arg Gly Gly
    210                 215                 220

Val Val Leu Ser Asp Leu Val Leu Phe Ser Trp Ile Gly Cys Leu Leu
225                 230                 235                 240

Tyr Ala Gly Gln Thr Ala Gly Trp Gly Trp Leu Phe Lys Ser Tyr Phe
                245                 250                 255

Val Pro Tyr Ile Ile Val Asn Phe Trp Leu Val Leu Ile Thr His Leu
            260                 265                 270

Gln His Thr Asp Val Arg Leu Pro His Tyr Arg Ser Gln Glu Trp Thr
        275                 280                 285

Trp Leu Lys Gly Ala Leu Cys Thr Met Asp Arg Asp Tyr Gly His Leu
    290                 295                 300

Asn Ile Leu His His His Ile Ser Asp Thr His Val Val His His Leu
305                 310                 315                 320

Phe Ser Tyr Leu Pro His Tyr His Ala Glu Glu Ala Leu Ala Ala Ile
                325                 330                 335

Lys Pro Ile Leu Gly Glu Tyr Tyr Leu Lys Asp Ser Val Ser Pro Gly
            340                 345                 350

Leu Gln Gly Val Met Glu Ala Leu Trp Asn Ser Met Thr Tyr Cys Arg
        355                 360                 365

Val Val Glu Asn Thr Gly Glu Val Leu Trp Phe Lys Asp Arg
    370                 375                 380
```

<210> SEQ ID NO 13
<211> LENGTH: 1779

<212> TYPE: DNA
<213> ORGANISM: Mycospaerella graminicola

<400> SEQUENCE: 13
ttttgccctt gccaagggac ccgtggcaga atggatcatc ttctgcggtg aattgggaga 60
gtcgggggag agaggacgtg caccgcctat cacttgcggg tctttctgcc tgtaagcctg 120
ggaaggggtc cgcctcacca ataaatttgt ctctggagct tcttctatct ccacgtctcc 180
ttcttcttgc gacatcctgt tccaccctct cccacacatt ctcagacgcc attatgagca 240
gaacagtcac attagaagcc gctccggcga cgacgctgtc ggtcgagaag aaaactccga 300
ccattcgcca aatccgcaat gccatccccg agcactgctt caagcccaca gcgtggaaat 360
cctccgccca cgccatcttc gactgctccg tcgccgcgct gatcgccttc gccgcctaca 420
agaccatccc tcttgtcgag tactggcccg ctcgctgggc attgtgggcg ctgtacggtt 480
acatcgaagg tctcgtcttc acgggcatct ggatcgtggc ccacgagtgc ggacacggcg 540
gtctctacac cagcaactgg gccaacgaca tcgtcggata caccctccac acatccctct 600
tggtgccgta ctttccctgg aagtacaccc acgcccgtca tcatcgctac accggacaca 660
tggagaagga caccgcgttc gtgccgcacc gagcgggcga gaagagtatt gggagcaaga 720
ttgcggaggt gattggacac gctgaggacg ctcctctgta tatgtttggt ggacttgtga 780
tgcatcagct tttgggctgg caggcgtacc tcctcttcta cgtgagcgcc ggggcgcggt 840
ccactcctaa ggctttggag ggctcgagct gggcgggaag ccatttcgac ccgatggcca 900
acttgtggac gccttcgcag cggccattcg tgttcttgtc gacagtcggt ctcggtgcgg 960
tcatgttcgc tctgtaccag ctctccggcg tgattggcgt agccaacaca ttcctgttat 1020
acggcctgcc ctacctctgg gtcaacaact ggttgggtat gttatcctgc gatcctcgct 1080
gggttgtctc ttcaattgct gacctgtgct ctttagtcgc catcacttac ctccaccaca 1140
ctcacccgga cagccaccac tacgaggcct cgcgctggac cttcctcgac ggcgccttga 1200
ccactgtcga ccgaccattt ggcttcatcg gccgcaaggt cttccacggc atcatcgact 1260
tccacgtcgt tcaccacctc ttcccgtgag cattatcgta gcaactcctt tctgtgatcc 1320
agaactgact tccctcctct tccagatcca tgccattcta ccacgccgaa gaagccacca 1380
aagccatgag gcccgttctc ggcgactact accgccgtga cgacaccccg ttctggatcg 1440
cattgtggaa gacattctca agctgccagg cggtgcagcc caaagaggga gaggagggag 1500
ttctcgaatg ggagacgaag aagacgcatg ttaagagcgc gtgatcgttt ggcatattga 1560
gcgaggcgtt gcatatcgtg actctctcga atgagtcttc gtggattctg aaaagcatta 1620
gaatgagaac ggatacatta aaggcgaatt atagaggcta gatgatgtat tacatgagga 1680
atttcatgat catgcggatg atgtgtcgcg tgaggggtct gtgacactgt tgccgctgag 1740
atccgtcgag ctgatgcaat gtggtggtct gtgcttttg 1779

<210> SEQ ID NO 14
<211> LENGTH: 1191
<212> TYPE: DNA
<213> ORGANISM: Mycospaerella graminicola

<400> SEQUENCE: 14
atgagcagaa cagtcacatt agaagccgct ccggcgacga cgctgtcggt cgagaagaaa 60
actccgacca ttcgccaaat ccgcaatgcc atccccgagc actgcttcaa gcccacagcg 120
tggaaatcct ccgcccacgc catcttcgac tgctccgtcg ccgcgctgat cgccttcgcc 180

-continued

```
gcctacaaga ccatccctct tgtcgagtac tggcccgctc gctgggcatt gtgggcgctg    240

tacggttaca tcgaaggtct cgtcttcacg ggcatctgga tcgtggccca cgagtgcgga    300

cacggcggtc tctacaccag caactgggcc aacgacatcg tcggatacac cctccacaca    360

tccctcttgg tgccgtactt tccctggaag tacacccacg cccgtcatca tcgctacacc    420

ggacacatgg agaaggacac cgcgttcgtg ccgcaccgag cgggcgagaa gagtattggg    480

agcaagattg cggaggtgat tggacacgct gaggacgctc ctctgtatat gtttggtgga    540

cttgtgatgc atcagctttt gggctggcag gcgtacctcc tcttctacgt gagcgccggg    600

gcgcggtcca ctcctaaggc tttggagggc tcgagctggg cgggaagcca tttcgacccg    660

atggccaact tgtggacgcc ttcgcagcgg ccattcgtgt tcttgtcgac agtcggtctc    720

ggtgcggtca tgttcgctct gtaccagctc tccggcgtga ttggcgtagc caacacattc    780

ctgttatacg gcctgcccta cctctgggtc aacaactggt tggtcgccat cacttacctc    840

caccacactc acccggacag ccaccactac gaggcctcgc gctggacctt cctcgacggc    900

gccttgacca ctgtcgaccg accatttggc ttcatcggcc gcaaggtctt ccacggcatc    960

atcgacttcc acgtcgttca ccacctcttc ccatccatgc cattctacca cgccgaagaa   1020

gccaccaaag ccatgaggcc cgttctcggc gactactacc gccgtgacga caccccgttc   1080

tggatcgcat tgtggaagac attctcaagc tgccaggcgg tgcagcccaa agagggagag   1140

gagggagttc tcgaatggga gacgaagaag acgcatgtta agagcgcgtg a            1191
```

```
<210> SEQ ID NO 15
<211> LENGTH: 396
<212> TYPE: PRT
<213> ORGANISM: Mycospaerella graminicola

<400> SEQUENCE: 15

Met Ser Arg Thr Val Thr Leu Glu Ala Ala Pro Ala Thr Thr Leu Ser
1               5                   10                  15

Val Glu Lys Lys Thr Pro Thr Ile Arg Gln Ile Arg Asn Ala Ile Pro
            20                  25                  30

Glu His Cys Phe Lys Pro Thr Ala Trp Lys Ser Ser Ala His Ala Ile
        35                  40                  45

Phe Asp Cys Ser Val Ala Ala Leu Ile Ala Phe Ala Ala Tyr Lys Thr
    50                  55                  60

Ile Pro Leu Val Glu Tyr Trp Pro Ala Arg Trp Ala Leu Trp Ala Leu
65                  70                  75                  80

Tyr Gly Tyr Ile Glu Gly Leu Val Phe Thr Gly Ile Trp Ile Val Ala
                85                  90                  95

His Glu Cys Gly His Gly Gly Leu Tyr Thr Ser Asn Trp Ala Asn Asp
            100                 105                 110

Ile Val Gly Tyr Thr Leu His Thr Ser Leu Leu Val Pro Tyr Phe Pro
        115                 120                 125

Trp Lys Tyr Thr His Ala Arg His His Arg Tyr Thr Gly His Met Glu
    130                 135                 140

Lys Asp Thr Ala Phe Val Pro His Arg Ala Gly Glu Lys Ser Ile Gly
145                 150                 155                 160

Ser Lys Ile Ala Glu Val Ile Gly His Ala Glu Asp Ala Pro Leu Tyr
                165                 170                 175

Met Phe Gly Gly Leu Val Met His Gln Leu Leu Gly Trp Gln Ala Tyr
            180                 185                 190

Leu Leu Phe Tyr Val Ser Ala Gly Ala Arg Ser Thr Pro Lys Ala Leu
```

```
        195                 200                 205

Glu Gly Ser Ser Trp Ala Gly Ser His Phe Asp Pro Met Ala Asn Leu
    210                 215                 220

Trp Thr Pro Ser Gln Arg Pro Phe Val Phe Leu Ser Thr Val Gly Leu
225                 230                 235                 240

Gly Ala Val Met Phe Ala Leu Tyr Gln Leu Ser Gly Val Ile Gly Val
                245                 250                 255

Ala Asn Thr Phe Leu Leu Tyr Gly Leu Pro Tyr Leu Trp Val Asn Asn
            260                 265                 270

Trp Leu Val Ala Ile Thr Tyr Leu His His Thr His Pro Asp Ser His
        275                 280                 285

His Tyr Glu Ala Ser Arg Trp Thr Phe Leu Asp Gly Ala Leu Thr Thr
    290                 295                 300

Val Asp Arg Pro Phe Gly Phe Ile Gly Arg Lys Val Phe His Gly Ile
305                 310                 315                 320

Ile Asp Phe His Val Val His His Leu Phe Pro Ser Met Pro Phe Tyr
                325                 330                 335

His Ala Glu Glu Ala Thr Lys Ala Met Arg Pro Val Leu Gly Asp Tyr
            340                 345                 350

Tyr Arg Arg Asp Asp Thr Pro Phe Trp Ile Ala Leu Trp Lys Thr Phe
        355                 360                 365

Ser Ser Cys Gln Ala Val Gln Pro Lys Glu Gly Glu Glu Gly Val Leu
    370                 375                 380

Glu Trp Glu Thr Lys Lys Thr His Val Lys Ser Ala
385                 390                 395


<210> SEQ ID NO 16
<211> LENGTH: 2301
<212> TYPE: DNA
<213> ORGANISM: Mycospaerella graminicola

<400> SEQUENCE: 16

actgtctccg atcaatggca aagagtgagc aaagaaagag tcggtgtatg ggaatctggt      60

cggaccgctg ggaccaggtc tagaagaccc ttggttcagt cccatctcac tctaatgcga     120

gccccggcgc tagctcaaaa tctcccaaat catacaacaa aactgccatt ccccgaggcc     180

acagttcctc ctttgctaca caatccgctc gtccttggtc tcgtctgcgt tgtgttcttg     240

tcttctgcca ttcgacgtct tgcagctgca gtatcgcctt accaccgtct ctatcctcag     300

ctccccacct ctcccactgg gcgacctctt tcccaacgcg ccaagtttca agagctgtgc     360

tctcaaccac ttgagacggc agcgacatct ctcgccagaa cttcgaccga gaagacactc     420

ttctctcgaa ataactccac cacacggcac gccgcagtct atacgataca gtcgccaaaa     480

tgagcaccac cgccctctcc cagaagccgg ccatgagacg ccatgtcacg gcggagtcct     540

ctccctcgac cgccgctggt tcccccaatg attcgccggc agcctccgcc tcgtcgacat     600

ccctctcatc gatgggcgac gacgactacc agcaaaagcc agcctccagc aagctcatcg     660

atacctacgg caacgagttc aagatgccag actacacaat caaggacatc cgtgatgcca     720

ttcccaagca ttgctttgag cgatccgccg caacgggcct gtactatgtc gccagggata     780

tcgtgctcct gagcaccaca tttttcttgt tcaacaagtt ctgcacaccg gaatacgttc     840

cctcataccc agctcgtgca gctctgtggg cagcatacac attcattcag ggtcttttcg     900

gcacaggtct gtgggtcttg gcccacgagt gcggtcacca gtccttctcg cccagcaaga     960

ctctcaatga caccgttgga tggatctgcc actctgctct tcttgtcccg tacttcagct    1020
```

```
ggaaaatctc ccacggcaag caccacaagg cgactggcaa catggagcgc gacatggtct   1080
ttctcccacg cactcgcgat gagcacgcta cccgcactgg cgcccttctc cacgagatgc   1140
acgagctgat ggaggagact ccaatctaca ccgccgtctc catgatcgtc cagcagctcg   1200
gcggatggcc aatgtacctg atccagaacc tgaccggcca caacaaccac gagaagcagc   1260
ctgagggcaa gggtgtcggc aaaaagaatg gcaacggcag cgtcaaccac ttcttgccaa   1320
gcagccctct ctacgagaag aaggacgagc acctcatcct cctctccgac ttgggtcttg   1380
ccattaccgc ttccgtcttg acctacgtcg gcaagaccta cggcttcacc aacctcctcg   1440
tctggtacat cctcccatac ctctgggtga accactggct cgtggccatc acctacctcc   1500
agcacaccga tccttctctc cctcactaca ctggtgacgc ctggaacttc gcccgcggtg   1560
ccgccgcgac catcgaccgc gaattcggct tcatcggccg caacctcctc cacggtatcg   1620
tcgagaccca cgttctccac cactacgtct ctaccatccc cttctaccac gccgacgagg   1680
cgaccgaggc catcaagcca atcatgggcc agcactaccg cgccgatgtc gagggcggct   1740
cgatcggatt cttgaaggca atgtggaagt ccgctcgttg gtgccagtgg gtcgagcctc   1800
tgcctggtac cactggcgag gaatccaagg tgctgttctt caggaacagg aacggtcttg   1860
gtgtgccgcc ggcgaagctc tctcccaagg ccggcaagag ggccatggtt gaggatgatt   1920
ccgaatagac tccgaataga ttagaacatc gaaagagatg gacatggaaa tgaatgggtg   1980
gttttgaaag tgtctttagc cggctttatt taggggttta aggtggcgtt ttccgacgag   2040
gtggtatgtc gaggcagatg acgcttagaa gcaagttatt gtatacatct tgttcgtcaa   2100
gatcactttc cgcacctgat cgatttgatg taatgcaggg caagtgttga acgtggacag   2160
gttcgatgcg acatgacttg agcttgagat gcccagttgc aaagtcacat ggttaagcag   2220
gttacgcaag ctctcgttgc aggaacgtcg gtttggatcg atcgatgagt gtccattact   2280
ggctttcacg ccacgccgta t                                             2301
```

```
<210> SEQ ID NO 17
<211> LENGTH: 1449
<212> TYPE: DNA
<213> ORGANISM: Mycospaerella graminicola

<400> SEQUENCE: 17
```

```
atgagcacca ccgccctctc ccagaagccg gccatgagac gccatgtcac ggcggagtcc     60
tctccctcga ccgccgctgg ttcccccaat gattcgccgg cagcctccgc ctcgtcgaca    120
tccctctcat cgatgggcga cgacgactac cagcaaaagc cagcctccag caagctcatc    180
gatacctacg gcaacgagtt caagatgcca gactacacaa tcaaggacat ccgtgatgcc    240
attcccaagc attgctttga gcgatccgcc gcaacgggcc tgtactatgt cgccagggat    300
atcgtgctcc tgagcaccac atttttcttg ttcaacaagt tctgcacacc ggaatacgtt    360
ccctcatacc cagctcgtgc agctctgtgg gcagcataca cattcattca gggtcttttc    420
ggcacaggtc tgtgggtctt ggcccacgag tgcggtcacc agtccttctc gcccagcaag    480
actctcaatg acaccgttgg atggatctgc cactctgctc ttcttgtccc gtacttcagc    540
tggaaaatct cccacggcaa gcaccacaag gcgactggca acatggagcg cgacatggtc    600
tttctcccac gcactcgcga tgagcacgct acccgcactg gcgcccttct ccacgagatg    660
cacgagctga tggaggagac tccaatctac accgccgtct ccatgatcgt ccagcagctc    720
ggcggatggc caatgtacct gatccagaac ctgaccggcc acaacaacca cgagaagcag    780
```

-continued

```
cctgagggca agggtgtcgg caaaaagaat ggcaacggca gcgtcaacca cttcttgcca     840

agcagccctc tctacgagaa gaaggacgag cacctcatcc tcctctccga cttgggtctt     900

gccattaccg cttccgtctt gacctacgtc ggcaagacct acggcttcac caacctcctc     960

gtctggtaca tcctcccata cctctgggtg aaccactggc tcgtggccat cacctacctc    1020

cagcacaccg atccttctct ccctcactac actggtgacg cctggaactt cgcccgcggt    1080

gccgccgcga ccatcgaccg cgaattcggc ttcatcggcc gcaacctcct ccacggtatc    1140

gtcgagaccc acgttctcca ccactacgtc tctaccatcc ccttctacca cgccgacgag    1200

gcgaccgagg ccatcaagcc aatcatgggc cagcactacc gcgccgatgt cgagggcggc    1260

tcgatcggat tcttgaaggc aatgtggaag tccgctcgtt ggtgccagtg ggtcgagcct    1320

ctgcctggta ccactggcga ggaatccaag gtgctgttct tcaggaacag gaacggtctt    1380

ggtgtgccgc cggcgaagct ctctcccaag gccggcaaga gggccatggt tgaggatgat    1440

tccgaatag                                                             1449


<210> SEQ ID NO 18
<211> LENGTH: 482
<212> TYPE: PRT
<213> ORGANISM: Mycospaerella graminicola

<400> SEQUENCE: 18

Met Ser Thr Thr Ala Leu Ser Gln Lys Pro Ala Met Arg Arg His Val
1               5                   10                  15

Thr Ala Glu Ser Ser Pro Ser Thr Ala Ala Gly Ser Pro Asn Asp Ser
            20                  25                  30

Pro Ala Ala Ser Ala Ser Ser Thr Ser Leu Ser Ser Met Gly Asp Asp
        35                  40                  45

Asp Tyr Gln Gln Lys Pro Ala Ser Ser Lys Leu Ile Asp Thr Tyr Gly
    50                  55                  60

Asn Glu Phe Lys Met Pro Asp Tyr Thr Ile Lys Asp Ile Arg Asp Ala
65                  70                  75                  80

Ile Pro Lys His Cys Phe Glu Arg Ser Ala Ala Thr Gly Leu Tyr Tyr
                85                  90                  95

Val Ala Arg Asp Ile Val Leu Leu Ser Thr Thr Phe Phe Leu Phe Asn
            100                 105                 110

Lys Phe Cys Thr Pro Glu Tyr Val Pro Ser Tyr Pro Ala Arg Ala Ala
        115                 120                 125

Leu Trp Ala Ala Tyr Thr Phe Ile Gln Gly Leu Phe Gly Thr Gly Leu
    130                 135                 140

Trp Val Leu Ala His Glu Cys Gly His Gln Ser Phe Ser Pro Ser Lys
145                 150                 155                 160

Thr Leu Asn Asp Thr Val Gly Trp Ile Cys His Ser Ala Leu Leu Val
                165                 170                 175

Pro Tyr Phe Ser Trp Lys Ile Ser His Gly Lys His His Lys Ala Thr
            180                 185                 190

Gly Asn Met Glu Arg Asp Met Val Phe Leu Pro Arg Thr Arg Asp Glu
        195                 200                 205

His Ala Thr Arg Thr Gly Ala Leu Leu His Glu Met His Glu Leu Met
    210                 215                 220

Glu Glu Thr Pro Ile Tyr Thr Ala Val Ser Met Ile Val Gln Gln Leu
225                 230                 235                 240

Gly Gly Trp Pro Met Tyr Leu Ile Gln Asn Leu Thr Gly His Asn Asn
                245                 250                 255
```

His Glu Lys Gln Pro Glu Gly Lys Gly Val Gly Lys Lys Asn Gly Asn
260 265 270

Gly Ser Val Asn His Phe Leu Pro Ser Ser Pro Leu Tyr Glu Lys Lys
275 280 285

Asp Glu His Leu Ile Leu Leu Ser Asp Leu Gly Leu Ala Ile Thr Ala
290 295 300

Ser Val Leu Thr Tyr Val Gly Lys Thr Tyr Gly Phe Thr Asn Leu Leu
305 310 315 320

Val Trp Tyr Ile Leu Pro Tyr Leu Trp Val Asn His Trp Leu Val Ala
325 330 335

Ile Thr Tyr Leu Gln His Thr Asp Pro Ser Leu Pro His Tyr Thr Gly
340 345 350

Asp Ala Trp Asn Phe Ala Arg Gly Ala Ala Ala Thr Ile Asp Arg Glu
355 360 365

Phe Gly Phe Ile Gly Arg Asn Leu Leu His Gly Ile Val Glu Thr His
370 375 380

Val Leu His His Tyr Val Ser Thr Ile Pro Phe Tyr His Ala Asp Glu
385 390 395 400

Ala Thr Glu Ala Ile Lys Pro Ile Met Gly Gln His Tyr Arg Ala Asp
405 410 415

Val Glu Gly Gly Ser Ile Gly Phe Leu Lys Ala Met Trp Lys Ser Ala
420 425 430

Arg Trp Cys Gln Trp Val Glu Pro Leu Pro Gly Thr Thr Gly Glu Glu
435 440 445

Ser Lys Val Leu Phe Phe Arg Asn Arg Asn Gly Leu Gly Val Pro Pro
450 455 460

Ala Lys Leu Ser Pro Lys Ala Gly Lys Arg Ala Met Val Glu Asp Asp
465 470 475 480

Ser Glu

<210> SEQ ID NO 19
<211> LENGTH: 1906
<212> TYPE: DNA
<213> ORGANISM: Naegleria gruberi

<400> SEQUENCE: 19
gcatcctaaa cagtatgaca gagttactgt tcggatagca atccggtctt tttatccatc 60
gcactaggat atgcttgaaa tttccgtatt ttcaaaaaga tctcgaaaga aaaaaaatgt 120
cagctgccac atcagaatct tgcgctcaac aagctgaaaa gtatgacaaa ctctcttcac 180
tctaccacgg agatgccatt cccttcactc ttcgtgaatt aaaggaagcc atcccaaaac 240
attgcttcca aagacctgtc atgaccagta tgctccatct catttcagat ttggttcaat 300
taattgccta tactgttgcc tattattact tttccaattt gttagaatcg tggtggtttg 360
ctaatttgaa tcaaattgta gtgttgagtc caatttatta cttgttgcag ggtgtcttgt 420
tttgtggtta tgtttttatt gaaggtttta catttactgg attgtgggtt cttcaggtag 480
gttaattatt attcgattag gtttatatat tatggatttc atctttatgt ttcgaataat 540
tcgtgtgaaa ttgtgtgaaa tatttcgaac aatttgtgtg aatattttat tatgattgta 600
gcatgaatgt ggacattatg cttttgctga tagtcctctt gtttgtgata ttgtcggtta 660
cattgtcgga agtgccttgt tggttccata ttttgcttgg caagtaagtt tagtcaacca 720
gagaatttgt taattttta ctggaatatt tgaatatttt ttgaaattct tcagaaatca 780

-continued

```
catgctattc accatgcaaa taccaatcac atgacaagag atcaaacctg ggttcctcaa    840

aatgtccaac caattccttc taataatcca gctcaaaaat ctcaagttga caaacaagtt    900

gaaatgaaac caaaatctga atcatctctt tctgccatta ctgatatgat tgttatggca    960

actattggtt ggccacttca cttggtgctc aatgtttctg gtccagttaa ggaaaatgtt   1020

gtggcctatt atgcaaaggg cattcgttat gaaccaacta ttattaccga aagtgatgga   1080

aactctcaag atgatgaaaa tgaatattct gactataagc aaatttcaca aaagtatcca   1140

atcaaattca cctctcactt tttaccatcc tctccaatct ttaatagtag agaaacctta   1200

aagatttact tgtctaattt tggagtaatt gccatgttat tcattctcta tcaattattc   1260

caaatttatg gatggcaagt gatggtcact gtctatgtct taccactcag tattaatttc   1320

ttcctattga cctcaattac ctttttacaa cacgtccacg atgacgttcc tcatttggat   1380

gaaggtgagt ggaattggtt gaagggagct ttgtgtacca ttgatcgttc gatgggttca   1440

ttcttggatt ccaaattgca tcacattact gatacacatg tgtgtcatca tgtcttttca   1500

aagattccat tctatcatgc tgaggaagca acgaaagcaa ttaagggaaa acttggaaat   1560

tattatagag atgagactga taagagtttc tttggtgctt tattcgaaaa tttgaagaat   1620

tgtgttgcct tgaagagaaa tgaaaagttt agaggaattt tgtggtggga tcattaaact   1680

tgaataaata gcagattcat ttacaatatt ctaaaggttt cttctttttc aataatattt   1740

aactccttct tgaaagattg atatcaaaga cgaaaacata ataagcaaaa ggttcagata   1800

agtttgatga aatactttct gtttattgag attcaaaatt aatttagaaa gcaatgaaga   1860

aggatgaaac caaagcaaca ataaccatga tgagcatatt cattcc                  1906
```

<210> SEQ ID NO 20
<211> LENGTH: 1197
<212> TYPE: DNA
<213> ORGANISM: Naegleria gruberi

<400> SEQUENCE: 20

```
atgtcagctg ccacatcaga atcttgcgct caacaagctg aaaagtatga caaactctct     60

tcactctacc acggagatgc cattcccttc actcttcgtg aattaaagga agccatccca    120

aaacattgct tccaaagacc tgtcatgacc agtatgctcc atctcatttc agatttggtt    180

caattaattg cctatactgt tgcctattat tacttttcca atttgttaga atctccaatt    240

tattacttgt tgcagggtgt cttgttttgt ggttatgttt ttattgaagg ttttacattt    300

actggattgt gggttcttca gcatgaatgt ggacattatg cttttgctga tagtcctctt    360

gtttgtgata ttgtcggtta cattgtcgga agtgccttgt tggttccata ttttgcttgg    420

caaaaatcac atgctattca ccatgcaaat accaatcaca tgacaagaga tcaaacctgg    480

gttcctcaaa atgtccaacc aattccttct aataatccag ctcaaaaatc tcaagttgac    540

aaacaagttg aaatgaaacc aaaatctgaa tcatctcttt ctgccattac tgatatgatt    600

gttatggcaa ctattggttg gccacttcac ttggtgctca atgtttctgg tccatatcca    660

atcaaattca cctctcactt tttaccatcc tctccaatct ttaatagtag agaaacctta    720

aagatttact tgtctaattt tggagtaatt gccatgttat tcattctcta tcaattattc    780

caaatttatg gatggcaagt gatggtcact gtctatgtct taccactcag tattaatttc    840

ttcctattga cctcaattac ctttttacaa cacgtccacg atgacgttcc tcatttggat    900

gaaggtgagt ggaattggtt gaagggagct ttgtgtacca ttgatcgttc gatgggttca    960

ttcttggatt ccaaattgca tcacattact gatacacatg tgtgtcatca tgtcttttca   1020
```

```
aagattccat tctatcatgc tgaggaagca acgaaagcaa ttaagggaaa acttggaaat   1080

tattatagag atgagactga taagagtttc tttggtgctt tattcgaaaa tttgaagaat   1140

tgtgttgcct tgaagagaaa tgaaaagttt agaggaattt tgtggtggga tcattaa      1197


<210> SEQ ID NO 21
<211> LENGTH: 398
<212> TYPE: PRT
<213> ORGANISM: Naegleria gruberi

<400> SEQUENCE: 21

Met Ser Ala Ala Thr Ser Glu Ser Cys Ala Gln Gln Ala Glu Lys Tyr
1               5                   10                  15

Asp Lys Leu Ser Ser Leu Tyr His Gly Asp Ala Ile Pro Phe Thr Leu
            20                  25                  30

Arg Glu Leu Lys Glu Ala Ile Pro Lys His Cys Phe Gln Arg Pro Val
        35                  40                  45

Met Thr Ser Met Leu His Leu Ile Ser Asp Leu Val Gln Leu Ile Ala
    50                  55                  60

Tyr Thr Val Ala Tyr Tyr Tyr Phe Ser Asn Leu Leu Glu Ser Pro Ile
65                  70                  75                  80

Tyr Tyr Leu Leu Gln Gly Val Leu Phe Cys Gly Tyr Val Phe Ile Glu
                85                  90                  95

Gly Phe Thr Phe Thr Gly Leu Trp Val Leu Gln His Glu Cys Gly His
            100                 105                 110

Tyr Ala Phe Ala Asp Ser Pro Leu Val Cys Asp Ile Val Gly Tyr Ile
        115                 120                 125

Val Gly Ser Ala Leu Leu Val Pro Tyr Phe Ala Trp Gln Lys Ser His
    130                 135                 140

Ala Ile His His Ala Asn Thr Asn His Met Thr Arg Asp Gln Thr Trp
145                 150                 155                 160

Val Pro Gln Asn Val Gln Pro Ile Pro Ser Asn Asn Pro Ala Gln Lys
                165                 170                 175

Ser Gln Val Asp Lys Gln Val Glu Met Lys Pro Lys Ser Glu Ser Ser
            180                 185                 190

Leu Ser Ala Ile Thr Asp Met Ile Val Met Ala Thr Ile Gly Trp Pro
        195                 200                 205

Leu His Leu Val Leu Asn Val Ser Gly Pro Tyr Pro Ile Lys Phe Thr
    210                 215                 220

Ser His Phe Leu Pro Ser Ser Pro Ile Phe Asn Ser Arg Glu Thr Leu
225                 230                 235                 240

Lys Ile Tyr Leu Ser Asn Phe Gly Val Ile Ala Met Leu Phe Ile Leu
                245                 250                 255

Tyr Gln Leu Phe Gln Ile Tyr Gly Trp Gln Val Met Val Thr Val Tyr
            260                 265                 270

Val Leu Pro Leu Ser Ile Asn Phe Phe Leu Leu Thr Ser Ile Thr Phe
        275                 280                 285

Leu Gln His Val His Asp Asp Val Pro His Leu Asp Glu Gly Glu Trp
    290                 295                 300

Asn Trp Leu Lys Gly Ala Leu Cys Thr Ile Asp Arg Ser Met Gly Ser
305                 310                 315                 320

Phe Leu Asp Ser Lys Leu His His Ile Thr Asp Thr His Val Cys His
                325                 330                 335

His Val Phe Ser Lys Ile Pro Phe Tyr His Ala Glu Glu Ala Thr Lys
```

```
            340                 345                 350

Ala Ile Lys Gly Lys Leu Gly Asn Tyr Tyr Arg Asp Glu Thr Asp Lys
        355                 360                 365

Ser Phe Phe Gly Ala Leu Phe Glu Asn Leu Lys Asn Cys Val Ala Leu
    370                 375                 380

Lys Arg Asn Glu Lys Phe Arg Gly Ile Leu Trp Trp Asp His
385                 390                 395
```

<210> SEQ ID NO 22
<211> LENGTH: 1740
<212> TYPE: DNA
<213> ORGANISM: Phycomyces blakesleeanus

<400> SEQUENCE: 22

```
caaggggga gaagggggga gaaggaaaca tacggttact atattctgat aggtaaatct      60

tgctgttcaa tgtctgtgta ataaaaccgg agttatttta acttttgtat attcctacaa     120

aaaaaacttg tttaaaagac actggtttaa ccaaagcttt tcgtttttta tttgtgtctt     180

tcatccttat attatttctt atgtcggata acactgaatc aatcaagaca gaaaagcaag     240

cactcaattt agacgaggca attgccaaag gatgggagat tccggatttt actatcaagg     300

aaatccgtga tgctattcct tcccactgct tccgtattga cacttttcgg tcctttggat     360

atgttttaca cgatttcttt tttgtcgcac tactaatgta cggtgccagc aagattgaca     420

ctctgtcatc tccatatatt cgatttgtcc tatgggctac ctacagtgtc ttacaaggaa     480

ttgtgggtac tggtctttgg gttatcggtc atgaatgtgg acatcaagca ttcagtcctt     540

caaaggtaca tggatcaatt atatatttat agtatgcgct tttttcttac taacactaac     600

attattatta ttattatata tagacaataa acaatagcgt tggtataatt atccacagcc     660

tattgcttgt tccatactac tcttggaaga tttctcattc aaagcatcac aagtctaatg     720

ggcacttgta caatgatatg gtaactatct cttctatata aaagctatat tatcgcaaac     780

agccatatta ttaaactatt acttatataa atacatgccc atctttttgc aggtatatgt     840

tcctagaaca cgatcgcata gaaagctagg acctaaagaa gaggaccatg agctcgacgg     900

acctcacagt gctcttatgg aatcccctat tgtagaaaca gcaaagatct tcagactggt     960

tgtgttcggg tgggtttgtt atgtcttact tgacgtaacc ggaaagcgtc caaagaaaac    1020

ctggacatca catttcaact tcaattgcca catctttgag gaacataact atgcagactt    1080

tgtcaagtca aacattggat tagctgtcgc aatctctggc ctagtctgtg ctggccaaat    1140

ttacggctcg atgactgtaa tgaagtatta tgtgttccct tatctttttg tcaactgctg    1200

gcttgtcttg atcacctatc tccagcacac cgactcagcg attccccgtt atagtcccaa    1260

tgtgtggaac ttccaacgtg gcgctgctct cacagttgat cgctcatatg ggcccatact    1320

gaatcatttc caccaccaca tttcggacac tcatgtagcc catcatttct tttctaatat    1380

gccacactat catgcagtag aagccactaa gcacatcaag aaggttttgg gaaaacatta    1440

tatgtctgat gacaccccta ttcttcaggc attgtacaaa tcatacagag aatgtaaatt    1500

tattgaagac gaaggcgacg ttcgtttcct caagaattaa agaagaagaa aaagaaaata    1560

atcacacaca cacacacaca cacacatata tatatatata tatccattac acatacacac    1620

acgatataca catcacaaat cacatatcat acattagata tcgcttttgt atttctatta    1680

ttattattca atacatgtat tcaaaataaa ataaacggaa atatttaacc acaaatcaaa    1740
```

<210> SEQ ID NO 23

<211> LENGTH: 1170
<212> TYPE: DNA
<213> ORGANISM: Phycomyces blakesleeanus

<400> SEQUENCE: 23
atgtcggata acactgaatc aatcaagaca gaaaagcaag cactcaattt agacgaggca 60
attgccaaag gatgggagat tccggatttt actatcaagg aaatccgtga tgctattcct 120
tcccactgct tccgtattga cacttttcgg tcctttggat atgttttaca cgatttcttt 180
tttgtcgcac tactaatgta cggtgccagc aagattgaca ctctgtcatc tccatatatt 240
cgatttgtcc tatgggctac ctacagtgtc ttacaaggaa ttgtgggtac tggtctttgg 300
gttatcggtc atgaatgtgg acatcaagca ttcagtcctt caaagacaat aaacaatagc 360
gttggtataa ttatccacag cctattgctt gttccatact actcttggaa gatttctcat 420
tcaaagcatc acaagtctaa tgggcacttg tacaatgata tggtatatgt tcctagaaca 480
cgatcgcata gaaagctagg acctaaagaa gaggaccatg agctcgacgg acctcacagt 540
gctcttatgg aatcccctat tgtagaaaca gcaaagatct tcagactggt tgtgttcggg 600
tgggtttgtt atgtcttact tgacgtaacc ggaaagcgtc caaagaaaac ctggacatca 660
catttcaact tcaattgcca catctttgag gaacataact atgcagactt tgtcaagtca 720
aacattggat tagctgtcgc aatctctggc ctagtctgtg ctggccaaat ttacggctcg 780
atgactgtaa tgaagtatta tgtgttccct tatctttttg tcaactgctg gcttgtcttg 840
atcacctatc tccagcacac cgactcagcg attccccgtt atagtcccaa tgtgtggaac 900
ttccaacgtg gcgctgctct cacagttgat cgctcatatg ggcccatact gaatcatttc 960
caccaccaca tttcggacac tcatgtagcc catcatttct tttctaatat gccacactat 1020
catgcagtag aagccactaa gcacatcaag aaggttttgg gaaaacatta tatgtctgat 1080
gacaccccta ttcttcaggc attgtacaaa tcatacagag aatgtaaatt tattgaagac 1140
gaaggcgacg ttcgtttcct caagaattaa 1170

<210> SEQ ID NO 24
<211> LENGTH: 389
<212> TYPE: PRT
<213> ORGANISM: Phycomyces blakesleeanus

<400> SEQUENCE: 24

```
Met Ser Asp Asn Thr Glu Ser Ile Lys Thr Glu Lys Gln Ala Leu Asn
1               5                   10                  15

Leu Asp Glu Ala Ile Ala Lys Gly Trp Glu Ile Pro Asp Phe Thr Ile
            20                  25                  30

Lys Glu Ile Arg Asp Ala Ile Pro Ser His Cys Phe Arg Ile Asp Thr
        35                  40                  45

Phe Arg Ser Phe Gly Tyr Val Leu His Asp Phe Phe Phe Val Ala Leu
    50                  55                  60

Leu Met Tyr Gly Ala Ser Lys Ile Asp Thr Leu Ser Ser Pro Tyr Ile
65                  70                  75                  80

Arg Phe Val Leu Trp Ala Thr Tyr Ser Val Leu Gln Gly Ile Val Gly
                85                  90                  95

Thr Gly Leu Trp Val Ile Gly His Glu Cys Gly His Gln Ala Phe Ser
            100                 105                 110

Pro Ser Lys Thr Ile Asn Asn Ser Val Gly Ile Ile Ile His Ser Leu
        115                 120                 125

Leu Leu Val Pro Tyr Tyr Ser Trp Lys Ile Ser His Ser Lys His His
```

```
    130                 135                 140

Lys Ser Asn Gly His Leu Tyr Asn Asp Met Val Tyr Val Pro Arg Thr
145                 150                 155                 160

Arg Ser His Arg Lys Leu Gly Pro Lys Glu Glu Asp His Glu Leu Asp
                165                 170                 175

Gly Pro His Ser Ala Leu Met Glu Ser Pro Ile Val Glu Thr Ala Lys
            180                 185                 190

Ile Phe Arg Leu Val Val Phe Gly Trp Val Cys Tyr Val Leu Leu Asp
        195                 200                 205

Val Thr Gly Lys Arg Pro Lys Lys Thr Trp Thr Ser His Phe Asn Phe
    210                 215                 220

Asn Cys His Ile Phe Glu Glu His Asn Tyr Ala Asp Phe Val Lys Ser
225                 230                 235                 240

Asn Ile Gly Leu Ala Val Ala Ile Ser Gly Leu Val Cys Ala Gly Gln
                245                 250                 255

Ile Tyr Gly Ser Met Thr Val Met Lys Tyr Tyr Val Phe Pro Tyr Leu
            260                 265                 270

Phe Val Asn Cys Trp Leu Val Leu Ile Thr Tyr Leu Gln His Thr Asp
        275                 280                 285

Ser Ala Ile Pro Arg Tyr Ser Pro Asn Val Trp Asn Phe Gln Arg Gly
    290                 295                 300

Ala Ala Leu Thr Val Asp Arg Ser Tyr Gly Pro Ile Leu Asn His Phe
305                 310                 315                 320

His His His Ile Ser Asp Thr His Val Ala His His Phe Phe Ser Asn
                325                 330                 335

Met Pro His Tyr His Ala Val Glu Ala Thr Lys His Ile Lys Lys Val
            340                 345                 350

Leu Gly Lys His Tyr Met Ser Asp Asp Thr Pro Ile Leu Gln Ala Leu
        355                 360                 365

Tyr Lys Ser Tyr Arg Glu Cys Lys Phe Ile Glu Asp Glu Gly Asp Val
    370                 375                 380

Arg Phe Leu Lys Asn
385


<210> SEQ ID NO 25
<211> LENGTH: 2243
<212> TYPE: DNA
<213> ORGANISM: Nematostella vectensis

<400> SEQUENCE: 25

tatgcgctga ataaaatcat aaaaatagtt tgataacact tgattttgta aaacatagag      60

ttccgatgga tgatataaag tattctacat ttaaaccacc attttaaaga gaaaaaagat     120

acattttata tggaaaaata ttattccctc aatattggcg atacttgtaa ttatccatta     180

cattatttat caattgtttc aatgttttaa atccgattat cttccagctt ttggcagtta     240

tgttcacttt ttgtgtgagc gcgaactgtt ttttttaga cgtaaacatt gcgtgcgttg      300

ttacactctc tttcacacac aactcgtgct ttccatcaga cccgacaaac gcgccaaaca     360

tgccgccgtg tcacgcaaca accggaagtg gcgagcagca agtcatgcaa tccacatctg     420

atgacaccaa aaacgaacac gagaaaacct tgccattcaa gccgaaaatc gtttggttaa     480

acgtgggttt tattctggtt cttcacgtta tggccttcta tgggatattt cttcttccac     540

agctgaaatt ctggacgatg atttggacga tagcttgtca ctttgccggc ggctatggcg     600

tgacaatagg tgcgcaccga ctgtgggctc acaggacctt caaggcaaaa tggccgcttc     660
```

```
gcctcgtgat tatgctaatg aacagcatgg ctgcgcagaa cgacatcttc gagtggtcac    720
gtgatcatcg cgtgcatcac aagtactcgg agaccgatgc tgacccccat aatgcaaagc    780
gcgggttctt tttctctcac gtgggctggc tgatgcagag aaaacacccg gatgttatac    840
ggaaagggaa aggaattgac ctgagcgact tgtacgccga cagcgtggtc atgttccaaa    900
ggaggtaagt tggagaggaa ctggatttgg gggggggggg gggggtattt aggggaggga    960
gagggggggg ggtactcccg tatatagctg ggtgtctaaa taactttttt caccaccgct   1020
gccagcctcc ttcttaagaa aaaaatcttg ctcgctgtga acaacagccc acattttccc   1080
gaaagctctg ccactgatcc ttctcaaaac tgcggccagt tcccgtttaa cccggtagat   1140
tccctgtaaa caggggtacg caagtgtata aggcagatat tcagatagac ggtgaaaaca   1200
gacaaaagga ataaacagat aaaagcaaaa ttgtttggaa aacgaataga aaaaagatga   1260
cacttagaaa actaagggga cttaatgtaa cttagagtcc gttcaagatc gttgtattaa   1320
aaatggctgt gacagaccgc taaaaatagg caaatgcaga caggcagaaa actgactggc   1380
gaacagacgg aaagggtata tttacgtcaa tgacactatg tttcttcgtt cttaaggcat   1440
tacaagaaaa tctccatgtt gatgtgtgtg cttatcccta cgctggtacc cagtctctgg   1500
ggcgagtctc tgtggaacgc ctacttcaca tcattcgcac tccgttacgt catcaccctc   1560
aacgtcacgt ggtgtgtcaa cagcatcgcg cacatgtggg gcgacaagcc ttatgacgtc   1620
accattaacc cagcagagaa cctcttcgtt accttggcaa cgtcaggcga gggttaccat   1680
aactaccatc acacttttcc ccaggactac gcggctagcg agtttggtac tcgcctcaac   1740
atgagtacga ggcttattga tatgtgggcc gcgatgggac tagtcagcga tcgaaaggtg   1800
gttcccaagg agacgattcg taagaggatg atgcggactg gcgcgctaag gagcttggga   1860
gaaaactgtg aaaaggacta aatacttatc agacttcata cacgcatttg caattaaaga   1920
atataactta ttggatatat agattttttg tatcataggc atgacttttt tatatcaagt   1980
ccggataatc gagaaaaaat aatttattta attttgctga atttgtattt tgcgccctaa   2040
tgtgcaacgg caacggccac agttttcaga aactaacata acgatgcggg agacgtactt   2100
tttgattgac attcacttca attagccaat gaagagctca ggaagccaat gaagtgccca   2160
gaggctcgct tcgaaatgag aatgatgtaa ccaacatcag tgatattgat aagctattgt   2220
tgttatttat tttcgttggt tgc                                           2243
```

<210> SEQ ID NO 26
<211> LENGTH: 990
<212> TYPE: DNA
<213> ORGANISM: Nematostella vectensis

<400> SEQUENCE: 26

```
atgccgccgt gtcacgcaac aaccggaagt ggcgagcagc aagtcatgca atccacatct     60
gatgacacca aaaacgaaca cgagaaaacc ttgccattca agccgaaaat cgtttggtta    120
aacgtgggtt ttattctggt tcttcacgtt atggccttct atgggatatt tcttcttcca    180
cagctgaaat tctggacgat gatttggacg atagcttgtc actttgccgg cggctatggc    240
gtgacaatag gtgcgcaccg actgtgggct cacaggacct tcaaggcaaa atggccgctt    300
cgcctcgtga ttatgctaat gaacagcatg gctgcgcaga acgacatctt cgagtggtca    360
cgtgatcatc gcgtgcatca caagtactcg gagaccgatg ctgaccccca taatgcaaag    420
cgcgggttct ttttctctca cgtgggctgg ctgatgcaga gaaaacaccc ggatgttata    480
```

```
cggaaaggga aaggaattga cctgagcgac ttgtacgccg acagcgtggt catgttccaa    540

aggaggcatt acaagaaaat ctccatgttg atgtgtgtgc ttatccctac gctggtaccc    600

agtctctggg gcgagtctct gtggaacgcc tacttcacat cattcgcact ccgttacgtc    660

atcaccctca acgtcacgtg gtgtgtcaac agcatcgcgc acatgtgggg cgacaagcct    720

tatgacgtca ccattaaccc agcagagaac ctcttcgtta ccttggcaac gtcaggcgag    780

ggttaccata actaccatca cacttttccc caggactacg cggctagcga gtttggtact    840

cgcctcaaca tgagtacgag gcttattgat atgtgggccg cgatgggact agtcagcgat    900

cgaaaggtgg ttcccaagga gacgattcgt aagaggatga tgcggactgg cgcgctaagg    960

agcttgggag aaaactgtga aaaggactaa                                     990
```

<210> SEQ ID NO 27
<211> LENGTH: 329
<212> TYPE: PRT
<213> ORGANISM: Nematostella vectensis

<400> SEQUENCE: 27

```
Met Pro Pro Cys His Ala Thr Thr Gly Ser Gly Glu Gln Gln Val Met
1               5                   10                  15

Gln Ser Thr Ser Asp Asp Thr Lys Asn Glu His Glu Lys Thr Leu Pro
            20                  25                  30

Phe Lys Pro Lys Ile Val Trp Leu Asn Val Gly Phe Ile Leu Val Leu
        35                  40                  45

His Val Met Ala Phe Tyr Gly Ile Phe Leu Leu Pro Gln Leu Lys Phe
    50                  55                  60

Trp Thr Met Ile Trp Thr Ile Ala Cys His Phe Ala Gly Gly Tyr Gly
65                  70                  75                  80

Val Thr Ile Gly Ala His Arg Leu Trp Ala His Arg Thr Phe Lys Ala
                85                  90                  95

Lys Trp Pro Leu Arg Leu Val Ile Met Leu Met Asn Ser Met Ala Ala
            100                 105                 110

Gln Asn Asp Ile Phe Glu Trp Ser Arg Asp His Arg Val His His Lys
        115                 120                 125

Tyr Ser Glu Thr Asp Ala Asp Pro His Asn Ala Lys Arg Gly Phe Phe
    130                 135                 140

Phe Ser His Val Gly Trp Leu Met Gln Arg Lys His Pro Asp Val Ile
145                 150                 155                 160

Arg Lys Gly Lys Gly Ile Asp Leu Ser Asp Leu Tyr Ala Asp Ser Val
                165                 170                 175

Val Met Phe Gln Arg Arg His Tyr Lys Lys Ile Ser Met Leu Met Cys
            180                 185                 190

Val Leu Ile Pro Thr Leu Val Pro Ser Leu Trp Gly Glu Ser Leu Trp
        195                 200                 205

Asn Ala Tyr Phe Thr Ser Phe Ala Leu Arg Tyr Val Ile Thr Leu Asn
    210                 215                 220

Val Thr Trp Cys Val Asn Ser Ile Ala His Met Trp Gly Asp Lys Pro
225                 230                 235                 240

Tyr Asp Val Thr Ile Asn Pro Ala Glu Asn Leu Phe Val Thr Leu Ala
                245                 250                 255

Thr Ser Gly Glu Gly Tyr His Asn Tyr His His Thr Phe Pro Gln Asp
            260                 265                 270

Tyr Ala Ala Ser Glu Phe Gly Thr Arg Leu Asn Met Ser Thr Arg Leu
        275                 280                 285
```

```
Ile Asp Met Trp Ala Ala Met Gly Leu Val Ser Asp Arg Lys Val Val
    290                 295                 300

Pro Lys Glu Thr Ile Arg Lys Arg Met Met Arg Thr Gly Ala Leu Arg
305                 310                 315                 320

Ser Leu Gly Glu Asn Cys Glu Lys Asp
                325


<210> SEQ ID NO 28
<211> LENGTH: 1380
<212> TYPE: DNA
<213> ORGANISM: Pythium irregulare

<400> SEQUENCE: 28

atggtggacc tcaagcctgg agtgaagcgc ctggtgagct ggaaggagat ccgcgagcac      60

gcgacgcccg cgaccgcgtg gatcgtgatt caccacaagg tctacgacat ctccaagtgg     120

gactcgcacc cgggtggctc cgtgatgctc acgcaggccg gcgaggacgc cacggacgcc     180

ttcgcggtct tccacccgtc ctcggcgctc aagctgctcg agcagttcta cgtcggcgac     240

gtggacgaaa cctccaaggc cgagatcgag ggggagccgg cgagcgacga ggagcgcgcg     300

cgccgcgagc gcatcaacga gttcatcgcg tcctaccgtc gtctgcgcgt caaggtcaag     360

ggcatggggc tctacgacgc cagcgcgctc tactacgcgt ggaagctcgt gagcacgttc     420

ggcatcgcgg tgctctcgat ggcgatctgc ttcttcttca acagtttcgc catgtacatg     480

gtcgccggcg tgattatggg gctcttctac cagcagtccg gatggctggc gcacgacttc     540

ttgcacaacc aggtgtgcga gaaccgcacg ctcggcaacc ttatcggctg cctcgtgggc     600

aacgcctggc agggcttcag cgtgcagtgg tggaagaaca agcacaacct gcaccacgcg     660

gtgccgaacc tgcacagcgc caaggacgag ggcttcatcg gcgacccgga catcgacacc     720

atgccgctgc tggcgtggtc taaggagatg gcgcgcaagg cgttcgagtc ggcgcacggc     780

ccgttcttca tccgcaacca ggcgttccta tacttcccgc tgctgctgct cgcgcgcctg     840

agctggctcg cgcagtcgtt cttctacgtg ttcaccgagt tctcgttcgg catcttcgac     900

aaggtcgagt tcgacggacc ggagaaggcg ggtctgatcg tgcactacat ctggcagctc     960

gcgatcccgt acttctgcaa catgagcctg tttgagggcg tggcatactt cctcatgggc    1020

caggcgtcct gcggcttgct cctggcgctg gtgttcagta ttggccacaa cggcatgtcg    1080

gtgtacgagc gcgaaaccaa gccggacttc tggcagctgc aggtgaccac gacgcgcaac    1140

atccgcgcgt cggtattcat ggactggttc accggtggct tgaactacca gatcgaccat    1200

cacctgttcc cgctcgtgcc gcgccacaac ttgccaaagg tcaacgtgct catcaagtcg    1260

ctatgcaagg agttcgacat cccgttccac gagaccggct tctgggaggg catctacgag    1320

gtcgtggacc acctggcgga catcagcaag gaattcatca ccgagttccc agcgatgtaa    1380


<210> SEQ ID NO 29
<211> LENGTH: 1320
<212> TYPE: DNA
<213> ORGANISM: Thraustochytrium ssp.

<400> SEQUENCE: 29

atgggcaagg gcagcgaggg ccgcagcgcg gcgcgcgaga tgacggccga ggcgaacggc      60

gacaagcgga aaacgattct gatcgagggc gtcctgtacg acgcgacgaa ctttaagcac     120

ccgggcggtt cgatcatcaa cttcttgacc gagggcgagg ccggcgtgga cgcgacgcag     180

gcgtaccgcg agtttcatca gcggtccggc aaggccgaca agtacctcaa gtcgctgccg     240
```

aagctggatg cgtccaaggt ggagtcgcgg ttctcggcca aagagcaggc gcggcgcgac 300
gccatgacgc gcgactacgc ggcctttcgc gaggagctcg tcgccgaggg gtactttgac 360
ccgtcgatcc cgcacatgat ttaccgcgtc gtggagatcg tggcgctctt cgcgctctcg 420
ttctggctca tgtccaaggc ctcgcccacc tcgctcgtgc tgggcgtggt gatgaacggc 480
attgcgcagg gccgctgcgg ctgggtcatg cacgagatgg gccacgggtc gttcacgggc 540
gtcatctggc tcgacgaccg gatgtgcgag ttcttctacg gcgtcggctg cggcatgagc 600
gggcactact ggaagaacca gcacagcaag caccacgccg cgcccaaccg cctcgagcac 660
gatgtcgatc tcaacacgct gcccctggtc gcctttaacg agcgcgtcgt gcgcaaggtc 720
aagccgggat cgctgctggc gctctggctg cgcgtgcagg cgtacctctt tgcgcccgtc 780
tcgtgcctgc tcatcggcct tggctggacg ctctacctgc acccgcgcta catgctgcgc 840
accaagcggc acatggagtt cgtctggatc ttcgcgcgct acattggctg gttctcgctc 900
atgggcgctc tcggctactc gccgggcacc tcggtcggga tgtacctgtg ctcgttcggc 960
ctcggctgca tttacatttt cctgcagttc gccgtcagcc acacgcacct gccggtgacc 1020
aacccggagg accagctgca ctggctcgag tacgcggccg accacacggt gaacattagc 1080
accaagtcct ggctcgtcac gtggtggatg tcgaacctga actttcagat cgagcaccac 1140
ctcttcccca cggcgccgca gttccgcttc aaggaaatca gtcctcgcgt cgaggccctc 1200
ttcaagcgcc acaacctccc gtactacgac ctgccctaca cgagcgcggt ctcgaccacc 1260
tttgccaatc tttattccgt cggccactcg gtcggcgccg acaccaagaa gcaggactga 1320

<210> SEQ ID NO 30
<211> LENGTH: 1086
<212> TYPE: DNA
<213> ORGANISM: Phytophtora infestans

<400> SEQUENCE: 30
atggcgacga aggaggcgta tgtgttcccc actctgacgg agatcaagcg gtcgctacct 60
aaagactgtt tcgaggcttc ggtgcctctg tcgctctact acaccgtgcg ttgtctggtg 120
atcgcggtgg ctctaacctt cggtctcaac tacgctcgcg ctctgcccga ggtcgagagc 180
ttctgggctc tggacgccgc actctgcacg ggctacatct tgctgcaggg catcgtgttc 240
tggggcttct tcacggtggg ccacgatgcc ggccacggcg ccttctcgcg ctaccacctg 300
cttaacttcg tggtgggcac tttcatgcac tcgctcatcc tcacgccctt cgagtcgtgg 360
aagctcacgc accgtcacca ccacaagaac acgggcaaca ttgaccgtga cgaggtcttc 420
tacccgcaac gcaaggccga cgaccacccg ctgtctcgca acctgattct ggcgctcggg 480
gcagcgtggc tcgcctattt ggtcgagggc ttccctcctc gtaaggtcaa ccacttcaac 540
ccgttcgagc ctctgttcgt gcgtcaggtg tcagctgtgg taatctctct tctcgcccac 600
ttcttcgtgg ccggactctc catctatctg agcctccagc tgggccttaa gacgatggca 660
atctactact atggacctgt ttttgtgttc ggcagcatgc tggtcattac caccttccta 720
caccacaatg atgaggagac cccatggtac gccgactcgg agtggacgta cgtcaagggc 780
aacctctcgt ccgtggaccg atcgtacggc gcgctcattg acaacctgag ccacaacatc 840
ggcacgcacc agatccacca ccttttccct atcattccgc actacaaact caagaaagcc 900
actgcggcct tccaccaggc tttccctgag ctcgtgcgca agagcgacga gccaattatc 960
aaggctttct tccgggttgg acgtctctac gcaaactacg gcgttgtgga ccaggaggcg 1020
aagctcttca cgctaaagga agccaaggcg gcgaccgagg cggcggccaa gaccaagtcc 1080
acgtaa 1086

<210> SEQ ID NO 31
<211> LENGTH: 873
<212> TYPE: DNA
<213> ORGANISM: Physcomitrella patens

<400> SEQUENCE: 31
atggaggtcg tggagagatt ctacggtgag ttggatggga aggtctcgca gggcgtgaat 60
gcattgctgg gtagttttgg ggtggagttg acggatacgc ccactaccaa aggcttgccc 120
ctcgttgaca gtcccacacc catcgtcctc ggtgtttctg tatacttgac tattgtcatt 180
ggagggcttt tgtggataaa ggccagggat ctgaaaccgc gcgcctcgga gccatttttg 240
ctccaagctt tggtgcttgt gcacaacctg ttctgttttg cgctcagtct gtatatgtgc 300
gtgggcatcg cttatcaggc tattacctgg cggtactctc tctggggcaa tgcatacaat 360
cctaaacata aagagatggc gattctggta tacttgttct acatgtctaa gtacgtggaa 420
ttcatggata ccgttatcat gatactgaag cgcagcacca ggcaaataag cttcctccac 480
gtttatcatc attcttcaat ttccctcatt tggtgggcta ttgctcatca cgctcctggc 540
ggtgaagcat attggtctgc ggctctgaac tcaggagtgc atgttctcat gtatgcgtat 600
tacttcttgg ctgcctgcct tcgaagtagc ccaaagttaa aaaataagta cctttttgg 660 ggcaggtact tgacacaatt ccaaatgttc cagtttatgc tgaacttagt gcaggcttac 720
tacgacatga aaacgaatgc gccatatcca caatggctga tcaagatttt gttctactac 780
atgatctcgt tgctgtttct tttcggcaat ttttacgtac aaaaatacat caaaccctct 840
gacggaaagc aaaagggagc taaaactgag tga 873

<210> SEQ ID NO 32
<211> LENGTH: 903
<212> TYPE: DNA
<213> ORGANISM: Ostreococcus tauri

<400> SEQUENCE: 32
atgagcgcct ccggtgcgct gctgcccgcg atcgcgttcg ccgcgtacgc gtacgcgacg 60
tacgcctacg cctttgagtg gtcgcacgcg aatggcatcg acaacgtcga cgcgcgcgag 120
tggatcggtg cgctgtcgtt gaggctcccg gcgatcgcga cgacgatgta cctgttgttc 180
tgcctggtcg gaccgaggtt gatggcgaag cgcgaggcgt tcgacccgaa ggggttcatg 240
ctggcgtaca atgcgtatca gacggcgttc aacgtcgtcg tgctcgggat gttcgcgcga 300
gagatctcgg ggctggggca gcccgtgtgg gggtcaacca tgccgtggag cgatagaaaa 360
tcgtttaaga tcctcctcgg ggtgtggttg cactacaaca acaaatattt ggagctattg 420
gacactgtgt tcatggttgc gcgcaagaag acgaagcagt tgagcttctt gcacgtttat 480
catcacgccc tgttgatctg ggcgtggtgg ttggtgtgtc acttgatggc cacgaacgat 540
tgtatcgatg cctacttcgg cgcggcgtgc aactcgttca ttcacatcgt gatgtactcg 600
tattatctca tgtcggcgct cggcattcga tgcccgtgga agcgatacat cacccaggct 660
caaatgctcc aattcgtcat tgtcttcgcg cacgccgtgt tcgtgctgcg tcagaagcac 720
tgcccggtca cccttccttg ggcgcaaatg ttcgtcatga cgaacatgct cgtgctcttc 780
gggaacttct acctcaaggc gtactcgaac aagtcgcgcg gcgacggcgc gagttccgtg 840
aaaccagccg agaccacgcg cgcgcccagc gtgcgacgca cgcgatctcg aaaaattgac 900
taa 903

<210> SEQ ID NO 33
<211> LENGTH: 1560
<212> TYPE: DNA
<213> ORGANISM: Thraustochytrium ssp.

<400> SEQUENCE: 33
atgacggtcg gctacgacga ggagatcccg ttcgagcagg tccgcgcgca caacaagccg 60
gatgacgcct ggtgcgcgat ccacgggcac gtgtacgatg tgaccaagtt cgcgagcgtg 120
cacccgggcg gcgacattat cctgctggcc gcaggcaagg aggccaccgt gctgtacgag 180
acttaccatg tgcggggcgt ctcggacgcg gtgctgcgca agtaccgcat cggcaagctg 240
ccggacggcc aaggcggcgc gaacgagaag gaaaagcgga cgctctcggg cctctcgtcg 300
gcctcgtact acacgtggaa cagcgacttt tacagggtaa tgcgcgagcg cgtcgtggct 360
cggctcaagg agcgcggcaa ggcccgccgc ggaggctacg agctctggat caaggcgttc 420
ctgctgctcg tcggcttctg gagctcgctg tactggatgt gcacgctgga cccctcgttc 480
ggggccatcc tggccgccat gtcgctgggc gtctttgccg cctttgtggg cacgtgcatc 540
cagcacgacg gcaaccacgg cgcctttgcc cagtcgcgat gggtcaacaa ggttgccggg 600
tggacgctcg acatgatcgg cgccagcggc atgacgtggg agttccagca cgtcctgggc 660
caccatccgt acacgaacct gatcgaggag gagaacggcc tgcaaaaggt gagcggcaag 720
aagatggaca ccaagctggc cgaccaggag agcgatccgg acgtcttttc cacgtacccg 780
atgatgcgcc tgcacccgtg gcaccagaag cgctggtacc accgtttcca gcacatttac 840
ggccccttca tctttggctt catgaccatc aacaaggtgg tcacgcagga cgtcggtgtg 900
gtgctccgca agcggctctt ccagattgac gccgagtgcc ggtacgcgag cccaatgtac 960
gtggcgcgtt tctggatcat gaaggcgctc acggtgctct acatggtggc cctgccgtgc 1020
tacatgcagg gcccgtggca cggcctcaag ctgttcgcga tcgcgcactt tacgtgcggc 1080
gaggtgctcg caaccatgtt cattgtgaac cacatcatcg agggcgtctc gtacgcttcc 1140
aaggacgcgg tcaagggcac gatggcgccg ccgaagacga tgcacggcgt gacgcccatg 1200
aacaacacgc gcaaggaggt ggaggcggag gcgtccaagt ctggcgccgt ggtcaagtca 1260
gtcccgctcg acgactgggc cgccgtccag tgccagacct cggtgaactg gagcgtcggc 1320
tcgtggttct ggaatcactt ttccggcggc ctcaaccacc agattgagca ccacctgttc 1380
cccgggctca gccacgagac gtactaccac atccaggacg tcgttcagtc cacctgcgcc 1440
gagtacggcg tcccgtacca gcacgagcct tcgctctgga ccgcgtactg gaagatgctc 1500
gagcacctcc gtcagctcgg caatgaggag acccacgagt cctggcagcg cgctgcctga 1560

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
atggcttcta cggctgtgcc 20

<210> SEQ ID NO 35
<211> LENGTH: 19
<212> TYPE: DNA

-continued

<213> ORGANISM: Artificial
<220> FEATURE:
<223> OTHER INFORMATION: Primer

<400> SEQUENCE: 35
ttaggcggcg ggagggtcg 19

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
atggctactc gacagcgtac 20

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
ctactccttg gcccatcgca tg 22

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
atggctacta ccacgacggt 20

<210> SEQ ID NO 39
<211> LENGTH: 23
<212> TYPE: DNA
<213> ORGANISM: Artificial
<220> FEATURE:
<223> OTHER INFORMATION: Primer

<400> SEQUENCE: 39
tcattgcgcc cagtgcagag ctc 23

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
atgacggtgg cttcccaggt g 21

<210> SEQ ID NO 41
<211> LENGTH: 21
<212> TYPE: DNA
<213> ORGANISM: Artificial
<220> FEATURE:
<223> OTHER INFORMATION: Primer

<400> SEQUENCE: 41
ttacctgtcc ttgaaccaaa g 21

<210> SEQ ID NO 42
<211> LENGTH: 21
<212> TYPE: DNA
<213> ORGANISM: Artificial
<220> FEATURE:
<223> OTHER INFORMATION: Primer

<400> SEQUENCE: 42
atgagcagaa cagtcacatt a 21

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
tcacgcgctc ttaacatgcg 20

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
atgagcacca ccgccctctc 20

<210> SEQ ID NO 45
<211> LENGTH: 19
<212> TYPE: DNA
<213> ORGANISM: Artificial
<220> FEATURE:
<223> OTHER INFORMATION: Primer

<400> SEQUENCE: 45
ctattcggaa tcatcctca 19

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
atgtcagctg ccacatcaga 20

<210> SEQ ID NO 47
<211> LENGTH: 20
<212> TYPE: DNA
<213> ORGANISM: Artificial
<220> FEATURE:
<223> OTHER INFORMATION: Primer

<400> SEQUENCE: 47
ttaatgatcc caccacaaaa 20

<210> SEQ ID NO 48
<211> LENGTH: 20
<212> TYPE: DNA
<213> ORGANISM: Artificial
<220> FEATURE:

<223> OTHER INFORMATION: Primer

<400> SEQUENCE: 48
atgtcggata acactgaatc 20

<210> SEQ ID NO 49
<211> LENGTH: 20
<212> TYPE: DNA
<213> ORGANISM: Artificial
<220> FEATURE:
<223> OTHER INFORMATION: Primer

<400> SEQUENCE: 49
ttaattcttg aggaaacgaa 20

<210> SEQ ID NO 50
<211> LENGTH: 20
<212> TYPE: DNA
<213> ORGANISM: Artificial
<220> FEATURE:
<223> OTHER INFORMATION: Primer

<400> SEQUENCE: 50
atgccgccgt gtcacgcaac 20

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
ttagtccttt tcacagtttt c 21

<210> SEQ ID NO 52
<211> LENGTH: 31
<212> TYPE: DNA
<213> ORGANISM: Artificial
<220> FEATURE:
<223> OTHER INFORMATION: Primer

<400> SEQUENCE: 52
gcggccgcgc catggtggac ctcaagcctg g 31

<210> SEQ ID NO 53
<211> LENGTH: 27
<212> TYPE: DNA
<213> ORGANISM: Artificial
<220> FEATURE:
<223> OTHER INFORMATION: Primer

<400> SEQUENCE: 53
gcggccgtta catcgctggg aactcgg 27

<210> SEQ ID NO 54
<211> LENGTH: 31
<212> TYPE: DNA
<213> ORGANISM: Artificial
<220> FEATURE:
<223> OTHER INFORMATION: Primer

<400> SEQUENCE: 54
gcggccgcgc catgggcaag ggcagcgagg g 31

<210> SEQ ID NO 55
<211> LENGTH: 32
<212> TYPE: DNA
<213> ORGANISM: Artificial
<220> FEATURE:
<223> OTHER INFORMATION: Primer

<400> SEQUENCE: 55
gcggccgcgc ctcagtcctg cttcttggtg tc 32

<210> SEQ ID NO 56
<211> LENGTH: 31
<212> TYPE: DNA
<213> ORGANISM: Artificial
<220> FEATURE:
<223> OTHER INFORMATION: Primer

<400> SEQUENCE: 56
gcggccgcgc catggcgacg aaggaggcgt a 31

<210> SEQ ID NO 57
<211> LENGTH: 31
<212> TYPE: DNA
<213> ORGANISM: Artificial
<220> FEATURE:
<223> OTHER INFORMATION: Primer

<400> SEQUENCE: 57
gcggccgcgt tacgtggact tggtcttggc c 31

<210> SEQ ID NO 58
<211> LENGTH: 32
<212> TYPE: DNA
<213> ORGANISM: Artificial
<220> FEATURE:
<223> OTHER INFORMATION: Primer

<400> SEQUENCE: 58
gcggccgcgc catggaggtc gtggagagat tc 32

<210> SEQ ID NO 59
<211> LENGTH: 28
<212> TYPE: DNA
<213> ORGANISM: Artificial
<220> FEATURE:
<223> OTHER INFORMATION: Primer

<400> SEQUENCE: 59
gcggccgcgt cactcagttt tagctccc 28

<210> SEQ ID NO 60
<211> LENGTH: 31
<212> TYPE: DNA
<213> ORGANISM: Artificial
<220> FEATURE:
<223> OTHER INFORMATION: Primer

<400> SEQUENCE: 60
gcggccgcgc catggcttct acggctgtgc c 31

<210> SEQ ID NO 61
<211> LENGTH: 29
<212> TYPE: DNA
<213> ORGANISM: Artificial
<220> FEATURE:
<223> OTHER INFORMATION: Primer -continued

<400> SEQUENCE: 61
gcggccgcgt taggcggcgg gagggtcga 29

<210> SEQ ID NO 62
<211> LENGTH: 31
<212> TYPE: DNA
<213> ORGANISM: Artificial
<220> FEATURE:
<223> OTHER INFORMATION: Primer

<400> SEQUENCE: 62
gcggccgcgc catggctact cgacagcgta c 31

<210> SEQ ID NO 63
<211> LENGTH: 31
<212> TYPE: DNA
<213> ORGANISM: Artificial
<220> FEATURE:
<223> OTHER INFORMATION: Primer

<400> SEQUENCE: 63
gcggccgcgc tactccttgg cccatcgcat g 31

<210> SEQ ID NO 64
<211> LENGTH: 32
<212> TYPE: DNA
<213> ORGANISM: Artificial
<220> FEATURE:
<223> OTHER INFORMATION: Primer

<400> SEQUENCE: 64
gcggccgcgc catggctact accacgacgg tc 32

<210> SEQ ID NO 65
<211> LENGTH: 29
<212> TYPE: DNA
<213> ORGANISM: Artificial
<220> FEATURE:
<223> OTHER INFORMATION: Primer

<400> SEQUENCE: 65
gcggccgcgt cattgcgccc agtgcagag 29

<210> SEQ ID NO 66
<211> LENGTH: 32
<212> TYPE: DNA
<213> ORGANISM: Artificial
<220> FEATURE:
<223> OTHER INFORMATION: Primer

<400> SEQUENCE: 66
gcggccgcgc catgacggtg gcttcccagg tg 32

<210> SEQ ID NO 67
<211> LENGTH: 30
<212> TYPE: DNA
<213> ORGANISM: Artificial
<220> FEATURE:
<223> OTHER INFORMATION: Primer

<400> SEQUENCE: 67
gcggccgcgt tacctgtcct tgaaccaaag 30

<210> SEQ ID NO 68
<211> LENGTH: 32

<212> TYPE: DNA
<213> ORGANISM: Artificial
<220> FEATURE:
<223> OTHER INFORMATION: Primer

<400> SEQUENCE: 68
gcggccgcgc catgagcaga acagtcacat ta 32

<210> SEQ ID NO 69
<211> LENGTH: 29
<212> TYPE: DNA
<213> ORGANISM: Artificial
<220> FEATURE:
<223> OTHER INFORMATION: Primer

<400> SEQUENCE: 69
gcggccgcgt cacgcgctct taacatgcg 29

<210> SEQ ID NO 70
<211> LENGTH: 31
<212> TYPE: DNA
<213> ORGANISM: Artificial
<220> FEATURE:
<223> OTHER INFORMATION: Primer

<400> SEQUENCE: 70
gcggccgcgc catgagcacc accgccctct c 31

<210> SEQ ID NO 71
<211> LENGTH: 30
<212> TYPE: DNA
<213> ORGANISM: Artificial
<220> FEATURE:
<223> OTHER INFORMATION: Primer

<400> SEQUENCE: 71
gcggccgcgc tattcggaat catcctcaac 30

<210> SEQ ID NO 72
<211> LENGTH: 30
<212> TYPE: DNA
<213> ORGANISM: Artificial
<220> FEATURE:
<223> OTHER INFORMATION: Primer

<400> SEQUENCE: 72
gcggccgcgc catgtcagct gccacatcag 30

<210> SEQ ID NO 73
<211> LENGTH: 29
<212> TYPE: DNA
<213> ORGANISM: Artificial
<220> FEATURE:
<223> OTHER INFORMATION: Primer

<400> SEQUENCE: 73
gcggccgcgt taatgatccc accacaaaa 29

<210> SEQ ID NO 74
<211> LENGTH: 31
<212> TYPE: DNA
<213> ORGANISM: Artificial
<220> FEATURE:
<223> OTHER INFORMATION: Primer

<400> SEQUENCE: 74
gcggccgcgc catgtcggat aacactgaat c 31

<210> SEQ ID NO 75
<211> LENGTH: 29
<212> TYPE: DNA
<213> ORGANISM: Artificial
<220> FEATURE:
<223> OTHER INFORMATION: Primer

<400> SEQUENCE: 75
gcggccgcgt taattcttga ggaaacgaa 29

<210> SEQ ID NO 76
<211> LENGTH: 31
<212> TYPE: DNA
<213> ORGANISM: Artificial
<220> FEATURE:
<223> OTHER INFORMATION: Primer

<400> SEQUENCE: 76
gcggccgcgc catgccgccg tgtcacgcaa c 31

<210> SEQ ID NO 77
<211> LENGTH: 30
<212> TYPE: DNA
<213> ORGANISM: Artificial
<220> FEATURE:
<223> OTHER INFORMATION: Primer

<400> SEQUENCE: 77
gcggccgcgt tagtcctttt cacagttttc 30

<210> SEQ ID NO 78
<211> LENGTH: 32
<212> TYPE: DNA
<213> ORGANISM: Artificial
<220> FEATURE:
<223> OTHER INFORMATION: Primer

<400> SEQUENCE: 78
gcggccgcgc catgagcgcc tccggtgcgc tg 32

<210> SEQ ID NO 79
<211> LENGTH: 23
<212> TYPE: DNA
<213> ORGANISM: Artificial
<220> FEATURE:
<223> OTHER INFORMATION: Primer

<400> SEQUENCE: 79
gcggccgcgt tagtcaattt ttc 23

<210> SEQ ID NO 80
<211> LENGTH: 32
<212> TYPE: DNA
<213> ORGANISM: Artificial
<220> FEATURE:
<223> OTHER INFORMATION: Primer

<400> SEQUENCE: 80
gcggccgcgc catgacggtc ggctacgacg ag 32

<210> SEQ ID NO 81
<211> LENGTH: 29
<212> TYPE: DNA
<213> ORGANISM: Artificial

<220> FEATURE:
<223> OTHER INFORMATION: Primer

<400> SEQUENCE: 81
gcggccgcgt caggcagcgc gctgccagg 29

<210> SEQ ID NO 82
<211> LENGTH: 60
<212> TYPE: DNA
<213> ORGANISM: Artificial
<220> FEATURE:
<223> OTHER INFORMATION: Sequencing Primer

<400> SEQUENCE: 82
gtcgacccgc ggactagtgg gccctctaga cccgggggat ccggatctgc tggctatgaa 60

<210> SEQ ID NO 83
<211> LENGTH: 9
<212> TYPE: PRT
<213> ORGANISM: Artificial
<220> FEATURE:
<223> OTHER INFORMATION: Desaturase Motif 1
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 83

Leu Xaa Xaa Ile Thr Xaa Leu Xaa His
1 5

<210> SEQ ID NO 84
<211> LENGTH: 8
<212> TYPE: PRT
<213> ORGANISM: Artificial
<220> FEATURE:
<223> OTHER INFORMATION: Desaturase Motif 2
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 84

Gly Ala Xaa Xaa Thr Xaa Asp Arg
1 5

<210> SEQ ID NO 85
<211> LENGTH: 5
<212> TYPE: PRT
<213> ORGANISM: Artificial
<220> FEATURE:
<223> OTHER INFORMATION: Desaturase Motif 3
<220> FEATURE:
<221> NAME/KEY: misc_feature
<222> LOCATION: (3)..(3)
<223> OTHER INFORMATION: Xaa can be any naturally occurring amino acid

<400> SEQUENCE: 85

-continued

```
His Val Xaa His His
1               5


<210> SEQ ID NO 86
<211> LENGTH: 29
<212> TYPE: DNA
<213> ORGANISM: Artificial
<220> FEATURE:
<223> OTHER INFORMATION: Primer

<400> SEQUENCE: 86

gcggccgcgc catggctgtt aaaacggac                                        29


<210> SEQ ID NO 87
<211> LENGTH: 29
<212> TYPE: DNA
<213> ORGANISM: Artificial
<220> FEATURE:
<223> OTHER INFORMATION: Primer

<400> SEQUENCE: 87

gcggccgcgc tatttttcaa cctcaatac                                        29


<210> SEQ ID NO 88
<211> LENGTH: 18
<212> TYPE: DNA
<213> ORGANISM: Artificial
<220> FEATURE:
<223> OTHER INFORMATION: Primer

<400> SEQUENCE: 88

atggctgtta aaacggac                                                    18


<210> SEQ ID NO 89
<211> LENGTH: 20
<212> TYPE: DNA
<213> ORGANISM: Artificial
<220> FEATURE:
<223> OTHER INFORMATION: Primer

<400> SEQUENCE: 89

ctatttttca acctcaatac                                                  20


<210> SEQ ID NO 90
<211> LENGTH: 2336
<212> TYPE: DNA
<213> ORGANISM: Laccaria bicolor

<400> SEQUENCE: 90

tttttctttt ctgtgggtcg tgtctgggat ttgggcgaag gctgggcaaa cttacgagtt      60

cataaatagc tcaaatacaa ttggcagttg gaatgccaag aaaatgatcc ccaggcgaaa     120

aaaaaaaaaa aaagactcgg caaactccgt ccaacccccca gaaaatgtag acgctaaaat    180

ccaatcgccg ctgtttacgt ctcttcgctc ttgccctctt aagtatacca caaggttccc     240

tcgccggtac ctacgttctc tcctttcaat ggctgttaaa acggacaaaa acggcgtcac     300

cgtcgtcgag caaggggtct acaacgttcc cgacatccct atcaaggatt tactcgacgc     360

tattccgtta gtcctctttg ttcttcatct cgctggcact aagttgtcca accaattagc     420

aaacactgct tccagcgttc tgctttgagg tcgtccgtct acatgtgcgt tcttttcctt     480

tccagacgtg caacgcacgt ggctcattgc tcgttccttt tccagtttct gggatatctt     540

cgttattggg tgcatctaca agactgcaag ttacctggac acgttcatca atcccgccac     600
```

```
tatatccctt ccccatcctt acctttatcc ttttgctcga ttcgctctct ggtcgttgta    660
cggtttctgg gttggcctct ttgcgacagg tctctgggtt gttgcccacg aatgtggtca    720
ccaggctttc tcagagtcaa aaaccatcaa caatacagtt ggctgggtcc ttcactcggc    780
gtaggtcgat cggcaattaa ttttcgtgtc actgctaacg tggcatgtga tttcagctta    840
ggggttccat accaagcttg gcgtatcacc cacgcaaagc atcacgcctc taccggccat    900
atgactcagg atcaggtctt cgtgccctct acccgctcag atgttggcct ccctagcctc    960
aacgtcgcaa aagaagaccg attgggttca cgtgtatcgg aggaagtgaa aagggaattc   1020
aaagaagcat taggcgattc gccgattggc gcaatcattg gttcggcaac ctacttggtc   1080
agttcgcgtc tggtttcgcg cactaactgt gtctgacgtg ttcttcactt ttaaaagctc   1140
ggaggatggc ccgcatatat ccttaccaac gcttctggcc agcgcagata ccccaaaggc   1200
accagtcgta cgtatcatca gcgacctgtt ggagggactg gttctcaatc ttgtcttaca   1260
gactttaatc ccaaggctgt gatgttctca ccccatcatt actcccagat cattgtttct   1320
aacatcggag tcgcactctg gttgggcatc attggtacat ggatatacta caagggcttt   1380
tcggaggtct tccgccttta cctcgtccct tacctttggt acattctcat caatcaaagg   1440
aagaatatca gttgattgac atttttttaac agggccaatc actggcttgt gttgatcacc   1500
ttcctccaac ataccgaccc tctcctcccc cattaccgtg cccctgagtt cacattccct   1560
cgtggtgctt tggccactct ggatcgcagc cttcttggag actgtggctc tatcatggcg   1620
tggatgggcg cacacgccac acatggtatt tctgagacgc atatccttca tcacgtttcg   1680
agcaagattc ctcattataa tgcgtaagtg ccagagttct accagttgtt ctatgccata   1740
atgttcttct tgtcagttgg gaagcgagtg cggccctcaa gaagaaactt gctagcgcag   1800
gtatcccgat gcaaggtggc cctggtggct ggcgtgaagt ttaccgcgtc tacagggaat   1860
gcaaggtttg tctcatgctt ccagtgttgg acctcttcta acgtatttga tagtttgttg   1920
aggatgaggg tgatgttgtc ttcttcaaaa actccgaagg catcgccaag atgaggccgg   1980
tcctccctga gtcgtccgca agtgactctg gtattgaggt tgaaaaatag atagagagtt   2040
agatttaacc atctagattc acctgccgtc gcctgcgctg taacatagag tggttggatt   2100
tgtcgcaaac ccctaatgag atttttcttg gatgatatct cgatgaatcc gaacgactag   2160
acaagaaacc tgctccacta tgggcatgct tgcaaattca tttattttga aatgatttat   2220
cttacaagaa cgcagattaa atcctactct ctttgacagt ttccttccaa atttctgcaa   2280
attcttcgat gttccgtcca tttcctaagc tgagagcctc gaatgggatc atattg       2336
```

```
<210> SEQ ID NO 91
<211> LENGTH: 1323
<212> TYPE: DNA
<213> ORGANISM: Laccaria bicolor

<400> SEQUENCE: 91
```

```
atggctgtta aaacggacaa aaacggcgtc accgtcgtcg agcaaggggt ctacaacgtt     60
cccgacatcc ctatcaagga tttactcgac gctattccca aacactgctt ccagcgttct    120
gctttgaggt cgtccgtcta cattttctgg gatatcttcg ttattgggtg catctacaag    180
actgcaagtt acctggacac gttcatcaat cccgccacta tatcccttcc ccatccttac    240
ctttatcctt ttgctcgatt cgctctctgg tcgttgtacg gtttctgggt tggcctcttt    300
gcgacaggtc tctgggttgt tgcccacgaa tgtggtcacc aggctttctc agagtcaaaa    360
accatcaaca atacagttgg ctgggtcctt cactcggcct taggggttcc ataccaagct    420
```

```
tggcgtatca cccacgcaaa gcatcacgcc tctaccggcc atatgactca ggatcaggtc    480

ttcgtgccct ctacccgctc agatgttggc ctccctagcc tcaacgtcgc aaaagaagac    540

cgattgggtt cacgtgtatc ggaggaagtg aaaagggaat tcaaagaagc attaggcgat    600

tcgccgattg gcgcaatcat tggttcggca acctacttgc tcggaggatg gcccgcatat    660

atccttacca acgcttctgg ccagcgcaga taccccaaag gcaccagtca ctttaatccc    720

aaggctgtga tgttctcacc ccatcattac tcccagatca ttgtttctaa catcggagtc    780

gcactctggt tgggcatcat tggtacatgg atatactaca agggcttttc ggaggtcttc    840

cgcctttacc tcgtccctta cctttgggcc aatcactggc ttgtgttgat caccttcctc    900

caacataccg accctctcct cccccattac cgtgcccctg agttcacatt ccctcgtggt    960

gctttggcca ctctggatcg cagccttctt ggagactgtg gctctatcat ggcgtggatg   1020

ggcgcacacg ccacacacgg tatttctgag acgcacatcc ttcaccacgt ttcgagcaag   1080

attcctcact ataatgcttg ggaagcgagt gcggccctca agaagaaact tgctagcgca   1140

ggtatcccga tgcaaggtgg ccctggtggc tggcgtgaag tttaccgcgt ctacagggaa   1200

tgcaagtttg ttgaggatga gggtgatgtt gtcttcttca aaaactccga aggcatcgcc   1260

aagatgaggc cggtcctccc tgagtcgtcc gcaagtgact ctggtattga ggttgaaaaa   1320

tag                                                                 1323


<210> SEQ ID NO 92
<211> LENGTH: 440
<212> TYPE: PRT
<213> ORGANISM: Laccaria bicolor

<400> SEQUENCE: 92

Met Ala Val Lys Thr Asp Lys Asn Gly Val Thr Val Val Glu Gln Gly
1               5                   10                  15

Val Tyr Asn Val Pro Asp Ile Pro Ile Lys Asp Leu Leu Asp Ala Ile
            20                  25                  30

Pro Lys His Cys Phe Gln Arg Ser Ala Leu Arg Ser Ser Val Tyr Ile
        35                  40                  45

Phe Trp Asp Ile Phe Val Ile Gly Cys Ile Tyr Lys Thr Ala Ser Tyr
    50                  55                  60

Leu Asp Thr Phe Ile Asn Pro Ala Thr Ile Ser Leu Pro His Pro Tyr
65                  70                  75                  80

Leu Tyr Pro Phe Ala Arg Phe Ala Leu Trp Ser Leu Tyr Gly Phe Trp
                85                  90                  95

Val Gly Leu Phe Ala Thr Gly Leu Trp Val Val Ala His Glu Cys Gly
            100                 105                 110

His Gln Ala Phe Ser Glu Ser Lys Thr Ile Asn Asn Thr Val Gly Trp
        115                 120                 125

Val Leu His Ser Ala Leu Gly Val Pro Tyr Gln Ala Trp Arg Ile Thr
    130                 135                 140

His Ala Lys His His Ala Ser Thr Gly His Met Thr Gln Asp Gln Val
145                 150                 155                 160

Phe Val Pro Ser Thr Arg Ser Asp Val Gly Leu Pro Ser Leu Asn Val
                165                 170                 175

Ala Lys Glu Asp Arg Leu Gly Ser Arg Val Ser Glu Glu Val Lys Arg
            180                 185                 190

Glu Phe Lys Glu Ala Leu Gly Asp Ser Pro Ile Gly Ala Ile Ile Gly
        195                 200                 205
```

```
Ser Ala Thr Tyr Leu Leu Gly Gly Trp Pro Ala Tyr Ile Leu Thr Asn
    210                 215                 220

Ala Ser Gly Gln Arg Arg Tyr Pro Lys Gly Thr Ser His Phe Asn Pro
225                 230                 235                 240

Lys Ala Val Met Phe Ser Pro His His Tyr Ser Gln Ile Ile Val Ser
                245                 250                 255

Asn Ile Gly Val Ala Leu Trp Leu Gly Ile Ile Gly Thr Trp Ile Tyr
            260                 265                 270

Tyr Lys Gly Phe Ser Glu Val Phe Arg Leu Tyr Leu Val Pro Tyr Leu
        275                 280                 285

Trp Ala Asn His Trp Leu Val Leu Ile Thr Phe Leu Gln His Thr Asp
    290                 295                 300

Pro Leu Leu Pro His Tyr Arg Ala Pro Glu Phe Thr Phe Pro Arg Gly
305                 310                 315                 320

Ala Leu Ala Thr Leu Asp Arg Ser Leu Leu Gly Asp Cys Gly Ser Ile
                325                 330                 335

Met Ala Trp Met Gly Ala His Ala Thr His Gly Ile Ser Glu Thr His
            340                 345                 350

Ile Leu His His Val Ser Ser Lys Ile Pro His Tyr Asn Ala Trp Glu
        355                 360                 365

Ala Ser Ala Ala Leu Lys Lys Lys Leu Ala Ser Ala Gly Ile Pro Met
    370                 375                 380

Gln Gly Gly Pro Gly Gly Trp Arg Glu Val Tyr Arg Val Tyr Arg Glu
385                 390                 395                 400

Cys Lys Phe Val Glu Asp Glu Gly Asp Val Val Phe Phe Lys Asn Ser
                405                 410                 415

Glu Gly Ile Ala Lys Met Arg Pro Val Leu Pro Glu Ser Ser Ala Ser
            420                 425                 430

Asp Ser Gly Ile Glu Val Glu Lys
        435                 440
```

<210> SEQ ID NO 93
<211> LENGTH: 19
<212> TYPE: DNA
<213> ORGANISM: Artificial
<220> FEATURE:
<223> OTHER INFORMATION: Primer

<400> SEQUENCE: 93
atgaactgtg taactgagg 19

<210> SEQ ID NO 94
<211> LENGTH: 21
<212> TYPE: DNA
<213> ORGANISM: Artificial
<220> FEATURE:
<223> OTHER INFORMATION: Primer

<400> SEQUENCE: 94
tatttgtaat aaacctctaa c 21

<210> SEQ ID NO 95
<211> LENGTH: 20
<212> TYPE: DNA
<213> ORGANISM: Artificial
<220> FEATURE:
<223> OTHER INFORMATION: Primer

<400> SEQUENCE: 95
atggaaacca aatcaggaag 20

<210> SEQ ID NO 96
<211> LENGTH: 18
<212> TYPE: DNA
<213> ORGANISM: Artificial
<220> FEATURE:
<223> OTHER INFORMATION: Primer

<400> SEQUENCE: 96
ttatgtataa atatgtac 18

<210> SEQ ID NO 97
<211> LENGTH: 21
<212> TYPE: DNA
<213> ORGANISM: Artificial
<220> FEATURE:
<223> OTHER INFORMATION: Primer

<400> SEQUENCE: 97
atgaatgaag ccaataacca c 21

<210> SEQ ID NO 98
<211> LENGTH: 22
<212> TYPE: DNA
<213> ORGANISM: Artificial
<220> FEATURE:
<223> OTHER INFORMATION: Primer

<400> SEQUENCE: 98
ttatttatag taatgaattt tg 22

<210> SEQ ID NO 99
<211> LENGTH: 19
<212> TYPE: DNA
<213> ORGANISM: Artificial
<220> FEATURE:
<223> OTHER INFORMATION: Primer

<400> SEQUENCE: 99
atgcaatcaa acacagttc 19

<210> SEQ ID NO 100
<211> LENGTH: 22
<212> TYPE: DNA
<213> ORGANISM: Artificial
<220> FEATURE:
<223> OTHER INFORMATION: Primer

<400> SEQUENCE: 100
ttagtttgat cgcggatgtt tg 22

<210> SEQ ID NO 101
<211> LENGTH: 22
<212> TYPE: DNA
<213> ORGANISM: Artificial
<220> FEATURE:
<223> OTHER INFORMATION: Primer

<400> SEQUENCE: 101
atgtttctcg ccggaagtga tg 22

<210> SEQ ID NO 102
<211> LENGTH: 20
<212> TYPE: DNA

<213> ORGANISM: Artificial
<220> FEATURE:
<223> OTHER INFORMATION: Primer

<400> SEQUENCE: 102
tcaggctcct agatctttcc 20

<210> SEQ ID NO 103
<211> LENGTH: 30
<212> TYPE: DNA
<213> ORGANISM: Artificial
<220> FEATURE:
<223> OTHER INFORMATION: Primer

<400> SEQUENCE: 103
gcggccgcgc catgaactgt gtaactgagg 30

<210> SEQ ID NO 104
<211> LENGTH: 30
<212> TYPE: DNA
<213> ORGANISM: Artificial
<220> FEATURE:
<223> OTHER INFORMATION: Primer

<400> SEQUENCE: 104
gcggccgcgt atttgtaata aacctctaac 30

<210> SEQ ID NO 105
<211> LENGTH: 31
<212> TYPE: DNA
<213> ORGANISM: Artificial
<220> FEATURE:
<223> OTHER INFORMATION: Primer

<400> SEQUENCE: 105
gcggccgcgc catggaaacc aaatcaggaa g 31

<210> SEQ ID NO 106
<211> LENGTH: 27
<212> TYPE: DNA
<213> ORGANISM: Artificial
<220> FEATURE:
<223> OTHER INFORMATION: Primer

<400> SEQUENCE: 106
gcggccgcgt tatgtataaa tatgtac 27

<210> SEQ ID NO 107
<211> LENGTH: 32
<212> TYPE: DNA
<213> ORGANISM: artificial
<220> FEATURE:
<223> OTHER INFORMATION: Primer

<400> SEQUENCE: 107
gcggccgcgc catgaatgaa gccaataacc ac 32

<210> SEQ ID NO 108
<211> LENGTH: 31
<212> TYPE: DNA
<213> ORGANISM: Artificial
<220> FEATURE:
<223> OTHER INFORMATION: Primer

<400> SEQUENCE: 108
gcggccgcgt tatttatagt aatgaatttt g 31

<210> SEQ ID NO 109
<211> LENGTH: 30
<212> TYPE: DNA
<213> ORGANISM: Artificial
<220> FEATURE:
<223> OTHER INFORMATION: Primer

<400> SEQUENCE: 109
gcggccgcgc catgcaatca aacacagttc 30

<210> SEQ ID NO 110
<211> LENGTH: 31
<212> TYPE: DNA
<213> ORGANISM: Artificial
<220> FEATURE:
<223> OTHER INFORMATION: Primer

<400> SEQUENCE: 110
gcggccgcgt tagtttgatc gcggatgttt g 31

<210> SEQ ID NO 111
<211> LENGTH: 33
<212> TYPE: DNA
<213> ORGANISM: Artificial
<220> FEATURE:
<223> OTHER INFORMATION: Primer

<400> SEQUENCE: 111
gcggccgcgc catgtttctc gccggaagtg atg 33

<210> SEQ ID NO 112
<211> LENGTH: 29
<212> TYPE: DNA
<213> ORGANISM: Artificial
<220> FEATURE:
<223> OTHER INFORMATION: Primer

<400> SEQUENCE: 112
gcggccgcgt caggctccta gatctttcc 29

<210> SEQ ID NO 113
<211> LENGTH: 7
<212> TYPE: PRT
<213> ORGANISM: Artificial
<220> FEATURE:
<223> OTHER INFORMATION: Desaturase motif 4
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 113

Thr Xaa Xaa Gln His Xaa Xaa
1               5

<210> SEQ ID NO 114
<211> LENGTH: 7
<212> TYPE: PRT
<213> ORGANISM: Artificial
<220> FEATURE:
<223> OTHER INFORMATION: Desaturase motif 5
<220> FEATURE:
<221> NAME/KEY: Variant
<222> LOCATION: (2)..(2)
<223> OTHER INFORMATION: Xaa in position 2 is Tyr or Phe
<220> FEATURE:
<221> NAME/KEY: Variant
<222> LOCATION: (3)..(3)
<223> OTHER INFORMATION: Xaa in position 3 is Leu or Met
<220> FEATURE:
<221> NAME/KEY: Variant
<222> LOCATION: (6)..(6)
<223> OTHER INFORMATION: Xaa in position 6 is Thr or Ser or Gln
<220> FEATURE:
<221> NAME/KEY: Variant
<222> LOCATION: (7)..(7)
<223> OTHER INFORMATION: Xaa in position 7 is Asp or His or Asn

<400> SEQUENCE: 114

Thr Xaa Xaa Gln His Xaa Xaa
1               5

<210> SEQ ID NO 115
<211> LENGTH: 7
<212> TYPE: PRT
<213> ORGANISM: Artificial
<220> FEATURE:
<223> OTHER INFORMATION: Desaturase motif 6
<220> FEATURE:
<221> NAME/KEY: Variant
<222> LOCATION: (2)..(2)
<223> OTHER INFORMATION: Xaa in position 2 is Tyr or Phe
<220> FEATURE:
<221> NAME/KEY: Variant
<222> LOCATION: (6)..(6)
<223> OTHER INFORMATION: Xaa in position 6 is Thr or Ser
<220> FEATURE:
<221> NAME/KEY: Variant
<222> LOCATION: (7)..(7)
<223> OTHER INFORMATION: Xaa in position 7 is Asp or His

<400> SEQUENCE: 115

Thr Xaa Leu Gln His Xaa Xaa
1               5

<210> SEQ ID NO 116
<211> LENGTH: 9
<212> TYPE: PRT
<213> ORGANISM: Artificial
<220> FEATURE:
<223> OTHER INFORMATION: Desaturase motif 7
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: Variant
<222> LOCATION: (7)..(7)
<223> OTHER INFORMATION: Xaa in position 7 is Gly or no amino acid
<220> FEATURE:
<221> NAME/KEY: Variant
<222> LOCATION: (8)..(8)
<223> OTHER INFORMATION: Xaa in position 8 can be any naturally
      occurring amino acid or no amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 116

Thr Xaa Xaa His His Xaa Xaa Xaa Xaa
1               5

<210> SEQ ID NO 117
<211> LENGTH: 9
<212> TYPE: PRT
<213> ORGANISM: Artificial
<220> FEATURE:
<223> OTHER INFORMATION: Desaturase motif 8
<220> FEATURE:
<221> NAME/KEY: Variant
<222> LOCATION: (2)..(2)
<223> OTHER INFORMATION: Xaa in position 3 is Tyr or Phe
<220> FEATURE:
<221> NAME/KEY: Variant
<222> LOCATION: (3)..(3)
<223> OTHER INFORMATION: Xaa in position 3 is Leu or Met
<220> FEATURE:
<221> NAME/KEY: Variant
<222> LOCATION: (6)..(6)
<223> OTHER INFORMATION: Xaa in position 6 is His or Thr or Ser or Val
<220> FEATURE:
<221> NAME/KEY: Variant
<222> LOCATION: (7)..(7)
<223> OTHER INFORMATION: Xaa in position 7 is Gly or no amino acid
<220> FEATURE:
<221> NAME/KEY: Variant
<222> LOCATION: (8)..(8)
<223> OTHER INFORMATION: Xaa in position 8 is His or Tyr or no amino
      acid
<220> FEATURE:
<221> NAME/KEY: Variant
<222> LOCATION: (9)..(9)
<223> OTHER INFORMATION: Xaa in position 9 is His or Asp or Glu or Gly

<400> SEQUENCE: 117

Thr Xaa Xaa His His Xaa Xaa Xaa Xaa
1               5

<210> SEQ ID NO 118
<211> LENGTH: 7
<212> TYPE: PRT
<213> ORGANISM: Artificial
<220> FEATURE:
<223> OTHER INFORMATION: Desaturase motif 9
<220> FEATURE:
<221> NAME/KEY: Variant
<222> LOCATION: (2)..(2)
<223> OTHER INFORMATION: Xaa in position 2 is Tyr or Phe
<220> FEATURE:
<221> NAME/KEY: Variant
<222> LOCATION: (3)..(3)
<223> OTHER INFORMATION: Xaa in position 3 is Leu or Met
<220> FEATURE:
<221> NAME/KEY: Variant
<222> LOCATION: (6)..(6)
<223> OTHER INFORMATION: Xaa in position 6 is His or Thr or Ser
<220> FEATURE:
<221> NAME/KEY: Variant
<222> LOCATION: (7)..(7)
<223> OTHER INFORMATION: Xaa in position 7 is His or Asp or Glu

<400> SEQUENCE: 118

Thr Xaa Xaa His His Xaa Xaa
1               5

<210> SEQ ID NO 119
<211> LENGTH: 9
<212> TYPE: PRT
<213> ORGANISM: Artificial
<220> FEATURE:
<223> OTHER INFORMATION: Desaturase motif 10
<220> FEATURE:
<221> NAME/KEY: Variant
<222> LOCATION: (2)..(2)
<223> OTHER INFORMATION: Xaa in position 2 is Tyr or Phe
<220> FEATURE:

<221> NAME/KEY: Variant
<222> LOCATION: (3)..(3)
<223> OTHER INFORMATION: Xaa in position 3 is Leu or Met
<220> FEATURE:
<221> NAME/KEY: Variant
<222> LOCATION: (6)..(6)
<223> OTHER INFORMATION: Xaa in position 6 is His or Thr or Ser or Val
<220> FEATURE:
<221> NAME/KEY: Variant
<222> LOCATION: (8)..(8)
<223> OTHER INFORMATION: Xaa in position 8 is His or Tyr
<220> FEATURE:
<221> NAME/KEY: Variant
<222> LOCATION: (9)..(9)
<223> OTHER INFORMATION: Xaa in position 9 is His or Asp or Glu or Gly

<400> SEQUENCE: 119

Thr Xaa Xaa His His Xaa Gly Xaa Xaa
1               5

<210> SEQ ID NO 120
<211> LENGTH: 7
<212> TYPE: PRT
<213> ORGANISM: Artificial
<220> FEATURE:
<223> OTHER INFORMATION: Desaturase motif 11
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 120

Thr Xaa Xaa His His Asn Xaa
1               5

<210> SEQ ID NO 121
<211> LENGTH: 7
<212> TYPE: PRT
<213> ORGANISM: Artificial
<220> FEATURE:
<223> OTHER INFORMATION: Desaturase motif 12
<220> FEATURE:
<221> NAME/KEY: Variant
<222> LOCATION: (2)..(2)
<223> OTHER INFORMATION: Xaa in position 2 is Tyr or Phe
<220> FEATURE:
<221> NAME/KEY: Variant
<222> LOCATION: (3)..(3)
<223> OTHER INFORMATION: Xaa in position 3 is Leu or Met
<220> FEATURE:
<221> NAME/KEY: Variant
<222> LOCATION: (7)..(7)
<223> OTHER INFORMATION: Xaa in position 7 is His or Asp or Glu or Gly

<400> SEQUENCE: 121

Thr Xaa Xaa His His Asn Xaa
1               5

<210> SEQ ID NO 122
<211> LENGTH: 1975
<212> TYPE: DNA
<213> ORGANISM: Helobdella robusta

<400> SEQUENCE: 122
attacaaaac tcttcttaaa agagccgttg atatgataca aaagttttca tacatatttt      60
tcctctgtta atttataaac agttgttaat tgacgttcaa taatagttac tataaaaaga     120

-continued

```
attaatttg aaacaatcct ataaaaatct gcaaacttac ccaagccctc tgttaaatga    180

tgttcccact gagcgatcta atgaactgtg taactgaggt taactccata atagcaagcc    240

taataaaagc agcgttcctg tattcaaacc cgcaaactaa aatccgagga ataaacctgg    300

acacccaact accaaaaaat ctgccatcag tcattgagat caagcgagtg ataccaagcc    360

actgttttgt gccgagcacc tgccgatctc ttttgtacgc cctgaaggat gtggtgcaga    420

tattatttgc ctgggtgctg ttgtggtacc tcctacccct gaccaattgg attgcgttga    480

aggttttgat gattttcgtc tactggggta ttcaggggac ttttttcatg ggcctgtttg    540

tgatggggca tgattgcggg catgggtcgt tctccaagta tcgtctgctt aatgatgtcg    600

tagggaccat cagccacgct ttcctgttcg tcccttacta ccagtggaag ctcacccatc    660

agaaccacca caaattcacc gggaatatgg acaaggatga ggtgagtttg cagtgttgct    720

gacacgattg ttgtgaacaa tttcttcatt ttttttcttt gcgttatttg atgtgacgta    780

gttgaagatt ggtttcatta aaaaacatga cgcacaggcg aaataatatg tttgaagtat    840

aaaaatgatt attataacca tttataattg tttataatta ttataaatat tataattatt    900

gataatttcc aggtcttcta cccagcccga gcttcgcaga agccgagcat caacagcgtc    960

ctccctggct ttggctacgg aatcggttgg ttcacgtacc tcttcattgg ctactttcca   1020

cgaagggtca gccatttcaa tttgtttgac gagatgttca ggggccacga agttgcttgc   1080

accctctcgt tgctcactta cgggatgaac gggactctct gctactggtt ttatttgagt   1140

tacggattca agattctctt cgttttctac ctagcaccgc ttttcattta tgggagttat   1200

atggttatcg ttaccttttt gcaccacagt gaagtcaata ttccttggta tgctgatcaa   1260

aagttagtcg ctctcttcag tcattcattt caatttgttc aaattattca cattttaaaa   1320

attttaagaa ttatttaaaa agcaatttca aagaaaaaat ttttttacat taaacaacaa   1380

ctgaaactta aaatcaactt caactacaca tacttactca ctaaaaaaac accacaaaac   1440

cgccacgaaa ccaccaaaaa tccacccacc acaaaattaa aaaaaaaatc ttgcccagct   1500

ggaactacgt aaaaggtcaa ctctcaacca ttgaccgtaa ctacgggctg gtccaccacg   1560

caatccactg cataggcacc caccaaatgc accacatgtt caccaaaata ccccactacc   1620

acctcgagga ggccaccaga cattttagga gtgctttccc ggagttagtg aaatcctgcg   1680

acgagcccat actttcgtca ttcgtacgca tgttcaagaa gtacaatcag cagcaggtgg   1740

tcgctgataa cgcgttagag gtttattaca aataaataat aataaatatt attattatat   1800

tatttattta ttactattat tattattatc gttattatta ctattattat taatactatc   1860

attattgtta ttattattat tattttaata attttggctg cgggcattta cgattacaga   1920

aagctttaca tcttcttttc agacttattg tgatatataa atgaaattat tactt        1975
```

<210> SEQ ID NO 123
<211> LENGTH: 1128
<212> TYPE: DNA
<213> ORGANISM: Helobdella robusta

<400> SEQUENCE: 123

```
atgaactgtg taactgaggt taactccata atagcaagcc taataaaagc agcgttcctg     60

tattcaaacc cgcaaactaa aatccgagga ataaacctgg acacccaact accaaaaaat    120

ctgccatcag tcattgagat caagcgagtg ataccaagcc actgttttgt gccgagcacc    180

tgccgatctc ttttgtacgc cctgaaggat gtggtgcaga tattatttgc ctgggtgctg    240

ttgtggtacc tcctacccct gaccaattgg attgcgttga aggttttgat gattttcgtc    300
```

-continued

```
tactggggta ttcaggggac ttttttcatg ggcctgtttg tgatggggca tgattgcggg    360

catgggtcgt tctccaagta tcgtctgctt aatgatgtcg tagggaccat cagccacgct    420

ttcctgttcg tcccttacta ccagtggaag ctcacccatc agaaccacca caaattcacc    480

gggaatatgg acaaggatga ggtcttctac ccagcccgag cttcgcagaa gccgagcatc    540

aacagcgtcc tccctggctt tggctacgga atcggttggt tcacgtacct cttcattggc    600

tactttccac gaagggtcag ccatttcaat ttgtttgacg agatgttcag ggccacgaa     660

gttgcttgca ccctctcgtt gctcacttac gggatgaacg ggactctctg ctactggttt    720

tatttgagtt acggattcaa gattctcttc gttttctacc tagcaccgct tttcatttat    780

gggagttata tggttatcgt taccttttg caccacagtg aagtcaatat tccttggtat     840

gctgatcaaa actggaacta cgtaaaaggt caactctcaa ccattgaccg taactacggg    900

ctggtccacc acgcaatcca ctgcataggc acccaccaaa tgcaccacat gttcaccaaa    960

ataccccact accacctcga ggaggccacc agacatttta ggagtgcttt cccggagtta   1020

gtgaaatcct gcgacgagcc catactttcg tcattcgtac gcatgttcaa gaagtacaat   1080

cagcagcagg tggtcgctga taacgcgtta gaggtttatt acaaataa                1128


<210> SEQ ID NO 124
<211> LENGTH: 375
<212> TYPE: PRT
<213> ORGANISM: Helobdella robusta

<400> SEQUENCE: 124

Met Asn Cys Val Thr Glu Val Asn Ser Ile Ile Ala Ser Leu Ile Lys
1               5                   10                  15

Ala Ala Phe Leu Tyr Ser Asn Pro Gln Thr Lys Ile Arg Gly Ile Asn
            20                  25                  30

Leu Asp Thr Gln Leu Pro Lys Asn Leu Pro Ser Val Ile Glu Ile Lys
        35                  40                  45

Arg Val Ile Pro Ser His Cys Phe Val Pro Ser Thr Cys Arg Ser Leu
    50                  55                  60

Leu Tyr Ala Leu Lys Asp Val Val Gln Ile Leu Phe Ala Trp Val Leu
65                  70                  75                  80

Leu Trp Tyr Leu Leu Pro Leu Thr Asn Trp Ile Ala Leu Lys Val Leu
                85                  90                  95

Met Ile Phe Val Tyr Trp Gly Ile Gln Gly Thr Phe Phe Met Gly Leu
            100                 105                 110

Phe Val Met Gly His Asp Cys Gly His Gly Ser Phe Ser Lys Tyr Arg
        115                 120                 125

Leu Leu Asn Asp Val Val Gly Thr Ile Ser His Ala Phe Leu Phe Val
    130                 135                 140

Pro Tyr Tyr Gln Trp Lys Leu Thr His Gln Asn His His Lys Phe Thr
145                 150                 155                 160

Gly Asn Met Asp Lys Asp Glu Val Phe Tyr Pro Ala Arg Ala Ser Gln
                165                 170                 175

Lys Pro Ser Ile Asn Ser Val Leu Pro Gly Phe Gly Tyr Gly Ile Gly
            180                 185                 190

Trp Phe Thr Tyr Leu Phe Ile Gly Tyr Phe Pro Arg Arg Val Ser His
        195                 200                 205

Phe Asn Leu Phe Asp Glu Met Phe Arg Gly His Glu Val Ala Cys Thr
    210                 215                 220
```

```
Leu Ser Leu Leu Thr Tyr Gly Met Asn Gly Thr Leu Cys Tyr Trp Phe
225                 230                 235                 240

Tyr Leu Ser Tyr Gly Phe Lys Ile Leu Phe Val Phe Tyr Leu Ala Pro
                245                 250                 255

Leu Phe Ile Tyr Gly Ser Tyr Met Val Ile Val Thr Phe Leu His His
            260                 265                 270

Ser Glu Val Asn Ile Pro Trp Tyr Ala Asp Gln Asn Trp Asn Tyr Val
        275                 280                 285

Lys Gly Gln Leu Ser Thr Ile Asp Arg Asn Tyr Gly Leu Val His His
    290                 295                 300

Ala Ile His Cys Ile Gly Thr His Gln Met His His Met Phe Thr Lys
305                 310                 315                 320

Ile Pro His Tyr His Leu Glu Glu Ala Thr Arg His Phe Arg Ser Ala
                325                 330                 335

Phe Pro Glu Leu Val Lys Ser Cys Asp Glu Pro Ile Leu Ser Ser Phe
            340                 345                 350

Val Arg Met Phe Lys Lys Tyr Asn Gln Gln Gln Val Val Ala Asp Asn
        355                 360                 365

Ala Leu Glu Val Tyr Tyr Lys
    370                 375


<210> SEQ ID NO 125
<211> LENGTH: 1390
<212> TYPE: DNA
<213> ORGANISM: Lottia gigantea

<400> SEQUENCE: 125

taatccattg ttattttttc taatttcaga atatggaaac caaatcagga agtcgtttga     60

agtcattttg gttatttttg gccaaaatag ccttggtaac attagtacaa gaagaatcaa    120

ccaaaacaga ggaacaagaa aatacagtca cggctgtttc acaagagact gatgagttat    180

ccaagaccca tctgccaaat gaacttccaa ccataataga cattaaaaga gcaattccta    240

gtcactgctt tcagtccaat gttatcacct caatgtacca tgcgatgaag gacgtcgtat    300

tcgtcatagg actttacatt ttgggagagc ttctgttgac gtatcttcct ttctgggcag    360

ttctagtcac agcaccagtg ttttggtttg ctcagggaac aatgtttaca gcactattcg    420

tgattggtca tgattgcgga catggttcgt tctcgaaata cgatctgttg aacgacactg    480

tgggtactgt tatgcattcg tttctgatga cgccctacta cggatggaag gtgtcccata    540

agaaccacca caaaaacact ggaaacattg acaaagatga ggttttctac ccagtaagga    600

aaagtttgaa aactcccggc agagcacttc caggctttgg acttggattg ggctattttg    660

gatatcttgt tttcggctat aacccacgac cagttagaca tttcaatcct ttcgagaaaa    720

tcttttccaa acatgtcctc ggatgcatcc tatctctagt gacccttacg gtttggagtt    780

cctacgtgta ccagtattac atgatctttg ggttcttccg attattctac cattatattg    840

tgcctttatt catctttgct accaacactg ttcttataac atttctgcac cacaccgaag    900

aggaaattcc ttggtactcc gatagcaagt gggacaacgt tcgtggacag ttaagctccg    960

ttgatcgtca ctatggaatc gtccacgata ttttgcacaa catcaccacc catcagatac   1020

atcacttatt cccaaaggtt cctcattacc atcttgaaga agcaactagt cattttagag   1080

cagcatttcc agaactagtc aatatccgca cggatcgaac atttccagcg ttctaccgaa   1140

tgttcaagaa atacgtcaaa cagtgtgtca ttccggacaa tactcatgta catatttata   1200

cataatttta tcaaatgttc cacctactgc caaatgtatt ggatgtaaaa tttaagtaga   1260
```

gctatttgca atcgtgtaac atttttcgta aaattggttg atcatacgaa gctgcatatc 1320
gttcttccat tgaaataaca cacacgaacg taaaatgctg aaatattacc ccaaagcttt 1380
caaatcacat 1390

<210> SEQ ID NO 126
<211> LENGTH: 1101
<212> TYPE: DNA
<213> ORGANISM: Lottia gigantea

<400> SEQUENCE: 126
atggaaacca aatcaggaag tcgtttgaag tcattttggt tatttttggc caaaatagcc 60
ttgactgatg agttatccaa gacccatctg ccaaatgaac ttccaaccat aatagacatt 120
aaaagagcaa ttcctagtca ctgctttcag tccaatgtta tcacctcaat gtaccatgcg 180
atgaaggacg tcgtattcgt cataggactt tacattttgg gagagcttct gttgacgtat 240
cttcctttct gggcagttct agtcacagca ccagtgtttt ggtttgctca gggaacaatg 300
tttacagcac tattcgtgat tggtcatgat tgcggacatg gttcgttctc gaaatacgat 360
ctgttgaacg acactgtggg tactgttatg cattcgtttc tgatgacgcc ctactacgga 420
tggaaggtgt cccataagaa ccaccacaaa aacactggaa acattgacaa agatgaggtt 480
ttctacccag taaggaaaag tttgaaaact cccggcagag cacttccagg ctttggactt 540
ggattgggct attttggata tcttgttttc ggctataacc cacgaccagt tagacatttc 600
aatcctttcg agaaaatctt ttccaaacat gtcctcggat gcatcctatc tctagtgacc 660
cttacggttt ggagttccta cgtgtaccag tattacatga tctttgggtt cttccgatta 720
ttctaccatt atattgtgcc tttattcatc tttgctacca acactgttct tataacattt 780
ctgcaccaca ccgaagagga aattccttgg tactccgata gcaagtggga caacgttcgt 840
ggacagttaa gctccgttga tcgtcactat ggaatcgtcc acgatatttt gcacaacatc 900
accacccatc agatacatca cttattccca aaggttcctc attaccatct tgaagaagca 960
actagtcatt ttagagcagc atttccagaa ctagtcaata tccgcacgga tcgaacattt 1020
ccagcgttct accgaatgtt caagaaatac gtcaaacagt gtgtcattcc ggacaatact 1080
catgtacata tttatacata a 1101

<210> SEQ ID NO 127
<211> LENGTH: 366
<212> TYPE: PRT
<213> ORGANISM: Lottia gigantea

<400> SEQUENCE: 127

Met Glu Thr Lys Ser Gly Ser Arg Leu Lys Ser Phe Trp Leu Phe Leu
1 5 10 15

Ala Lys Ile Ala Leu Thr Asp Glu Leu Ser Lys Thr His Leu Pro Asn
20 25 30

Glu Leu Pro Thr Ile Ile Asp Ile Lys Arg Ala Ile Pro Ser His Cys
35 40 45

Phe Gln Ser Asn Val Ile Thr Ser Met Tyr His Ala Met Lys Asp Val
50 55 60

Val Phe Val Ile Gly Leu Tyr Ile Leu Gly Glu Leu Leu Leu Thr Tyr
65 70 75 80

Leu Pro Phe Trp Ala Val Leu Val Thr Ala Pro Val Phe Trp Phe Ala
85 90 95

```
Gln Gly Thr Met Phe Thr Ala Leu Phe Val Ile Gly His Asp Cys Gly
            100                 105                 110

His Gly Ser Phe Ser Lys Tyr Asp Leu Leu Asn Asp Thr Val Gly Thr
        115                 120                 125

Val Met His Ser Phe Leu Met Thr Pro Tyr Tyr Gly Trp Lys Val Ser
    130                 135                 140

His Lys Asn His His Lys Asn Thr Gly Asn Ile Asp Lys Asp Glu Val
145                 150                 155                 160

Phe Tyr Pro Val Arg Lys Ser Leu Lys Thr Pro Gly Arg Ala Leu Pro
                165                 170                 175

Gly Phe Gly Leu Gly Leu Gly Tyr Phe Gly Tyr Leu Val Phe Gly Tyr
            180                 185                 190

Asn Pro Arg Pro Val Arg His Phe Asn Pro Phe Glu Lys Ile Phe Ser
        195                 200                 205

Lys His Val Leu Gly Cys Ile Leu Ser Leu Val Thr Leu Thr Val Trp
    210                 215                 220

Ser Ser Tyr Val Tyr Gln Tyr Tyr Met Ile Phe Gly Phe Phe Arg Leu
225                 230                 235                 240

Phe Tyr His Tyr Ile Val Pro Leu Phe Ile Phe Ala Thr Asn Thr Val
                245                 250                 255

Leu Ile Thr Phe Leu His His Thr Glu Glu Glu Ile Pro Trp Tyr Ser
            260                 265                 270

Asp Ser Lys Trp Asp Asn Val Arg Gly Gln Leu Ser Ser Val Asp Arg
        275                 280                 285

His Tyr Gly Ile Val His Asp Ile Leu His Asn Ile Thr Thr His Gln
    290                 295                 300

Ile His His Leu Phe Pro Lys Val Pro His Tyr His Leu Glu Glu Ala
305                 310                 315                 320

Thr Ser His Phe Arg Ala Ala Phe Pro Glu Leu Val Asn Ile Arg Thr
                325                 330                 335

Asp Arg Thr Phe Pro Ala Phe Tyr Arg Met Phe Lys Lys Tyr Val Lys
            340                 345                 350

Gln Cys Val Ile Pro Asp Asn Thr His Val His Ile Tyr Thr
        355                 360                 365
```

<210> SEQ ID NO 128
<211> LENGTH: 1513
<212> TYPE: DNA
<213> ORGANISM: Lottia gigantea

<400> SEQUENCE: 128

```
caaagaaaag cggcagtact cttgtccata ttcgtcgtca ataaccaaaa gtttctgttt      60

ttaattaatc caaacaacga attgcacaaa tggccattga aagaaatgtc aaagtaaatg     120

gctcaatgga tatcttacag accagtgaag atattggaaa tggtctgtct actgcaaaga     180

atgggcatat aagtaatgat atgaatgaag ccaataacca cgtgttcgac acaacgactg     240

gcgaggaaca acatctatcc aaacgaaacg gttcttccaa cggtacaagc aagaacgggg     300

ttgccaacaa aatacccagt atttcagaaa tcaaggcagc tatccccaac cattgtttta     360

aatcaactat caaacagtct atgtattacg ttttcaaaga cattatcctt ataatagcgt     420

tatactgttt tggacattgg gtcttacagt gcaattccat aatactcaag acggcactgt     480

cgccagtata ttggttctta caaggtacgc tgttattcgc ggtatttgta ttgggacatg     540

attgtaatca tggctcgttt tctagctatg cattattgaa cgattgcctt ggtactgttc     600
```

```
tacattcatt tgtaatgacg ccgtattacc cctggaaaat ttcgcatcgt catcaccaca    660

acaatactgg taatatggac aaagatgaga tattttatcc cattaggaag aaagacaaca    720

ataagaactc ttttgcatta ttttttggtc ttggattcgg ctggttggcg tatctgtggc    780

gcggattcgg accacggcaa atgaatcatt ggataccacg acatgcgatc ttcgctaaac    840

atgtcgtagg gtgtatattg tctataggcg ttgtgggtat atgggtcggt atattaggat    900

attatgtgca actgatgggt atggtgagtt tggtatacca ttatatgata ccggtcttta    960

tatgtggatg ttatatcgtc atggtaacgt ttctacacca tagtgatatc aaccttccat   1020

ggtacagcga cgacaactgg gacagtgtta aaggcaaact aagctcagtc gacagagact   1080

atgggatttt tcacgacgtt atccatacta taggaacgca ccaagttcac catttgtttc   1140

ccataattcc tcattataat ctacgcgaag caacgacgca cttccggaag gcattcccgc   1200

aattagtgca tatcaacgat aaaagcattt ttccagcatt tactgaaatg ttctttaaat   1260

attccagtca gtgtatagta gaaaatgatg ccaaaattca ttactataaa taattaaata   1320

tggcattaag tatatggagt agggcataaa aaatattaaa acagaacctg aaacatgttg   1380

ttactcagag taacatgata tttatttctt ttcattcttg tttcatattt attcttttaa   1440

acgatcgtat atttttagca tctatttgca atattttcaa attcaaaaat ggctttttgt   1500

gcaacataat cta                                                      1513
```

<210> SEQ ID NO 129
<211> LENGTH: 1113
<212> TYPE: DNA
<213> ORGANISM: Lottia gigantea

<400> SEQUENCE: 129

```
atgaatgaag ccaataacca cgtgttcgac acaacgactg gcgaggaaca acatctatcc     60

aaacgaaacg gttcttccaa cggtacaagc aagaacgggg ttgccaacaa aatacccagt    120

atttcagaaa tcaaggcagc tatccccaac cattgtttta aatcaactat caaacagtct    180

atgtattacg ttttcaaaga cattatcctt ataatagcgt tatactgttt tggacattgg    240

gtcttacagt gcaattccat aatactcaag acggcactgt cgccagtata ttggttctta    300

caaggtacgc tgttattcgc ggtatttgta ttgggacatg attgtaatca tggctcgttt    360

tctagctatg cattattgaa cgattgcctt ggtactgttc tacattcatt tgtaatgacg    420

ccgtattacc cctggaaaat ttcgcatcgt catcaccaca acaatactgg taatatggac    480

aaagatgaga tattttatcc cattaggaag aaagacaaca ataagaactc ttttgcatta    540

ttttttggtc ttggattcgg ctggttggcg tatctgtggc gcggattcgg accacggcaa    600

atgaatcatt ggataccacg acatgcgatc ttcgctaaac atgtcgtagg gtgtatattg    660

tctataggcg ttgtgggtat atgggtcggt atattaggat attatgtgca actgatgggt    720

atggtgagtt tggtatacca ttatatgata ccggtcttta tatgtggatg ttatatcgtc    780

atggtaacgt ttctacacca tagtgatatc aaccttccat ggtacagcga cgacaactgg    840

gacagtgtta aaggcaaact aagctcagtc gacagagact atgggatttt tcacgacgtt    900

atccatacta taggaacgca ccaagttcac catttgtttc ccataattcc tcattataat    960

ctacgcgaag caacgacgca cttccggaag gcattcccgc aattagtgca tatcaacgat   1020

aaaagcattt ttccagcatt tactgaaatg ttctttaaat attccagtca gtgtatagta   1080

gaaaatgatg ccaaaattca ttactataaa taa                                1113
```

-continued

<210> SEQ ID NO 130
<211> LENGTH: 370
<212> TYPE: PRT
<213> ORGANISM: Lottia gigantea

<400> SEQUENCE: 130

```
Met Asn Glu Ala Asn Asn His Val Phe Asp Thr Thr Thr Gly Glu Glu
1               5                   10                  15

Gln His Leu Ser Lys Arg Asn Gly Ser Ser Asn Gly Thr Ser Lys Asn
            20                  25                  30

Gly Val Ala Asn Lys Ile Pro Ser Ile Ser Glu Ile Lys Ala Ala Ile
        35                  40                  45

Pro Asn His Cys Phe Lys Ser Thr Ile Lys Gln Ser Met Tyr Tyr Val
    50                  55                  60

Phe Lys Asp Ile Ile Leu Ile Ile Ala Leu Tyr Cys Phe Gly His Trp
65                  70                  75                  80

Val Leu Gln Cys Asn Ser Ile Ile Leu Lys Thr Ala Leu Ser Pro Val
                85                  90                  95

Tyr Trp Phe Leu Gln Gly Thr Leu Leu Phe Ala Val Phe Val Leu Gly
            100                 105                 110

His Asp Cys Asn His Gly Ser Phe Ser Ser Tyr Ala Leu Leu Asn Asp
        115                 120                 125

Cys Leu Gly Thr Val Leu His Ser Phe Val Met Thr Pro Tyr Tyr Pro
    130                 135                 140

Trp Lys Ile Ser His Arg His His His Asn Asn Thr Gly Asn Met Asp
145                 150                 155                 160

Lys Asp Glu Ile Phe Tyr Pro Ile Arg Lys Lys Asp Asn Asn Lys Asn
                165                 170                 175

Ser Phe Ala Leu Phe Phe Gly Leu Gly Phe Gly Trp Leu Ala Tyr Leu
            180                 185                 190

Trp Arg Gly Phe Gly Pro Arg Gln Met Asn His Trp Ile Pro Arg His
        195                 200                 205

Ala Ile Phe Ala Lys His Val Val Gly Cys Ile Leu Ser Ile Gly Val
    210                 215                 220

Val Gly Ile Trp Val Gly Ile Leu Gly Tyr Tyr Val Gln Leu Met Gly
225                 230                 235                 240

Met Val Ser Leu Val Tyr His Tyr Met Ile Pro Val Phe Ile Cys Gly
                245                 250                 255

Cys Tyr Ile Val Met Val Thr Phe Leu His His Ser Asp Ile Asn Leu
            260                 265                 270

Pro Trp Tyr Ser Asp Asp Asn Trp Asp Ser Val Lys Gly Lys Leu Ser
        275                 280                 285

Ser Val Asp Arg Asp Tyr Gly Ile Phe His Asp Val Ile His Thr Ile
    290                 295                 300

Gly Thr His Gln Val His His Leu Phe Pro Ile Ile Pro His Tyr Asn
305                 310                 315                 320

Leu Arg Glu Ala Thr Thr His Phe Arg Lys Ala Phe Pro Gln Leu Val
                325                 330                 335

His Ile Asn Asp Lys Ser Ile Phe Pro Ala Phe Thr Glu Met Phe Phe
            340                 345                 350

Lys Tyr Ser Ser Gln Cys Ile Val Glu Asn Asp Ala Lys Ile His Tyr
        355                 360                 365

Tyr Lys
    370
```

<210> SEQ ID NO 131
<211> LENGTH: 3060
<212> TYPE: DNA
<213> ORGANISM: Microcoleus chthonoplastes

<400> SEQUENCE: 131

```
aaaattctgt agaagatgat atagccatcc agaggtatac ctcgcaaatc aggacgtatt     60
tctgtataat ttatacctaa cttagggaaa ttgactaatt gttggcagcg acgcgcaaaa    120
ttttgaaaaa agcgctcacc ggcttcgata ttattagcag taaagtaatc ggcaatttcg    180
ttgaggtctt ggctggcgag aacgttgata agatagcgtt tcatgtttga gtctcgcgtg    240
cttgctggaa gcgatccaaa atctctgcga taaagggttc gccatcaatg ggtggagtct    300
gttcggagac agcaatagca gcatctattt ttgaccgtac agagttgagc cactcgttgt    360
cagcacgctc atattcatct aacaactgca aggcgatttc gaggacttct tcagccgagc    420
gatatttgcc tgttcgcaat ttggtttgaa taaattgctc ttgggtcttt gttagactaa    480
tactcatcgt agtcagccag aaagtttgct ctaattctag caatctcact tgtcagatgt    540
cattcatata gaggtagcca tctagcggcg ttcctcaatg attgtctcag aaataggttt    600
accctgcacc tgaatcagac gccgttcagg ttgctgatta tcagaagcgt gtttaacttg    660
tttaactaaa ccagaggtta acagcgcttg gtgaaatttt gtacgttgag cagctacttc    720
tttgtcagta agatgttttt ggatagccag attaagttgc tgtagttcct ctgactcaag    780
catctctaac tgattgagga tttgattcaa gattgtttgt ggcatagcct tctacttttt    840
cgtcatcgag tttgtctcct attttacgac ggatattcaa aaagtatgag aattaatttg    900
gatctggttg ggcgcgatcg cacaagcatg aaggaatggc aatcccttct gtatactgta    960
ggttatcgcc atataagatg ttgggtttcg gcgcgtcaac ccaatctaca agcattacac   1020
cgtgggactt tagcttaatt cataagactt gattatcacc cgaagtacgg gagaaccgtt   1080
tccagcttca tacaaggtgg gctaatcctt ggtaatcccc agaatgatgg tgcgttgagg   1140
taatcattga taccgaaaac gatttgactg aaatggctag aaaaagggtg ctatcagttt   1200
tttcgtagtg agaagctaga tcggcttcac tggatgaaga tgaacgcgat cgcacgttta   1260
ttattgtagg ttgggttgag gttgcttaaa ccaacacatc tagttatagt attagagcta   1320
cgtctgattg actactgaat acatatttat agtattatgt caactccgtt ttccactgac   1380
tgatactata ggatatcgct atggggatca aaagcaacat ctggcataaa cgctattttg   1440
gtgctaatgg gatgagccgc gaagcgatcg cgtagttatt gactgacaaa caactgatcc   1500
gctaatttta gatttatttg aacaactaag gtcataaaag gttacaatca agcttgtgta   1560
attcaagcct atatttaccc gctttacctg gcatattgtg tgtggcaggt agttgattaa   1620
atgtaggttt ttcaattaaa ttagaagttt catgcaatca aacacagttc tcaagcaggc   1680
aacgattaca gcctcatcca ctcctaaaga agagttaccc tttactctcc aagacttaaa   1740
agcggcaatt cccgcctact gttttgaacc ttctgtttgg aagtctctca gttatttctt   1800
tctagacatt ggcataatcg ctggatttta tgccatcgcc tataaactgg attcctggtt   1860
atttttcccc atcttttggg tactgcaagg aactatgttt tgggcgttgt ttgtggtggg   1920
tcatgactgc ggtcatggct ctttctctaa gattaaatgg ctgaataacc tgattggaca   1980
tctgtctcac actcccatcc tggttccctt ccacgggtgg cgcatcagtc acagaactca   2040
tcatgccaat acgggtagcc tggaaaccga tgaaagttgg tatccggtat ctcagactaa   2100
gtataagcag atgcggtggt atgaaaagct atttcgctat aatttaccat tgctagctta   2160
```

tcccctctat ctatttaagc gatcgcctaa tcgcgagggt tcccattttc tgcccaatag 2220
tccattattt cgtccctcgg aaaaatggga tattgtcacc agttccgttc tctgggtgtt 2280
aatggttgcc tttttagggg gactgacgtt tcagttcggt tggctatttc tggtgaagta 2340
ttacctggtt ccttatgttg tatttgtcat gtggctagat ttggtcacat tcctgcatca 2400
tactgaacca gatattccct ggtatcgggg agatgattgg tatttcctga aaggggcatt 2460
atcaacgatt gatcgggatt atggctttat taatcccatt catcatgata tcgggactca 2520
tgtggcgcat catattttct tgaatatgcc ccactatcac ttgaagacgg caactgaggc 2580
acttaaaccc gtgttaggcg agtattatcg ctgttccaat gagccgattt ggaagagttt 2640
tatgcgttct tactgggctt gtcatttcgt gaaggatcaa ggatctcccg tttactatga 2700
atctcccaaa catccgcgat caaactaaag tatagaacgc ggatttacta cattagaact 2760
gtagagacat tcccaggaat gtctctatgg ctattatgct tattttccgg agtcatgttt 2820
gagtctcgcg tgcttgctgg aagcgatcca aaatctctgc gataaagggt tcgccatcaa 2880
tgggtggagt ctgttcggag acagcaatag cagcatcgat ttttgcccgt acagagttgt 2940
tccactcgct gtcagcacgc tcatattcat ccaacaactg caaggcaatt tcgagaactt 3000
cttcagccga gcgatatttg cctgttcgca atttggtttg aataaattgc tcttgggtct 3060

<210> SEQ ID NO 132
<211> LENGTH: 1077
<212> TYPE: DNA
<213> ORGANISM: Microcoleus chthonoplastes

<400> SEQUENCE: 132
atgcaatcaa acacagttct caagcaggca acgattacag cctcatccac tcctaaagaa 60
gagttaccct ttactctcca agacttaaaa gcggcaattc ccgcctactg ttttgaacct 120
tctgtttgga agtctctcag ttatttcttt ctagacattg gcataatcgc tggattttat 180
gccatcgcct ataaactgga ttcctggtta tttttcccca tcttttgggt actgcaagga 240
actatgtttt gggcgttgtt tgtggtgggt catgactgcg gtcatggctc tttctctaag 300
attaaatggc tgaataacct gattggacat ctgtctcaca ctcccatcct ggttcccttc 360
cacgggtggc gcatcagtca cagaactcat catgccaata cgggtagcct ggaaaccgat 420
gaaagttggt atccggtatc tcagactaag tataagcaga tgcggtggta tgaaaagcta 480
tttcgctata atttaccatt gctagcttat cccctctatc tatttaagcg atcgcctaat 540
cgcgagggtt cccattttct gcccaatagt ccattatttc gtccctcgga aaaatgggat 600
attgtcacca gttccgttct ctgggtgtta atggttgcct ttttaggggg actgacgttt 660
cagttcggtt ggctatttct ggtgaagtat tacctggttc cttatgttgt atttgtcatg 720
tggctagatt tggtcacatt cctgcatcat actgaaccag atattccctg gtatcgggga 780
gatgattggt atttcctgaa aggggcatta tcaacgattg atcgggatta tggctttatt 840
aatcccattc atcatgatat cgggactcat gtggcgcatc atattttctt gaatatgccc 900
cactatcact tgaagacggc aactgaggca cttaaacccg tgttaggcga gtattatcgc 960
tgttccaatg agccgatttg gaagagtttt atgcgttctt actgggcttg tcatttcgtg 1020
aaggatcaag gatctcccgt ttactatgaa tctcccaaac atccgcgatc aaactaa 1077

<210> SEQ ID NO 133
<211> LENGTH: 358
<212> TYPE: PRT

<213> ORGANISM: Microcoleus chthonoplastes

<400> SEQUENCE: 133

```
Met Gln Ser Asn Thr Val Leu Lys Gln Ala Thr Ile Thr Ala Ser Ser
1               5                   10                  15

Thr Pro Lys Glu Glu Leu Pro Phe Thr Leu Gln Asp Leu Lys Ala Ala
            20                  25                  30

Ile Pro Ala Tyr Cys Phe Glu Pro Ser Val Trp Lys Ser Leu Ser Tyr
        35                  40                  45

Phe Phe Leu Asp Ile Gly Ile Ile Ala Gly Phe Tyr Ala Ile Ala Tyr
    50                  55                  60

Lys Leu Asp Ser Trp Leu Phe Phe Pro Ile Phe Trp Val Leu Gln Gly
65                  70                  75                  80

Thr Met Phe Trp Ala Leu Phe Val Val Gly His Asp Cys Gly His Gly
                85                  90                  95

Ser Phe Ser Lys Ile Lys Trp Leu Asn Asn Leu Ile Gly His Leu Ser
            100                 105                 110

His Thr Pro Ile Leu Val Pro Phe His Gly Trp Arg Ile Ser His Arg
        115                 120                 125

Thr His His Ala Asn Thr Gly Ser Leu Glu Thr Asp Glu Ser Trp Tyr
    130                 135                 140

Pro Val Ser Gln Thr Lys Tyr Lys Gln Met Arg Trp Tyr Glu Lys Leu
145                 150                 155                 160

Phe Arg Tyr Asn Leu Pro Leu Leu Ala Tyr Pro Leu Tyr Leu Phe Lys
                165                 170                 175

Arg Ser Pro Asn Arg Glu Gly Ser His Phe Leu Pro Asn Ser Pro Leu
            180                 185                 190

Phe Arg Pro Ser Glu Lys Trp Asp Ile Val Thr Ser Ser Val Leu Trp
        195                 200                 205

Val Leu Met Val Ala Phe Leu Gly Gly Leu Thr Phe Gln Phe Gly Trp
    210                 215                 220

Leu Phe Leu Val Lys Tyr Tyr Leu Val Pro Tyr Val Val Phe Val Met
225                 230                 235                 240

Trp Leu Asp Leu Val Thr Phe Leu His His Thr Glu Pro Asp Ile Pro
                245                 250                 255

Trp Tyr Arg Gly Asp Asp Trp Tyr Phe Leu Lys Gly Ala Leu Ser Thr
            260                 265                 270

Ile Asp Arg Asp Tyr Gly Phe Ile Asn Pro Ile His His Asp Ile Gly
        275                 280                 285

Thr His Val Ala His His Ile Phe Leu Asn Met Pro His Tyr His Leu
    290                 295                 300

Lys Thr Ala Thr Glu Ala Leu Lys Pro Val Leu Gly Glu Tyr Tyr Arg
305                 310                 315                 320

Cys Ser Asn Glu Pro Ile Trp Lys Ser Phe Met Arg Ser Tyr Trp Ala
                325                 330                 335

Cys His Phe Val Lys Asp Gln Gly Ser Pro Val Tyr Tyr Glu Ser Pro
            340                 345                 350

Lys His Pro Arg Ser Asn
        355
```

<210> SEQ ID NO 134
<211> LENGTH: 10047
<212> TYPE: DNA
<213> ORGANISM: Mycosphaerella fijiensis

<400> SEQUENCE: 134

```
ctatcacatc tcgcggctcg acggatacat tatgtgttga cctgatgtag cagacgcatt     60
tcttcgacaa gtcatcgccg ctgaactttc tcgaccaagt tggtctgcgc tgaggtgtgg    120
tcatcttgtc tgttggagtt cctgtgtggt ttgtatggat acgtcgcagc aggctattaa    180
atgtcatctc gctcaggaca atgtgttgtg gcccccacga ctcgggcggg cggcctctgc    240
taaatatgtg tttccagatc acagccacct acccagcgga gatgctgtgg aaccttgcgt    300
cacctgtgag gcccagccag accacacacc ggtcgcatcg agtgatgctc gtgcactgca    360
gtcccgctct cttcgtgacg caggcgcttt ggaggcagtg cttgtgcgcg ctcccctctg    420
cccgcagcct tcgagccata cgcaccggcc tcgcttccat catcgcctcc agccgctcgg    480
ttagcctgcc gccagctcac cagttggctg caatgactgt caccgcgacc tgcttatttg    540
gagtacgtcg gctgtggaca tcgctaagga catcatgctg tggtattatc accatgaagg    600
cgcacgtccg gttgtgtttg tagttgcagc cctccgacat gcatcacaag gcgcagtaca    660
tcgccagagg agaggctgga gatgttgcac gcagattgac cattccacag gagcctgagt    720
tctcgtatta aactttgccg taagttctct cttcactatc gaactaacat tatagcctct    780
ataatggcct cacagtcgga tgttcttgtg tcaggcgagc agtcagcagt tgtcggtagc    840
gccgacagtg gtatagtcat acctagaacc ttgcctaaat gcggccggcg atacaattcc    900
gacacttcag ccaggagtcc atggcgaaga aaaattattc tatcactagg tacggaaaac    960
ctcgatcgac atcatatttc caggatcaac cacttgactg acagacttcg cagacggtgg   1020
aggaattcga ggctatgcgt cgctgaaaat tctggaacgt ctcatgcaga aggtcgagcg   1080
gatggagcag agcaatgaga ctagatacca cgctgcctac ggacagatca cgagcagcgc   1140
cgcatatccg tggaatagca cacaagtacc cgcaggcctt tcagtctcca atcccgatgt   1200
ccctcgccag tctttcgacg cgggctttcg tcctcatcat tactttgatt acttcttcgg   1260
caccagtaca ggagggtgag tactatagca acctgacgaa gttatcggct tctcatgtgc   1320
ttcttgcaac gcatcgtccc gtggctttta gctgatttca ctcctgcaga ttgagctcca   1380
ttatgctcgg ccgccttcag atgtcagttt ctaccgcgct taagcaatac gacgtggttg   1440
gaaacagcgt atttgcccgc ggacggccgt atgtcactgc cttgggcagt attatggtgc   1500
caaagtacag aagtcgcgac atggagcaag ctttgtccaa agtgttgcag aacggcctag   1560
tagggaagac gctgacgagg ccggcggatg agctcgcact tcagaatgag aatgagggtg   1620
cggcacgaac gtaagtcagc ctccacctcg tgaagccttt cgctcggcct gcatatgtat   1680
actctgtcgc cgtgtcgggc tgttcggttg aaggtctcga cttccaagta tcgtcaacta   1740
atgatcacag cgttgtcgtc tcccatggac catcaaccct tggcggtgtc tcgatgcgat   1800
atctctttcg gagctacgaa catccaaaac cgtccactcg gcttaccgat ggccaagaag   1860
aagatcactt gaatccaggc ccgttacctc caactacgat catagaagcg gcgagagcca   1920
caagtgctgc gccgacctat ttctctgaga aggaagtcgg aggtcttctc tacatggatg   1980
gcgccgttga tgccaacaat cccgtgcaac tcgcatataa tgaggtcacg cagatgcatc   2040
actctcagca acctcgcttg atcatctcaa taggcactgg agaagcagca gaatggcagc   2100
cgcacagtgc ttggcgggtg ctcaagaccg tcaagcgcac cgcagaccac ttaagcgact   2160
ttgctcgaaa tctcacagat acggagggcc cgcacaaaga gctcaagaag acgatcagac   2220
atctgcccaa gagtaaacag ccgctatact ttcgattcaa tattccgagc tcttctggta   2280
tttgcgatat tggtctcgac gagtggcagc caagaaaagc cagccaccgg gcatcggccg   2340
```

```
ggcacgaaac caagtcaaag atgacagacg ctgtcaacga gtactgtaag actatcgatg   2400
accaactaga agagtgtgcc agaattctag tcgaggttcg aagggagaga gcagaaaccg   2460
aacgctggga gagattcgct ttgcataggt cctactcctg ccccgaagca gattgcgagg   2520
cgcctagttt ccctggcaga caagacctac gacagcatct cttcgactca cacggcatcg   2580
tgcgccacgt ttggtgccgg ggcgagttgc caagttatca gaaacatcaa tttgcttgca   2640
tttggcacga ttgtggcgat tatactatca caacctttga tcactcgcaa tctggcatct   2700
gcgatcatct agatgcacgt acgagatcta tcgtggaaag ttatatgaag agtgagcacg   2760
gcgtacctga tgcgaaggtc atgacgagtg aggattttga agaattactt gatcggggtc   2820
gagacctaga cttgctgaag aaggcgagga cgatgaagac ttgaggtttt cgtcattttt   2880
gcgcacctgg aaattcgagt attaccctgg accatcacca ccctctcgtc tctggatctc   2940
tcacatccga atccggaatc ttcacaaaaa tatgcttcca gtacacgaca agaatatccg   3000
ccagcagccc cgcgaagctc atcttcctcc gtctagtccc aggccaccca tccggcagtc   3060
tctcttccgt ataaaagacc gtaatatcct tgaccgcaat cctctcgcca aacgtctgca   3120
acaggataca cgtctgcgac caggtcgtac catacaatct caaccccaaa ctccgcaacc   3180
ctttataccc aaaagctact ttacactctt tatcgcgcct aacacgagtt ctcgcaagac   3240
tctcacgcgt aattccaccg cctggagcag catcttcgag aaaggcttga aacatcgcgg   3300
gctggaaagt gaaattatcg ccttgccgat catctagtct ggtgaaagag gcatcgtgct   3360
cgatcacgtt gtgtttgcgt agatcgagta gtgtgaaagt tccgtctgag tggaggaggg   3420
gtttcacgat gctggataag acgtccgcga gcagaggtgt gcagtcggca gagactagca   3480
atgcggcttt gaggtgcgat tgtgttatgc cggtgccgtc tcgagggcta tcgtggtcaa   3540
caattctggc tggtctacga agtttccatt tatcaccgta ggcggcactt acagataccc   3600
atgattagaa agactgttca aaaacggaca tggagaccgc gtgctcggat cgccgcggat   3660
ataggtatgg tctgcttctc gaatttcttg gatttccttt ttgggcggag atttgaagaa   3720
agctattagc ggctggaaca gacttgatac ttgaatccca cacattttgg gtcggacatc   3780
gctagggata ttctagatgg gctttgggat ggcaatgatc ttgtgtcgag aggtctgaca   3840
tatttgactg aaatggtctg actacgccca ttctgtcagc tagaccagta gtgacagatg   3900
ccatgtgcac tcagctggtg gtaggagcag ccacagccag caggtttcgg ttttaccgtc   3960
gcctgcatag atgttgaata ctgaatattc agtatttaga gggtatattc agtgaatatg   4020
aatataactt ttcgtatatt caggtgaata gttagtattc agtcttccgc ggaggtggat   4080
agatagatta atagctacct ctacgtcgtt atcgctgtct attaatacta ttgttataga   4140
tactattatt atagatacta ttgttataga tactgcttct atagatacta taataataat   4200
actatcgata tattactaca aggcgcctac tatatagtac tatatatcta ataagtcttc   4260
tatcttatct ttattaatag tactgttatc tattactagt aatgtaatac tagccttcta   4320
ctattgttta gaaggctcta ttatacgcac tgtcttacta tctagttagc ttcggtccta   4380
tagaatagta cgccttgcta tactaaaggt acgctcgctc ttagcggata tagcgaaggt   4440
agataagacg tcgatagtaa gctacgataa taaaggctac gcctatcgct aagctagtta   4500
taactactat tgtaatagac ctattcggac gtcgttacta ctgctatctt agataacagg   4560
caataggcac ggagcggcat agacgaagct attaaactcg tccttaaccg tatcgataac   4620
ctccgcggct aattactacg actcgaagct agtaaggtct ataaccgcta tagtagtagt   4680
```

-continued

```
tagttttgct aaaggctcgt acctgtcctt atattcttac tataatgccc tcgctcttac   4740
tattgctagc tctaactagt tagtgttctt tactctagtc tagcgcttct aaagctaagt   4800
aagtcgcttt aaagggtata gtaagagagc cgctacgtac gtaccggatt cgtcgataag   4860
ttagtagtac ttactaaaca ggtgccaaga gacaataata gacttcgtaa tagcaggtct   4920
atacttatat agctcgagag acttctcgta atagttaacg aggtattcta tagcttctta   4980
gaagctatct agtatatagt tatagctcta taggcgtatt ataacctcct taaatagata   5040
taggaagttg cgagcgtgtt taattactat ctagtcggct atagttagct ctacgtctta   5100
tagtaaaggc tctcgtacga atagaaggtc taatgttagc ttagctttaa tagcctcgtc   5160
tataagcaag agctagctat tctgccgagt cttactaggt gtctttagta ccgctgctat   5220
agtagcggct ctagctaaga acttaaatat agcctatata atatcgtctt agaggcggag   5280
taacaggtta tatagcttct gtatagtctc ttgcttagta aacgaggctg tatcgatatt   5340
aagctatata gagacggaga cattatcgtt actagtagca gcggcattat aagcagctat   5400
ctgctactta ataaaggcac gctcgttatt ctttgccttc tcgaaggcta tcttagccga   5460
ctcttaagac tccgagaata taaaggctta tatagcgagg ttaataatat atctaatata   5520
gcgaagccgg cgtatcttct cgtactacta agtaatacct tcggagcgta gaaagcgctc   5580
aatcttacgt attaacgtat tattagacgt aacgttatcg cttgtaatcc aaccgatatt   5640
gttaacaata ttaaactgct taaaggcctt aataagaagc tgtataagct cggctctagt   5700
atagcgtata ataacgatag gaaggtcgag aagtacttat tatagcttac tatctttgtc   5760
gacgaattgg cagttaatag cttaatagta cttatagcta tactacgact tctaggtgtc   5820
tatatagagg tgaatatagc taatagctat agagaggtat ttcactactt aatagcgtat   5880
ataatagaag aggcggaaga ctcgtaagta gagcgaagta tataactata ggaagactcg   5940
taaagcctat agattaacgg ctaatataat gttatagaaa ctaggtgaaa ctagcttgtt   6000
aaaggctata ctctactcgg aggcgaaggc agcgagagcg ttacgatatt gctatgtttt   6060
agctacgtta cgtaggatta atagtacgtg ttcctctcga gaagatgcct tagtaagtac   6120
ttaaatagct atactatcgc gaatatcggc ttgcttctat ctcggctcct tgcctttgta   6180
tttactagta tataagctat gccttcttat taaataatag tcggtattgc ttatcgtact   6240
atactataga cctaagtcta gctcgaaggc tgttttatag caatcctcga atatatagta   6300
ctataccttg tatctatagt tatctatata ctctgcctcc tacggataag gctctcttat   6360
acatgctagt attttaggat ctaccgcttt ctgtcttgtc ttcttgcttc taggtaccga   6420
taatagcttt agtacttata gcaaagaagg tgtcgattat tgtatagatt tagtcgacta   6480
cgtattaata gaaggtatct cgactagtat cggatttagg accgcttcga ggtcgctatc   6540
gcttttatag ctagcgctat cgctacgctt acgttttcga tataggtcgt tttcccgtta   6600
cgaagcctag ctatttagca aattttcttg tactttgtat attaatttat atatagtgcg   6660
gaagttaact atagcggtgt tagtagtcga ggtataatta ttagtataga tttgaaaaat   6720
ttaagtttac tagaaatata cggccggaaa ggcccgatcg cggaccgctc tcggttatac   6780
tatccggata cgattattag gctacttaag ccttatataa cgctatagga ccctagataa   6840
gcagtaatag tatataaagc aactaatacc ttctatattc tatcttcttt atttataaca   6900
ctactactaa tatactcctt tactatcgct attgccgcta aagcgttacg agcgcgctac   6960
gtagcgagct cttcctttag cttatattcc ttaccgctat atagcatata taggttataa   7020
ctatacgggt ccgcgaatct aaagtgcctc gctttctctt ctattctacg aatacggtcg   7080
```

agatatacct cgcaacgata gtctctcgga tatactagca catagttgct actcttccga 7140
atatactcgt cgaaagcctc taccttcttt agataaatat cgagcttagc attcttcgca 7200
attatcctat attctatagc cttatatccc ttcctaatct cctagcgttg ttctagtagc 7260
cgccctatta ccttatacta agtatctatc tcggctcgct attccttaag ctactctatc 7320
gccttcgacg tcttcttcgg attcttataa agcctcttcg taataggctc tttaattagt 7380
aacggtttac gctcgatagt aggctcggtc ttaataatag gcttagttat tagcggcggc 7440
aatattagcg gcggcaatat tactagcgac gatattagct taggtttaga ctccgagtct 7500
aacagctaat tacgagttag cactactact agaataacta gtattattac ctatctacct 7560
cgattacttc tacgcgcttt atacctatta ttatataaag aaagagccca aaataccgta 7620
aaattgaaaa tctatatagg atctatatac gccgacgtat agcctgccta aatataaata 7680
tacctactat ttagtctacc tatatttaag gttcatttaa ttaaatataa atatatattc 7740
aaactgaata ttcacaattc aacatctata gtcgcctgat cggtttggct tttgagatga 7800
ccacagcttc gctgtcactg gcttgaggac tatgcaaagt gcctatttgg gcatggcgtg 7860
ggagtgctgg aggtgagctc tttgtggtgt tcttgttctt ggatctggat ctgctcacgt 7920
ggtcccggac ctgaaacaga ctgctggctg actattagca cacgcagcga gatgtttgac 7980
attcgtttct tgtcagtgtc gccttcctga tctcctatga ctatgacaga tcgactcttc 8040
agctctgggc acgttctcag ttagacgacc tatatagtcc tcacaagtgt aaccggtctc 8100
ttggcagtgt agccacagat tttcggtgta ggttcggttt caaaaccgaa cccaacccaa 8160
ccaaaccaat gggtggttta cttagaagaa gcgatttaga tatcaaatcg cggtatacgt 8220
gctcgccaac aaaggctctt cggaattata cggcttccct gccagccgac caaaaggctt 8280
tcggaattcc tacgtctagc atagaactcc aatgcatagc ctacctaaca tgaagggttg 8340
actccggagt ccgaacggct caagaccggc tcaatgtgtg catttacact ttggaagcat 8400
tggagcacca cagacacaaa aagataagag caccgtctat ccctatctcg aacaatgttc 8460
caatcttcga agtcatgttt ctcgccggaa gtgatgaggt cggagaaatt tccggactgt 8520
cgagtattcc aaccaggaca acgaccagca agatttcgtt gcagcggctt cgaaaagcga 8580
tcccagaggc atgttttcgt ccaagcgtgg tgagatctgc tgcacacgtt cttgcagatg 8640
ttctcctggc tgtaggtctt gcattcgcag ctctcgaact cgtcccgcaa atcggcagtc 8700
gagcacttcg tgttgctctg tggatgcttt acgggtatgt ccaaggcttg gtgttcactg 8760
gaatctggat tcttgcacac gagtgcggac attacgcatt atttccgggc agaaaggtca 8820
atgatgcgat cgggtttttc ctgcatagtg ctcttcttgt tccatatttc tcttgggtga 8880
gttcaacgag tccaagactc aggttcttga tggggtgtct gctgataccg aactctacaa 8940
cctggtagaa gtacacgcat gctcgtcatc atcgatacac aaaccatatt gagaaagata 9000
cggcgtatgt gccttccagg gaagaggaga taacatggtc cagacgaatt tctgaagttc 9060
ttcatcagac ggaggacgct cctttgcatt ctgccattct gcttgtctgc catcagcttt 9120
tcggctggca ggcgtacatc gcatgctatg caagtggtgg acctggctcg ttggtgagag 9180
cgtcgagggg caagacgttt gatcgatgcc atttgaatcc agcagcgtgc atctttacgg 9240
cgtcagaagc ggcattcgta gggttgtcca cgctggggtt gttgggaatg ctgttgctcc 9300
tcgccatggc agctagcaag atcggttggg ccaatgtggc actcctctac ggagttccat 9360
atgcctgggt caacaattgg ctggtcgcga tcacatatct tcatcacaca catcgagaca 9420

-continued ttcagcactt cgccagctcg ggctggacgt acatgaatgg tgtgctgtcc acaattgatc 9480
ggcctttcgg catcgtggga cgatatgtgt tccacggcat aatcgacttc catgtcgtcc 9540
atcatctctt tccgtaagtg ctcgctcata catctgggcc ggtcccaact tctggcggca 9600
actctaagca gtcatacagc cagataccat tctaccatgc ggaagaagcg acagaagcag 9660
tcaagaagga attgggtgag cgctactgct tcgacgacac gcctttctgg cttgctcttt 9720
ggcggacgtt ccgggaatgt caggtcgtgg tgccatcgaa gcatgcatcc gatgtgcttg 9780
tctggaaaga tctaggagcc tgagcctgag agtaagaaag tgagaagagc caagccaagc 9840
caagcgcaca tggcagcagt ccttgccatt cctcgccgtc gcaaatactg caaactcacc 9900
accttacatt catgactctg acatcgcagg cgcgcattct cgtcaccaac tgcaaatcta 9960
tacttccagc ctcgctgttg cactcatctt cctcgccgta tcaagaccca gctttcgagt 10020
caaatgtttc cccagcctaa cgcatgg 10047

<210> SEQ ID NO 135
<211> LENGTH: 1191
<212> TYPE: DNA
<213> ORGANISM: Mycosphaerella fijiensis

<400> SEQUENCE: 135
atgtttctcg ccggaagtga tgaggtcgga gaaatttccg gactgtcgag tattccaacc 60
aggacaacga ccagcaagat ttcgttgcag cggcttcgaa aagcgatccc agaggcatgt 120
tttcgtccaa gcgtggtgag atctgctgca cacgttcttg cagatgttct cctggctgta 180
ggtcttgcat tcgcagctct cgaactcgtc ccgcaaatcg gcagtcgagc acttcgtgtt 240
gctctgtgga tgctttacgg gtatgtccaa ggcttggtgt tcactggaat ctggattctt 300
gcacacgagt gcggacatta cgcattattt ccgggcagaa aggtcaatga tgcgatcggg 360
tttttcctgc atagtgctct tcttgttcca tatttctctt ggaagtacac gcatgctcgt 420
catcatcgat acacaaacca tattgagaaa gatacggcgt atgtgccttc cagggaagag 480
gagataacat ggtccagacg aatttctgaa gttcttcatc agacggagga cgctcctttg 540
cattctgcca ttctgcttgt ctgccatcag cttttcggct ggcaggcgta catcgcatgc 600
tatgcaagtg gtggacctgg ctcgttggtg agagcgtcga ggggcaagac gtttgatcga 660
tgccatttga atccagcagc gtgcatcttt acggcgtcag aagcggcatt cgtagggttg 720
tccacgctgg ggttgttggg aatgctgttg ctcctcgcca tggcagctag caagatcggt 780
tgggccaatg tggcactcct ctacggagtt ccatatgcct gggtcaacaa ttggctggtc 840
gcgatcacat atcttcatca cacacatcga gacattcagc acttcgccag ctcgggctgg 900
acgtacatga atggtgtgct gtccacaatt gatcggcctt tcggcatcgt gggacgatat 960
gtgttccacg gcataatcga cttccatgtc gtccatcatc tctttcccca gataccattc 1020
taccatgcgg aagaagcgac agaagcagtc aagaaggaat tgggtgagcg ctactgcttc 1080
gacgacacgc ctttctggct tgctctttgg cggacgttcc gggaatgtca ggtcgtggtg 1140
ccatcgaagc atgcatccga tgtgcttgtc tggaaagatc taggagcctg a 1191

<210> SEQ ID NO 136
<211> LENGTH: 396
<212> TYPE: PRT
<213> ORGANISM: Mycosphaerella fijiensis

<400> SEQUENCE: 136

Met Phe Leu Ala Gly Ser Asp Glu Val Gly Glu Ile Ser Gly Leu Ser

-continued

```
1               5                   10                  15

Ser Ile Pro Thr Arg Thr Thr Thr Ser Lys Ile Ser Leu Gln Arg Leu
            20                  25                  30

Arg Lys Ala Ile Pro Glu Ala Cys Phe Arg Pro Ser Val Val Arg Ser
        35                  40                  45

Ala Ala His Val Leu Ala Asp Val Leu Leu Ala Val Gly Leu Ala Phe
    50                  55                  60

Ala Ala Leu Glu Leu Val Pro Gln Ile Gly Ser Arg Ala Leu Arg Val
65                  70                  75                  80

Ala Leu Trp Met Leu Tyr Gly Tyr Val Gln Gly Leu Val Phe Thr Gly
                85                  90                  95

Ile Trp Ile Leu Ala His Glu Cys Gly His Tyr Ala Leu Phe Pro Gly
            100                 105                 110

Arg Lys Val Asn Asp Ala Ile Gly Phe Phe Leu His Ser Ala Leu Leu
        115                 120                 125

Val Pro Tyr Phe Ser Trp Lys Tyr Thr His Ala Arg His His Arg Tyr
    130                 135                 140

Thr Asn His Ile Glu Lys Asp Thr Ala Tyr Val Pro Ser Arg Glu Glu
145                 150                 155                 160

Glu Ile Thr Trp Ser Arg Arg Ile Ser Glu Val Leu His Gln Thr Glu
                165                 170                 175

Asp Ala Pro Leu His Ser Ala Ile Leu Leu Val Cys His Gln Leu Phe
            180                 185                 190

Gly Trp Gln Ala Tyr Ile Ala Cys Tyr Ala Ser Gly Gly Pro Gly Ser
        195                 200                 205

Leu Val Arg Ala Ser Arg Gly Lys Thr Phe Asp Arg Cys His Leu Asn
    210                 215                 220

Pro Ala Ala Cys Ile Phe Thr Ala Ser Glu Ala Ala Phe Val Gly Leu
225                 230                 235                 240

Ser Thr Leu Gly Leu Leu Gly Met Leu Leu Leu Leu Ala Met Ala Ala
                245                 250                 255

Ser Lys Ile Gly Trp Ala Asn Val Ala Leu Leu Tyr Gly Val Pro Tyr
            260                 265                 270

Ala Trp Val Asn Asn Trp Leu Val Ala Ile Thr Tyr Leu His His Thr
        275                 280                 285

His Arg Asp Ile Gln His Phe Ala Ser Ser Gly Trp Thr Tyr Met Asn
    290                 295                 300

Gly Val Leu Ser Thr Ile Asp Arg Pro Phe Gly Ile Val Gly Arg Tyr
305                 310                 315                 320

Val Phe His Gly Ile Ile Asp Phe His Val Val His His Leu Phe Pro
                325                 330                 335

Gln Ile Pro Phe Tyr His Ala Glu Glu Ala Thr Glu Ala Val Lys Lys
            340                 345                 350

Glu Leu Gly Glu Arg Tyr Cys Phe Asp Asp Thr Pro Phe Trp Leu Ala
        355                 360                 365

Leu Trp Arg Thr Phe Arg Glu Cys Gln Val Val Val Pro Ser Lys His
    370                 375                 380

Ala Ser Asp Val Leu Val Trp Lys Asp Leu Gly Ala
385                 390                 395
```

<210> SEQ ID NO 137
<211> LENGTH: 28346
<212> TYPE: DNA
<213> ORGANISM: Artificial
<220> FEATURE:
<223> OTHER INFORMATION: Binary T-plasmid LJB765 (synthetic)

<400> SEQUENCE: 137
gacatacaaa tggacgaacg gataaacctt ttcacgccct tttaaatatc cgattattct 60
aataaacgct cttttctctt aggtttaccc gccaatatat cctgtcaaac actgatagtt 120
taaactgaag gcgggaaacg acaatcagat ctagtaggaa acagctatga ccatgattac 180
gccaagcttg catgcctgca ggtcgactct agactagtgg atccgatatc gattacgcca 240
agctatcaac tttgtataga aaagttgcca tgattacgcc aagcttcccg ggctgcagca 300
aatttacaca ttgccactaa acgtctaaac ccttgtaatt tgtttttgtt ttactatgtg 360
tgttatgtat ttgatttgcg ataaattttt atatttggta ctaaatttat aacacctttt 420
atgctaacgt ttgccaacac ttagcaattt gcaagttgat taattgattc taaattattt 480
ttgtcttcta aatacatata ctaatcaact ggaaatgtaa atatttgcta atatttctac 540
tataggagaa ttaaagtgag tgaatatggt accacaaggt ttggagattt aattgttgca 600
atgctgcatg gatggcatat acaccaaaca ttcaataatt cttgaggata ataatggtac 660
cacacaagat ttgaggtgca tgaacgtcac gtggacaaaa ggtttagtaa tttttcaaga 720
caacaatgtt accacacaca agttttgagg tgcatgcatg gatgccctgt ggaaagttta 780
aaaatatttt ggaaatgatt tgcatggaag ccatgtgtaa aaccatgaca tccacttgga 840
ggatgcaata atgaagaaaa ctacaaattt acatgcaact agttatgcat gtagtctata 900
taatgaggat tttgcaatac tttcattcat acacactcac taagttttac acgattataa 960
tttcttcata gccagtacca tggaagttgt tgagaggttc tacggagagt tggatggaaa 1020
ggtttcccaa ggagtgaacg ctttgttggg atctttcgga gttgagttga ctgatacccc 1080
aactactaag ggattgccac tcgttgattc tccaactcca attgtgttgg gagtgtctgt 1140
ttacttgacc atcgtgatcg gaggattgct ttggatcaag gctagagatc tcaagccaag 1200
agcttctgag ccattcttgt tgcaagcttt ggtgttggtg cacaacttgt tctgcttcgc 1260
tttgtctctt tacatgtgcg tgggtatcgc ttaccaagct atcacctgga gatattcctt 1320
gtggggaaac gcttataacc caaagcacaa ggagatggct atcctcgttt acctcttcta 1380
catgtccaag tacgtggagt tcatggatac cgtgatcatg atcctcaaga gatccaccag 1440
acagatttct ttcctccacg tgtaccacca ttcttctatc tcccttatct ggtgggctat 1500
tgctcatcat gctccaggag gagaggctta ttggagtgct gctctcaact ctggagtgca 1560
tgtgttgatg tacgcttact acttcttggc tgcttgcttg agatcttccc caaagctcaa 1620
gaacaagtac ctcttctggg gaagatacct cacccaattc cagatgttcc agttcatgct 1680
caacttggtg caagcttact acgatatgaa aaccaacgct ccatatccac aatggctcat 1740
caagatcctc ttctactaca tgatctccct cttgttcctc ttcggaaact tctacgtgca 1800
aaagtacatc aagccatccg atggaaagca aaagggagct aagaccgagt gattaattaa 1860
ggccgcagat ctccaccgcg gtggcggccg ctctagcccg atatctcgac aagctcgagt 1920
ttctccataa taatgtgtga gtagttccca gataagggaa ttagggttcc tatagggttt 1980
cgctcatgtg ttgagcatat aagaaaccct tagtatgtat ttgtatttgt aaaatacttc 2040
tatcaataaa atttctaatt cctaaaacca aaatccagta ctaaaatcca gatcccccga 2100
attaattcgg cgttaattca ggatatcggg cggatcgatc ctctagcata tgctcgagtt 2160
accatttctt tttcctgcat ctcaatagta tatagggtat caaatagtga ttatccaaac 2220

-continued ttaaataagt tagaggaaac accaagatat gccatatact ctcatatttg acactatgat 2280
tcaaagttgc acttgcataa aacttattaa ttcaatagta aaaccaaact tgtgcgtgat 2340
acagttaaaa tgactaaact actaattaag gtccctccca ttagtaaata agttattttc 2400
ttagaaaaag aaaataataa aaagaatgac gagtctatct aaatcatatt aacaagtaat 2460
acatattgat tcattcgatg gaggaggcca ataattgtag taaacaagca gtgccgaggt 2520
taatatatgc tcaagacagt aaataatcta aatgaattaa gacagtgatt tgcaaagagt 2580
agatgcagag aagagaacta aagatttgct gctacacgta tataagaata gcaacagata 2640
ttcattctgt ctctttgtgg aatatggata tctactaatc atcatctatc tgtgaagaat 2700
aaaagaagcg gccacaagcg cagcgtcgca catatgatgt gtatcaaatt aggactccat 2760
agccatgcat gctgaagaat gtcacacacg ttctgtcaca cgtgttactc tctcactgtt 2820
ctcctcttcc tataaatcac cgcgccacag cttctccact tcaccacttc accacttcac 2880
tcacaatcct tcattagttg tttactatca cagtcacaga tctagagcgg ccgcggcgcg 2940
ccggggccca aaatggtgga cctcaagcct ggagtgaagc gcctggtgag ctggaaggag 3000
atccgcgagc acgcgacgcc cgcgaccgcg tggatcgtga ttcaccacaa ggtctacgac 3060
atctccaagt gggactcgca cccgggtggc tccgtgatgc tcacgcaggc cggcgaggac 3120
gccacggacg ccttcgcggt cttccacccg tcctcggcgc tcaagctgct cgagcagttc 3180
tacgtcggcg acgtggacga aacctccaag gccgagatcg agggggagcc ggcgagcgac 3240
gaggagcgcg cgcgccgcga gcgcatcaac gagttcatcg cgtcctaccg ccgtctgcgc 3300
gtcaaggtca agggcatggg gctctacgac gccagcgcgc tctactacgc gtggaagctc 3360
gtgagcacgt tcggcatcgc ggtgctctcg atggcgatct gcttcttctt caacagtttc 3420
gccatgtaca tggtcgccgg cgtgattatg gggctcttct accagcagtc cggatggctg 3480
gcgcacgact tcttgcacaa ccaggtgtgc gagaaccgca cgctcggcaa ccttatcggc 3540
tgcctcgtgg gcaacgcctg gcagggcttc agcatgcagt ggtggaagaa caagcacaac 3600
ctgcaccacg cggtgccgaa cctgcacagc gccaaggacg agggcttcat cggcgacccg 3660
gacatcgaca ccatgccgct gctggcgtgg tctaaggaga tggcgcgcaa ggcgttcgag 3720
tcggcgcacg gcccgttctt catccgcaac caggcgttcc tatacttccc gctgctgctg 3780
ctcgcgcgcc tgagctggct cgcgcagtcg ttcttctacg tgttcaccga gttctcgttc 3840
ggcatcttcg acaaggtcga gttcgacgga ccggagaagg cgggtctgat cgtgcactac 3900
atctggcagc tcgcgatccc gtacttctgc aacatgagcc tgtttgaggg cgtggcatac 3960
ttcctcatgg gccaggcgtc ctgcggcttg ctcctggcgc tggtgttcag tattggccac 4020
aacggcatgt cggtgtacga gcgcgaaacc aagccggact tctggcagct gcaggtgacc 4080
acgacgcgca acatccgcgc gtcggtattc atggactggt tcaccggtgg cttgaactac 4140
cagatcgacc atcacctgtt cccgctcgtg ccgcgccaca acttgccaaa ggtcaacgtg 4200
ctcatcaagt cgctatgcaa ggagttcgac atcccgttcc acgagaccgg cttctgggag 4260
ggcatctacg aggtcgtgga ccacctggcg gacatcagca aggaatttat caccgagttc 4320
ccagcgatgt aagttaactt aattaaggcc gcagatatca gatctggtcg accgatcctg 4380
caatagaatg ttgaggtgac cactttctgt aataaaataa ttataaaata aatttagaat 4440
tgctgtagtc aagaacatca gttctaaaat attaataaag ttatggcctt ttgacatatg 4500
tgtttcgata aaaaaatcaa aataaattga gatttattcg aaatacaatg aaagtttgca 4560
gatatgagat atgtttctac aaaataataa cttaaaactc aactatatgc taatgttttt 4620

-continued

```
cttggtgtgt ttcatagaaa attgtatccg tttcttagaa aatgctcgta aggatcggca   4680
tgcaagctga tccccgggta cccaagtttg tacaaaaaag caggctgcga tcgctaagga   4740
tgacctaccc attcttgaga caaatgttac attttagtat cagagtaaaa tgtgtaccta   4800
taactcaaat tcgattgaca tgtatccatt caacataaaa ttaaaccagc ctgcacctgc   4860
atccacattt caagtatttt caaaccgttc ggctcctatc caccgggtgt aacaagacgg   4920
attccgaatt tggaagattt tgactcaaat tcccaattta tattgaccgt gactaaatca   4980
actttaactt ctataattct gattaagctc ccaatttata ttcccaacgg cactacctcc   5040
aaaatttata gactctcatc cccttttaaa ccaacttagt aaacgttttt tttttaattt   5100
tatgaagtta agtttttacc ttgtttttaa aaagaatcgt tcataagatg ccatgccaga   5160
acattagcta cacgttacac atagcatgca gccgcggaga attgtttttc ttcgccactt   5220
gtcactccct tcaaacacct aagagcttct ctctcacagc acacacatac aatcacatgc   5280
gtgcatgcat tattacacgt gatcgccatg caaatctcct ttatagccta taaattaact   5340
catcggcttc actctttact caaaccaaaa ctcatcaata caaacaagat taaaaacaac   5400
catggctaca aaggaggctt acgttttccc aactctcacc gagatcaaga gatctctccc   5460
aaaggattgc ttcgaggctt ctgtgccttt gtctctctac tacactgtga gatgcttggt   5520
tattgctgtg gctttgacct tcggattgaa ctacgctaga gctttgccag aggttgagtc   5580
tttctgggct ttggatgctg ctttgtgcac tggatatatc ctcctccagg gaattgtgtt   5640
ctggggattc ttcactgttg gacacgatgc tggacacgga gctttctcta gataccacct   5700
cttgaacttc gttgtgggaa ccttcatgca ctctctcatc ttgaccccat tcgagtcttg   5760
gaagttgacc cacagacacc accacaagaa caccggaaac atcgatagag atgaggtgtt   5820
ctacccacag agaaaggctg atgatcaccc attgtccagg aacttgatct tggctttggg   5880
agctgcttgg cttgcttatt tggtggaggg attcccacca agaaaggtga accacttcaa   5940
cccattcgag ccactttttg tgagacaagt gtccgctgtg gttatctctt tgctcgctca   6000
cttcttcgtt gctggactct ctatctactt gtctctccag ttgggactta agaccatggc   6060
tatctactac tacggaccag ttttcgtgtt cggatctatg ttggtgatta ccaccttctt   6120
gcaccacaac gatgaggaga ctccatggta tgctgattct gagtggactt acgtgaaggg   6180
aaacttgtcc tctgtggata gatcttacgg tgctctcatc gataacctct cccacaacat   6240
cggaactcac cagatccacc acctcttccc aattatccca cactacaagc tcaagaaggc   6300
tactgctgct ttccaccaag ctttcccaga gcttgtgaga aagtccgatg agccaatcat   6360
caaggctttc ttcagagtgg gaaggttgta tgctaactac ggagtggttg atcaagaggc   6420
taagctcttc actttgaagg aggctaaggc tgctactgaa gctgctgcta agaccaagtc   6480
tacctgagtt cgagtattat ggcattggga aaactgtttt tcttgtacca tttgttgtgc   6540
ttgtaattta ctgtgttttt tattcggttt tcgctatcga actgtgaaat ggaaatggat   6600
ggagaagagt taatgaatga tatggtcctt ttgttcattc tcaaattaat attatttgtt   6660
ttttctctta tttgttgtgt gttgaatttg aaattataag agatatgcaa acattttgtt   6720
ttgagtaaaa atgtgtcaaa tcgtggcctc taatgaccga agttaatatg aggagtaaaa   6780
cacttgtagt tgtaccatta tgcttattca ctaggcaaca aatatatttt cagacctaga   6840
aaagctgcaa atgttactga atacaagtat gtcctcttgt gttttagaca tttatgaact   6900
ttcctttatg taattttcca gaatccttgt cagattctaa tcattgcttt ataattatag   6960
```

-continued

```
ttatactcat ggatttgtag ttgagtatga aaatattttt taatgcattt tatgacttgc   7020
caattgattg acaacatgca tcaatattta aattcgacgg cccggactgt atccaacttc   7080
tgatctttga atctctctgt tccaacatgt tctgaaggag ttctaagact tttcagaaag   7140
cttgtaacat gctttgtaga ctttctttga attactcttg caaactctga ttgaacctac   7200
gtgaaaactg ctccagaagt tctaaccaaa ttccgtcttg ggaaggccca aaatttattg   7260
agtacttcag tttcatggac gtgtcttcaa agatttataa cttgaaatcc catcattttt   7320
aagagaagtt ctgttccgca atgtcttaga tctcattgaa atctacaact cttgtgtcag   7380
aagttcttcc agaatcaact tgcatcatgg tgaaaatctg gccagaagtt ctgaacttgt   7440
catatttctt aacagttaga aaaatttcta agtgtttaga attttgactt ttccaaagca   7500
aacttgactt ttgactttct taataaaaca aacttcatat tctaacatgt cttgatgaaa   7560
tgtgattctt gaaatttgat gttgatgcaa aagtcaaagt ttgacttttc agtgtgcaat   7620
tgaccatttt gctcttgtgc caattccaaa cctaaattga tgtatcagtg ctgcaaactt   7680
gatgtcatgg aagatcttat gagaaaattc ttgaagactg agaggaaaaa ttttgtagta   7740
caacacaaag aatcctgttt ttcatagtcg gactagacac attaacataa aacaccactt   7800
cattcgaaga gtgattgaag aaggaaatgt gcagttacct ttctgcagtt cataagagca   7860
acttacagac acttttacta aaatactaca aagaggaaga ttttaacaac ttagagaagt   7920
aatgggagtt aaagagcaac acattaaggg ggagtgttaa aattaatgtg ttgtaaccac   7980
cactaccttt agtaagtatt ataagaaaat tgtaatcatc acattataat tattgtcctt   8040
atttaaaatt atgataaagt tgtatcatta agattgagaa aaccaaatag tcctcgtctt   8100
gatttttgaa ttattgtttt ctatgttact tttcttcaag cctatataaa aactttgtaa   8160
tgctaaattg tatgctggaa aaaaatgtgt aatgaattca atagaaatta tggtatttca   8220
aagtccaaaa tccatcaata gaaatttagt acaaaacgta actcaaaaat attctcttat   8280
tttaaatttt acaacaatat aaaaatattc tcttatttta aattttacaa taatataatt   8340
tatcacctgt cacctttaga ataccaccaa caatattaat acttagatat tttattctta   8400
ataattttga gatctctcaa tatatctgat atttatttta tatttgtgtc atattttctt   8460
atgttttaga gttaaccctt atatcttggt caaactagta attcaatata tgagtttgtg   8520
aaggacacat tgacatcttg aaacattggt tttaaccttg ttggaatgtt aaaggtaata   8580
aaacattcag aattatgacc atctattaat atacttcctt tgtcttttaa aaaagtgtgc   8640
atgaaaatgc tctatggtaa gctagagtgt cttgctggcc tgtgtatatc aattccattt   8700
ccagatggta gaaactgcca ctacgaataa ttagtcataa gacacgtatg ttaacacacg   8760
tccccttgca tgttttttgc catatattcc gtctctttct ttttcttcac gtataaaaca   8820
atgaactaat taatagagcg atcaagctga accatggatg cttataacgc tgctatggat   8880
aagattggag ctgctatcat cgattggagt gatccagatg gaaagttcag agctgatagg   8940
gaggattggt ggttgtgcga tttcagatcc gctatcacca ttgctctcat ctacatcgct   9000
ttcgtgatct tgggatctgc tgtgatgcaa tctctcccag ctatggaccc ataccctatc   9060
aagttcctct acaacgtgtc tcaaatcttc ctctgcgctt acatgactgt tgaggctgga   9120
ttcctcgctt ataggaacgg atacaccgtt atgccatgca accacttcaa cgtgaacgat   9180
ccaccagttg ctaacttgct ctggctcttc tacatctcca aagtgtggga tttctgggat   9240
accatcttca ttgtgctcgg aaagaagtgg agacaactct ctttcttgca cgtgtaccac   9300
cacaccacca tcttcctctt ctactggttg aacgctaacg tgctctacga tggagatatc   9360
```

```
ttcttgacca tcctcctcaa cggattcatt cacaccgtga tgtacaccta ctacttcatc   9420
tgcatgcaca ccaaggattc taagaccgga aagtctttgc caatctggtg gaagtcatct   9480
ttgaccgctt tccaactctt gcaattcacc atcatgatgt cccaagctac ctacttggtt   9540
ttccacggat gcgataaggt ttccctcaga atcaccatcg tgtacttcgt gtacattctc   9600
tccctttcct tcctcttcgc tcagttcttc gtgcaatcct acatggctcc aaagaagaag   9660
aagtccgctt gacctgcaga tagactatac tatgttttag cctgcctgct ggctagctac   9720
tatgttatgt tatgttgtaa aataaacacc tgctaaggta tatctatcta tattttagca   9780
tggctttctc aataaattgt ctttccttat cgtttactat cttataccta ataatgaaat   9840
aataatatca catatgagga acggggcagg tttaggcata tatatacgag tgtagggcgg   9900
agtggggggg cccctgtgca tatgtcaata tcgtaaatta taatcattgt atttattggt   9960
aattttgtca tttatctgag ggatacgcaa gtccaaacat cttaaaaata cgttcgaata  10020
catcaatctt tttctctatt ttggttagac gccatattta tcgaatacag aagcgctaac  10080
tgaaaaacac agcttatgtt gacgacatca taataacata tgatcgcgca actattaaat  10140
attttgaata taaaatttta aaatcttgtt aggtgtccaa agaattggaa aaacgataag  10200
agacctgggc aggcggaaac atcaaaagcg ttaaacgata aatcgtatat gacaccacag  10260
aagtcatgca tgataacaca acttcagtga caaaaataca atttaaaccc atgacatata  10320
attggtcttg cgatacaaac tatgcatctc ttttgtttat acatttaata cattatcatc  10380
aacggttctt atcagcccaa tctttccatg tattttagcg ggtaatttga actcctatca  10440
aaagaaccat gcactcaagc acgtgtccaa acacttaaga cacgtatcaa ttgtgaactt  10500
ttgagttctc tctccctctc atcacctccc cttccttata ccatgtgtgt tgagaccgag  10560
aacaacgatg gaatccctac tgtggagatc gctttcgatg gagagagaga aagagctgag  10620
gctaacgtga agttgtctgc tgagaagatg gaacctgctg ctttggctaa gaccttcgct  10680
agaagatacg tggttatcga gggagttgag tacgatgtga ccgatttcaa acaccctgga  10740
ggaaccgtga ttttctacgc tctctctaac actggagctg atgctactga ggctttcaag  10800
gagttccacc acagatctag aaaggctagg aaggctttgg ctgctttgcc ttctagacct  10860
gctaagaccg ctaaagtgga tgatgctgag atgctccagg atttcgctaa gtggagaaag  10920
gagttggaga gggacggatt cttcaagcct tctcctgctc acgttgctta cagattcgct  10980
gagttggctg ctatgtacgc tttgggaacc tacttgatgt acgctagata cgttgtgtcc  11040
tctgtgttgg tttacgcttg cttcttcgga gctagatgtg gatgggttca acacgaggga  11100
ggacactctt ctttgaccgg aaacatctgg tgggataaga gaatccaagc tttcactgct  11160
ggattcggat tggctggatc tggagatatg tggaactcca tgcacaacaa gcaccacgct  11220
actcctcaaa aagtgaggca cgatatggat ttggatacca ctcctgctgt tgctttcttc  11280
aacaccgctg tggaggataa tagacctagg ggattctcta agtactggct cagattgcaa  11340
gcttggacct tcattcctgt gacttctgga ttggtgttgc tcttctggat gttcttcctc  11400
caccccttcta aggctttgaa gggaggaaag tacgaggagc ttgtgtggat gttggctgct  11460
cacgtgatta gaacctggac cattaaggct gttactggat tcaccgctat gcaatcctac  11520
ggactcttct tggctacttc ttgggtttcc ggatgctact tgttcgctca cttctctact  11580
tctcacaccc acttggatgt tgttcctgct gatgagcact tgtcttgggt taggtacgct  11640
gtggatcaca ccattgatat cgatccttct cagggatggg ttaactggtt gatgggatac  11700
```

```
ttgaactgcc aagtgattca ccacctcttc ccttctatgc ctcaattcag acaacctgag  11760
gtgtccagaa gattcgttgc tttcgctaag aagtggaacc tcaactacaa ggtgatgact  11820
tatgctggag cttggaaggc tactttggga aacctcgata atgtgggaaa gcactactac  11880
gtgcacggac aacactctgg aaagaccgct tgagccggag gagtaaaaga gaaggccaac  11940
gtacgtcaag agtgtgtttg gtttgttgtt agtggttaga actttggttc tgacctctct  12000
tgtaactttt tttttccata gtcttgttta tttgttaatg tacttttgca ttgtttttgt  12060
tgttgccatg tttaaagttg tattgtgttt gtataatgtt ttgttttgtt taaatctttg  12120
tagatggtaa atgagaaata agtaaatatt tccgagagac tgttgagtga cgacgttact  12180
tcttgtcctg caggacccag ctttcttgta caaagtggcc atgattacgc caagcttccc  12240
gggctgcagc aaatttacac attgccacta aacgtctaaa cccttgtaat ttgtttttgt  12300
tttactatgt gtgttatgta tttgatttgc gataaatttt tatatttggt actaaattta  12360
taacaccttt tatgctaacg tttgccaaca cttagcaatt tgcaagttga ttaattgatt  12420
ctaaattatt tttgtcttct aaatacatat actaatcaac tggaaatgta aatatttgct  12480
aatatttcta ctataggaga attaaagtga gtgaatatgg taccacaagg tttggagatt  12540
taattgttgc aatgctgcat ggatggcata tacaccaaac attcaataat tcttgaggat  12600
aataatggta ccacacaaga tttgaggtgc atgaacgtca cgtggacaaa aggtttagta  12660
atttttcaag acaacaatgt taccacacac aagttttgag gtgcatgcat ggatgccctg  12720
tggaaagttt aaaaatattt tggaaatgat ttgcatggaa gccatgtgta aaaccatgac  12780
atccacttgg aggatgcaat aatgaagaaa actacaaatt tacatgcaac tagttatgca  12840
tgtagtctat ataatgagga ttttgcaata ctttcattca tacacactca ctaagtttta  12900
cacgattata atttcttcat agccagtggc gcgccaccat ggcgactaga caaagaactg  12960
ctactactgt ggtggttgag gatttgccaa aggttacctt ggaggctaag tctgagccag  13020
ttttcccaga tatcaagacc atcaaggatg ctattccagc tcattgcttc caaccatctc  13080
tcgtgacttc cttctactac gtgttcaggg atttcgctat ggtttctgct cttgtgtggg  13140
ctgctttgac ttacatccca tccatcccag atcaaacctt gagagtggct gcttggatgg  13200
tttacggatt cgtgcaagga cttttctgta ccggagtgtg gattttggga catgagtgtg  13260
gacatggagc tttctccctt catggaaagg ttaacaacgt gaccggatgg ttcttgcatt  13320
ctttcctcct cgtgccatac ttctcttgga agtactctca tcacagacac catagattca  13380
ccggacacat ggatttggat atggctttcg tgccaaagac tgagccaaag ccatctaagt  13440
ctctcatgat cgctggaatt gatgttgctg agttggttga ggatactcca gctgctcaaa  13500
tggtgaagct catcttccat caactcttcg gatggcaggc ttacttgttc ttcaacgctt  13560
cttccggaaa gggatctaag caatgggagc caaagactgg attgtccaag tggttcagag  13620
tgtctcattt cgagccaacc tctgctgttt tcagaccaaa cgaggctatc ttcatcctca  13680
tctcagatat cggattggct ttgatgggaa ccgctctcta tttcgcttct aagcaagttg  13740
gagtgtccac tatcttgttc ttgtacctcg tgccttattt gtgggttcac cattggttgg  13800
tggctattac ttacttgcat caccaccata ctgagttgcc acattacact gctgagggat  13860
ggacttatgt gaagggagct ttggctactg ttgataggga gttcggattc atcggaaagc  13920
acctcttcca cggaattatt gagaagcacg tggtgcatca tttgttccca aagatcccat  13980
tctacaaggc tgatgaggct actgaggcta ttaagccagt gatcggagat cattactgcc  14040
acgatgatag atctttcctc ggacaactct ggactatttt cggaaccctc aagtacgttg  14100
```

agcatgatcc agctagacca ggtgctatga ggtggaacaa ggattgatta attaaggccg 14160
cagatctcca ccgcggtggc ggccgctcta gcccgatatc tcgacaagct cgagtttctc 14220
cataataatg tgtgagtagt tcccagataa gggaattagg gttcctatag ggtttcgctc 14280
atgtgttgag catataagaa acccttagta tgtatttgta tttgtaaaat acttctatca 14340
ataaaatttc taattcctaa aaccaaaatc cagtactaaa atccagatcc cccgaattaa 14400
ttcggcgtta attcaggata tcgggcggat ccccgggtac ccaactttat tatacatagt 14460
tgataattca ctggccgatt tggtttaaac gaattcgccc ttctttagca gatatttggt 14520
gtctaaatgt ttattttgtg atatgttcat gtttgaaatg gtggtttcga aaccagggac 14580
aacgttggga tctgataggg tgtcaaagag tattatggat tgggacaatt tcggtcatga 14640
gttgcaaatt caagtatatc gttcgattat gaaaattttc gaagaatatc ccatttgaga 14700
gagtctttac ctcattaatg tttttagatt atgaaatttt atcatagttc atcgtagtct 14760
ttttggtgta aaggctgtaa aaagaaattg ttcacttttg ttttcgttta tgtgaaggct 14820
gtaaaagatt gtaaaagact attttggtgt tttggataaa atgatagttt ttatagattc 14880
ttttgctttt agaagaaata catttgaaat tttttccatg ttgagtataa aataccgaaa 14940
tcgattgaag atcatagaaa tattttaact gaaaacaaat ttataactga ttcaattctc 15000
tccattttta tacctattta accgtaatcg attctaatag atgatcgatt ttttatataa 15060
tcctaattaa ccaacggcat gtattggata attaaccgat caactctcac ccctaataga 15120
atcagtattt tccttcgacg ttaattgatc ctacactatg taggtcatat ccatcgtttt 15180
aatttttggc caccattcaa ttctgtcttg cctttaggga tgtgaatatg aacggccaag 15240
gtaagagaat aaaaataatc caaattaaag caagagaggc caagtaagat aatccaaatg 15300
tacacttgtc attgccaaaa ttagtaaaat actcggcata ttgtattccc acacattatt 15360
aaaataccgt atatgtattg gctgcatttg catgaataat actacgtgta agcccaaaag 15420
aacccacgtg tagcccatgc aaagttaaca ctcacgaccc cattcctcag tctccactat 15480
ataaacccac catccccaat ctcaccaaac ccaccacaca actcacaact cactctcaca 15540
ccttctagag gatctgatat ctgcggccgc ggcgcgccac catgggaaaa ggatctgagg 15600
gaagatctgc tgctagagag atgactgctg aggctaacgg agataagaga aagaccatcc 15660
tcattgaggg agtgttgtac gatgctacca acttcaaaca cccaggaggt tccattatta 15720
acttcctcac cgagggagaa gctggagttg atgctaccca agcttacaga gagttccatc 15780
agagatccgg aaaggctgat aagtacctca agtccctccc aaagttggat gcttctaagg 15840
tggagtctag gttctctgct aaggagcagg ctagaaggga cgctatgacc agggattacg 15900
ctgctttcag agaggagttg gttgctgagg gatacttcga tccatctatc ccacacatga 15960
tctacagagt ggtggagatt gtggctttgt tcgctttgtc tttctggttg atgtctaagg 16020
cttctccaac ctctttggtt ttgggagtgg tgatgaacgg aatcgctcaa ggaagatgcg 16080
gatgggttat gcatgagatg ggacacggat ctttcactgg agttatctgg ctcgatgata 16140
ggatgtgcga gttcttctac ggagttggat gtggaatgtc tggacactac tggaagaacc 16200
agcattctaa gcaccatgct gctccaaaca gattggagca cgatgtggat ttgaacacct 16260
tgccactcgt tgctttcaac gagagagttg tgaggaaggt taagccagga tctttgttgg 16320
ctttgtggct cagagttcag gcttatttgt tcgctccagt gtcttgcttg ttgatcggat 16380
tgggatggac cttgtacttg cacccaagat atatgctcag gaccaagaga catatggagt 16440
ttgtgtggat cttcgctaga tatatcggat ggttctcctt gatgggagct ttgggatatt 16500
ctcctggaac ttctgtggga atgtacctct gctctttcgg acttggatgc atctacatct 16560
tcctccaatt cgctgtgtct catacccatt tgccagttac caacccagag gatcaattgc 16620
attggcttga gtacgctgct gatcataccg tgaacatctc taccaagtct tggttagtta 16680
cctggtggat gtctaacctc aacttccaaa tcgagcatca tttgttccca accgctccac 16740
aattcaggtt caaggagatc tctccaagag ttgaggctct cttcaagaga cataacctcc 16800
cttactacga tttgccatac acctctgctg tttctactac cttcgctaac ctctactctg 16860
ttggacattc tgttggagct gataccaaga agcaggattg attaattaag gccgcctcga 16920
gcatgcatct agagggcccg ctagcgttaa ccctgcttta atgagatatg cgagacgcct 16980
atgatcgcat gatatttgct ttcaattctg ttgtgcacgt tgtaaaaaac ctgagcatgt 17040
gtagctcaga tccttaccgc cggtttcggt tcattctaat gaatatatca cccgttacta 17100
tcgtattttt atgaataata ttctccgttc aatttactga ttgtccgtcc acgggcagga 17160
catagggact actacaagca tagtatgctt cagacaaaga gctaggaaag aactcttgat 17220
ggaggttaag agaaaaaagt gctagagggg catagtaatc aaacttgtca aaaccgtcat 17280
catgatgagg gatgacataa tataaaaagt tgactaaggt cttggtagta ctctttgatt 17340
agtattatat attggtgaga acatgagtca agaggagaca agaaaccgag gaaccatagt 17400
ttagcaacaa gatggaagtt gcaaagttga gctagccgct cgattagtta catctcctaa 17460
gcagtactac aaggaatggt ctctatactt tcatgtttag cacatggtag tgcggattga 17520
caagttagaa acagtgctta ggagacaaag agtcagtaaa ggtattgaaa gagtgaagtt 17580
gatgctcgac aggtcaggag aagtccctcc gccagatggt gactaccaag ggggttggtat 17640
cagctgagac ccaaataaga ttcttcggtt gaaccagtgg ttcgaccgag actcttaggg 17700
tgggatttca ctgtaagatt tgtgcatttt gttgaatata aattgacaat ttttttttatt 17760
taattataga ttatttagaa tgaattacat atttagtttc taacaaggat agcaatggat 17820
gggtatgggt acaggttaaa catatctatt acccacccat ctagtcgtcg ggttttacac 17880
gtacccaccc gtttacataa accagaccgg aattttaaac cgtacccgtc cgttagcggg 17940
tttcagattt acccgtttaa tcgggtaaaa cctgattact aaatatatat tttttatttg 18000
ataaacaaaa caaaaatgtt aatattttca tattggatgc aattttaaga aacacatatt 18060
cataaatttc catatttgta ggaaaataaa aagaaaaata tattcaagaa cacaaatttc 18120
accgacatga cttttattac agagttggaa ttagatctaa caattgaaaa attaaaatta 18180
agatagaata tgttgaggaa catgacatag tataatgctg ggttacccgt cgggtaggta 18240
tcgaggcgga tactactaaa tccatcccac tcgctatccg ataatcactg gtttcgggta 18300
tacccattcc cgtcaacagg cctttttaac cggataattt caacttatag tgaatgaatt 18360
ttgaataaat agttagaata ccaaaatcct ggattgcatt tgcaatcaaa ttttgtgaac 18420
cgttaaattt tgcatgtact tgggatagat ataatagaac cgaattttca ttagtttaat 18480
ttataactta ctttgttcaa agaaaaaaaa tatctatcca atttacttat aataaaaaat 18540
aatctatcca agttacttat tataatcaac ttgtaaaaag gtaagaatac aaatgtggta 18600
gcgtacgtgt gattatatgt gacgaaatgt tatatctaac aaaagtccaa attcccatgg 18660
taaaaaaaat caaaatgcat ggcaggctgt ttgtaacctt ggaataagat gttggccaat 18720
tctggagccg ccacgtacgc aagactcagg gccacgttct cttcatgcaa ggatagtaga 18780
acaccactcc acccacctcc tatattagac ctttgcccaa ccctccccaa ctttcccatc 18840
ccatccacaa agaaaccgac atttttatca taaatcggcg cgccgttaac gctagcgcca 18900
tgggtgcagg cggtcgaatg caagatccca ccaacggtgg caacaaaacc gagcccgaac 18960
caatccaacg ggtcccacat gaaaaacccc cattcacagt tggagacatc aagaaagcga 19020
tcccacctca ttgtttcaac cgatcggtaa ttcgttcatt ttcatacgtc ttttacgacc 19080
tcacaatcgc gtcaatcttg tactacattg ccaacaatta catctctacc ctccctagcc 19140
cgctcgccta cgtggcatgg cccgtttact gggccgtcca agggtgcgtc ttaaccgggg 19200
tgtgggtcat agcccacgaa tgtggccatc atgcttttag cgaccaccaa tggctcgatg 19260
acaccgtggg tctcgtcttg cactcgttcc tactcgtgcc ctacttttcg tggaaatata 19320
gccaccgtag gcaccactcg aacacgggtt cgatcgagca cgatgaggtt ttcgtcccga 19380
agttgaaatc gggcgtccgg tcaaccgccc ggtacctaaa caacccaccg ggccgaatct 19440
tgaccctact cgtaacccta accctcggtt ggcctctata cctcacgttc aacgtttcgg 19500
gccgttacta cgaccggttc gcgtgccatt tcgacccgaa tagcccgatc tactcgaagc 19560
gcgaacgggc tcaaatcttc atatccgacg ccgggatctt agccgtagtc ttcgtactct 19620
tccgactcgc aatgaccaaa gggctcacgt gggtcctaac catgtacggt ggcccgttac 19680
tcgtggtcaa cggtttccta gtcttgatca cattcctaca acacactcac ccttcgctcc 19740
cgcactatga ctcaaccgaa tgggattggt tacgtggggc cctcaccaca atcgaccgtg 19800
attacgggat cctaaacaaa gtgttccata acataaccga cactcacgtg gcccaccatt 19860
tgttctctac aatgcctcat taccatgcaa tggaagccac gaaggtgatc aaaccgattt 19920
tgggcgatta ttatcagttt gacgggacct cgatttttaa ggcgatgtat cgggaaacaa 19980
aggagtgcat ttatgttgat aaggatgagg aggtgaaaga tggtgtttat tggtatcgta 20040
ataagattta agttaacgct agcttaatta aggccgcaga tatcagatct ggtcgaccta 20100
gaggatcccc ggccgcaaag ataataacaa aagcctacta tataacgtac atgcaagtat 20160
tgtatgatat taatgttttt acgtacgtgt aaacaaaaat aattacgttt gtaacgtatg 20220
gtgatgatgt ggtgcactag gtgtaggcct tgtattaata aaaagaagtt tgttctatat 20280
agagtggttt agtacgacga tttatttact agtcggattg gaatagagaa ccgaattctt 20340
caatccttgc ttttgatcaa gaattgaaac cgaatcaaat gtaaaagttg atatatttga 20400
aaaacgtatt gagcttatga aaatgctaat actctcatct gtatggaaaa gtgactttaa 20460
aaccgaactt aaaagtgaca aaaggggaat atcgcatcaa accgaatgaa accgatagaa 20520
gggcgaattc gcggccgcta aattcaattc gccctatagt gagtcgtatt acaattcact 20580
ggccgtcgtt ttacaacgtc gtgactggga aaaccctggc gttacccaac ttaatcgcct 20640
tgcagcacat ccccctttcg ccagctggcg taatagcgaa gaggcccgca ccgatcgccc 20700
ttcccaacag ttgcaaatga tatcgcccgg gctcgaggta ccatcgttca aacatttggc 20760
aataaagttt cttaagattg aatcctgttg ccggtcttgc gatgattatc atataatttc 20820
tgttgaatta cgttaagcat gtaataatta acatgtaatg catgacgtta tttatgagat 20880
gggtttttat gattagagtc ccgcaattat acatttaata cgcgatagaa aacaaaatat 20940
agcgcgcaaa ctaggataaa ttatcgcgcg cggtgtcatc tatgttacta gatcgggcat 21000
taccctgtta tccctagagc tcgaattcac tggccgtcgt tttacaacga ctcaggatcc 21060
tgtcaaacac tgatagttta aactgaaggc gggaaacgac aatctgatca tgagcggaga 21120
attaagggag tcacgttatg acccccgccg atgacgcggg acaagccgtt ttacgtttgg 21180

-continued

```
aactgacaga accgcaacgt tgaaggagcc actcagccgc gggtttctgg agtttaatga  21240
gctaagcaca tacgtcagaa accattattg cgcgttcaaa agtcgcctaa ggtcactatc  21300
agctagcaaa tatttcttgt caaaaatgct ccactgacgt tccataaatt cccctcggta  21360
tccaattaga gtctcatatt cactctcaat ccaaataatc tgcaccggat ctggatcgtt  21420
tcgcatgatt gaacaagatg gattgcacgc aggttctccg gccgcttggg tggagaggct  21480
attcggctat gactgggcac aacagacaat cggctgctct gatgccgccg tgttccggct  21540
gtcagcgcag gggcgcccgg ttctttttgt caagaccgac ctgtccggtg ccctgaatga  21600
actgcaggac gaggcagcgc ggctatcgtg gctggccacg acgggcgttc cttgcgcagc  21660
tgtgctcgac gttgtcactg aagcgggaag ggactggctg ctattgggcg aagtgccggg  21720
gcaggatctc ctgtcatctc accttgctcc tgccgagaaa gtatccatca tggctgatgc  21780
aatgcggcgg ctgcatacgc ttgatccggc tacctgccca ttcgaccacc aagcgaaaca  21840
tcgcatcgag cgagcacgta ctcggatgga agccggtctt gtcgatcagg atgatctgga  21900
cgaagagcat caggggctcg cgccagccga actgttcgcc aggctcaagg cgcgcatgcc  21960
cgacggcgag gatctcgtcg tgacccatgg cgatgcctgc ttgccgaata tcatggtgga  22020
aaatggccgc ttttctggat tcatcgactg tggccggctg ggtgtggcgg accgctatca  22080
ggacatagcg ttggctaccc gtgatattgc tgaagagctt ggcggcgaat gggctgaccg  22140
cttcctcgtg ctttacggta tcgccgctcc cgattcgcag cgcatcgcct tctatcgcct  22200
tcttgacgag ttcttctgag ctagggataa cagggtaatt gagcgggacc caagctctag  22260
atcttgctgc gttcggatat tttcgtggag ttcccgccac agacccggat gatccccgat  22320
cgttcaaaca tttggcaata aagtttctta agattgaatc ctgttgccgg tcttgcgatg  22380
attatcatat aatttctgtt gaattacgtt aagcatgtaa taattaacat gtaatgcatg  22440
acgttattta tgagatgggt ttttatgatt agagtcccgc aattatacat ttaatacgcg  22500
atagaaaaca aaatatagcg cgcaaactag gataaattat cgcgcgcggt gtcatctatg  22560
ttactagatc gggcctcctg tcaagctctg cttggtaata attgtcatta gattgttttt  22620
atgcatagat gcactcgaaa tcagccaatt ttagacaagt atcaaacgga tgttaattca  22680
gtacattaaa gacgtccgca atgtgttatt aagttgtcta agcgtcaatt tgtttacacc  22740
acaatatatc ctgccaccag ccagccaaca gctccccgac cggcagctcg gcacaaaatc  22800
accacgcgtt accaccacgc cggccggccg catggtgttg accgtgttcg ccggcattgc  22860
cgagttcgag cgttccctaa tcatcgaccg cacccggagc gggcgcgagg ccgccaaggc  22920
ccgaggcgtg aagtttggcc cccgccctac cctcaccccg gcacagatcg cgcacgcccg  22980
cgagctgatc gaccaggaag gccgcaccgt gaaagaggcg gctgcactgc ttggcgtgca  23040
tcgctcgacc ctgtaccgcg cacttgagcg cagcgaggaa gtgacgccca ccgaggccag  23100
gcggcgcggt gccttccgtg aggacgcatt gaccgaggcc gacgccctgg cggccgccga  23160
gaatgaacgc caagaggaac aagcatgaaa ccgcaccagg acggccagga cgaaccgttt  23220
ttcattaccg aagagatcga ggcggagatg atcgcggccg ggtacgtgtt cgagccgccc  23280
gcgcacgtct caaccgtgcg gctgcatgaa atcctggccg gtttgtctga tgccaagctg  23340
gcggcctggc cggccagctt ggccgctgaa gaaaccgagc gccgccgtct aaaaaggtga  23400
tgtgtatttg agtaaaacag cttgcgtcat gcggtcgctg cgtatatgat gcgatgagta  23460
aataaacaaa tacgcaaggg gaacgcatga aggttatcgc tgtacttaac cagaaaggcg  23520
ggtcaggcaa gacgaccatc gcaacccatc tagcccgcgc cctgcaactc gccggggccg  23580
```

atgttctgtt agtcgattcc gatccccagg gcagtgcccg cgattgggcg gccgtgcggg 23640
aagatcaacc gctaaccgtt gtcggcatcg accgcccgac gattgaccgc gacgtgaagg 23700
ccatcggccg gcgcgacttc gtagtgatcg acggagcgcc ccaggcggcg gacttggctg 23760
tgtccgcgat caaggcagcc gacttcgtgc tgattccggt gcagccaagc ccttacgaca 23820
tatgggccac cgccgacctg gtggagctgg ttaagcagcg cattgaggtc acggatggaa 23880
ggctacaagc ggcctttgtc gtgtcgcggg cgatcaaagg cacgcgcatc ggcggtgagg 23940
ttgccgaggc gctggccggg tacgagctgc ccattcttga gtcccgtatc acgcagcgcg 24000
tgagctaccc aggcactgcc gccgccggca caaccgttct tgaatcagaa cccgagggcg 24060
acgctgcccg cgaggtccag gcgctggccg ctgaaattaa atcaaaactc atttgagtta 24120
atgaggtaaa gagaaaatga gcaaaagcac aaacacgcta agtgccggcc gtccgagcgc 24180
acgcagcagc aaggctgcaa cgttggccag cctggcagac acgccagcca tgaagcgggt 24240
caactttcag ttgccggcgg aggatcacac caagctgaag atgtacgcgg tacgccaagg 24300
caagaccatt accgagctgc tatctgaata catcgcgcag ctaccagagt aaatgagcaa 24360
atgaataaat gagtagatga attttagcgg ctaaaggagg cggcatggaa aatcaagaac 24420
aaccaggcac cgacgccgtg gaatgcccca tgtgtggagg aacgggcggt tggccaggcg 24480
taagcggctg ggttgtctgc cggccctgca atggcactgg aacccccaag cccgaggaat 24540
cggcgtgagc ggtcgcaaac catccggccc ggtacaaatc ggcgcggcgc tgggtgatga 24600
cctggtggag aagttgaagg ccgcgcaggc cgcccagcgg caacgcatcg aggcagaagc 24660
acgccccggt gaatcgtggc aagcggccgc tgatcgaatc cgcaaagaat cccggcaacc 24720
gccggcagcc ggtgcgccgt cgattaggaa gccgcccaag ggcgacgagc aaccagattt 24780
tttcgttccg atgctctatg acgtgggcac ccgcgatagt cgcagcatca tggacgtggc 24840
cgttttccgt ctgtcgaagc gtgaccgacg agctggcgag gtgatccgct acgagcttcc 24900
agacgggcac gtagaggttt ccgcagggcc ggccggcatg gccagtgtgt gggattacga 24960
cctggtactg atggcggttt cccatctaac cgaatccatg aaccgatacc gggaagggaa 25020
gggagacaag cccggccgcg tgttccgtcc acacgttgcg gacgtactca agttctgccg 25080
gcgagccgat ggcggaaagc agaaagacga cctggtagaa acctgcattc ggttaaacac 25140
cacgcacgtt gccatgcagc gtacgaagaa ggccaagaac ggccgcctgg tgacggtatc 25200
cgagggtgaa gccttgatta gccgctacaa gatcgtaaag agcgaaaccg ggcggccgga 25260
gtacatcgag atcgagctag ctgattggat gtaccgcgag atcacagaag gcaagaaccc 25320
ggacgtgctg acggttcacc ccgattactt tttgatcgat cccggcatcg gccgttttct 25380
ctaccgcctg gcacgccgcg ccgcaggcaa ggcagaagcc agatggttgt tcaagacgat 25440
ctacgaacgc agtggcagcg ccggagagtt caagaagttc tgtttcaccg tgcgcaagct 25500
gatcgggtca aatgacctgc cggagtacga tttgaaggag gaggcggggc aggctggccc 25560
gatcctagtc atgcgctacc gcaacctgat cgagggcgaa gcatccgccg gttcctaatg 25620
tacggagcag atgctagggc aaattgccct agcaggggaa aaaggtcgaa aaggtctctt 25680
tcctgtggat agcacgtaca ttgggaaccc aaagccgtac attgggaacc ggaacccgta 25740
cattgggaac ccaaagccgt acattgggaa ccggtcacac atgtaagtga ctgatataaa 25800
agagaaaaaa ggcgattttt ccgcctaaaa ctctttaaaa cttattaaaa ctcttaaaac 25860
ccgcctggcc tgtgcataac tgtctggcca gcgcacagcc gaagagctgc aaaaagcgcc 25920

-continued

```
taccc ttcgg tcgctgcgct ccctacgccc cgccgcttcg cgtcggccta tcgcggccgc  25980
tggccgctca aaaatggctg gcctacggcc aggcaatcta ccagggcgcg gacaagccgc  26040
gccgtcgcca ctcgaccgcc ggcgcccaca tcaaggcacc ctgcctcgcg cgtttcggtg  26100
atgacggtga aaacctctga cacatgcagc tcccggagac ggtcacagct tgtctgtaag  26160
cggatgccgg gagcagacaa gcccgtcagg gcgcgtcagc gggtgttggc gggtgtcggg  26220
gcgcagccat gacccagtca cgtagcgata gcggagtgta tactggctta actatgcggc  26280
atcagagcag attgtactga gagtgcacca tatgcggtgt gaaataccgc acagatgcgt  26340
aaggagaaaa taccgcatca ggcgctcttc cgcttcctcg ctcactgact cgctgcgctc  26400
ggtcgttcgg ctgcggcgag cggtatcagc tcactcaaag gcggtaatac ggttatccac  26460
agaatcaggg gataacgcag gaaagaacat gtgagcaaaa ggccagcaaa aggccaggaa  26520
ccgtaaaaag gccgcgttgc tggcgttttt ccataggctc cgcccccctg acgagcatca  26580
caaaaatcga cgctcaagtc agaggtggcg aaacccgaca ggactataaa gataccaggc  26640
gtttccccct ggaagctccc tcgtgcgctc tcctgttccg accctgccgc ttaccggata  26700
cctgtccgcc tttctccctt cgggaagcgt ggcgctttct catagctcac gctgtaggta  26760
tctcagttcg gtgtaggtcg ttcgctccaa gctgggctgt gtgcacgaac cccccgttca  26820
gcccgaccgc tgcgccttat ccggtaacta tcgtcttgag tccaacccgg taagacacga  26880
cttatcgcca ctggcagcag ccactggtaa caggattagc agagcgaggt atgtaggcgg  26940
tgctacagag ttcttgaagt ggtggcctaa ctacggctac actagaagga cagtatttgg  27000
tatctgcgct ctgctgaagc cagttacctt cggaaaaaga gttggtagct cttgatccgg  27060
caaacaaacc accgctggta gcggtggttt ttttgtttgc aagcagcaga ttacgcgcag  27120
aaaaaaagga tctcaagaag atcctttgat cttttctacg gggtctgacg ctcagtggaa  27180
cgaaaactca cgttaaggga ttttggtcat gcatgatata tctcccaatt tgtgtagggc  27240
ttattatgca cgcttaaaaa taataaaagc agacttgacc tgatagtttg gctgtgagca  27300
attatgtgct tagtgcatct aacgcttgag ttaagccgcg ccgcgaagcg gcgtcggctt  27360
gaacgaattt ctagctagac attatttgcc gactaccttg gtgatctcgc ctttcacgta  27420
gtggacaaat tcttccaact gatctgcgcg cgaggccaag cgatcttctt cttgtccaag  27480
ataagcctgt ctagcttcaa gtatgacggg ctgatactgg gccggcaggc gctccattgc  27540
ccagtcggca gcgacatcct tcggcgcgat tttgccggtt actgcgctgt accaaatgcg  27600
ggacaacgta agcactacat ttcgctcatc gccagcccag tcgggcggcg agttccatag  27660
cgttaaggtt tcatttagcg cctcaaatag atcctgttca ggaaccggat caaagagttc  27720
ctccgccgct ggacctacca aggcaacgct atgttctctt gcttttgtca gcaagatagc  27780
cagatcaatg tcgatcgtgg ctggctcgaa gatacctgca agaatgtcat tgcgctgcca  27840
ttctccaaat tgcagttcgc gcttagctgg ataacgccac ggaatgatgt cgtcgtgcac  27900
aacaatggtg acttctacag cgcggagaat ctcgctctct ccaggggaag ccgaagtttc  27960
caaaaggtcg ttgatcaaag ctcgccgcgt tgtttcatca agccttacgg tcaccgtaac  28020
cagcaaatca atatcactgt gtggcttcag gccgccatcc actgcggagc cgtacaaatg  28080
tacggccagc aacgtcggtt cgagatggcg ctcgatgacg ccaactacct ctgatagttg  28140
agtcgatact tcggcgatca ccgcttcccc catgatgttt aactttgttt tagggcgact  28200
gccctgctgc gtaacatcgt tgctgctcca taacatcaaa catcgaccca cggcgtaacg  28260
cgcttgctgc ttggatgccc gaggcataga ctgtacccca aaaaaacagt cataacaagc  28320
```

catgaaaacc gccactgcgt tccatg 28346

<210> SEQ ID NO 138
<211> LENGTH: 819
<212> TYPE: DNA
<213> ORGANISM: Thalassiosira pseudonana

<400> SEQUENCE: 138
atggatgctt ataacgctgc tatggataag attggagctg ctatcatcga ttggagtgat 60
ccagatggaa agttcagagc tgatagggag gattggtggt tgtgcgattt cagatccgct 120
atcaccattg ctctcatcta catcgctttc gtgatcttgg gatctgctgt gatgcaatct 180
ctcccagcta tggacccata ccctatcaag ttcctctaca acgtgtctca aatcttcctc 240
tgcgcttaca tgactgttga ggctggattc ctcgcttata ggaacggata caccgttatg 300
ccatgcaacc acttcaacgt gaacgatcca ccagttgcta acttgctctg gctcttctac 360
atctccaaag tgtgggattt ctgggatacc atcttcattg tgctcggaaa gaagtggaga 420
caactctctt tcttgcacgt gtaccaccac accaccatct tcctcttcta ctggttgaac 480
gctaacgtgc tctacgatgg agatatcttc ttgaccatcc tcctcaacgg attcattcac 540
accgtgatgt acacctacta cttcatctgc atgcacacca aggattctaa gaccggaaag 600
tctttgccaa tctggtggaa gtcatctttg accgctttcc aactcttgca attcaccatc 660
atgatgtccc aagctaccta cttggttttc cacggatgcg ataaggtttc cctcagaatc 720
accatcgtgt acttcgtgta cattctctcc cttttcttcc tcttcgctca gttcttcgtg 780
caatcctaca tggctccaaa gaagaagaag tccgcttga 819

<210> SEQ ID NO 139
<211> LENGTH: 1371
<212> TYPE: DNA
<213> ORGANISM: Ostreococcus tauri

<400> SEQUENCE: 139
atgtgtgttg agaccgagaa caacgatgga atccctactg tggagatcgc tttcgatgga 60
gagagagaaa gagctgaggc taacgtgaag ttgtctgctg agaagatgga acctgctgct 120
ttggctaaga ccttcgctag aagatacgtg gttatcgagg gagttgagta cgatgtgacc 180
gatttcaaac accctggagg aaccgtgatt ttctacgctc tctctaacac tggagctgat 240
gctactgagg ctttcaagga gttccaccac agatctagaa aggctaggaa ggctttggct 300
gctttgcctt ctagacctgc taagaccgct aaagtggatg atgctgagat gctccaggat 360
ttcgctaagt ggagaaagga gttggagagg gacggattct tcaagccttc tcctgctcac 420
gttgcttaca gattcgctga gttggctgct atgtacgctt tgggaaccta cttgatgtac 480
gctagatacg ttgtgtcctc tgtgttggtt tacgcttgct tcttcggagc tagatgtgga 540
tgggttcaac acgagggagg acactcttct ttgaccggaa acatctggtg ggataagaga 600
atccaagctt tcactgctgg attcggattg gctggatctg gagatatgtg gaactccatg 660
cacaacaagc accacgctac tcctcaaaaa gtgaggcacg atatggattt ggataccact 720
cctgctgttg ctttcttcaa caccgctgtg gaggataata gacctagggg attctctaag 780
tactggctca gattgcaagc ttggaccttc attcctgtga cttctggatt ggtgttgctc 840
ttctggatgt tcttcctcca cccttctaag gctttgaagg gaggaaagta cgaggagctt 900
gtgtggatgt tggctgctca cgtgattaga acctggacca ttaaggctgt tactggattc 960

```
accgctatgc aatcctacgg actcttcttg gctacttctt gggtttccgg atgctacttg   1020
ttcgctcact tctctacttc tcacacccac ttggatgttg ttcctgctga tgagcacttg   1080
tcttgggtta ggtacgctgt ggatcacacc attgatatcg atccttctca gggatgggtt   1140
aactggttga tgggatactt gaactgccaa gtgattcacc acctcttccc ttctatgcct   1200
caattcagac aacctgaggt gtccagaaga ttcgttgctt tcgctaagaa gtggaacctc   1260
aactacaagg tgatgactta tgctggagct tggaaggcta ctttgggaaa cctcgataat   1320
gtgggaaagc actactacgt gcacggacaa cactctggaa agaccgcttg a            1371
```

<210> SEQ ID NO 140
<211> LENGTH: 1209
<212> TYPE: DNA
<213> ORGANISM: Fusarium monoliforme

<400> SEQUENCE: 140

```
atggcgacta gacaaagaac tgctactact gtggtggttg aggatttgcc aaaggttacc     60
ttggaggcta agtctgagcc agttttccca gatatcaaga ccatcaagga tgctattcca    120
gctcattgct tccaaccatc tctcgtgact tccttctact acgtgttcag ggatttcgct    180
atggtttctg ctcttgtgtg ggctgctttg acttacatcc catccatccc agatcaaacc    240
ttgagagtgg ctgcttggat ggtttacgga ttcgtgcaag gacttttctg taccggagtg    300
tggattttgg gacatgagtg tggacatgga gctttctccc ttcatggaaa ggttaacaac    360
gtgaccggat ggttcttgca ttctttcctc ctcgtgccat acttctcttg gaagtactct    420
catcacagac accatagatt caccggacac atggatttgg atatggcttt cgtgccaaag    480
actgagccaa agccatctaa gtctctcatg atcgctggaa ttgatgttgc tgagttggtt    540
gaggatactc cagctgctca aatggtgaag ctcatcttcc atcaactctt cggatggcag    600
gcttacttgt tcttcaacgc ttcttccgga aagggatcta agcaatggga gccaaagact    660
ggattgtcca agtggttcag agtgtctcat ttcgagccaa cctctgctgt tttcagacca    720
aacgaggcta tcttcatcct catctcagat atcggattgg ctttgatggg aaccgctctc    780
tatttcgctt ctaagcaagt tggagtgtcc actatcttgt tcttgtacct cgtgccttat    840
ttgtgggttc accattggtt ggtggctatt acttacttgc atcaccacca tactgagttg    900
ccacattaca ctgctgaggg atggacttat gtgaagggag ctttggctac tgttgatagg    960
gagttcggat tcatcggaaa gcacctcttc cacggaatta ttgagaagca cgtggtgcat   1020
catttgttcc caaagatccc attctacaag gctgatgagg ctactgaggc tattaagcca   1080
gtgatcggag atcattactg ccacgatgat agatctttcc tcggacaact ctggactatt   1140
ttcggaaccc tcaagtacgt tgagcatgat ccagctagac caggtgctat gaggtggaac   1200
aaggattga                                                           1209
```

<210> SEQ ID NO 141
<211> LENGTH: 1152
<212> TYPE: DNA
<213> ORGANISM: Calendula officinalis

<400> SEQUENCE: 141

```
atgggtgcag gcggtcgaat gcaagatccc accaacggtg gcaacaaaac cgagcccgaa     60
ccaatccaac gggtcccaca tgaaaaaccc ccattcacag ttggagacat caagaaagcg    120
atcccacctc attgtttcaa ccgatcggta attcgttcat tttcatacgt cttttacgac    180
ctcacaatcg cgtcaatctt gtactacatt gccaacaatt acatctctac cctccctagc    240
```

-continued

```
ccgctcgcct acgtggcatg gcccgtttac tgggccgtcc aagggtgcgt cttaaccggg    300

gtgtgggtca tagcccacga atgtggccat catgctttta gcgaccacca atggctcgat    360

gacaccgtgg gtctcgtctt gcactcgttc ctactcgtgc cctacttttc gtggaaatat    420

agccaccgta ggcaccactc gaacacgggt tcgatcgagc acgatgaggt tttcgtcccg    480

aagttgaaat cgggcgtccg gtcaaccgcc cggtacctaa acaacccacc gggccgaatc    540

ttgaccctac tcgtaaccct aaccctcggt tggcctctat acctcacgtt caacgtttcg    600

ggccgttact acgaccggtt cgcgtgccat ttcgacccga atagcccgat ctactcgaag    660

cgcgaacggg ctcaaatctt catatccgac gccgggatct tagccgtagt cttcgtactc    720

ttccgactcg caatgaccaa agggctcacg tgggtcctaa ccatgtacgg tggcccgtta    780

ctcgtggtca acggtttcct agtcttgatc acattcctac aacacactca cccttcgctc    840

ccgcactatg actcaaccga atgggattgg ttacgtgggg ccctcaccac aatcgaccgt    900

gattacggga tcctaaacaa agtgttccat aacataaccg acactcacgt ggcccaccat    960

ttgttctcta caatgcctca ttaccatgca atggaagcca cgaaggtgat caaaccgatt   1020

ttgggcgatt attatcagtt tgacgggacc tcgattttta aggcgatgta tcgggaaaca   1080

aaggagtgca tttatgttga taaggatgag gaggtgaaag atggtgttta ttggtatcgt   1140

aataagattt aa                                                       1152
```

<210> SEQ ID NO 142
<211> LENGTH: 3201
<212> TYPE: DNA
<213> ORGANISM: Physcomitrella patens

<400> SEQUENCE: 142

```
tccagaagag gctgcccgtt gcgctggggc tcaggcggac ccggtgggcc agagctgggg     60

ggggggggga gccacgtttg ttttgggaca tgagcgacgc agcagaaggg gcaagaccgc    120

agagggaggg agtgagagag agggaagaag aagatctgct gctgcattgt taccatcgcc    180

gctttcatca cgtcgtgaca gaacgcagat atctaaatac atcgatttat tttttttatta    240

attaatttat tcaccacatg gccagcgtcc ataggtcacg tcgagaaaga cacagaccgt    300

acgtcaggtt tccacttttg gtaggcagac ggtgcggggc tgtcataata tttgtcatgc    360

caatacttgg agtaacttac aaacctcatg aaaatatgac atcgaatgcc cgattctgac    420

caagacccgc ccctccccct ccctgtcccc tcctccccac tcggcgtaaa tatgcagttc    480

ctgtctgttg ggtcgtctct ctatcattgc cttaggtagg agacaggcgc tgcgagtcca    540

ggaggttgac ccggggcgga gccaggagag ctcttggggc gaatagcgat gtcgtccaga    600

aggggcatga tctcgatgga tcaagccagt aagattgctg acaatccttc tgcggtatcg    660

ctacgcagcg cggaggacga tggcaagctg gctgcaatct ccgtgaagca tcagcataat    720

agggatgatg aggagttcga tgcgtcgacg cggccgccgt tcagtcttgg tcagatacgg    780

gccgccattc ccaagctctg ctgggaaaga agcattgtga ggtcgttcag ctacgtcggc    840

agggatgtta ccattgtagt ggcgctggcg tgtgtgacgg cgtatcttga tagctggttt    900

ctgtggccgt tctattggat tgcacagggg acgatgttct gggcgatctt cgttcttggc    960

cacgactgcg ggcatggcag cttctccaac agtaaaagat tgaacaacct agttggccac   1020

atcatgcact cgttcattct tgtgccgtat catgggtggc gcatcagcca taggacgcat   1080

cacgccaatc acgggcatgt cgaaaacgat gagtcctggt acccgatgac agaggcggtg   1140
```

```
ttcaagacac tgaatttctg ggctaaatgt gggcgtctca agtttccaac tactctgttt   1200
gcctatccag tgtacttgtg gacgaggagt ccagggaagg atggttccca tttcaatccc   1260
tccagcgact tatttgatca gagtgagtgg agcgaggtga cgatgtcgac cgcgtgctgg   1320
ttggcaatgg gggctatctt aacggcagca gtgtcacagt tcgggttcct ctggatgctt   1380
aagctctact tcgtcccgta tatcattaat gtgatgtggt tggatgccgt gacatacctt   1440
caccaccatg ggtacgataa aaagattccc tggtaccgag gtaaggagtg gaactatttg   1500
cggggaggac tgtccaccgt cgatcgtgac tacggttttt tcaacaagat ccaccacgac   1560
attggcacgc acgtcgtgca tcacctgttt cctcagatcc cgcattatca tttatgtgag   1620
gcaaccgcgg ctgtcaagtc tttgcttgga aatttctacc gagaaccaga gaagtcaggt   1680
cccattcctc ttcatctcat ccctgtcatt atgaagagtt tctctgagga tcacttcgtg   1740
gccgacgagg gtgacattgt cttttaccaa aaagatccaa aacagtgcaa ttgcagataa   1800
atctcttcca ggttacttgc tctcttcccc ttccattgta gcataagtcg cggattagga   1860
agctgtggat gatacactcg actcactgtc taaggaagct ggattttgac gcccctccct   1920
gtctagtcgt cattggcagc cattgatgat cgagcgatta agtaggaagg aaccatccac   1980
agacagatag aaatgcaaca ggaaaacaag tagagatcgg ctctcattct ccagtaagag   2040
aggcgcgtga gcacgcacag gggatcatct ggtgtccaag acggtgtgac gtggatctat   2100
tcgctatttt tgttcattgc gaaagaattt cttcacttgc atcgtgtttt catcgagctt   2160
ttggaaatgg cattgcttat tttttcgctg caaatatcca aacattagca gctgtttttg   2220
ttggtgcaca tgagccatcg ggagtgtgta tctttctcct ctgctggctt gcagttgcag   2280
cttggttcgt gaacttttaa agtcgatgat taggtttctg cttgatattt gcagctgtgt   2340
tgtgatcgat tgttccgagt ggaatatgga tttgagtatt catgacctgt ttaggaaatc   2400
accaattttt attcccgatt actgcaatcg gtcctttctt tataaatcat atctttgaca   2460
ttgtgacata gtcattgatc ttctaatcat ctctcataca atccccgtca accagagcag   2520
gcttttcaag gtgtctgaga aggatcgtga acatgggcgt gcctgcctac catatgatcc   2580
gccacaaaca tgtcttgccc atttgatgct atttgagatt ctctcatact ttgattcata   2640
actacatatt tttaattgtt atatagagtt gtgaccctcc cccactttgg agtaaagata   2700
ttctcatcta tttagtcatt tttatttgcc tctcttaact tttatcaaaa aatcacttaa   2760
gtgattttaa tttgttttct tctactcttt ggttttgtat agtcacatac tttcttatta   2820
aaagccgtga ttaatccttg tacatatctc aagtttcttt tatttatcca ttacaattca   2880
tgtggagggt aatctttgaa aatatacaag tattgaattc ccttcatatt tgtatgtttt   2940
ttttattaaa tattacttct acttgatcca taatttgatt ccacacctct ttttaaggtg   3000
aaatctttgc cttctttttg tagaagccac tcacatcttc tacaaatttc ttcctaagaa   3060
cacttacata aaaaatcgaa tgcctcatca atctcttcaa tatgtctaag atatatatat   3120
tcttgtataa tatgtttgca acttcataag gacctgccta ctattagatc catttgaaag   3180
tgagatgtat taggcaagtg a                                            3201
```

<210> SEQ ID NO 143
<211> LENGTH: 1185
<212> TYPE: DNA
<213> ORGANISM: Physcomitrella patens

<400> SEQUENCE: 143

```
atggatcaag ccagtaagat tgctgacaat ccttctgcgg tatcgctacg cagcgcggag     60
```

-continued gacgatggca agctggctgc aatctccgtg aagcatcagc ataataggga tgatgaggag 120
ttcgatgcgt cgacgcggcc gccgttcagt cttggtcaga tacgggccgc cattcccaag 180
ctctgctggg aaagaagcat tgtgaggtcg ttcagctacg tcggcaggga tgttaccatt 240
gtagtggcgc tggcgtgtgt gacggcgtat cttgatagct ggtttctgtg gccgttctat 300
tggattgcac aggggacgat gttctgggcg atcttcgttc ttggccacga ctgcgggcat 360
ggcagcttct ccaacagtaa aagattgaac aacctagttg gccacatcat gcactcgttc 420
attcttgtgc cgtatcatgg gtggcgcatc agccatagga cgcatcacgc caatcacggg 480
catgtcgaaa acgatgagtc ctggtacccg atgacagagg cggtgttcaa gacactgaat 540
ttctgggcta aatgtgggcg tctcaagttt ccaactactc tgtttgccta tccagtgtac 600
ttgtggacga ggagtccagg gaaggatggt tcccatttca atccctccag cgacttattt 660
gatcagagtg agtggagcga ggtgacgatg tcgaccgcgt gctggttggc aatgggggct 720
atcttaacgg cagcagtgtc acagttcggg ttcctctgga tgcttaagct ctacttcgtc 780
ccgtatatca ttaatgtgat gtggttggat gccgtgacat accttcacca ccatgggtac 840
gataaaaaga ttccctggta ccgaggtaag gagtggaact atttgcgggg aggactgtcc 900
accgtcgatc gtgactacgg tttttcaac aagatccacc acgacattgg cacgcacgtc 960
gtgcatcacc tgtttcctca gatcccgcat tatcatttat gtgaggcaac cgcggctgtc 1020
aagtctttgc ttggaaattt ctaccgagaa ccagagaagt caggtcccat tcctcttcat 1080
ctcatccctg tcattatgaa gagtttctct gaggatcact tcgtggccga cgagggtgac 1140
attgtctttt accaaaaaga tccaaaacag tgcaattgca gataa 1185

<210> SEQ ID NO 144
<211> LENGTH: 394
<212> TYPE: PRT
<213> ORGANISM: Physcomitrella patens

<400> SEQUENCE: 144

Met Asp Gln Ala Ser Lys Ile Ala Asp Asn Pro Ser Ala Val Ser Leu
1 5 10 15

Arg Ser Ala Glu Asp Asp Gly Lys Leu Ala Ala Ile Ser Val Lys His
20 25 30

Gln His Asn Arg Asp Asp Glu Glu Phe Asp Ala Ser Thr Arg Pro Pro
35 40 45

Phe Ser Leu Gly Gln Ile Arg Ala Ala Ile Pro Lys Leu Cys Trp Glu
50 55 60

Arg Ser Ile Val Arg Ser Phe Ser Tyr Val Gly Arg Asp Val Thr Ile
65 70 75 80

Val Val Ala Leu Ala Cys Val Thr Ala Tyr Leu Asp Ser Trp Phe Leu
85 90 95

Trp Pro Phe Tyr Trp Ile Ala Gln Gly Thr Met Phe Trp Ala Ile Phe
100 105 110

Val Leu Gly His Asp Cys Gly His Gly Ser Phe Ser Asn Ser Lys Arg
115 120 125

Leu Asn Asn Leu Val Gly His Ile Met His Ser Phe Ile Leu Val Pro
130 135 140

Tyr His Gly Trp Arg Ile Ser His Arg Thr His His Ala Asn His Gly
145 150 155 160

His Val Glu Asn Asp Glu Ser Trp Tyr Pro Met Thr Glu Ala Val Phe
165 170 175

```
Lys Thr Leu Asn Phe Trp Ala Lys Cys Gly Arg Leu Lys Phe Pro Thr
            180                 185                 190

Thr Leu Phe Ala Tyr Pro Val Tyr Leu Trp Thr Arg Ser Pro Gly Lys
        195                 200                 205

Asp Gly Ser His Phe Asn Pro Ser Ser Asp Leu Phe Asp Gln Ser Glu
    210                 215                 220

Trp Ser Glu Val Thr Met Ser Thr Ala Cys Trp Leu Ala Met Gly Ala
225                 230                 235                 240

Ile Leu Thr Ala Ala Val Ser Gln Phe Gly Phe Leu Trp Met Leu Lys
                245                 250                 255

Leu Tyr Phe Val Pro Tyr Ile Ile Asn Val Met Trp Leu Asp Ala Val
            260                 265                 270

Thr Tyr Leu His His His Gly Tyr Asp Lys Lys Ile Pro Trp Tyr Arg
        275                 280                 285

Gly Lys Glu Trp Asn Tyr Leu Arg Gly Gly Leu Ser Thr Val Asp Arg
    290                 295                 300

Asp Tyr Gly Phe Phe Asn Lys Ile His His Asp Ile Gly Thr His Val
305                 310                 315                 320

Val His His Leu Phe Pro Gln Ile Pro His Tyr His Leu Cys Glu Ala
                325                 330                 335

Thr Ala Ala Val Lys Ser Leu Leu Gly Asn Phe Tyr Arg Glu Pro Glu
            340                 345                 350

Lys Ser Gly Pro Ile Pro Leu His Leu Ile Pro Val Ile Met Lys Ser
        355                 360                 365

Phe Ser Glu Asp His Phe Val Ala Asp Glu Gly Asp Ile Val Phe Tyr
    370                 375                 380

Gln Lys Asp Pro Lys Gln Cys Asn Cys Arg
385                 390
```

<210> SEQ ID NO 145
<211> LENGTH: 1543
<212> TYPE: DNA
<213> ORGANISM: Physcomitrella patens

<400> SEQUENCE: 145

```
gcgctgcgag gtccagcacg tagagacgga ccgtgtctgt tcagtgtgtg gcaaaggcga      60

attcagagtg gttggaagaa gggggtggat caagctgctg ctgtgatcga tcgcgggagt     120

cagcgatggc ttcgcggaga ggcatgatct cgttggatca ggccaagtcc atgatcgaag     180

agctgccgcc agtggtgtcg atgcggagcg cggaggatga tgacaaaggc ggcggcggcg     240

gcggcggcgg cggcgtcgtc tctgtggaag ccaaaggtca ggaggaagcg tgggacgcgt     300

cgaagaagcc ccccttcacc ctcggccaga tccgagccgc cattccaaag cactgctggg     360

agcgcagcat tccacgctcg ttgcgatacg tcgcaaacga catcgccatt gtggtggcgc     420

tcgcggtggt tgctgcgtac gtcgatagtt ggttcttgtg gccgttttac tggttcgtcc     480

aagggacaat gttctggtcg ctcttcgtcc tcggccacga ttgcggacac ggtagcttct     540

ccccaagcag gcgattgaac aacttcgtcg gccacatcgt tcactcgttt atcctggtcc     600

cttaccatgg ctggcgcatc agccaccgga cgcatcacgc taaccacggc cacgtcgaga     660

acgacgagtc gtggtatccc atgacggagg cgctgtacag gactctcaac atctttgaga     720

aactgggtcg gttgcagttt ccattcccac tcttagcgta tcctttctac ctgtggacga     780

ggagcccagg caagaatgga acccattaca gcccttcgag cgacctgttt gattcgagcg     840
```

```
agtggaagga agtgatcacc tcaaccgctt gctggttcgc tatggtggcg atcctggccg    900
acgtcgtctt tcataaaggt ttcctctgga cgtttaagct ctatttcata ccttacatcg    960
tcaatgtcgt gtggctggac ttcgtcacat accttcatca ccatggctac gagaagaaaa   1020
ttccatggta tcgtgggcaa gagtggaact acatgcgcgg ggggttgtcc accatcgacc   1080
gcgactacgg gatcttcaac aaaatccatc acgacatcgg cacgcacgtt gtgcaccatt   1140
tgttccctca gattccgcat taccatttgg tcgaggcaac cgcggcggtg aagcctttgc   1200
ttgggaacta ctacagggag ccgaaaaggt caggtctgat tccactgcat ctcctcccca   1260
ttctcgtgaa gagcttcaac gaggatcatt atgtggccga cgagggcgac attgtctttt   1320
atcagaacga tgtaaagcag tgattcgtca cctcttcttg gccacagaaa aagaaaaaaa   1380
gaaaaaaaat catggctata gcgcggcccg tttgctctca acctttctag catgcactct   1440
cgcgttggaa atgatccatc aatcggcgat gcatcgtgca aggagggtca gactccgacg   1500
ggacgttgat tgaagacctc cttcaaagga tttagcgtct tat                     1543
```

<210> SEQ ID NO 146
<211> LENGTH: 1143
<212> TYPE: DNA
<213> ORGANISM: Physcomitrella patens

<400> SEQUENCE: 146

```
atgcggagcg cggaggatga tgacaaaggc ggcggcggcg gcggcggcgg cggcgtcgtc     60
tctgtggaag ccaaaggtca ggaggaagcg tgggacgcgt cgaagaagcc ccccttcacc    120
ctcggccaga tccgagccgc cattccaaag cactgctggg agcgcagcat tccacgctcg    180
ttgcgatacg tcgcaaacga catcgccatt gtggtggcgc tcgcggtggt tgctgcgtac    240
gtcgatagtt ggttcttgtg gccgttttac tggttcgtcc aagggacaat gttctggtcg    300
ctcttcgtcc tcggccacga ttgcggacac ggtagcttct ccccaagcag gcgattgaac    360
aacttcgtcg gccacatcgt tcactcgttt atcctggtcc cttaccatgg ctggcgcatc    420
agccaccgga cgcatcacgc taaccacggc cacgtcgaga acgacgagtc gtggtatccc    480
atgacggagg cgctgtacag gactctcaac atctttgaga aactgggtcg gttgcagttt    540
ccattcccac tcttagcgta tcctttctac ctgtggacga ggagcccagg caagaatgga    600
acccattaca gcccttcgag cgacctgttt gattcgagcg agtggaagga agtgatcacc    660
tcaaccgctt gctggttcgc tatggtggcg atcctggccg acgtcgtctt tcataaaggt    720
ttcctctgga cgtttaagct ctatttcata ccttacatcg tcaatgtcgt gtggctggac    780
ttcgtcacat accttcatca ccatggctac gagaagaaaa ttccatggta tcgtgggcaa    840
gagtggaact acatgcgcgg ggggttgtcc accatcgacc gcgactacgg gatcttcaac    900
aaaatccatc acgacatcgg cacgcacgtt gtgcaccatt tgttccctca gattccgcat    960
taccatttgg tcgaggcaac cgcggcggtg aagcctttgc ttgggaacta ctacagggag   1020
ccgaaaaggt caggtctgat tccactgcat ctcctcccca ttctcgtgaa gagcttcaac   1080
gaggatcatt atgtggccga cgagggcgac attgtctttt atcagaacga tgtaaagcag   1140
tga                                                                 1143
```

<210> SEQ ID NO 147
<211> LENGTH: 380
<212> TYPE: PRT
<213> ORGANISM: Physcomitrella patens

<400> SEQUENCE: 147

```
Met Arg Ser Ala Glu Asp Asp Asp Lys Gly Gly Gly Gly Gly Gly Gly
1               5                   10                  15

Gly Gly Val Val Ser Val Glu Ala Lys Gly Gln Glu Glu Ala Trp Asp
            20                  25                  30

Ala Ser Lys Lys Pro Pro Phe Thr Leu Gly Gln Ile Arg Ala Ala Ile
        35                  40                  45

Pro Lys His Cys Trp Glu Arg Ser Ile Pro Arg Ser Leu Arg Tyr Val
    50                  55                  60

Ala Asn Asp Ile Ala Ile Val Val Ala Leu Ala Val Val Ala Ala Tyr
65                  70                  75                  80

Val Asp Ser Trp Phe Leu Trp Pro Phe Tyr Trp Phe Val Gln Gly Thr
                85                  90                  95

Met Phe Trp Ser Leu Phe Val Leu Gly His Asp Cys Gly His Gly Ser
            100                 105                 110

Phe Ser Pro Ser Arg Arg Leu Asn Asn Phe Val Gly His Ile Val His
        115                 120                 125

Ser Phe Ile Leu Val Pro Tyr His Gly Trp Arg Ile Ser His Arg Thr
    130                 135                 140

His His Ala Asn His Gly His Val Glu Asn Asp Glu Ser Trp Tyr Pro
145                 150                 155                 160

Met Thr Glu Ala Leu Tyr Arg Thr Leu Asn Ile Phe Glu Lys Leu Gly
                165                 170                 175

Arg Leu Gln Phe Pro Phe Pro Leu Leu Ala Tyr Pro Phe Tyr Leu Trp
            180                 185                 190

Thr Arg Ser Pro Gly Lys Asn Gly Thr His Tyr Ser Pro Ser Ser Asp
        195                 200                 205

Leu Phe Asp Ser Ser Glu Trp Lys Glu Val Ile Thr Ser Thr Ala Cys
    210                 215                 220

Trp Phe Ala Met Val Ala Ile Leu Ala Asp Val Val Phe His Lys Gly
225                 230                 235                 240

Phe Leu Trp Thr Phe Lys Leu Tyr Phe Ile Pro Tyr Ile Val Asn Val
                245                 250                 255

Val Trp Leu Asp Phe Val Thr Tyr Leu His His His Gly Tyr Glu Lys
            260                 265                 270

Lys Ile Pro Trp Tyr Arg Gly Gln Glu Trp Asn Tyr Met Arg Gly Gly
        275                 280                 285

Leu Ser Thr Ile Asp Arg Asp Tyr Gly Ile Phe Asn Lys Ile His His
    290                 295                 300

Asp Ile Gly Thr His Val Val His His Leu Phe Pro Gln Ile Pro His
305                 310                 315                 320

Tyr His Leu Val Glu Ala Thr Ala Ala Val Lys Pro Leu Leu Gly Asn
                325                 330                 335

Tyr Tyr Arg Glu Pro Lys Arg Ser Gly Leu Ile Pro Leu His Leu Leu
            340                 345                 350

Pro Ile Leu Val Lys Ser Phe Asn Glu Asp His Tyr Val Ala Asp Glu
        355                 360                 365

Gly Asp Ile Val Phe Tyr Gln Asn Asp Val Lys Gln
    370                 375                 380
```

<210> SEQ ID NO 148
<211> LENGTH: 1495
<212> TYPE: DNA
<213> ORGANISM: Physcomitrella patens

<400> SEQUENCE: 148
ttctttccaa taagtgtctc gggaagggga gagtgagtga gagagagaga ctccagtgga 60
gagtcgcggc ggagctcttg tggactggag cgatgtcgtc tagaaggggc ttgatatcgc 120
tggatcagcc ccgaaagatt ggtcacaatc ttcccgtggt gtcgttggat agcattgaga 180
atgtcaggaa cgtgggtggg atgtccgtga agcatgagat taataggaag gatgaagaat 240
tcgatgcgtc tagaaagccg cccttcagcc ttggccagtt acgagccgcc attcccaagc 300
actgctggga gcggagtctg tcgagatctt tcagctatgt agtcagagat gttgccattg 360
tagtgacgct agcgtatgtg gcggtatact tcgatagctg gtttctgtgg ccagtgtatt 420
ggttggcaca ggggacaatg ttttgggcga tcttcgttct gggtcacgac tgtgggcatg 480
gcagcttttc aagcaacaag agcctgaaca acctggtcgg acacatcctg cactcgttca 540
ttctggtgcc atatcacggg tggcgcatca gtcacaggac acatcatgcc aaccatggcc 600
acgtcaagaa cgacgagtcc tggtacccga tgacagaggg gctgtttatc acactggatt 660
tctggggcaa atttggacgg ctgaactttc cggctacgct gtttgcgtat cccgcgtacc 720
tctggtggag aactcctggc aagtcgggtt cccatttcaa tccgtccagc gatttgtttg 780
acccgagtga gtggaaggag gtggcaacgt cgaccacatg ctggttgaca atggttgcca 840
tctcgatgac ttcggtgtcg caagtcgggt ttctttttgt gttcaagctt tacttcgtcc 900
cctacatcgt caacgtgatg tggttggacg ctgtgaccta ccttcaccac cacgggtatg 960
agaaacaaat cccctggtac cgaggtcagg aatggagtta cctgcggggt ggactgtcca 1020
ccatcgatcg cgactacggt ttgtttaatg agatccacca cgacattggc acacacgtcg 1080
tgcatcacct cttccctcag atcccgcatt atcatttgcg tgaagctaca gcagccgtaa 1140
ggcccttgtt aaaaagttac taccgcgagc cccaaaagtc gggtcttttt cctcttcacc 1200
tcatctctgt catgatgaag agtttctccg agcatcactt cgtggctgat gagtgcgata 1260
ttgtcttcta tcagaagagc acaaatgcta agtgaggttc tcgagcctag agaaatttcg 1320
ctaatgtttt ttgcttccac cctacaaatg tggatctttt atcaggtggg tcagtaatct 1380
tgtattctac attagaatcg gaatgggagc ctgtaactgg tattattgac caattctgga 1440
gttaaaagac gtcatttttg gattattctc cacatgtggc tctgtacaat aataa 1495

<210> SEQ ID NO 149
<211> LENGTH: 1095
<212> TYPE: DNA
<213> ORGANISM: Physcomitrella patens

<400> SEQUENCE: 149
atgtccgtga agcatgagat taataggaag gatgaagaat tcgatgcgtc tagaaagccg 60
cccttcagcc ttggccagtt acgagccgcc attcccaagc actgctggga gcggagtctg 120
tcgagatctt tcagctatgt agtcagagat gttgccattg tagtgacgct agcgtatgtg 180
gcggtatact tcgatagctg gtttctgtgg ccagtgtatt ggttggcaca ggggacaatg 240
ttttgggcga tcttcgttct gggtcacgac tgtgggcatg gcagcttttc aagcaacaag 300
agcctgaaca acctggtcgg acacatcctg cactcgttca ttctggtgcc atatcacggg 360
tggcgcatca gtcacaggac acatcatgcc aaccatggcc acgtcaagaa cgacgagtcc 420
tggtacccga tgacagaggg gctgtttatc acactggatt tctggggcaa atttggacgg 480
ctgaactttc cggctacgct gtttgcgtat cccgcgtacc tctggtggag aactcctggc 540
aagtcgggtt cccatttcaa tccgtccagc gatttgtttg acccgagtga gtggaaggag 600

```
gtggcaacgt cgaccacatg ctggttgaca atggttgcca tctcgatgac ttcggtgtcg    660

caagtcgggt ttctttttgt gttcaagctt tacttcgtcc cctacatcgt caacgtgatg    720

tggttggacg ctgtgaccta ccttcaccac cacgggtatg agaaacaaat cccctggtac    780

cgaggtcagg aatggagtta cctgcggggt ggactgtcca ccatcgatcg cgactacggt    840

ttgtttaatg agatccacca cgacattggc acacacgtcg tgcatcacct cttccctcag    900

atcccgcatt atcatttgcg tgaagctaca gcagccgtaa ggcccttgtt aaaaagttac    960

taccgcgagc cccaaaagtc gggtcttttt cctcttcacc tcatctctgt catgatgaag   1020

agtttctccg agcatcactt cgtggctgat gagtgcgata ttgtcttcta tcagaagagc   1080

acaaatgcta agtga                                                    1095
```

<210> SEQ ID NO 150
<211> LENGTH: 364
<212> TYPE: PRT
<213> ORGANISM: Physcomitrella patens

<400> SEQUENCE: 150

```
Met Ser Val Lys His Glu Ile Asn Arg Lys Asp Glu Glu Phe Asp Ala
1               5                   10                  15

Ser Arg Lys Pro Pro Phe Ser Leu Gly Gln Leu Arg Ala Ala Ile Pro
            20                  25                  30

Lys His Cys Trp Glu Arg Ser Leu Ser Arg Ser Phe Ser Tyr Val Val
        35                  40                  45

Arg Asp Val Ala Ile Val Val Thr Leu Ala Tyr Val Ala Val Tyr Phe
    50                  55                  60

Asp Ser Trp Phe Leu Trp Pro Val Tyr Trp Leu Ala Gln Gly Thr Met
65                  70                  75                  80

Phe Trp Ala Ile Phe Val Leu Gly His Asp Cys Gly His Gly Ser Phe
                85                  90                  95

Ser Ser Asn Lys Ser Leu Asn Asn Leu Val Gly His Ile Leu His Ser
            100                 105                 110

Phe Ile Leu Val Pro Tyr His Gly Trp Arg Ile Ser His Arg Thr His
        115                 120                 125

His Ala Asn His Gly His Val Lys Asn Asp Glu Ser Trp Tyr Pro Met
    130                 135                 140

Thr Glu Gly Leu Phe Ile Thr Leu Asp Phe Trp Gly Lys Phe Gly Arg
145                 150                 155                 160

Leu Asn Phe Pro Ala Thr Leu Phe Ala Tyr Pro Ala Tyr Leu Trp Trp
                165                 170                 175

Arg Thr Pro Gly Lys Ser Gly Ser His Phe Asn Pro Ser Ser Asp Leu
            180                 185                 190

Phe Asp Pro Ser Glu Trp Lys Glu Val Ala Thr Ser Thr Thr Cys Trp
        195                 200                 205

Leu Thr Met Val Ala Ile Ser Met Thr Ser Val Ser Gln Val Gly Phe
    210                 215                 220

Leu Phe Val Phe Lys Leu Tyr Phe Val Pro Tyr Ile Val Asn Val Met
225                 230                 235                 240

Trp Leu Asp Ala Val Thr Tyr Leu His His His Gly Tyr Glu Lys Gln
                245                 250                 255

Ile Pro Trp Tyr Arg Gly Gln Glu Trp Ser Tyr Leu Arg Gly Gly Leu
            260                 265                 270

Ser Thr Ile Asp Arg Asp Tyr Gly Leu Phe Asn Glu Ile His His Asp
```

```
        275                 280                 285

Ile Gly Thr His Val Val His His Leu Phe Pro Gln Ile Pro His Tyr
    290                 295                 300

His Leu Arg Glu Ala Thr Ala Ala Val Arg Pro Leu Leu Lys Ser Tyr
305                 310                 315                 320

Tyr Arg Glu Pro Gln Lys Ser Gly Leu Phe Pro Leu His Leu Ile Ser
                325                 330                 335

Val Met Met Lys Ser Phe Ser Glu His His Phe Val Ala Asp Glu Cys
            340                 345                 350

Asp Ile Val Phe Tyr Gln Lys Ser Thr Asn Ala Lys
        355                 360


<210> SEQ ID NO 151
<211> LENGTH: 2468
<212> TYPE: DNA
<213> ORGANISM: Postia placenta

<400> SEQUENCE: 151

cgcgctgggc tcctagcagc tccgtgtgat agatcattcg aagtcaggcg cgcttgtcgc     60

accagaaccc ggggggtgtc actgtcccag acaagctgtt ggaccgtggg cggcacgata    120

aaacgatctt taatcggaga gttctcttcc gccccctctt gagaagtcca ctccgcgctt    180

cttgctatcc accacccgca atggctacca cggctgattc tgcaggccca gcacggactc    240

agtcggcgtc cacgtactca gaggaccagc tccctgaatt cacacctatg ccatggtacg    300

tcaagattct cacaacttca tgaacagctc tcatgcgctg gcacaggact ctgagtgaga    360

ttcgcgctgc tatccctgca catctccacg cgcgccagac gtggaagggg atgctctacc    420

tcttgcgtga catcctaatg gcagccattg tatggaagct cgcgctctac atcgatcctt    480

cgttcaagag tgagactgcc gtgcgaacgt tgacgccggt aggagcggaa gccgcacgct    540

ggggcgcctg gcttgtttag tatgtgatct tactagtgta gtcaggcgct gcgactcaga    600

gcaacctaag ttggtggttc cagggtctga tcttcacagg gatctgggtg atcgggcacg    660

aggtgggtac ttgacagtac gcaaccttac ttgacccctt cgcttatatc agtcttagtg    720

cggtcacggc gcattctcgt ccaacaagcg tatttgcgat atcattggat ttgtgagtag    780

cacgtcgaag tcaagcgggg ttcacgtcgg tggctgatat ctacattgaa tagattacgc    840

acacgttcct gtggacaccc tacttcagct ggcagatctc tcatcatcgt catcacagca    900

atcatgcgtc catggagcgc gacgaggtat atgtgcccaa gacacgcgcc gacctgggca    960

tccctaagga gagtgagggt gcaatcgact atgaggatta cctcggcgat acaccaatct   1020

acacgttgtt tgcgcttatc cgacaacagg ttttggcctt cccggcatat cttcgtaagt   1080

ttgcttcttc gtattaacaa tggttagatt cacagcaggc tgttagtatt caacgtctca   1140

gggcagaaga actacccgaa atggaccaat cacttcgatc gtacgtaagc gccgtgtcga   1200

ggcatgaccc acgtcctaat ctcgttcaca gccaattcta ttcttttcac gaagaggcag   1260

cgcaatgccg tcatcatgtc gaatatcggc atcgctacta tggtctacat tgtgctcgag   1320

gccagtcgca cctggggcgc gagtgagatc atgaagtact atggcatccc atggctgtcg   1380

gtcactcact ggtaaattat atctgtcgtg acgtttatat gatgaggtta atcaggcgac   1440

taggttcatc atgatcactt accttcacca cacggacgtc gaactccctc actaccgcaa   1500

cggacagtgg aacttccagc ggggcgctgc ggcgactgta gatcgtaatt tcctcggctg   1560

gcaagggcgc ttcttcctgc acgatgtcgc ccacttccac gtcattcacc actttttccc   1620
```

```
tatgatgccc ttctgtgagt gtcttgcttt gaaatgcggt gcgcctgtca ggctgacgat   1680

gtgcggcaga ccacgggcct gaggcaacga aatatctcaa ggagttcatt ggcgaccact   1740

atcggtattc tgataagccc gtgttcaagg cgctctggga cacgtacaac aattgccaat   1800

ttgtcgaaga tgagggtgcg tcatctcctg aatttggtaa agccggtgct gatcctgcgc   1860

ccgtataggt gacattctct tctaccgtga ccgcaagggc caggcgcgcg tacgccccgc   1920

tgagcccttc agggaatcca ctatatcagc gagcgtgtct cgttgatctt caaaccaccg   1980

tatacagttc agaagtgtat catcgccgga ttgccctggc gcccttgctt ctacactgtt   2040

catctatcgt tcacgctgtc ttaccacgct atgttctgtg tttcggtagc ctgtcggcat   2100

tacttgttcc aacactgatg tctccttaga acccctctcc ccccttgtaa ccgcagcatg   2160

atgttgtatg ccttgtaatc gaggcatctt ttgtactggt atgggtcaga taatcagtgt   2220

tgttgtacga ccatcaccgt aatgccattt tcacgattcc atgatctcac ttctctattc   2280

agtctcctag actatctgcg tctcatatca tgatgtaatc tgtcgctact ggtaatgcat   2340

cgagacgagg tcccatcact atggttattc aaaaggaaga gatcggtgta caatctggcg   2400

atgtcacagt atgtgtttgc aagcgtgaag gagggctgaa aatgcagctg ctctcattgg   2460

cgacatct                                                              2468
```

<210> SEQ ID NO 152
<211> LENGTH: 1284
<212> TYPE: DNA
<213> ORGANISM: Postia placenta

<400> SEQUENCE: 152

```
atggctacca cggctgattc tgcaggccca gcacggactc agtcggcgtc cacgtactca     60

gaggaccagc tccctgaatt cacacctatg ccatggactc tgagtgagat tcgcgctgct    120

atccctgcac atctccacgc gcgccagacg tggaagggga tgctctacct cttgcgtgac    180

atcctaatgg cagccattgt atggaagctc gcgctctaca tcgatccttc gttcaagagt    240

gagactgccg tgcgaacgtt gacgccggta ggagcggaag ccgcacgctg gggcgcctgg    300

cttgtttatt ggtggttcca gggtctgatc ttcacaggga tctgggtgat cgggcacgag    360

tgcggtcacg gcgcattctc gtccaacaag cgtatttgcg atatcattgg atttattacg    420

cacacgttcc tgtggacacc ctacttcagc tggcagatct ctcatcatcg tcatcacagc    480

aatcatgcgt ccatggagcg cgacgaggta tatgtgccca agacacgcgc cgacctgggc    540

atccctaagg agagtgaggg tgcaatcgac tatgaggatt acctcggcga tacaccaatc    600

tacacgttgt ttgcgcttat ccgacaacag gttttggcct tcccggcata tcttctattc    660

aacgtctcag ggcagaagaa ctacccgaaa tggaccaatc acttcgatcc caattctatt    720

cttttcacga agaggcagcg caatgccgtc atcatgtcga atatcggcat cgctactatg    780

gtctacattg tgctcgaggc cagtcgcacc tggggcgcga gtgagatcat gaagtactat    840

ggcatcccat ggctgtcggt cactcactgg ttcatcatga tcacttacct tcaccacacg    900

gacgtcgaac tccctcacta ccgcaacgga cagtggaact tccagcgggg cgctgcggcg    960

actgtagatc gtaatttcct cggctggcaa gggcgcttct tcctgcacga tgtcgcccac   1020

ttccacgtca ttcaccactt tttccctatg atgcccttct accacgggcc tgaggcaacg   1080

aaatatctca aggagttcat tggcgaccac tatcggtatt ctgataagcc cgtgttcaag   1140

gcgctctggg acacgtacaa caattgccaa tttgtcgaag atgagggtga cattctcttc   1200

taccgtgacc gcaagggcca ggcgcgcgta cgccccgctg agcccttcag ggaatccact   1260
```

```
atatcagcga gcgtgtctcg ttga                                        1284


<210> SEQ ID NO 153
<211> LENGTH: 427
<212> TYPE: PRT
<213> ORGANISM: Postia placenta

<400> SEQUENCE: 153

Met Ala Thr Thr Ala Asp Ser Ala Gly Pro Ala Arg Thr Gln Ser Ala
1               5                   10                  15

Ser Thr Tyr Ser Glu Asp Gln Leu Pro Glu Phe Thr Pro Met Pro Trp
            20                  25                  30

Thr Leu Ser Glu Ile Arg Ala Ala Ile Pro Ala His Leu His Ala Arg
        35                  40                  45

Gln Thr Trp Lys Gly Met Leu Tyr Leu Leu Arg Asp Ile Leu Met Ala
    50                  55                  60

Ala Ile Val Trp Lys Leu Ala Leu Tyr Ile Asp Pro Ser Phe Lys Ser
65                  70                  75                  80

Glu Thr Ala Val Arg Thr Leu Thr Pro Val Gly Ala Glu Ala Ala Arg
                85                  90                  95

Trp Gly Ala Trp Leu Val Tyr Trp Trp Phe Gln Gly Leu Ile Phe Thr
            100                 105                 110

Gly Ile Trp Val Ile Gly His Glu Cys Gly His Gly Ala Phe Ser Ser
        115                 120                 125

Asn Lys Arg Ile Cys Asp Ile Ile Gly Phe Ile Thr His Thr Phe Leu
    130                 135                 140

Trp Thr Pro Tyr Phe Ser Trp Gln Ile Ser His His Arg His His Ser
145                 150                 155                 160

Asn His Ala Ser Met Glu Arg Asp Glu Val Tyr Val Pro Lys Thr Arg
                165                 170                 175

Ala Asp Leu Gly Ile Pro Lys Glu Ser Glu Gly Ala Ile Asp Tyr Glu
            180                 185                 190

Asp Tyr Leu Gly Asp Thr Pro Ile Tyr Thr Leu Phe Ala Leu Ile Arg
        195                 200                 205

Gln Gln Val Leu Ala Phe Pro Ala Tyr Leu Leu Phe Asn Val Ser Gly
    210                 215                 220

Gln Lys Asn Tyr Pro Lys Trp Thr Asn His Phe Asp Pro Asn Ser Ile
225                 230                 235                 240

Leu Phe Thr Lys Arg Gln Arg Asn Ala Val Ile Met Ser Asn Ile Gly
                245                 250                 255

Ile Ala Thr Met Val Tyr Ile Val Leu Glu Ala Ser Arg Thr Trp Gly
            260                 265                 270

Ala Ser Glu Ile Met Lys Tyr Tyr Gly Ile Pro Trp Leu Ser Val Thr
        275                 280                 285

His Trp Phe Ile Met Ile Thr Tyr Leu His His Thr Asp Val Glu Leu
    290                 295                 300

Pro His Tyr Arg Asn Gly Gln Trp Asn Phe Gln Arg Gly Ala Ala Ala
305                 310                 315                 320

Thr Val Asp Arg Asn Phe Leu Gly Trp Gln Gly Arg Phe Phe Leu His
                325                 330                 335

Asp Val Ala His Phe His Val Ile His His Phe Phe Pro Met Met Pro
            340                 345                 350

Phe Tyr His Gly Pro Glu Ala Thr Lys Tyr Leu Lys Glu Phe Ile Gly
        355                 360                 365
```

```
Asp His Tyr Arg Tyr Ser Asp Lys Pro Val Phe Lys Ala Leu Trp Asp
    370                 375                 380

Thr Tyr Asn Asn Cys Gln Phe Val Glu Asp Glu Gly Asp Ile Leu Phe
385                 390                 395                 400

Tyr Arg Asp Arg Lys Gly Gln Ala Arg Val Arg Pro Ala Glu Pro Phe
                405                 410                 415

Arg Glu Ser Thr Ile Ser Ala Ser Val Ser Arg
            420                 425


<210> SEQ ID NO 154
<211> LENGTH: 4066
<212> TYPE: DNA
<213> ORGANISM: Selaginella moellendorffii

<400> SEQUENCE: 154

cgcaaaatat ggggatttc ccccgttcct cgcagtcact ctccttgcct tcaaagcttt     60

gctacaagac gccgagatca tcgctaagtt ttcgatcgcc caagcaagcg tgtgtcatcg    120

ctggccttgg ctcttccttt tctccactct tggctcttaa aagaaggctc aagcccggct    180

cgagctcgcc atccattcca atggtcgctg ttccactccg aactgtcact gctcctcaaa    240

gcgatgtggt cggtgacttc tccaaggagt ttgatcctgc tgctccacca ccattttctc    300

tgggagatat cagagctgcc attccaaagc attgctggga gaagaatgtg tggagatcga    360

ttagctatgt cgtgagggac atagcggtgg ttctcggact ggctgctggt gctgcttact    420

tgaataattg gctcgtctgg ccactctact gggctgccca agggacgatg ttctgggctc    480

tctttgtgct cggccatgac tggtaagttt ttcttctccc aaaaacttgt ttttgctttc    540

tcgttcttac gcgtctttga tcagtggaca cgggagtttt tccaataaca agaagcttaa    600

ccatgtcttc ggccacattc tccattcttc catcctggtt ccataccacg ggtggtacgt    660

atgcttttcc atttcttgtt tggcttagag cttaaacttt gtggaaatcc aggaggataa    720

gccaccggac gcatcaccag aatcacggcc atgtcgagaa cgacgagtcc tggcatccag    780

taagtcgcct taagctcttc caagtgaaaa ccatttcgtt tttccttatc ttacactgtt    840

cttcatgtag atgaccgaga agctctacaa agacgcagat atctttactc gcttcggccg    900

gttccagctt ccatgggtca tgtttgctta tccgctttat ctggtattac tagaagttcc    960

attttgcttt gcctcgtttc taatctttct cacgaccagg cgacgaggag tccgggtaaa   1020

actggctctc acttccatcc ggacagctct ctcttcgtcc cgagcgagag aaacgacgtg   1080

ataacgtcga cagtgtgctg gtcggcgatg ttggcgttgc tggctgccat gaccgctgct   1140

gttggccccg tttggatgtt caagctttac gtcgtacctt acttggtaag ttttccagag   1200

ttctacgcaa tcgcttgatg cttgtgaccg cagatcaata ttgtttggct ggatgctgtg   1260

acttacatgc atcaccacgg gcacgaagtc aaggttccgt ggtacagagg aaaggtactg   1320

tgcaagcttt ttgtttttt tcaaggctct ttatgctgga actctaggag tggaactaca   1380

tgagaggggg actttccacc atagacagag actacggagt gatcaacaac atccaccacg   1440

atatcggcac tcacgtcgtg catcatttgt tccctcaaat tcctcactac aatttggtgg   1500

aagctgtgag ttcatcttag cgcttttttg cttcggaacg agctaatcgt ggttcttttt   1560

tcttttttc tttttcttt tttctttttt tttttgtttt cttggtgtag accaaagcga   1620

taaagcctgt gctgggaaaa tactacaggg aaccagaaaa atctggtctg cttcccttgc   1680

acttgtacaa aattcttaag tcgagcctcg aggaggacca ttttgtgccg aatgaaggcg   1740
```

```
acattgtctt ctaccagcgg gactccattt aaagaggaac aatgaaaaaa tcattttttg   1800
gcgaaaatgc gaagccaaca aaaaagaaaa cacgcaaaaa gcattctttt ctccagaaat   1860
gtcatataga gtttgatctt tataaagagt cccattcgaa agattcgttt gatcaggagg   1920
agcctaccta taaatataaa agaatgccag tggagagatg cgatacgggt tccctagaag   1980
cttttataca gcgctctttc tttcttttct tggcggcaat ccaggtggcg gctcttgcga   2040
tccgatcgat cgccattaga tcgattccat cgatcgatcc atggcggacg acggcgccaa   2100
ggggtttgat ccatcagcgc cgccgccgtt caccatcgcc gaggtccgcg ccgccatccc   2160
tagccactgc tggaacaaga gcctgggcag atctttgagc ttcctggcca gggatctggc   2220
gggcgtcgcg atcttggcct gcgttgccgg atatttcgat cactggctcg tctggcccgc   2280
gtattggatc gcgcaaggca cgctcttctg ggcgctcttc gtcatcggcc acgactggta   2340
agcaaaagct tccatttcca tcgactcgca ttggatttca ttgcacggca gtggtgagaa   2400
ttttgtctct ttggtttgct cttggatttc tggtgccctg cattgcgatt ctttcacctg   2460
aatacctcga agttcccttt ctcttggatt tcgcgctcga tacttatttt ttcttttact   2520
ttctgtgtac gtttgcgtgc gtgctttttt atttttgtt tttttatttc ttgcgttttt    2580
tgtgacttag aacatgtctc tagtttgtct tctacttccc ttgagcaact tgcgtgaaag   2640
ttactctatg aattcttttt ctatgcagtg gacacggaag cttttctgac aacaaggacg   2700
tgaacacagt cgtaggacat tttgtccact cgtttatttt ggtcccgtat catgggtggt   2760
gagtgatcag attctcttgt cctgtttttg tcctccccca tgactgattc cccggcctcg   2820
caggagaatc agccacagaa ctcatcatca aaatcacggt cacgcagaca atgacgagtc   2880
ctggtcacct gtaagccgtt ctgagcttgc aaattttcaa aattttcatg gtttttttcag  2940
atgaccgaga gcatgtataa gtcgtctcct ccactgaagc ttgttgcacg gttccaattg   3000
ccgtggccat tgttggtatt cccgttctat ctcgtaagga tttgtttatt ctccattgtt   3060
cgagcttgac accttcttgt gcttgtaggt gaaaagaact cctggcaagg atggttctca   3120
tttccatcca gagagcccct tgttcaagcc cagtgagagg ggtgatgttt tgacgtcaac   3180
cgcgtgttgg acggtcatgt tagccatcct gatcgccttg acgataagaa tcgggccact   3240
ctggatgttg aaactctact ttgttcctta cgtggtaagt cctgtacgct cttgagtatg   3300
ccatccagtg tagaactcta gcgtttttaa cttttcgttt ctttatcatt ttcagatcca   3360
gataatgtgg attgctggtg ttacttacat gcaccaccat ggccactacc agaaagtacc   3420
atggtatcgt gggaaggtac aagtattttc ctgttctgag gattcatttc tctcaaacga   3480
gctcttttac atctcaggaa tggaattaca tccgaggcgg cctatcaact atagaccgag   3540
actatggatt gttcaataac attcaccacg acattggaac gcatgtcgtg catcatttgt   3600
tcccgcagat tccacactac catttgatcg aagccgtaag tttctctgag tggtatcaag   3660
ggtcatcgat taacgttctt ttcaaatttc ctgtgtagac taaagccata aagccgattc   3720
tcgggaaata ctacagggac cctgagacgt ccggaccagt gccgatccat ttgttcaagg   3780
ttctaagcaa gagcctcaag gaagaccagt tcgtcgccga cgacggcgat gttgtcttct   3840
accagagcga tccaggcttg aagtaagtct gtttttttgt ctctggaaga ccaaagtttt   3900
ggagagtttt aataatccag ccggcgatgc taaggtaacg ataaaagcac ctcttttact   3960
gaccattttt tagtgttctt catcttagta ctcggttttg agaaaaaaaa aatccattcc   4020
atcgaagttt tcacgagctt gcaactcgaa ttttcacgaa tgttgc                  4066
```

<210> SEQ ID NO 155
<211> LENGTH: 1125
<212> TYPE: DNA
<213> ORGANISM: Selaginella moellendorffii

<400> SEQUENCE: 155
atggtcgctg ttccactccg aactgtcact gctcctcaaa gcgatgtggt cggtgacttc 60
tccaaggagt ttgatcctgc tgctccacca ccattttctc tgggagatat cagagctgcc 120
attccaaagc attgctggga gaagaatgtg tggagatcga ttagctatgt cgtgagggac 180
atagcggtgg ttctcggact ggctgctggt gctgcttact tgaataattg gctcgtctgg 240
ccactctact gggctgccca agggacgatg ttctgggctc tctttgtgct cggccatgac 300
tgtggacacg ggagtttttc caataacaag aagcttaacc atgtcttcgg ccacattctc 360
cattcttcca tcctggttcc ataccacggg tggaggataa gccaccggac gcatcaccag 420
aatcacggcc atgtcgagaa cgacgagtcc tggcatccaa tgaccgagaa gctctacaaa 480
gacgcagata tctttactcg cttcggccgg ttccagcttc catgggtcat gtttgcttat 540
ccgctttatc tggcgacgag gagtccgggt aaaactggct ctcacttcca tccggacagc 600
tctctcttcg tcccgagcga gagaaacgac gtgataacgt cgacagtgtg ctggtcggcg 660
atgttggcgt tgctggctgc catgaccgct gctgttggcc ccgtttggat gttcaagctt 720
tacgtcgtac cttacttgat caatattgtt tggctggatg ctgtgactta catgcatcac 780
cacgggcacg aagtcaaggt tccgtggtac agaggaaagg aatggaatta catccgaggc 840
ggcctatcaa ctatagaccg agactatgga ttgttcaata acattcacca cgacattgga 900
acgcatgtcg tgcatcattt gttcccgcag attccacact accatttgat cgaagccact 960
aaagccataa agccgattct cgggaaatac tacagggacc ctgagacgtc cggaccagtg 1020
ccgatccatt tgttcaaggt tctaagcaag agcctcaagg aagaccagtt cgtcgccgac 1080
gacggcgatg ttgtcttcta ccagagcgat ccaggcttga agtaa 1125

<210> SEQ ID NO 156
<211> LENGTH: 374
<212> TYPE: PRT
<213> ORGANISM: Selaginella moellendorffii

<400> SEQUENCE: 156

Met Val Ala Val Pro Leu Arg Thr Val Thr Ala Pro Gln Ser Asp Val
1               5                   10                  15

Val Gly Asp Phe Ser Lys Glu Phe Asp Pro Ala Ala Pro Pro Pro Phe
            20                  25                  30

Ser Leu Gly Asp Ile Arg Ala Ala Ile Pro Lys His Cys Trp Glu Lys
        35                  40                  45

Asn Val Trp Arg Ser Ile Ser Tyr Val Val Arg Asp Ile Ala Val Val
    50                  55                  60

Leu Gly Leu Ala Ala Gly Ala Ala Tyr Leu Asn Asn Trp Leu Val Trp
65                  70                  75                  80

Pro Leu Tyr Trp Ala Ala Gln Gly Thr Met Phe Trp Ala Leu Phe Val
                85                  90                  95

Leu Gly His Asp Cys Gly His Gly Ser Phe Ser Asn Asn Lys Lys Leu
            100                 105                 110

Asn His Val Phe Gly His Ile Leu His Ser Ser Ile Leu Val Pro Tyr
        115                 120                 125

His Gly Trp Arg Ile Ser His Arg Thr His His Gln Asn His Gly His
    130                 135                 140

```
Val Glu Asn Asp Glu Ser Trp His Pro Met Thr Glu Lys Leu Tyr Lys
145                 150                 155                 160

Asp Ala Asp Ile Phe Thr Arg Phe Gly Arg Phe Gln Leu Pro Trp Val
                165                 170                 175

Met Phe Ala Tyr Pro Leu Tyr Leu Ala Thr Arg Ser Pro Gly Lys Thr
            180                 185                 190

Gly Ser His Phe His Pro Asp Ser Ser Leu Phe Val Pro Ser Glu Arg
        195                 200                 205

Asn Asp Val Ile Thr Ser Thr Val Cys Trp Ser Ala Met Leu Ala Leu
    210                 215                 220

Leu Ala Ala Met Thr Ala Ala Val Gly Pro Val Trp Met Phe Lys Leu
225                 230                 235                 240

Tyr Val Val Pro Tyr Leu Ile Asn Ile Val Trp Leu Asp Ala Val Thr
                245                 250                 255

Tyr Met His His His Gly His Glu Val Lys Val Pro Trp Tyr Arg Gly
            260                 265                 270

Lys Glu Trp Asn Tyr Ile Arg Gly Gly Leu Ser Thr Ile Asp Arg Asp
        275                 280                 285

Tyr Gly Leu Phe Asn Asn Ile His His Asp Ile Gly Thr His Val Val
    290                 295                 300

His His Leu Phe Pro Gln Ile Pro His Tyr His Leu Ile Glu Ala Thr
305                 310                 315                 320

Lys Ala Ile Lys Pro Ile Leu Gly Lys Tyr Tyr Arg Asp Pro Glu Thr
                325                 330                 335

Ser Gly Pro Val Pro Ile His Leu Phe Lys Val Leu Ser Lys Ser Leu
            340                 345                 350

Lys Glu Asp Gln Phe Val Ala Asp Asp Gly Asp Val Val Phe Tyr Gln
        355                 360                 365

Ser Asp Pro Gly Leu Lys
    370
```

<210> SEQ ID NO 157
<211> LENGTH: 1209
<212> TYPE: DNA
<213> ORGANISM: Microdochium nivale

<400> SEQUENCE: 157

```
atgattgcga ccacccagac caagacggcc gtcacggacc gcgggacgac ccggatgaga      60

ggctcgtcaa cagcccagga gttcccagac atccagacca tccgcgatgc tatccccaag     120

cactgctttg agccctcaac agtccgttcc ttgagctatg tcgcccgcga tgtaaccatg     180

gcctcggccc tcatctgggc ggccgtccgc ttcatccccc agatcgagga ctcggtcctg     240

cgcttctcgg cctggatggt ctacggcctt gtccagggca tggtctgcac cggcgtctgg     300

atcctcgccc acgagtgcgg ccacggcgcc ttcagcaagc accagaccct caacgacttt     360

gtcggctggg tcctgcactc gagtctcggc gtcccctact tctcatggaa gttctcacac     420

caccgccacc accgcttcac tggcaacatg gagaaggaca tggtctttgt ccccgccgtc     480

aagaccgagg agccccctaa gcgccgcctc gcctccttct acctcgaccc tgagatcctc     540

gaggacgccc ccattgtcag cctcatccag ctcattgccc accagctcgc cggctggcag     600

atgtacatgc tcttcaacgt ctcatcgggc aaggacagca agcagcgcaa ccagtctggc     660

tggctgcgcg tcagccactt tgagcccacc agcgccgtct tccgccctag cgaggcctgg     720

tacatcttcc tcgccgacgt cggccttgct ctcaccggcg ccgccatcta ctacggctcc     780
```

-continued

```
acccttgtcg gctggcccac catgttcttt gtctactttg tcccctacat gtggtggaac    840

cactggctcg ttgccatcac ctacctccac cacacccacc cggaagtcca ccactacgag    900

gcggacagct ggacctacgt caagggcgcc ctcgccaccg tcgaccgcga ctttggctgg    960

attgacaagc acctcttcca cggcatcatt ggcttccacg tcatccacca catctttgcc   1020

aagatcccct tctactacgc cgaggaggcc accgcggcca tccagcccgt cattggcaac   1080

cactaccacc gtgctcccgg ctccttcctc ggcgacctct ggctcacttt caccaagtgc   1140

cgcttcgtcg agaaggaccc cgagcaccct ggcgccatgc gctgggtcgc accccgcaag   1200

gacctttag                                                           1209
```

<210> SEQ ID NO 158
<211> LENGTH: 402
<212> TYPE: PRT
<213> ORGANISM: Microdochium nivale

<400> SEQUENCE: 158

```
Met Ile Ala Thr Thr Gln Thr Lys Thr Ala Val Thr Asp Arg Gly Thr
1               5                   10                  15

Thr Arg Met Arg Gly Ser Ser Thr Ala Gln Glu Phe Pro Asp Ile Gln
            20                  25                  30

Thr Ile Arg Asp Ala Ile Pro Lys His Cys Phe Glu Pro Ser Thr Val
        35                  40                  45

Arg Ser Leu Ser Tyr Val Ala Arg Asp Val Thr Met Ala Ser Ala Leu
    50                  55                  60

Ile Trp Ala Ala Val Arg Phe Ile Pro Gln Ile Glu Asp Ser Val Leu
65                  70                  75                  80

Arg Phe Ser Ala Trp Met Val Tyr Gly Leu Val Gln Gly Met Val Cys
                85                  90                  95

Thr Gly Val Trp Ile Leu Ala His Glu Cys Gly His Gly Ala Phe Ser
            100                 105                 110

Lys His Gln Thr Leu Asn Asp Phe Val Gly Trp Val Leu His Ser Ser
        115                 120                 125

Leu Gly Val Pro Tyr Phe Ser Trp Lys Phe Ser His His Arg His His
    130                 135                 140

Arg Phe Thr Gly Asn Met Glu Lys Asp Met Val Phe Val Pro Ala Val
145                 150                 155                 160

Lys Thr Glu Glu Pro Pro Lys Arg Arg Leu Ala Ser Phe Tyr Leu Asp
                165                 170                 175

Pro Glu Ile Leu Glu Asp Ala Pro Ile Val Ser Leu Ile Gln Leu Ile
            180                 185                 190

Ala His Gln Leu Ala Gly Trp Gln Met Tyr Met Leu Phe Asn Val Ser
        195                 200                 205

Ser Gly Lys Asp Ser Lys Gln Arg Asn Gln Ser Gly Trp Leu Arg Val
    210                 215                 220

Ser His Phe Glu Pro Thr Ser Ala Val Phe Arg Pro Ser Glu Ala Trp
225                 230                 235                 240

Tyr Ile Phe Leu Ala Asp Val Gly Leu Ala Leu Thr Gly Ala Ala Ile
                245                 250                 255

Tyr Tyr Gly Ser Thr Leu Val Gly Trp Pro Thr Met Phe Phe Val Tyr
            260                 265                 270

Phe Val Pro Tyr Met Trp Trp Asn His Trp Leu Val Ala Ile Thr Tyr
        275                 280                 285
```

```
Leu His His Thr His Pro Glu Val His His Tyr Glu Ala Asp Ser Trp
    290                 295                 300

Thr Tyr Val Lys Gly Ala Leu Ala Thr Val Asp Arg Asp Phe Gly Trp
305                 310                 315                 320

Ile Asp Lys His Leu Phe His Gly Ile Ile Gly Phe His Val Ile His
                325                 330                 335

His Ile Phe Ala Lys Ile Pro Phe Tyr Tyr Ala Glu Glu Ala Thr Ala
            340                 345                 350

Ala Ile Gln Pro Val Ile Gly Asn His Tyr His Arg Ala Pro Gly Ser
        355                 360                 365

Phe Leu Gly Asp Leu Trp Leu Thr Phe Thr Lys Cys Arg Phe Val Glu
    370                 375                 380

Lys Asp Pro Glu His Pro Gly Ala Met Arg Trp Val Ala Pro Arg Lys
385                 390                 395                 400

Asp Leu
```

<210> SEQ ID NO 159
<211> LENGTH: 22
<212> TYPE: DNA
<213> ORGANISM: Artificial
<220> FEATURE:
<223> OTHER INFORMATION: Primer

<400> SEQUENCE: 159
atggatcaag ccagtaagat tg 22

<210> SEQ ID NO 160
<211> LENGTH: 23
<212> TYPE: DNA
<213> ORGANISM: Artificial
<220> FEATURE:
<223> OTHER INFORMATION: Primer

<400> SEQUENCE: 160
ttatctgcaa ttgcactgtt ttg 23

<210> SEQ ID NO 161
<211> LENGTH: 22
<212> TYPE: DNA
<213> ORGANISM: Artificial
<220> FEATURE:
<223> OTHER INFORMATION: Primer

<400> SEQUENCE: 161
atgcggagcg cggaggatga tg 22

<210> SEQ ID NO 162
<211> LENGTH: 21
<212> TYPE: DNA
<213> ORGANISM: Artificial
<220> FEATURE:
<223> OTHER INFORMATION: Primer

<400> SEQUENCE: 162
tcactgcttt acatcgttct g 21

<210> SEQ ID NO 163
<211> LENGTH: 20
<212> TYPE: DNA
<213> ORGANISM: Artificial
<220> FEATURE:
<223> OTHER INFORMATION: Primer

<400> SEQUENCE: 163
atgtccgtga agcatgagat 20

<210> SEQ ID NO 164
<211> LENGTH: 22
<212> TYPE: DNA
<213> ORGANISM: Artificial
<220> FEATURE:
<223> OTHER INFORMATION: Primer

<400> SEQUENCE: 164
tcacttagca tttgtgctct tc 22

<210> SEQ ID NO 165
<211> LENGTH: 22
<212> TYPE: DNA
<213> ORGANISM: Artificial
<220> FEATURE:
<223> OTHER INFORMATION: Primer

<400> SEQUENCE: 165
atggctacca cggctgattc tg 22

<210> SEQ ID NO 166
<211> LENGTH: 20
<212> TYPE: DNA
<213> ORGANISM: Artificial
<220> FEATURE:
<223> OTHER INFORMATION: Primer

<400> SEQUENCE: 166
tcaacgagac acgctcgctg 20

<210> SEQ ID NO 167
<211> LENGTH: 20
<212> TYPE: DNA
<213> ORGANISM: Artificial
<220> FEATURE:
<223> OTHER INFORMATION: Primer

<400> SEQUENCE: 167
atggtcgctg ttccactccg 20

<210> SEQ ID NO 168
<211> LENGTH: 22
<212> TYPE: DNA
<213> ORGANISM: Artificial
<220> FEATURE:
<223> OTHER INFORMATION: Primer

<400> SEQUENCE: 168
ttacttcaag cctggatcgc tc 22

<210> SEQ ID NO 169
<211> LENGTH: 21
<212> TYPE: DNA
<213> ORGANISM: Artificial
<220> FEATURE:
<223> OTHER INFORMATION: Primer

<400> SEQUENCE: 169
atgattgcga ccacccagac c 21

<210> SEQ ID NO 170
<211> LENGTH: 20

<212> TYPE: DNA
<213> ORGANISM: Artificial
<220> FEATURE:
<223> OTHER INFORMATION: Primer

<400> SEQUENCE: 170
ctaaaggtcc ttgcggggtg 20

<210> SEQ ID NO 171
<211> LENGTH: 33
<212> TYPE: DNA
<213> ORGANISM: Artificial
<220> FEATURE:
<223> OTHER INFORMATION: Primer

<400> SEQUENCE: 171
gcggccgcgc catggatcaa gccagtaaga ttg 33

<210> SEQ ID NO 172
<211> LENGTH: 32
<212> TYPE: DNA
<213> ORGANISM: Artificial
<220> FEATURE:
<223> OTHER INFORMATION: Primer

<400> SEQUENCE: 172
gcggccgcgt tatctgcaat tgcactgttt tg 32

<210> SEQ ID NO 173
<211> LENGTH: 33
<212> TYPE: DNA
<213> ORGANISM: Artificial
<220> FEATURE:
<223> OTHER INFORMATION: Primer

<400> SEQUENCE: 173
gcggccgcgc catgcggagc gcggaggatg atg 33

<210> SEQ ID NO 174
<211> LENGTH: 30
<212> TYPE: DNA
<213> ORGANISM: Artificial
<220> FEATURE:
<223> OTHER INFORMATION: Primer

<400> SEQUENCE: 174
gcggccgcgt cactgcttta catcgttctg 30

<210> SEQ ID NO 175
<211> LENGTH: 31
<212> TYPE: DNA
<213> ORGANISM: Artificial
<220> FEATURE:
<223> OTHER INFORMATION: Primer

<400> SEQUENCE: 175
gcggccgcgc catgtccgtg aagcatgaga t 31

<210> SEQ ID NO 176
<211> LENGTH: 31
<212> TYPE: DNA
<213> ORGANISM: Artificial
<220> FEATURE:
<223> OTHER INFORMATION: Primer

<400> SEQUENCE: 176

-continued gcggccgcgt cacttagcat ttgtgctctt c 31

<210> SEQ ID NO 177
<211> LENGTH: 33
<212> TYPE: DNA
<213> ORGANISM: Artificial
<220> FEATURE:
<223> OTHER INFORMATION: Primer

<400> SEQUENCE: 177
gcggccgcgc catggctacc acggctgatt ctg 33

<210> SEQ ID NO 178
<211> LENGTH: 29
<212> TYPE: DNA
<213> ORGANISM: Artificial
<220> FEATURE:
<223> OTHER INFORMATION: Primer

<400> SEQUENCE: 178
gcggccgcgt caacgagaca cgctcgctg 29

<210> SEQ ID NO 179
<211> LENGTH: 31
<212> TYPE: DNA
<213> ORGANISM: Artificial
<220> FEATURE:
<223> OTHER INFORMATION: Primer

<400> SEQUENCE: 179
gcggccgcgc catggtcgct gttccactcc g 31

<210> SEQ ID NO 180
<211> LENGTH: 31
<212> TYPE: DNA
<213> ORGANISM: Artificial
<220> FEATURE:
<223> OTHER INFORMATION: Primer

<400> SEQUENCE: 180
gcggccgcgt tacttcaagc ctggatcgct c 31

<210> SEQ ID NO 181
<211> LENGTH: 32
<212> TYPE: DNA
<213> ORGANISM: Artificial
<220> FEATURE:
<223> OTHER INFORMATION: Primer

<400> SEQUENCE: 181
gcggccgcgc catgattgcg accacccaga cc 32

<210> SEQ ID NO 182
<211> LENGTH: 29
<212> TYPE: DNA
<213> ORGANISM: Artificial
<220> FEATURE:
<223> OTHER INFORMATION: Primer

<400> SEQUENCE: 182
gcggccgcgc taaaggtcct tgcggggtg 29

<210> SEQ ID NO 183
<211> LENGTH: 16093
<212> TYPE: DNA
<213> ORGANISM: Artificial
<220> FEATURE:
<223> OTHER INFORMATION: Plasmid

<400> SEQUENCE: 183
aaaagttgcc atgattacgc caagcttggc cactaaggcc aatttaaatc tactaggccg 60
gccaaagtag gcgcctacta ccggtaattc ccgggattag cggccgctag tctgtgcgca 120
cttgtatcct gcaggtcaat cgtttaaaca ctgtacggac cgtggcctaa taggccggta 180
cccaagtttg tacaaaaaag caggctccat gattacgcca agcttggcca ctaaggccaa 240
tttaaatcta ctaggccggc catcgacggc ccggactgta tccaacttct gatctttgaa 300
tctctctgtt ccaacatgtt ctgaaggagt tctaagactt ttcagaaagc ttgtaacatg 360
ctttgtagac tttctttgaa ttactcttgc aaactctgat tgaacctacg tgaaaactgc 420
tccagaagtt ctaaccaaat tccgtcttgg gaaggcccaa aatttattga gtacttcagt 480
ttcatggacg tgtcttcaaa gatttataac ttgaaatccc atcattttta agagaagttc 540
tgttccgcaa tgtcttagat ctcattgaaa tctacaactc ttgtgtcaga agttcttcca 600
gaatcaactt gcatcatggt gaaaatctgg ccagaagttc tgaacttgtc atatttctta 660
acagttagaa aaatttctaa gtgtttagaa ttttgacttt tccaaagcaa acttgacttt 720
tgactttctt aataaaacaa acttcatatt ctaacatgtc ttgatgaaat gtgattcttg 780
aaatttgatg ttgatgcaaa agtcaaagtt tgacttttca gtgtgcaatt gaccattttg 840
ctcttgtgcc aattccaaac ctaaattgat gtatcagtgc tgcaaacttg atgtcatgga 900
agatcttatg agaaaattct tgaagactga gaggaaaaat tttgtagtac aacacaaaga 960
atcctgtttt tcatagtcgg actagacaca ttaacataaa acaccacttc attcgaagag 1020
tgattgaaga aggaaatgtg cagttacctt tctgcagttc ataagagcaa cttacagaca 1080
cttttactaa aatactacaa agaggaagat tttaacaact tagagaagta atgggagtta 1140
aagagcaaca cattaagggg gagtgttaaa attaatgtgt tgtaaccacc actaccttta 1200
gtaagtatta taagaaaatt gtaatcatca cattataatt attgtcctta tttaaaatta 1260
tgataaagtt gtatcattaa gattgagaaa accaaatagt cctcgtcttg atttttgaat 1320
tattgttttc tatgttactt ttcttcaagc ctatataaaa actttgtaat gctaaattgt 1380
atgctggaaa aaaatgtgta atgaattgaa tagaaattat ggtatttcaa agtccaaaat 1440
ccatcaatag aaatttagta caaaacgtaa ctcaaaaata ttctcttatt ttaaatttta 1500
caacaatata aaaatattct cttattttaa attttacaat aatataattt atcacctgtc 1560
acctttagaa taccaccaac aatattaata cttagatatt ttattcttaa taattttgag 1620
atctctcaat atatctgata tttattttat atttgtgtca tattttctta tgttttagag 1680
ttaaccctta tatcttggtc aaactagtaa ttcaatatat gagtttgtga aggacacatt 1740
gacatcttga aacattggtt ttaaccttgt tggaatgtta aaggtaataa aacattcaga 1800
attatgacca tctattaata tacttccttt gtcttttaaa aaagtgtgca tgaaaatgct 1860
ctatggtaag ctagagtgtc ttgctggcct gtgtatatca attccatttc cagatggtag 1920
aaactgccac tacgaataat tagtcataag acacgtatgt taacacacgt ccccttgcat 1980 gtttttttgcc atatattccg tctctttctt tttcttcacg tataaaacaa tgaactaatt 2040
aatagagcga tcaagctgaa ccgcgccacc atgagcagaa ctgttacttt agaggctgct 2100
cctgctacta ctttgagcgt ggagaagaaa acccctacca tccgtcaaat aaggaacgct 2160
atccctgagc attgcttcaa acctaccgct tggaaatcat ctgctcacgc tatcttcgat 2220

-continued tgctcagtag ctgctcttat tgctttcgct gcttacaaga ccatccctct cgttgaatac 2280
tggcctgcta gatgggcttt gtgggctctt tacggttaca tagagggatt agtgttcact 2340
ggaatctgga tcgttgctca tgagtgtgga catggtggac tttacacctc aaactgggct 2400
aacgatatag ttggttacac cttacatact tctcttttag tgccttactt cccttggaag 2460
tacactcatg ctagacacca cagatacacc ggacacatgg aaaaggatac cgctttcgtt 2520
cctcatagag ctggtgaaaa gtcaatagga agcaagatag ctgaggttat cggacatgct 2580
gaggatgctc cactttacat gttcggagga ttagttatgc atcaactttt aggatggcag 2640
gcttaccttc tcttctatgt gagcgctggt gctagatcta ctcctaaggc tctcgaggga 2700
tcatcttggg ctggatctca cttcgatcct atggctaacc tttggacccc ttctcaaaga 2760
cctttcgtgt tcttgagcac tgttggatta ggagctgtta tgttcgctct ctatcagctt 2820
tcaggtgtta tcggagtagc taacaccttc cttctctacg gacttcctta cctctgggta 2880
aacaactggc tagtggctat cacttacctt catcacaccc accctgattc tcatcattac 2940
gaggcttcta gatggacttt cttagatggt gctctaacta ccgtggatag gcctttcgga 3000
ttcatcggaa gaaaggtgtt ccacggaatc atagatttcc acgttgttca ccaccttttc 3060
ccttcaatgc ctttctatca tgctgaggaa gctactaagg ctatgagacc tgtgttagga 3120
gattactacc gtagagatga cactcctttc tggatagctt tatggaaaac cttctcttca 3180
tgccaagctg ttcagcctaa agagggtgaa gagggagttc ttgagtggga gaccaagaaa 3240
acccacgtga agagcgcttg atgattaatt aaggccgcct cgaccgtacc ccctgcagat 3300
agactatact atgttttagc ctgcctgctg gctagctact atgttatgtt atgttgtaaa 3360
ataaacacct gctaaggtat atctatctat attttagcat ggctttctca ataaattgtc 3420
tttccttatc gtttactatc ttatacctaa taatgaaata ataatatcac atatgaggaa 3480
cggggcaggt ttaggcatat atatacgagt gtagggcgga gtggggggcg cctactaccg 3540
gtaattcccg ggattagcgg ccgctagtct gtgcgcactt gtatcctgca ggtcaatcgt 3600
ttaaacactg tacggaccgt ggcctaatag gccggtacca cccagctttc ttgtacaaag 3660
tggccatgat tacgccaagc tctccaccgc ggtggcggcc gctctagccc aagctttaag 3720
gatgacctac ccattcttga gacaaatgtt acattttagt atcagagtaa aatgtgtacc 3780
tataactcaa attcgattga catgtatcca ttcaacataa aattaaacca gcctgcacct 3840
gcatccacat ttcaagtatt ttcaaaccgt tcggctccta tccaccgggt gtaacaagac 3900
ggattccgaa tttggaagat tttgactcaa attcccaatt tatattgacc gtgactaaat 3960
caactttaac ttctataatt ctgattaagc tcccaattta tattcccaac ggcactacct 4020
ccaaaattta tagactctca tccccttta aaccaactta gtaaacgttt ttttttaat 4080 tttatgaagt taagttttta ccttgttttt aaaaagaatc gttcataaga tgccatgcca 4140
gaacattagc tacacgttac acatagcatg cagccgcgga gaattgtttt tcttcgccac 4200
ttgtcactcc cttcaaacac ctaagagctt ctctctcaca gcacacacat acaatcacat 4260
gcgtgcatgc attattacac gtgatcgcca tgcaaatctc ctttatagcc tataaattaa 4320
ctcatcggct tcactcttta ctcaaaccaa aactcatcaa tacaaacaag attaaaaaca 4380
taaggcgcgc caattgacta gtaggcctat cgattaggag aataacaatg gtgcgctcct 4440
ccaagaacgt catcaaggag ttcatgcgct tcaaggtgcg catggagggc accgtgaacg 4500
gccacgagtt cgagatcgag ggcgagggcg agggccgccc ctacgagggc cacaacaccg 4560
tgaagctgaa ggtgaccaag ggcggccccc tgcccttcgc ctgggacatc ctgtcccccc 4620
agttccagta cggctccaag gtgtacgtga agcaccccgc cgacatcccc gactacaaga 4680
agctgtcctt ccccgagggc ttcaagtggg agcgcgtgat gaacttcgag gacggcggcg 4740
tggtgaccgt gacccaggac tcctccctgc aggacggctg cttcatctac aaggtgaagt 4800
tcatcggcgt gaacttcccc tccgacggcc ccgtaatgca gaagaagacc atgggctggg 4860
aggcctccac cgagcgcctg taccccccgcg acggcgtgct gaagggcgag atccacaagg 4920
ccctgaagct gaaggacggc ggccactacc tggtggagtt caagtccatc tacatggcca 4980
agaagcccgt gcagctgccc ggctactact acgtggactc caagctggac atcacctccc 5040
acaacgagga ctacaccatc gtggagcagt acgagcgcac cgagggccgc caccacctgt 5100
tcctgctcga gtctagaggt accggttgtt aacgttagcc ggctacgtat actccggaat 5160
attaataggc ctaggatgca tatggcggcc gcctgcagct ggcgccatcg attaattaag 5220
gccgcctcga gcatgcatct agagggcccg ctagcgttaa ccctgcttta atgagatatg 5280
cgagacgcct atgatcgcat gatatttgct ttcaattctg ttgtgcacgt tgtaaaaaac 5340
ctgagcatgt gtagctcaga tccttaccgc cggtttcggt tcattctaat gaatatatca 5400
cccgttacta tcgtattttt atgaataata ttctccgttc aatttactga ttgtccgtcg 5460
agcatatgct agaggatccc cgggtaccca actttattat acatagttga taattcactg 5520
gccggatgta ccgaattcgc ggccgcaagc ttgtacacta gtacgcgtca attggcgatc 5580
gcggatctga gatgaaaccg gtgattatca gaacctttta tggtctttgt atgcatatgg 5640
taaaaaaact tagtttgcaa tttcctgttt gttttggtaa tttgagtttc ttttagttgt 5700
tgatctgcct gctttttggt ttacgtcaga ctactactgc tgttgttgtt tggtttcctt 5760
tctttcattt tataaataaa taatccggtt cggtttactc cttgtgactg gctcagtttg 5820
gttattgcga aatgcgaatg gtaaattgag taattgaaat tcgttattag ggttctaagc 5880
tgttttaaca gtcactgggt taatatctct cgaatcttgc atggaaaatg ctcttaccat 5940
tggtttttaa ttgaaatgtg ctcatatggg ccgtggtttc caaattaaat aaaactacga 6000
tgtcatcgag aagtaaaatc aactgtgtcc acattatcag ttttgtgtat acgatgaaat 6060
agggtaattc aaaatctagc ttgatatgcc ttttggttca ttttaacctt ctgtaaacat 6120
tttttcagat tttgaacaag taaatccaaa aaaaaaaaaa aaaaatctca actcaacact 6180
aaattatttt aatgtataaa agatgcttaa aacatttggc ttaaaagaaa gaagctaaaa 6240
acatagagaa ctcttgtaaa ttgaagtatg aaaatatact gaattgggta ttatatgaat 6300
ttttctgatt taggattcac atgatccaaa aaggaaatcc agaagcacta atcagacatt 6360
ggaagtagga atatttcaaa aagttttttt tttttaagta agtgacaaaa gcttttaaaa 6420
aatagaaaag aaactagtat taaagttgta aatttaataa acaaaagaaa ttttttatat 6480
tttttcattt ctttttccag catgaggtta tgatggcagg atgtggattt catttttttc 6540
cttttgatag ccttttaatt gatctattat aattgacgaa aaaatattag ttaattatag 6600
atatatttta ggtagtatta gcaatttaca cttccaaaag actatgtaag ttgtaaatat 6660
gatgcgttga tctcttcatc attcaatggt tagtcaaaaa aataaaagct taactagtaa 6720
actaaagtag tcaaaaattg tactttagtt taaaatatta catgaataat ccaaaacgac 6780
atttatgtga aacaaaaaca atatagatcc attaccctgt tatccctaga ggggaaaatt 6840
cgaatccaaa aattacggat atgaatatag gcatatccgt atccgaatta tccgtttgac 6900
agctagcaac gattgtacaa ttgcttcttt aaaaaaggaa gaaagaaaga aagaaaagaa 6960
tcaacatcag cgttaacaaa cggccccgtt acggcccaaa cggtcatata gagtaacggc 7020
gttaagcgtt gaaagactcc tatcgaaata cgtaaccgca aacgtgtcat agtcagatcc 7080
cctcttcctt caccgcctca aacacaaaaa taatcttcta cagcctatat atacaacccc 7140
cccttctatc tctcctttct cacaattcat catctttctt tctctacccc caattttaag 7200
aaatcctctc ttctcctctt cattttcaag gtaaatctct ctctctctct ctctctctgt 7260
tattccttgt tttaattagg tatgtattat tgctagtttg ttaatctgct tatcttatgt 7320
atgccttatg tgaatatctt tatcttgttc atctcatccg tttagaagct ataaatttgt 7380
tgatttgact gtgtatctac acgtggttat gtttatatct aatcagatat gaatttcttc 7440
atattgttgc gtttgtgtgt accaatccga aatcgttgat ttttttcatt taatcgtgta 7500
gctaattgta cgtatacata tggatctacg tatcaattgt tcatctgttt gtgtttgtat 7560
gtatacagat ctgaaaacat cacttctctc atctgattgt gttgttacat acatagatat 7620
agatctgtta tatcattttt tttattaatt gtgtatatat atatgtgcat agatctggat 7680
tacatgattg tgattattta catgattttg ttatttacgt atgtatatat gtagatctgg 7740
actttttgga gttgttgact tgattgtatt tgtgtgtgta tatgtgtgtt ctgatcttga 7800
tatgttatgt atgtgcagct gaaccatggc ggcggcaaca acaacaacaa caacatcttc 7860
ttcgatctcc ttctccacca aaccatctcc ttcctcctcc aaatcaccat taccaatctc 7920
cagattctcc ctcccattct ccctaaaccc caacaaatca tcctcctcct cccgccgccg 7980
cggtatcaaa tccagctctc cctcctccat ctccgccgtg ctcaacacaa ccaccaatgt 8040
cacaaccact ccctctccaa ccaaacctac caaacccgaa acattcatct cccgattcgc 8100
tccagatcaa ccccgcaaag gcgctgatat cctcgtcgaa gctttagaac gtcaaggcgt 8160
agaaaccgta ttcgcttacc ctggaggtac atcaatggag attcaccaag ccttaacccg 8220
ctcttcctca atccgtaacg tccttcctcg tcacgaacaa ggaggtgtat tcgcagcaga 8280
aggatacgct cgatcctcag gtaaaccagg tatctgtata gccacttcag gtcccggagc 8340
tacaaatctc gttagcggat tagccgatgc gttgttagat agtgttcctc ttgtagcaat 8400
cacaggacaa gtccctcgtc gtatgattgg tacagatgcg tttcaagaga ctccgattgt 8460
tgaggtaacg cgttcgatta cgaagcataa ctatcttgtg atggatgttg aagatatccc 8520
taggattatt gaggaagctt tctttttagc tacttctggt agacctggac ctgttttggt 8580
tgatgttcct aaagatattc aacaacagct tgcgattcct aattgggaac aggctatgag 8640
attacctggt tatatgtcta ggatgcctaa acctccggaa gattctcatt tggagcagat 8700
tgttaggttg atttctgagt ctaagaagcc tgtgttgtat gttggtggtg gttgtttgaa 8760
ttctagcgat gaattgggta ggtttgttga gcttacgggg atccctgttg cgagtacgtt 8820
gatggggctg ggatcttatc cttgtgatga tgagttgtcg ttacatatgc ttggaatgca 8880
tgggactgtg tatgcaaatt acgctgtgga gcatagtgat ttgttgttgg cgtttggggt 8940
aaggtttgat gatcgtgtca cgggtaagct tgaggctttt gctagtaggg ctaagattgt 9000
tcatattgat attgactcgg ctgagattgg gaagaataag actcctcatg tgtctgtgtg 9060
tggtgatgtt aagctggctt tgcaagggat gaataaggtt cttgagaacc gagcggagga 9120
gcttaagctt gattttggag tttggaggaa tgagttgaac gtacagaaac agaagtttcc 9180
gttgagcttt aagacgtttg gggaagctat tcctccacag tatgcgatta aggtccttga 9240
tgagttgact gatggaaaag ccataataag tactggtgtc gggcaacatc aaatgtgggc 9300
ggcgcagttc tacaattaca agaaaccaag gcagtggcta tcatcaggag gccttggagc 9360

```
tatgggattt ggacttcctg ctgcgattgg agcgtctgtt gctaaccctg atgcgatagt   9420
tgtggatatt gacggagatg gaagctttat aatgaatgtg caagagctag ccactattcg   9480
tgtagagaat cttccagtga aggtactttt attaaacaac cagcatcttg gcatggttat   9540
gcaatgggaa gatcggttct acaaagctaa ccgagctcac acatttctcg ggatccggc    9600
tcaggaggac gagatattcc cgaacatgtt gctgtttgca gcagcttgcg ggattccagc   9660
ggcgagggtg acaaagaaag cagatctccg agaagctatt cagacaatgc tggatacacc   9720
aggaccttac ctgttggatg tgatttgtcc gcaccaagaa catgtgttgc cgatgatccc   9780
gaatggtggc actttcaacg atgtcataac ggaaggagat ggccggatta aatactgata   9840
gggataacag ggtaatctcg acgagatgaa accggtgatt atcagaacct tttatggtct   9900
ttgtatgcat atggtaaaaa aacttagttt gcaatttcct gtttgttttg gtaatttgag   9960
tttcttttag ttgttgatct gcctgctttt tggtttacgt cagactacta ctgctgttgt  10020
tgtttggttt cctttctttc attttataaa taaataatcc ggttcggttt actccttgtg  10080
actggctcag tttggttatt gcgaaatgcg aatggtaaat tgagtaattg aaattcgtta  10140
ttagggttct aagctgtttt aacagtcact gggttaatat ctctcgaatc ttgcatggaa  10200
aatgctctta ccattggttt ttaattgaaa tgtgctcata tgggccgtgg tttccaaatt  10260
aaataaaact acgatgtcat cgagaagtaa aatcaactgt gtccacatta tcagttttgt  10320
gtatacgatg aaatagggta attcaaaatc tagcttgata tgccttttgg ttcattttaa  10380
ccttctgtaa acatttttc agattttgaa caagtaaatc caaaaaaaaa aaaaaaaaat   10440
ctcaactcaa cactaaatta ttttaatgta taaaagatgc ttaaaacatt tggcttaaaa  10500
gaaagaagct aaaaacatag agaactcttg taaattgaag tatgaaaata tactgaattg  10560
ggtattatat gaatttttct gatttaggat tcacatgatc caaaaaggaa atccagaagc  10620
actaatcaga cattggaagt aggaatattt caaaaagttt ttttttttta agtaagtgac  10680
aaaagctttt aaaaaataga aaagaaacta gtattaaagt tgtaaattta ataaacaaaa  10740
gaaatttttt atatttttc atttcttttt ccagcatgag gttatgatgg caggatgtgg   10800
atttcatttt tttcctttg atagcctttt aattgatcta ttataattga cgaaaaaata   10860
ttagttaatt atagatatat tttaggtagt attagcaatt tacacttcca aaagactatg  10920
taagttgtaa atatgatgcg ttgatctctt catcattcaa tggttagtca aaaaaataaa  10980
agcttaacta gtaaactaaa gtagtcaaaa attgtacttt agtttaaaat attacatgaa  11040
taatccaaaa cgacatttat gtgaaacaaa aacaatatgt cgaggcgatc gcagtactta  11100
atcagtgatc agtaactaaa ttcagtacat taaagacgtc cgcaatgtgt tattaagttg  11160
tctaagcgtc aatttgttta caccacaata tatcctgcca ccagccagcc aacagctccc  11220
cgaccggcag ctcggcacaa aatcactgat catctaaaaa ggtgatgtgt atttgagtaa  11280
aacagcttgc gtcatgcggt cgctgcgtat atgatgcgat gagtaaataa acaaatacgc  11340
aaggggaacg catgaaggtt atcgctgtac ttaaccagaa aggcgggtca ggcaagacga  11400
ccatcgcaac ccatctagcc cgcgccctgc aactcgccgg ggccgatgtt ctgttagtcg  11460
attccgatcc ccagggcagt gcccgcgatt gggcggccgt gcgggaagat caaccgctaa  11520
ccgttgtcgg catcgaccgc ccgacgattg accgcgacgt gaaggccatc ggccggcgcg  11580
acttcgtagt gatcgacgga gcgccccagg cggcggactt ggctgtgtcc gcgatcaagg  11640
cagccgactt cgtgctgatt ccggtgcagc caagccctta cgacatttgg gccaccgccg  11700
```

```
acctggtgga gctggttaag cagcgcattg aggtcacgga tggaaggcta caagcggcct  11760
ttgtcgtgtc gcgggcgatc aaaggcacgc gcatcggcgg tgaggttgcc gaggcgctgg  11820
ccgggtacga gctgcccatt cttgagtccc gtatcacgca gcgcgtgagc tacccaggca  11880
ctgccgccgc cggcacaacc gttcttgaat cagaacccga gggcgacgct gcccgcgagg  11940
tccaggcgct ggccgctgaa attaaatcaa aactcatttg agttaatgag gtaaagagaa  12000
aatgagcaaa agcacaaaca cgctaagtgc cggccgtccg agcgcacgca gcagcaaggc  12060
tgcaacgttg gccagcctgg cagacacgcc agccatgaag cgggtcaact ttcagttgcc  12120
ggcggaggat cacaccaagc tgaagatgta cgcggtacgc caaggcaaga ccattaccga  12180
gctgctatct gaatacatcg cgcagctacc agagtaaatg agcaaatgaa taaatgagta  12240
gatgaatttt agcggctaaa ggaggcggca tggaaaatca agaacaacca ggcaccgacg  12300
ccgtggaatg ccccatgtgt ggaggaacgg gcggttggcc aggcgtaagc ggctgggttg  12360
tctgccggcc ctgcaatggc actggaaccc ccaagcccga ggaatcggcg tgagcggtcg  12420
caaaccatcc ggcccggtac aaatcggcgc ggcgctgggt gatgacctgg tggagaagtt  12480
gaaggccgcg caggccgccc agcggcaacg catcgaggca gaagcacgcc ccggtgaatc  12540
gtggcaaggg gccgctgatc gaatccgcaa agaatcccgg caaccgccgg cagccggtgc  12600
gccgtcgatt aggaagccgc ccaagggcga cgagcaacca gattttttcg ttccgatgct  12660
ctatgacgtg ggcacccgcg atagtcgcag catcatggac gtggccgttt tccgtctgtc  12720
gaagcgtgac cgacgagctg gcgaggtgat ccgctacgag cttccagacg ggcacgtaga  12780
ggtttccgca ggccccgccg gcatggccag tgtgtgggat tacgacctgg tactgatggc  12840
ggtttcccat ctaaccgaat ccatgaaccg ataccgggaa gggaagggag acaagcccgg  12900
ccgcgtgttc cgtccacacg ttgcggacgt actcaagttc tgccggcgag ccgatggcgg  12960
aaagcagaaa gacgacctgg tagaaacctg cattcggtta aacaccacgc acgttgccat  13020
gcagcgtacc aagaaggcca agaacggccg cctggtgacg gtatccgagg gtgaagcctt  13080
gattagccgc tacaagatcg taaagagcga aaccgggcgg ccggagtaca tcgagatcga  13140
gcttgctgat tggatgtacc gcgagatcac agaaggcaag aacccggacg tgctgacggt  13200
tcaccccgat actttttga tcgaccccgg catcggccgt tttctctacc gcctggcacg  13260
ccgcgccgca ggcaaggcag aagccagatg gttgttcaag acgatctacg aacgcagtgg  13320
cagcgccgga gagttcaaga agttctgttt caccgtgcgc aagctgatcg ggtcaaatga  13380
cctgccggag tacgatttga aggaggaggc ggggcaggct ggcccgatcc tagtcatgcg  13440
ctaccgcaac ctgatcgagg gcgaagcatc cgccggttcc taatgtacgg agcagatgct  13500
agggcaaatt gccctagcag gggaaaaagg tcgaaaaggt ctctttcctg tggatagcac  13560
gtacattggg aacccaaagc cgtacattgg gaaccggaac ccgtacattg ggaacccaaa  13620
gccgtacatt gggaaccggt cacacatgta agtgactgat ataaaagaga aaaaaggcga  13680
tttttccgcc taaaactctt taaaacttat taaaactctt aaaacccgcc tggcctgtgc  13740
ataactgtct ggccagcgca cagccgaaga gctgcaaaaa gcgcctaccc ttcggtcgct  13800
gcgctcccta cgccccgccg cttcgcgtcg gcctatcgcg gcctatgcgg tgtgaaatac  13860
cgcacagatg cgtaaggaga aaataccgca tcaggcgctc ttccgcttcc tcgctcactg  13920
actcgctgcg ctcggtcgtt cggctgcggc gagcggtatc agctcactca aaggcggtaa  13980
tacggttatc cacagaatca ggggataacg caggaaagaa catgtgagca aaaggccagc  14040
aaaaggccag gaaccgtaaa aaggccgcgt tgctggcgtt tttccatagg ctccgccccc  14100
```

ctgacgagca tcacaaaaat cgacgctcaa gtcagaggtg gcgaaacccg acaggactat 14160
aaagatacca ggcgtttccc cctggaagct ccctcgtgcg ctctcctgtt ccgaccctgc 14220
cgcttaccgg atacctgtcc gcctttctcc cttcgggaag cgtggcgctt tctcatagct 14280
cacgctgtag gtatctcagt tcggtgtagg tcgttcgctc caagctgggc tgtgtgcacg 14340
aaccccccgt tcagcccgac cgctgcgcct tatccggtaa ctatcgtctt gagtccaacc 14400
cggtaagaca cgacttatcg ccactggcag cagccactgg taacaggatt agcagagcga 14460
ggtatgtagg cggtgctaca gagttcttga agtggtggcc taactacggc tacactagaa 14520
ggacagtatt tggtatctgc gctctgctga agccagttac cttcggaaaa agagttggta 14580
gctcttgatc cggcaaacaa accaccgctg gtagcggtgg tttttttgtt tgcaagcagc 14640
agattacgcg cagaaaaaaa ggatctcaag aagatccttt gatcttttct acggggtcct 14700
tcaactcatc gatagtttgg ctgtgagcaa ttatgtgctt agtgcatcta acgcttgagt 14760
taagccgcgc cgcgaagcgg cgtcggcttg aacgaatttc tagctagaca ttatttgcca 14820
acgaccttcg tgatctcgcc cttgacatag tggacaaatt cttcgagctg gtcggcccgg 14880
gacgcgagac ggtcttcttc ttggcccaga taggcttggc gcgcttcgag gatcacgggc 14940
tggtattgcg ccggaaggcg ctccatcgcc cagtcggcgg cgacatcctt cggcgcgatc 15000
ttgccggtaa ccgccgagta ccaaatccgg ctcagcgtaa ggaccacatt gcgctcatcg 15060
cccgcccaat ccggcgggga gttccacagg gtcagcgtct cgttcagtgc ttcgaacaga 15120
tcctgttccg gcaccgggtc gaaaagttcc tcggccgcgg ggccgacgag ggccacgcta 15180
tgctcccggg ccttggtgag caggatcgcc agatcaatgt cgatggtggc cggttcaaag 15240
atacccgcca gaatatcatt acgctgccat tcgccgaact ggagttcgcg tttggccgga 15300
tagcgccagg ggatgatgtc atcgtgcacc acaatcgtca cctcaaccgc gcgcaggatt 15360
tcgctctcgc cgggggaggc ggacgtttcc agaaggtcgt tgataagcgc gcggcgcgtg 15420
gtctcgtcga gacggacggt aacggtgaca agcaggtcga tgtccgaatg gggcttaagg 15480
ccgccgtcaa cggcgctacc atacagatgc acggcgagga gggtcggttc gaggtggcgc 15540
tcgatgacac ccacgacttc cgacagctgg gtggacacct cggcgatgac cgcttcaccc 15600
atgatgttta actttgtttt agggcgactg ccctgctgcg taacatcgtt gctgctccat 15660
aacatcaaac atcgacccac ggcgtaacgc gcttgctgct tggatgcccg aggcatagac 15720
tgtaccccaa aaaaacagtc ataacaagcc atgaaaaccg ccactgcgtt ccatgaatat 15780
tcaaacaaac acatacagcg cgacttatca tggatattga catacaaatg gacgaacgga 15840
taaacctttt cacgcccttt taaatatccg attattctaa taaacgctct tttctcttag 15900
gtttacccgc caatatatcc tgtcaaacac tgatagttta aactgaaggc gggaaacgac 15960
aatctgatca ctgattagta actaaggcct ttaattaatc tagaggcgcg ccgggccccc 16020
tgcagggagc tcggccggcc aatttaaatt gatatcggta catcgattac gccaagctat 16080
caactttgta tag 16093

<210> SEQ ID NO 184
<211> LENGTH: 16097
<212> TYPE: DNA
<213> ORGANISM: Artificial
<220> FEATURE:
<223> OTHER INFORMATION: Plasmid

<400> SEQUENCE: 184

-continued

```
aaaagttgcc atgattacgc caagcttggc cactaaggcc aatttaaatc tactaggccg     60
gccaaagtag gcgcctacta ccggtaattc ccgggattag cggccgctag tctgtgcgca    120
cttgtatcct gcaggtcaat cgtttaaaca ctgtacggac cgtggcctaa taggccggta    180
cccaagtttg tacaaaaaag caggctccat gattacgcca agcttggcca ctaaggccaa    240
tttaaatcta ctaggccggc catcgacggc ccggactgta tccaacttct gatctttgaa    300
tctctctgtt ccaacatgtt ctgaaggagt tctaagactt ttcagaaagc ttgtaacatg    360
ctttgtagac tttctttgaa ttactcttgc aaactctgat tgaacctacg tgaaaactgc    420
tccagaagtt ctaaccaaat tccgtcttgg gaaggcccaa aatttattga gtacttcagt    480
ttcatggacg tgtcttcaaa gatttataac ttgaaatccc atcattttta agagaagttc    540
tgttccgcaa tgtcttagat ctcattgaaa tctacaactc ttgtgtcaga agttcttcca    600
gaatcaactt gcatcatggt gaaaatctgg ccagaagttc tgaacttgtc atatttctta    660
acagttagaa aaatttctaa gtgtttagaa ttttgacttt tccaaagcaa acttgacttt    720
tgactttctt aataaaacaa acttcatatt ctaacatgtc ttgatgaaat gtgattcttg    780
aaatttgatg ttgatgcaaa agtcaaagtt tgacttttca gtgtgcaatt gaccattttg    840
ctcttgtgcc aattccaaac ctaaattgat gtatcagtgc tgcaaacttg atgtcatgga    900
agatcttatg agaaaattct tgaagactga gaggaaaaat tttgtagtac aacacaaaga    960
atcctgtttt tcatagtcgg actagacaca ttaacataaa acaccacttc attcgaagag   1020
tgattgaaga aggaaatgtg cagttacctt tctgcagttc ataagagcaa cttacagaca   1080
cttttactaa aatactacaa agaggaagat tttaacaact tagagaagta atgggagtta   1140
aagagcaaca cattaagggg gagtgttaaa attaatgtgt tgtaaccacc actaccttta   1200
gtaagtatta taagaaaatt gtaatcatca cattataatt attgtcctta tttaaaatta   1260
tgataaagtt gtatcattaa gattgagaaa accaaatagt cctcgtcttg atttttgaat   1320
tattgttttc tatgttactt ttcttcaagc ctatataaaa actttgtaat gctaaattgt   1380
atgctggaaa aaaatgtgta atgaattgaa tagaaattat ggtatttcaa agtccaaaat   1440
ccatcaatag aaatttagta caaaacgtaa ctcaaaaata ttctcttatt ttaaatttta   1500
caacaatata aaaatattct cttattttaa attttacaat aatataattt atcacctgtc   1560
acctttagaa taccaccaac aatattaata cttagatatt ttattcttaa taattttgag   1620
atctctcaat atatctgata tttattttat atttgtgtca tattttctta tgttttagag   1680
ttaaccctta tatcttggtc aaactagtaa ttcaatatat gagtttgtga aggacacatt   1740
gacatcttga aacattggtt ttaaccttgt tggaatgtta aaggtaataa aacattcaga   1800
attatgacca tctattaata tacttccttt gtcttttaaa aaagtgtgca tgaaaatgct   1860
ctatggtaag ctagagtgtc ttgctggcct gtgtatatca attccatttc cagatggtag   1920
aaactgccac tacgaataat tagtcataag acacgtatgt taacacacgt ccccttgcat   1980
gttttttgcc atatattccg tctctttctt tttcttcacg tataaaacaa tgaactaatt   2040
aatagagcga tcaagctgaa ccatggctac tagacaaaga acttccacta ctgtggttgt   2100
ggagaagcca tctgctaagg ttacattgga gccacaacaa caaccacagt tcccagatat   2160
caagaccatc aaggatgcta ttccagctca ctgcttccaa ccatccctct tcacttcctt   2220
ctactacgtg ttcagggatt tcgctatggt tgctactctt gtgtgggctg ctttgactta   2280
cattccagct atcccagatc aaagactcag agtggctgct tggatggttt acggattcgt   2340
gcaaggattg gtgtgtactg gagtgtggat tttgggacac gagtgtggac acggagcttt   2400
```

```
ctctacccac ggaaagttga acaacgttgt gggatggttc ttgcactctt tcctcctcgt   2460
gccatacttc tcttggaagt actcacacca cagacatcac agattcaccg gacacatgga   2520
tttggatatg gctttcgtgc cagctactca acctaagaag cactctatcc tcgctggaat   2580
cgatttgaac gagttgttcg aggatactcc aatcgctcaa ctcatcagga ttgtgttcca   2640
ccaactcttc ggatggcaag tgtacttgct cttcaacgct tctgctggaa agggatctaa   2700
gcaatgggag ccaactggat tggctaagtg gttcagagtg tctcacttcg agccaacctc   2760
tgctgttttc agaccatccg aggctatctt catcttcatc tccgatttgg gattggctat   2820
taccttcacc gctctctact tcgcttctaa ggctgttgga acttctaccg tgttgttctt   2880
gtacgctgtg ccttatttct gggtgcacca ctggttggtt gctatcactt acttgcacca   2940
ccaccacact gaggtgccac actacactaa cgagggatgg acttacgtta agggagcttt   3000
ggctactgtt gatagggagt tcggattcat cggaaagcac ctcttccacg gaattattga   3060
gaagcacgtg gttcaccact tgttcccaag aatcccattc tacaaggctg atgaggctac   3120
tgaggctatt aagccattgc tcggagatct ctactaccac gatgagagga acttcatcgg   3180
acaactctgg tctgttttcg gttctctcaa gtacgttgag cacgatccaa ctaaccaggg   3240
agctatgaga tgggctaagg agtgatgatt aattaaggcc gcctcgaccg taccccctgc   3300
agatagacta tactatgttt tagcctgcct gctggctagc tactatgtta tgttatgttg   3360
taaaataaac acctgctaag gtatatctat ctatatttta gcatggcttt ctcaataaat   3420
tgtctttcct tatcgtttac tatcttatac ctaataatga aataataata tcacatatga   3480
ggaacggggc aggtttaggc atatatatac gagtgtaggg cggagtgggg ggcgcctact   3540
accggtaatt cccgggatta gcggccgcta gtctgtgcgc acttgtatcc tgcaggtcaa   3600
tcgtttaaac actgtacgga ccgtggccta ataggccggt accacccagc tttcttgtac   3660
aaagtggcca tgattacgcc aagctctcca ccgcggtggc ggccgctcta gcccaagctt   3720
taaggatgac ctacccattc ttgagacaaa tgttacattt tagtatcaga gtaaaatgtg   3780
tacctataac tcaaattcga ttgacatgta tccattcaac ataaaattaa accagcctgc   3840
acctgcatcc acatttcaag tattttcaaa ccgttcggct cctatccacc gggtgtaaca   3900
agacggattc cgaatttgga agattttgac tcaaattccc aatttatatt gaccgtgact   3960
aaatcaactt taacttctat aattctgatt aagctcccaa tttatattcc caacggcact   4020
acctccaaaa tttatagact ctcatcccct tttaaaccaa cttagtaaac gttttttttt   4080
taattttatg aagttaagtt tttaccttgt ttttaaaaag aatcgttcat aagatgccat   4140
gccagaacat tagctacacg ttacacatag catgcagccg cggagaattg tttttcttcg   4200
ccacttgtca ctcccttcaa acacctaaga gcttctctct cacagcacac acatacaatc   4260
acatgcgtgc atgcattatt acacgtgatc gccatgcaaa tctcctttat agcctataaa   4320
ttaactcatc ggcttcactc tttactcaaa ccaaaactca tcaatacaaa caagattaaa   4380
aacataaggc gcgccaattg actagtaggc ctatcgatta ggagaataac aatggtgcgc   4440
tcctccaaga acgtcatcaa ggagttcatg cgcttcaagg tgcgcatgga gggcaccgtg   4500
aacggccacg agttcgagat cgagggcgag ggcgagggcc gcccctacga gggccacaac   4560
accgtgaagc tgaaggtgac caagggcggc cccctgccct tcgcctggga catcctgtcc   4620
ccccagttcc agtacggctc caaggtgtac gtgaagcacc ccgccgacat ccccgactac   4680
aagaagctgt ccttccccga gggcttcaag tgggagcgcg tgatgaactt cgaggacggc   4740
```

ggcgtggtga ccgtgaccca ggactcctcc ctgcaggacg gctgcttcat ctacaaggtg 4800
aagttcatcg gcgtgaactt cccctccgac ggccccgtaa tgcagaagaa gaccatgggc 4860
tgggaggcct ccaccgagcg cctgtacccc cgcgacggcg tgctgaaggg cgagatccac 4920
aaggccctga agctgaagga cggcggccac tacctggtgg agttcaagtc catctacatg 4980
gccaagaagc ccgtgcagct gcccggctac tactacgtgg actccaagct ggacatcacc 5040
tcccacaacg aggactacac catcgtggag cagtacgagc gcaccgaggg ccgccaccac 5100
ctgttcctgc tcgagtctag aggtaccggt tgttaacgtt agccggctac gtatactccg 5160
gaatattaat aggcctagga tgcatatggc ggccgcctgc agctggcgcc atcgattaat 5220
taaggccgcc tcgagcatgc atctagaggg cccgctagcg ttaaccctgc tttaatgaga 5280
tatgcgagac gcctatgatc gcatgatatt tgctttcaat tctgttgtgc acgttgtaaa 5340
aaacctgagc atgtgtagct cagatcctta ccgccggttt cggttcattc taatgaatat 5400
atcacccgtt actatcgtat ttttatgaat aatattctcc gttcaattta ctgattgtcc 5460
gtcgagcata tgctagagga tccccgggta cccaacttta ttatacatag ttgataattc 5520
actggccgga tgtaccgaat tcgcggccgc aagcttgtac actagtacgc gtcaattggc 5580
gatcgcggat ctgagatgaa accggtgatt atcagaacct tttatggtct ttgtatgcat 5640
atggtaaaaa aacttagttt gcaatttcct gtttgttttg gtaatttgag tttcttttag 5700
ttgttgatct gcctgctttt tggtttacgt cagactacta ctgctgttgt tgtttggttt 5760
cctttctttc attttataaa taaataatcc ggttcggttt actccttgtg actggctcag 5820
tttggttatt gcgaaatgcg aatggtaaat tgagtaattg aaattcgtta ttagggttct 5880
aagctgtttt aacagtcact gggttaatat ctctcgaatc ttgcatggaa aatgctctta 5940
ccattggttt ttaattgaaa tgtgctcata tgggccgtgg tttccaaatt aaataaaact 6000
acgatgtcat cgagaagtaa aatcaactgt gtccacatta tcagttttgt gtatacgatg 6060
aaatagggta attcaaaatc tagcttgata tgccttttgg ttcattttaa ccttctgtaa 6120 acatttttc agattttgaa caagtaaatc caaaaaaaaa aaaaaaaaat ctcaactcaa 6180
cactaaatta ttttaatgta taaaagatgc ttaaaacatt tggcttaaaa gaaagaagct 6240
aaaaacatag agaactcttg taaattgaag tatgaaaata tactgaattg ggtattatat 6300
gaatttttct gatttaggat tcacatgatc caaaaaggaa atccagaagc actaatcaga 6360
cattggaagt aggaatattt caaaaagttt tttttttta agtaagtgac aaaagctttt 6420
aaaaaataga aaagaaacta gtattaaagt tgtaaattta ataaacaaaa gaaatttttt 6480
atattttttc atttcttttt ccagcatgag gttatgatgg caggatgtgg atttcatttt 6540
tttccttttg atagcctttt aattgatcta ttataattga cgaaaaaata ttagttaatt 6600
atagatatat tttaggtagt attagcaatt tacacttcca aaagactatg taagttgtaa 6660
atatgatgcg ttgatctctt catcattcaa tggttagtca aaaaaataaa agcttaacta 6720
gtaaactaaa gtagtcaaaa attgtacttt agtttaaaat attacatgaa taatccaaaa 6780
cgacatttat gtgaaacaaa aacaatatag atccattacc ctgttatccc tagaggggaa 6840
aattcgaatc caaaaattac ggatatgaat ataggcatat ccgtatccga attatccgtt 6900
tgacagctag caacgattgt acaattgctt ctttaaaaaa ggaagaaaga aagaaagaaa 6960
agaatcaaca tcagcgttaa caaacggccc cgttacggcc caaacggtca tatagagtaa 7020
cggcgttaag cgttgaaaga ctcctatcga aatacgtaac cgcaaacgtg tcatagtcag 7080
atcccctctt ccttcaccgc ctcaaacaca aaaataatct tctacagcct atatatacaa 7140
cccccccttc tatctctcct ttctcacaat tcatcatctt tctttctcta cccccaattt 7200
taagaaatcc tctcttctcc tcttcatttt caaggtaaat ctctctctct ctctctctct 7260
ctgttattcc ttgttttaat taggtatgta ttattgctag tttgttaatc tgcttatctt 7320
atgtatgcct tatgtgaata tctttatctt gttcatctca tccgtttaga agctataaat 7380
ttgttgattt gactgtgtat ctacacgtgg ttatgtttat atctaatcag atatgaattt 7440
cttcatattg ttgcgtttgt gtgtaccaat ccgaaatcgt tgattttttt catttaatcg 7500
tgtagctaat tgtacgtata catatggatc tacgtatcaa ttgttcatct gtttgtgttt 7560
gtatgtatac agatctgaaa acatcacttc tctcatctga ttgtgttgtt acatacatag 7620
atatagatct gttatatcat ttttttattt aattgtgtat atatatatgt gcatagatct 7680
ggattacatg attgtgatta tttacatgat tttgttattt acgtatgtat atatgtagat 7740
ctggactttt tggagttgtt gacttgattg tatttgtgtg tgtatatgtg tgttctgatc 7800
ttgatatgtt atgtatgtgc agctgaacca tggcggcggc aacaacaaca acaacaacat 7860
cttcttcgat ctccttctcc accaaaccat ctccttcctc ctccaaatca ccattaccaa 7920
tctccagatt ctccctccca ttctccctaa accccaacaa atcatcctcc tcctcccgcc 7980
gccgcggtat caaatccagc tctccctcct ccatctccgc cgtgctcaac acaaccacca 8040
atgtcacaac cactccctct ccaaccaaac ctaccaaacc cgaaacattc atctcccgat 8100
tcgctccaga tcaaccccgc aaaggcgctg atatcctcgt cgaagcttta gaacgtcaag 8160
gcgtagaaac cgtattcgct taccctggag gtacatcaat ggagattcac caagccttaa 8220
cccgctcttc ctcaatccgt aacgtccttc ctcgtcacga acaaggaggt gtattcgcag 8280
cagaaggata cgctcgatcc tcaggtaaac caggtatctg tatagccact tcaggtcccg 8340
gagctacaaa tctcgttagc ggattagccg atgcgttgtt agatagtgtt cctcttgtag 8400
caatcacagg acaagtccct cgtcgtatga ttggtacaga tgcgtttcaa gagactccga 8460
ttgttgaggt aacgcgttcg attacgaagc ataactatct tgtgatggat gttgaagata 8520
tccctaggat tattgaggaa gctttctttt tagctacttc tggtagacct ggacctgttt 8580
tggttgatgt tcctaaagat attcaacaac agcttgcgat tcctaattgg gaacaggcta 8640
tgagattacc tggttatatg tctaggatgc ctaaacctcc ggaagattct catttggagc 8700
agattgttag gttgatttct gagtctaaga agcctgtgtt gtatgttggt ggtggttgtt 8760
tgaattctag cgatgaattg ggtaggtttg ttgagcttac ggggatccct gttgcgagta 8820
cgttgatggg gctgggatct tatccttgtg atgatgagtt gtcgttacat atgcttggaa 8880
tgcatgggac tgtgtatgca aattacgctg tggagcatag tgatttgttg ttggcgtttg 8940
gggtaaggtt tgatgatcgt gtcacgggta agcttgaggc ttttgctagt agggctaaga 9000
ttgttcatat tgatattgac tcggctgaga ttgggaagaa taagactcct catgtgtctg 9060
tgtgtggtga tgttaagctg gctttgcaag ggatgaataa ggttcttgag aaccgagcgg 9120
aggagcttaa gcttgatttt ggagtttgga ggaatgagtt gaacgtacag aaacagaagt 9180
ttccgttgag ctttaagacg tttggggaag ctattcctcc acagtatgcg attaaggtcc 9240
ttgatgagtt gactgatgga aaagccataa taagtactgg tgtcgggcaa catcaaatgt 9300
gggcggcgca gttctacaat tacaagaaac caaggcagtg gctatcatca ggaggccttg 9360
gagctatggg atttggactt cctgctgcga ttggagcgtc tgttgctaac cctgatgcga 9420
tagttgtgga tattgacgga gatggaagct ttataatgaa tgtgcaagag ctagccacta 9480

-continued ttcgtgtaga gaatcttcca gtgaaggtac ttttattaaa caaccagcat cttggcatgg 9540
ttatgcaatg ggaagatcgg ttctacaaag ctaaccgagc tcacacattt ctcggggatc 9600
cggctcagga ggacgagata ttcccgaaca tgttgctgtt tgcagcagct tgcgggattc 9660
cagcggcgag ggtgacaaag aaagcagatc tccgagaagc tattcagaca atgctggata 9720
caccaggacc ttacctgttg gatgtgattt gtccgcacca agaacatgtg ttgccgatga 9780
tcccgaatgg tggcactttc aacgatgtca taacggaagg agatggccgg attaaatact 9840
gatagggata acagggtaat ctcgacgaga tgaaaccggt gattatcaga accttttatg 9900
gtctttgtat gcatatggta aaaaaactta gtttgcaatt tcctgtttgt tttggtaatt 9960
tgagtttctt ttagttgttg atctgcctgc tttttggttt acgtcagact actactgctg 10020
ttgttgtttg gtttcctttc tttcatttta taaataaata atccggttcg gtttactcct 10080
tgtgactggc tcagtttggt tattgcgaaa tgcgaatggt aaattgagta attgaaattc 10140
gttattaggg ttctaagctg ttttaacagt cactgggtta atatctctcg aatcttgcat 10200
ggaaaatgct cttaccattg gtttttaatt gaaatgtgct catatgggcc gtggtttcca 10260
aattaaataa aactacgatg tcatcgagaa gtaaaatcaa ctgtgtccac attatcagtt 10320
ttgtgtatac gatgaaatag ggtaattcaa aatctagctt gatatgcctt ttggttcatt 10380
ttaaccttct gtaaacattt tttcagattt tgaacaagta aatccaaaaa aaaaaaaaaa 10440
aaatctcaac tcaacactaa attattttaa tgtataaaag atgcttaaaa catttggctt 10500
aaaagaaaga agctaaaaac atagagaact cttgtaaatt gaagtatgaa aatatactga 10560
attgggtatt atatgaattt ttctgattta ggattcacat gatccaaaaa ggaaatccag 10620
aagcactaat cagacattgg aagtaggaat atttcaaaaa gttttttttt tttaagtaag 10680
tgacaaaagc ttttaaaaaa tagaaaagaa actagtatta aagttgtaaa tttaataaac 10740
aaaagaaatt ttttatattt tttcatttct ttttccagca tgaggttatg atggcaggat 10800
gtggatttca ttttttttcct tttgatagcc ttttaattga tctattataa ttgacgaaaa 10860
aatattagtt aattatagat atattttagg tagtattagc aatttacact tccaaaagac 10920
tatgtaagtt gtaaatatga tgcgttgatc tcttcatcat tcaatggtta gtcaaaaaaa 10980
taaaagctta actagtaaac taaagtagtc aaaaattgta ctttagttta aaatattaca 11040
tgaataatcc aaaacgacat ttatgtgaaa caaaaacaat atgtcgaggc gatcgcagta 11100
cttaatcagt gatcagtaac taaattcagt acattaaaga cgtccgcaat gtgttattaa 11160
gttgtctaag cgtcaatttg tttacaccac aatatatcct gccaccagcc agccaacagc 11220
tccccgaccg gcagctcggc acaaaatcac tgatcatcta aaaaggtgat gtgtatttga 11280
gtaaaacagc ttgcgtcatg cggtcgctgc gtatatgatg cgatgagtaa ataaacaaat 11340
acgcaagggg aacgcatgaa ggttatcgct gtacttaacc agaaaggcgg gtcaggcaag 11400
acgaccatcg caacccatct agcccgcgcc ctgcaactcg ccggggccga tgttctgtta 11460
gtcgattccg atccccaggg cagtgcccgc gattgggcgg ccgtgcggga agatcaaccg 11520
ctaaccgttg tcggcatcga ccgcccgacg attgaccgcg acgtgaaggc catcggccgg 11580
cgcgacttcg tagtgatcga cggagcgccc caggcggcgg acttggctgt gtccgcgatc 11640
aaggcagccg acttcgtgct gattccggtg cagccaagcc cttacgacat ttgggccacc 11700
gccgacctgg tggagctggt taagcagcgc attgaggtca cggatggaag gctacaagcg 11760
gcctttgtcg tgtcgcgggc gatcaaaggc acgcgcatcg gcggtgaggt tgccgaggcg 11820
ctggccgggt acgagctgcc cattcttgag tcccgtatca cgcagcgcgt gagctaccca 11880
ggcactgccg ccgccggcac aaccgttctt gaatcagaac ccgagggcga cgctgcccgc 11940
gaggtccagg cgctggccgc tgaaattaaa tcaaaactca tttgagttaa tgaggtaaag 12000
agaaaatgag caaaagcaca aacacgctaa gtgccggccg tccgagcgca cgcagcagca 12060
aggctgcaac gttggccagc ctggcagaca cgccagccat gaagcgggtc aactttcagt 12120
tgccggcgga ggatcacacc aagctgaaga tgtacgcggt acgccaaggc aagaccatta 12180
ccgagctgct atctgaatac atcgcgcagc taccagagta aatgagcaaa tgaataaatg 12240
agtagatgaa ttttagcggc taaaggaggc ggcatggaaa atcaagaaca accaggcacc 12300
gacgccgtgg aatgccccat gtgtggagga acgggcggtt ggccaggcgt aagcggctgg 12360
gttgtctgcc ggccctgcaa tggcactgga acccccaagc ccgaggaatc ggcgtgagcg 12420
gtcgcaaacc atccggcccg gtacaaatcg gcgcggcgct gggtgatgac ctggtggaga 12480
agttgaaggc cgcgcaggcc gcccagcggc aacgcatcga ggcagaagca cgccccggtg 12540
aatcgtggca aggggccgct gatcgaatcc gcaaagaatc ccggcaaccg ccggcagccg 12600
gtgcgccgtc gattaggaag ccgcccaagg gcgacgagca accagatttt ttcgttccga 12660
tgctctatga cgtgggcacc cgcgatagtc gcagcatcat ggacgtggcc gttttccgtc 12720
tgtcgaagcg tgaccgacga gctggcgagg tgatccgcta cgagcttcca gacgggcacg 12780
tagaggtttc cgcaggcccc gccggcatgg ccagtgtgtg ggattacgac ctggtactga 12840
tggcggtttc ccatctaacc gaatccatga accgataccg ggaagggaag ggagacaagc 12900
ccggccgcgt gttccgtcca cacgttgcgg acgtactcaa gttctgccgg cgagccgatg 12960
gcggaaagca gaaagacgac ctggtagaaa cctgcattcg gttaaacacc acgcacgttg 13020
ccatgcagcg taccaagaag gccaagaacg gccgcctggt gacggtatcc gagggtgaag 13080
ccttgattag ccgctacaag atcgtaaaga gcgaaaccgg gcggccggag tacatcgaga 13140
tcgagcttgc tgattggatg taccgcgaga tcacagaagg caagaacccg gacgtgctga 13200
cggttcaccc cgattacttt ttgatcgacc ccggcatcgg ccgttttctc taccgcctgg 13260
cacgccgcgc cgcaggcaag gcagaagcca gatggttgtt caagacgatc tacgaacgca 13320
gtggcagcgc cggagagttc aagaagttct gtttcaccgt gcgcaagctg atcgggtcaa 13380
atgacctgcc ggagtacgat ttgaaggagg aggcggggca ggctggcccg atcctagtca 13440
tgcgctaccg caacctgatc gagggcgaag catccgccgg ttcctaatgt acggagcaga 13500
tgctagggca aattgcccta gcaggggaaa aaggtcgaaa aggtctcttt cctgtggata 13560
gcacgtacat tgggaaccca aagccgtaca ttgggaaccg gaacccgtac attgggaacc 13620
caaagccgta cattgggaac cggtcacaca tgtaagtgac tgatataaaa gagaaaaaag 13680
gcgatttttc cgcctaaaac tctttaaaac ttattaaaac tcttaaaacc cgcctggcct 13740
gtgcataact gtctggccag cgcacagccg aagagctgca aaaagcgcct acccttcggt 13800
cgctgcgctc cctacgcccc gccgcttcgc gtcggcctat cgcggcctat gcggtgtgaa 13860
ataccgcaca gatgcgtaag gagaaaatac cgcatcaggc gctcttccgc ttcctcgctc 13920
actgactcgc tgcgctcggt cgttcggctg cggcgagcgg tatcagctca ctcaaaggcg 13980
gtaatacggt tatccacaga atcaggggat aacgcaggaa agaacatgtg agcaaaaggc 14040
cagcaaaagg ccaggaaccg taaaaaggcc gcgttgctgg cgtttttcca taggctccgc 14100
ccccctgacg agcatcacaa aaatcgacgc tcaagtcaga ggtggcgaaa cccgacagga 14160
ctataaagat accaggcgtt tccccctgga agctccctcg tgcgctctcc tgttccgacc 14220

-continued

```
ctgccgctta ccggatacct gtccgccttt ctcccttcgg gaagcgtggc gctttctcat  14280
agctcacgct gtaggtatct cagttcggtg taggtcgttc gctccaagct gggctgtgtg  14340
cacgaacccc ccgttcagcc cgaccgctgc gccttatccg gtaactatcg tcttgagtcc  14400
aacccggtaa gacacgactt atcgccactg gcagcagcca ctggtaacag gattagcaga  14460
gcgaggtatg taggcggtgc tacagagttc ttgaagtggt ggcctaacta cggctacact  14520
agaaggacag tatttggtat ctgcgctctg ctgaagccag ttaccttcgg aaaaagagtt  14580
ggtagctctt gatccggcaa acaaaccacc gctggtagcg gtggtttttt tgtttgcaag  14640
cagcagatta cgcgcagaaa aaaaggatct caagaagatc ctttgatctt ttctacgggg  14700
tccttcaact catcgatagt ttggctgtga gcaattatgt gcttagtgca tctaacgctt  14760
gagttaagcc gcgccgcgaa gcggcgtcgg cttgaacgaa tttctagcta gacattattt  14820
gccaacgacc ttcgtgatct cgcccttgac atagtggaca aattcttcga gctggtcggc  14880
ccgggacgcg agacggtctt cttcttggcc cagataggct tggcgcgctt cgaggatcac  14940
gggctggtat tgcgccggaa ggcgctccat cgcccagtcg gcggcgacat ccttcggcgc  15000
gatcttgccg gtaaccgccg agtaccaaat ccggctcagc gtaaggacca cattgcgctc  15060
atcgcccgcc caatccggcg gggagttcca cagggtcagc gtctcgttca gtgcttcgaa  15120
cagatcctgt tccggcaccg ggtcgaaaag ttcctcggcc gcggggccga cgagggccac  15180
gctatgctcc cgggccttgg tgagcaggat cgccagatca atgtcgatgg tggccggttc  15240
aaagataccc gccagaatat cattacgctg ccattcgccg aactggagtt cgcgtttggc  15300
cggatagcgc caggggatga tgtcatcgtg caccacaatc gtcacctcaa ccgcgcgcag  15360
gatttcgctc tcgccggggg aggcggacgt ttccagaagg tcgttgataa gcgcgcggcg  15420
cgtggtctcg tcgagacgga cggtaacggt gacaagcagg tcgatgtccg aatggggctt  15480
aaggccgccg tcaacggcgc taccatacag atgcacggcg aggagggtcg gttcgaggtg  15540
gcgctcgatg acacccacga cttccgacag ctgggtggac acctcggcga tgaccgcttc  15600
acccatgatg tttaactttg ttttagggcg actgccctgc tgcgtaacat cgttgctgct  15660
ccataacatc aaacatcgac ccacggcgta acgcgcttgc tgcttggatg cccgaggcat  15720
agactgtacc ccaaaaaaac agtcataaca agccatgaaa accgccactg cgttccatga  15780
atattcaaac aaacacatac agcgcgactt atcatggata ttgacataca aatggacgaa  15840
cggataaacc ttttcacgcc cttttaaata tccgattatt ctaataaacg ctcttttctc  15900
ttaggtttac ccgccaatat atcctgtcaa acactgatag tttaaactga aggcgggaaa  15960
cgacaatctg atcactgatt agtaactaag gcctttaatt aatctagagg cgcgccgggc  16020
cccctgcagg gagctcggcc ggccaattta aattgatatc ggtacatcga ttacgccaag  16080
ctatcaactt tgtatag                                                 16097
```